US009352028B2

(12) United States Patent
Barner et al.

(10) Patent No.: US 9,352,028 B2
(45) Date of Patent: May 31, 2016

(54) COMPOSITION FOR TREATING LUNG CANCER, PARTICULARLY OF NON-SMALL LUNG CANCERS (NSCLC)

(71) Applicant: CUREVAC GMBH, Tubingen (DE)

(72) Inventors: Marijke Barner, Stuttgart (DE); Jochen Probst, Wolfschlugen (DE); Thomas Lander, Konigstein I. Taunus (DE); Ingmar Hoerr, Tubingen (DE)

(73) Assignee: CureVac AG, Tübingen (DE)

( * ) Notice: Subject to any disclaimer, the term of this patent is extended or adjusted under 35 U.S.C. 154(b) by 262 days.

(21) Appl. No.: 13/750,664

(22) Filed: Jan. 25, 2013

(65) Prior Publication Data
US 2013/0202645 A1 Aug. 8, 2013

Related U.S. Application Data

(63) Continuation of application No. 12/682,213, filed as application No. PCT/EP2008/008503 on Oct. 8, 2008, now abandoned.

(30) Foreign Application Priority Data

Oct. 9, 2007 (WO) .................. PCT/EP2007/008770

(51) Int. Cl.
*A61K 39/00* (2006.01)
(52) U.S. Cl.
CPC ......... *A61K 39/0011* (2013.01); *A61K 2039/53* (2013.01)
(58) Field of Classification Search
None
See application file for complete search history.

(56) References Cited

U.S. PATENT DOCUMENTS

| 5,804,381 | A | 9/1998 | Chen et al. |
|---|---|---|---|
| 2005/0003484 | A1 | 1/2005 | Hirano et al. |
| 2005/0032730 | A1 | 2/2005 | Von Der Mulbe et al. |
| 2005/0054624 | A1 | 3/2005 | Covey |
| 2005/0249748 | A1 | 11/2005 | Oubensky, Jr. et al. |
| 2005/0250723 | A1 | 11/2005 | Hoerr et al. |
| 2006/0188440 | A1 | 8/2006 | Adams et al. |
| 2008/0025944 | A1 | 1/2008 | Hoerr et al. |
| 2008/0171711 | A1 | 7/2008 | Hoerr et al. |
| 2008/0267873 | A1 | 10/2008 | Hoerr et al. |
| 2010/0203076 | A1 | 8/2010 | Fotin-Mleczek et al. |
| 2010/0305196 | A1 | 12/2010 | Probst et al. |
| 2011/0053829 | A1 | 3/2011 | Baumhof et al. |
| 2011/0269950 | A1 | 11/2011 | Von Der Mülbe et al. |

FOREIGN PATENT DOCUMENTS

| EP | 1604688 | 12/2005 |
|---|---|---|
| WO | WO 02/098443 | 12/2002 |
| WO | WO 2004/004743 | 1/2004 |
| WO | WO 2006/008154 | 1/2006 |
| WO | WO 2006/024518 | 3/2006 |
| WO | WO 2007/008780 | 1/2007 |
| WO | WO 2008/014979 | 2/2008 |
| WO | WO 2008/077592 | 7/2008 |
| WO | WO 2008/083949 | 7/2008 |

OTHER PUBLICATIONS

Jager et al. Recombinant vaccinia/fowlpox NY-ESO-1 vaccines induce both humoral and cellular NY-ESO-1-specific immune responses in cancer patients. Proceedings of the National Academy of Sciences, USA, vol. 103, No. 39, pp. 14453-14458, Sep. 2006.*
Lucas et al. MAGE-B5, MAGE-B6, MAGE-C2, and MAGE-C3: Four new members of the MAGE family with tumor-specific expression. International Journal of Cancer, vol. 87, No. 1, pp. 55-60, 2000.*
Kopreski et al. Circulating RNA as a tumor marker: Detection of 5T4 mRNA in breast and lung cancer patient serum. Annals of the NY Academy of Sciences, vol. 945, pp. 172-178, Sep. 2001.*
Duffy et al. Survivin: a promising tumor marker. Cancer Letters, vol. 249, pp. 49-60, Apr. 2007, Epub Feb. 1, 2007.*
Lee et al. The nucleotide sequence of human protamine 1 cDNA. Nucleic Acids Research, vol. 15, No. 18, p. 7639, 1987.*
Scheel et al. Toll-like receptor-dependent activation of several human blood cell types by protamine-condensed mRNA. European Journal of Immunology, vol. 35, pp. 1557-1566, 2005.*
Godelaine et al., "A new tumor specific antigen encoded by MAGE-C2 and presented to cytolytic T lymphocytes by HLA-B44." Cancer Immunology Immunotherapy, vol. 56(6):753-759, 2007 (Epub 2006).
Jungbluth et al., "CT7 (MAGE-C1) antigen expression in normal and neoplastic tissues," International Journal of Cancer, vol. 99:839-845, 2002.
Kobayashi et al., "Peptide epitope identification for tumor-reactive CD4 T Cells." Current Opinion Immunology: vol 20:221-227, 2008.
Mitchell et al., "mRNA turnover." Current Opinion in Cell Biology, vol. 13(3):320-325, 2001.
Mulyran et al., "Attenuated recombinant vaccinia virus expressing oncofetal antigen (Tumor-associated antigen) 5T4 induces active therapy of established tumors." Molecular Cancer Therapeutics, vol. 1:1129-1137, 2002.
Pesole et al., "UTRdb and UTRsite: specialized databases of sequences and functional elements of 5' and 3' untranslated regions of eukaryotic mRNAs, Update 2002." Nucleic Acids Research, vol. 30(1):335-340, 2002.
Ross et al., "Control of messenger RNA stability in higher eukaryotes." Trends in Genetics, vol. 12(5):171-175, 1996.

(Continued)

*Primary Examiner* — Jennifer Dunston
(74) *Attorney, Agent, or Firm* — Parker Highlander PLLC

(57) ABSTRACT

The present invention relates to an active (immunostimulatory) composition comprising at least one RNA, preferably a mRNA, encoding at least two (preferably different) antigens capable of eliciting an (adaptive) immune response in a mammal. The invention furthermore relates to a vaccine comprising the active (immunostimulatory) composition, and to the use of the active (immunostimulatory) composition (for the preparation of a vaccine) and/or of the vaccine for eliciting an (adaptive) immune response for the treatment of lung cancer, particularly of non-small cell lung cancers (NSCLC), preferably selected from the three main sub-types squamous cell lung carcinoma, adenocarcinoma and large cell lung carcinoma, or of disorders related thereto. Finally, the invention relates to kits, particularly to kits of parts, containing the active (immunostimulatory) composition and/or the vaccine.

67 Claims, 34 Drawing Sheets

(56) References Cited

OTHER PUBLICATIONS

Figure 27:
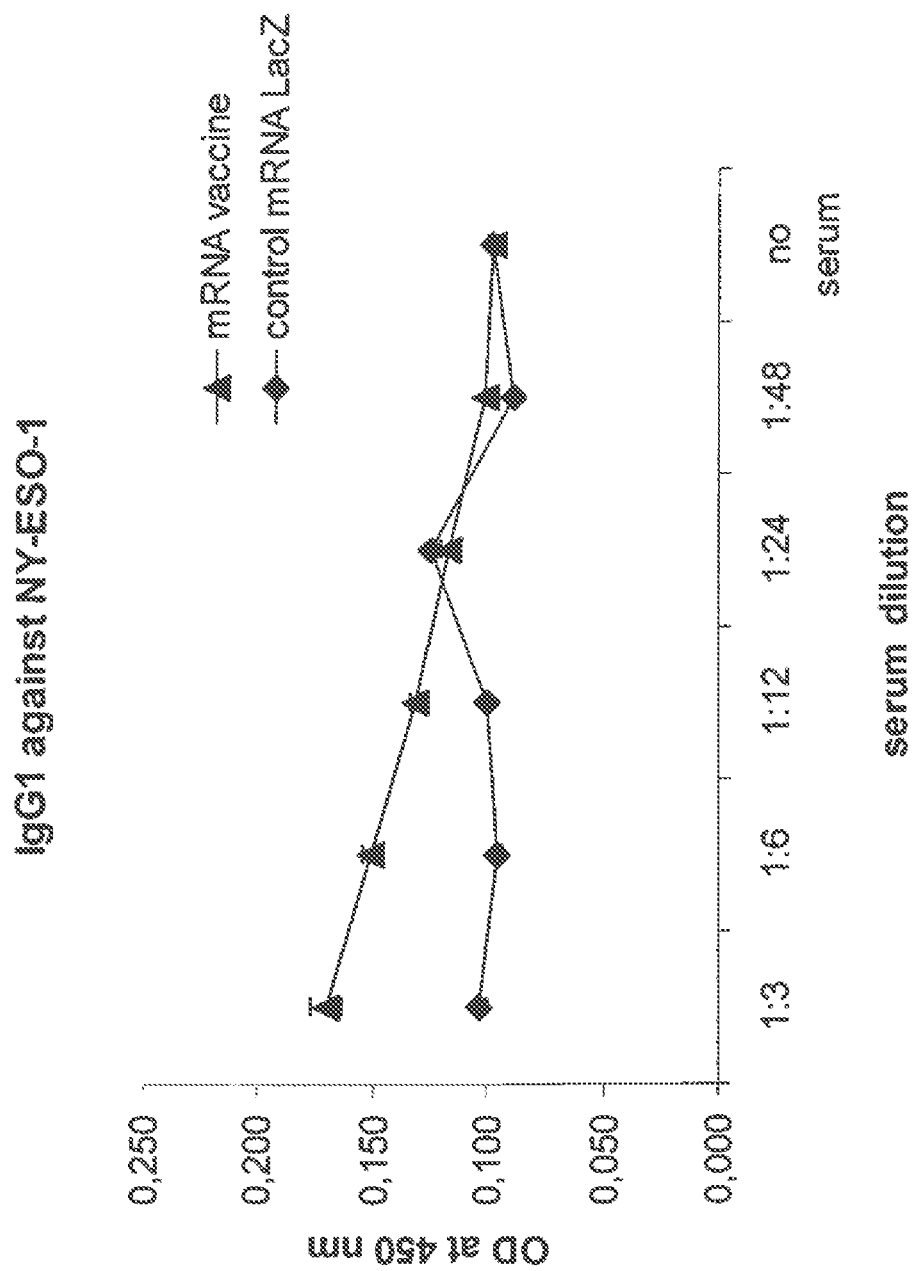

Tajima et al., "Identification of an epitope from the epithelial cell adhesion molecule eliciting HLA-A*2402-restricted cytotoxic T-lymphocyte responses." Tissue Antigens, vol. 64(6):650-659, 2004.

Tourriere et al., "mRNA degradation machines in eukaryotic dells." Biochimie, vol. 84(8):821-837, 2002.

Wilusz et al., "Bringing the role of mRNA decay in the control of gene expression into focus." Trends in Genetics, vol. 20(10):491-497, 2004.

Xiang et al., "A DNA vaccine targeting survivin compines apoptosis with suppresion of angiogenesis in lung tumor eradication," Cancer Research vol. 65(2):553-561, 2005.

Aug. 29, 2012 Office Action issued in parent U.S. Appl. No. 12/682,213, 41 pages.

Rüttinger et al., "Adjuvant therapeutic vaccination in patients with non-small cell lung cancer made lymphopenic and reconstituted with autologous PBMC: first clinical experience and evidence of an immune response", *Journal of Translational Medicine*, 5:43, 2007.

Rittig et al., "Intradermal vaccinations with RNA coding for TAA generate CD8+ and CD4+ immune responses and induce clinical benefit in vaccinated patients", *Mol Ther.*, 19(5):990-9, 2011.

Ciuleanu et al., "Maintenance pemetrexed plus best supportive care versus placebo plus best supportive care for non-small-cell lung cancer: a randomised, double-blind, phase 3 study," *Lancet*, 374:1432-1440, 2009.

Kallen et al., "A novel, disruptive vaccination technology, Self-adjuvanted RNActive® vaccines," *Human Vaccines & Immunotherapetuics*, 9:10:2263-2276, 2013.

Office Action issued in European Application No. 08 838 033.2, mailed Aug. 5, 2015.

Paz-Ares et al., "Maintenance therapy with pemetrexed plus best supportive care versus placebo plus best supportive care after induction therapy with pemetrexed plus cisplatin for advanced non squamous non-small-cell lung cancer (PARAMOUNT): a double-blind, phase 3, randomised controlled trial," *Lancet Oncol.* 13:247-255, 2012.

Scheel et al., "Therapeutic anti-tumor immunity triggered by injections of immunostimulating single-stranded RNA," *European Journal of Immunology*, 36:2807-2816, 2006.

* cited by examiner

```
ATGACACCGGGCACCCAGTCTCCTTTCTTCCTGCTGCTGCTCCTCACAGTGCTTACAGTTGTTACAGGTTCTGGT
CATGCAAGCTCTACCCCAGGTGGAGAAAAGGAGACTTCGGCTACCCAGAGAAGTTCAGTGCCCAGCTCTACTGAG
AAGAATGCTGTGAGTATGACCAGCAGCGTACTCTCCAGCCACAGCCCCGGTTCAGGCTCCTCCACCACTCAGGGA
CAGGATGTCACTCTGGCCCCGGCCACGGAACCAGCTTCAGGTTCAGCTGCCACCTGGGGACAGGATGTCACCTCG
GTCCCAGTCACCAGGCCAGCCCTGGGCTCCACCACCCCGCCAGCCCACGATGTCACCTCAGCCCCGGACAACAAG
CCAGCCCCGGGCTCCACCGCCCCCCAGCCCACGGTGTCACCTCGGCCCCGGACACCAGGCCGGCCCCGGGCTCC
ACCGCCCCCCAGCCCACGGTGTCACCTCGGCCCCGGACACCAGGCCGGCCCCGGGCTCCACCGCCCCCCAGCC
CACGGTGTCACCTCGGCCCCGGACACCAGGCCGGCCCCGGGCTCCACCGCCCCCCAGCCCACGGTGTCACCTCG
GCCCCGGACACCAGGCCGGCCCCGGGCTCCACCGCCCCCCAGCCCACGGTGTCACCTCGGCCCCGGACACCAGG
CCGGCCCCGGGCTCCACCGCCCCCCAGCCCACGGTGTCACCTCGGCCCCGGACAACAGGCCCGCCTTGGGCTCC
ACCGCCCCTCCAGTCCACAATGTCACCTCGGCCTCAGGCTCTGCATCAGGCTCAGCTTCTACTCTGGTGCACAAC
GGCACCTCTGCCAGGGCTACCACAACCCCAGCCAGCAAGAGCACTCCATTCTCAATTCCCAGCCACCACTCTGAT
ACTCCTACCACCCTTGCCAGCCATAGCACCAAGACTGATGCCAGTAGCACTCACCATAGCTCGGTACCTCCTCTC
ACCTCCTCCAATCACAGCACTTCTCCCCAGTTGTCTACTGGGGTCTCTTTCTTTTTCCTGTCTTTTCACATTTCA
AACCTCCAGTTTAATTCCTCTCTGGAAGATCCCAGCACCGACTACTACCAAGAGCTGCAGAGAGACATTTCTGAA
ATGTTTTTGCAGATTTATAAACAAGGGGGTTTTCTGGGCCTCTCCAATATTAAGTTCAGGCCAGGATCTGTGGTG
GTACAATTGACTCTGGCCTTCCGAGAAGGTACCATCAATGTCCACGACGTGGAGACACAGTTCAATCAGTATAAA
ACGGAAGCAGCCTCTCGATATAACCTGACGATCTCAGACGTCAGCGTGAGTGATGTGCCATTTCCTTTCTCTGCC
CAGTCTGGGGCTGGGGTGCCAGGCTGGGGCATCGCGCTGCTGGTGCTGGTCTGTGTTCTGGTTGCGCTGGCCATT
GTCTATCTCATTGCCTTGGCTGTCTGTCAGTGCCGCCGAAAGAACTACGGGCAGCTGGACATCTTTCCAGCCCGG
GATACCTACCATCCTATGAGCGAGTACCCCACCTACCACACCCATGGGCGCTATGTGCCCCCTAGCAGTACCGAT
CGTAGCCCCTATGAGAAGGTTTCTGCAGGTAACGGTGGCAGCAGCCTCTCTTACACAAACCCAGCAGTGGCAGCC
GCTTCTGCCAACTTGTAG
```

Fig. 1

ATGACCCCCGGCACCCAGAGCCCGTTCTTCCTGCTCCTGCTGCTCACGGTGCTGACCGTCGTGACCGGGTCCGGC
CACGCCAGCTCCACCCCCGGGGGCGAGAAGGAGACGAGCGCCACCCAGCGGTCCAGCGTGCCCTCCAGCACCGAG
AAGAACGCGGTCTCCATGACCAGCTCCGTGCTGAGCTCCACAGCCCCGGGTCCGGCAGCTCCACGACCCAGGGC
CAGGACGTGACCCTCGCCCCGGCCACCGAGCCCGCCAGCGGGTCCGCCGCGACGTGGGGCCAGGACGTCACCAGC
GTGCCCGTGACCCGCCCCGCCCTGGGGAGCACCACGCCGCCCGCCCACGACGTCACCTCCGCCCCCGACAACAAG
CCCGCGCCGGGCAGCACCGCCCCCCCCGCCCACGGGGTGACCTCCGCCCCCGACACGCGGCCGGCCCCCGGCAGC
ACCGCGCCCCCGCCCACGGCGTGACCTCCGCCCCGGACACCCGCCCCGCCCCCGGGAGCACGGCCCCGCCGGCG
CACGGCGTCACCTCCGCCCCCGACACCCGGCCCGCCCCCGGGAGCACCGCCCCGCCCGCCCACGGCGTGACGTCC
GCGCCCGACACCCGCCCGGCCCCCGGCAGCACCGCCCCCCCGCCCACGGGGTGACCTCCGCCCCGGACACGCGG
CCCGCGCCCGGCAGCACCGCCCCGCCGGCCCACGGGGTCACCTCCGCCCCCGACAACCGCCCCGCGCTGGGCAGC
ACCGCCCCCCGGTGCACAACGTGACGTCCGCCAGCGGGTCCGCCAGCGGCTCCGCCAGCACCCTCGTCCACAAC
GGCACCAGCGCGCGGGCCACCACCACGCCCGCCTCCAAGAGCACCCCCTTCTCCATCCCCAGCCACCACTCCGAC
ACCCCGACCACGCTGGCCAGCCACTCCACCAAGACCGACGCCAGCTCCACCACCACAGCTCCGTGCCGCCGCTG
ACGAGCTCCAACCACAGCACCTCCCCCAGCTCAGCACCGGGGTGTCCTTCTTCTTCCTGAGCTTCCACATCAGC
AACCTGCAGTTCAACTCCAGCCTCGAGGACCCGTCCACCGACTACTACCAGGAGCTGCAGCGCGACATCAGCGAG
ATGTTCCTGCAGATCTACAAGCAGGGCGGGTTCCTCGGCCTGTCCAACATCAAGTTCCGGCCCGGGAGCGTCGTG
GTGCAGCTGACGCTCGCGTTCCGCGAGGGCACCATCAACGTCCACGACGTGGAGACCCAGTTCAACCAGTACAAG
ACCGAGGCCGCCTCCCGGTACAACCTGACGATCAGCGACGTCTCCGTGAGCGACGTGCCCTTCCCCTTCTCCGCC
CAGAGCGGCGCCGGGGTCCCGGGCTGGGGATCGCGCTGCTCGTGCTGGTGTGCGTCCTGGTGGCCCTCGCCATC
GTGTACCTGATCGCCCTGGCGGTCTCGCCAGTGCCGCCGGAAGAACTACGGCCAGCTCGACATCTTCCCCGCCCGC
GACACCTACCACCCCATGTCCGAGTACCCGACCTACCACACCCACGGGCGGTACGTGCCCCCCAGCTCCACGGAC
CGCAGCCCCTACGAGAAGGTGTCCGCCGGCAACGGCGGGAGCTCCCTGAGCTACACCAACCCGGCCGTCGCCGCG
GCCAGCGCCAACCTGTGA

Fig. 2 atgcctggggggtgctcccggggcccgccgccggggacgggcgtctgcggctggcgcgactagcgctggtactc
ctgggctgggtctcctcgtcttctcccacctcctcggcatcctccttctcctcctcggcgcgcgttcctggcttcc
gccgtgtccgccagccccgctgccggaccagtgcccgcgctgtgcgagtgctccgaggcagcgcgcacagtc
aagtgcgttaaccgcaatctgaccgaggtgcccacggacctgccgcctacgtgcgcaacctcttccttaccggc
aaccagctggccgtgctccctgccggcgccttcgccgccggccgccgctggcggagctggccgcgctcaacctc
agcggcagccgcctggacgaggtgcgcgcgggcgccttcgagcatctgcccagcctgcgccagctcgacctcagc
cacaacccactggccgacctcagtcccttcgctttctcgggcagcaatgccagcgtctcggcccccagtcccctt
gtggaactgatcctgaaccacatcgtgcccctgaagatgagcggcagaaccggagcttcgagggcatggtggtg
gcggccctgctggcgggccgtgcactgcaggggctccgccgcttggagctggccagcaaccacttcctttacctg
ccgcgggatgtgctggcccaactgcccagcctcaggcacctggacttaagtaataattcgctggtgagcctgacc
tacgtgtccttccgcaacctgacacatctagaaagcctccacctggaggacaatgccctcaaggtccttcacaat
ggcaccctggctgagttgcaaggtctaccccacattagggttttcctggacaacaatccctgggtctgcgactgc
cacatggcagacatggtgacctggctcaaggaaacagaggtagtgcagggcaaagaccggctcacctgtgcatat
ccggaaaaaatgaggaatcgggtcctcttggaactcaacagtgctgacctggactgtgaccgattcttcccca
tccctgcaaacctcttatgtcttcctgggtattgttttagccctgataggcgctatttcctcctggttttgtat
ttgaaccgcaaggggataaaaaagtggatgcataacatcagagatgcctgcagggatcacatggaagggtatcat
tacagatatgaaatcaatgcggaccccagattaacgaacctcagttctaactcggatgtctga

Fig. 3

ATGCCCGGCGGGTGCAGCCGGGGCCCGGCCGCCGGGGACGGCCGCCTGCGGCTCGCGCGCCTGGCCCTGGTGCTC
CTGGGGTGGGTCTCCAGCTCCAGCCCCACCTCCAGCGCCTCCAGCTTCTCCAGCTCCGCCCCCTTCCTGGCCAGC
GCGGTGTCCGCCCAGCCCCCGCTCCCCGACCAGTGCCCCGCCCTGTGCGAGTGCAGCGAGGCCGCGCGGACCGTG
AAGTGCCTCAACCGCAACCTGACGGAGGTGCCCACCGACCTCCCCGGCCTACGTGCGGAACCTGTTCCTGACCGGC
AACCAGCTCGCCGTCCTGCCCGCCGGCGCCTTCGCGCGCCGGCCGCCCCTGGCCGAGCTCGCCGCCCTGAACCTG
TCCGGGAGCCGCCTCGACGAGGTGCGGGCCGGCGCGTTCGAGCACCTGCCGTCCCTGCGCCAGCTCGACCTGAGC
CACAACCCCCTGGCCGACCTCTCCCCCTTCGCCTTCAGCGGGAGCAACGCCTCCGTGAGCGCCCCCTCCCCGCTG
GTCGAGCTGATCCTCAACCACATCGTGCCCCCCGAGGACGAGCGGCAGAACCGCAGCTTCGAGGGCATGGTGGTC
GCGGCCCTGCTGGCCGGGCGGGCCCTCCAGGGCCTGCGCCGGCTGGAGCTCGCCTCCAACCACTTCCTGTACCTG
CCCCGCGACGTGCTCGCGCAGCTGCCGAGCCTGCGGCACCTCGACCTGTCCAACAACAGCCTGGTGTCCCTCACC
TACGTCAGCTTCCGCAACCTGACGCACCTGGAGTCCCTCCACCTGGAGGACAACGCCCTGAAGGTGCTGCACAAC
GGCACCCTCGCCGAGCTGCAGGGGCTGCCCCACATCCGGGTGTTCCTCGACAACAACCCCCTGGGTCTGCGACTGC
CACATGGCCGACATGGTGACCTGGCTGAAGGAGACCGAGGTGGTCCAGGGCAAGGACCGCCTGACGTGCGCGTAC
CCCGAGAAGATGCGGAACCGGGTGCTCCTGGAGCTGAACAGCGCCGACCTCGACTGCGACCCGATCCTGCCCCCC
TCCCTGCAGACCAGCTACGTGTTCCTCGGGATCGTCCTGGCCCTGATCGGCGCCATCTTCCTCCTGGTGCTGTAC
CTCAACCGCAAGGGCATCAAGAAGTGGATGCACAACATCCGGGACGCCTGCCGCGACCACATGGAGGGGTACCAC
TACCGGTACGAGATCAACGCGGACCCCCGCCTGACCAACCTGTCCAGCAACTCCGACGTCTGA

Fig. 4

```
ATGGAGCTGGCGGCCTTGTGCCGCTGGGGGCTCCTCCTCGCCCTCTTGCCCCCGGAGCCGCGAGCACCCAAGTG
TGCACCGGCACAGACATGAAGCTGCGGCTCCCTGCCAGTCCCGAGACCCACCTGGACATGCTCCGCCACCTCTAC
CAGGGCTGCCAGGTGGTGCAGGGAAACCTGGAACTCACCTACCTGCCCACCAATGCCAGCCTGTCCTTCCTGCAG
GATATCCAGGAGGTGCAGGGCTACGTGCTCATCGCTCACAACCAAGTGAGGCAGGTCCCACTGCAGAGGCTGCGG
ATTGTGCGAGGCACCCAGCTCTTTGAGGACAACTATGCCCTGGCCGTGCTAGACAATGGAGACCCGCTGAACAAT
ACCACCCCTGTCACAGGGGCCTCCCCAGGAGGCCTGCGGGAGCTGCAGCTTCGAAGCCTCACAGAGATCTTGAAA
GGAGGGGTCTTGATCCAGCGGAACCCCCAGCTCTGCTACCAGGACACGATTTTGTGGAAGGACATCTTCCACAAG
AACAACCAGCTGGCTCTCACACTGATAGACACCAACCGCTCTCGGGCCTGCCACCCCTGTTCTCCGATGTGTAAG
GGCTCCCGCTGCTGGGGAGAGAGTTCTGAGGATTGTCAGAGCCTGACGCGCACTGTCTGTGCCGGTGGCTGTGCC
CGCTGCAAGGGGCCACTGCCCACTGACTGCTGCCATGAGCAGTGTGCTGCCGGCTGCACGGGCCCCAAGCACTCT
GACTGCCTGGCCTGCCTCCACTTCAACCACAGTGGCATCTGTGAGCTGCACTGCCCAGCCCTGGTCACCTACAAC
ACAGACACGTTTGAGTCCATGCCCAATCCCGAGGGCCGGTATACATTCGGCGCCAGCTGTGTGACTGCCTGTCCC
TACAACTACCTTTCTACGGACGTGGGATCCTGCACCCTCGTCTGCCCCCTGCACAACCAAGAGGTGACAGCAGAG
GATGGAACACAGCGGTGTGAGAAGTGCAGCAAGCCCTGTGCCCGAGTGTGCTATGGTCTGGGCATGGAGCACTTG
CGAGAGGTGAGGGCAGTTACCAGTGCCAATATCCAGGAGTTTGCTGGCTGCAAGAAGATCTTTGGGAGCCTGGCA
TTTCTGCCGGAGAGCTTTGATGGGGACCCAGCCTCCAACACTGCCCCGCTCCAGCCAGGACAGCTCCAAGTGTTT
GAGACTCTGGAAGAGATCACAGGTTACCTATACATCTCAGCATGGCCGGACGCCTGCCTCAGCGTCTTC
CAGAACCTGCAAGTAATCCGGGGACGAATTCTGCACAATGGCGCCTACTCGCTGACCCTGCAAGGGCTGGGCATC
AGCTGGCTGGGGCTGCGCTCACTGAGGGAACTGGGCAGTGGACTGGCCCTCATCCACCATAACACCCACCTCTGC
TTCGTGCACACGGTGCCCTGGGACCAGCTCTTTCGGAACCCCGCACCAAGCTCTGCTCCACACTGCCAACCGGCCA
GAGGACGAGTGTGTGGGCGAGGGCCTGGCCTGCCACCAGCTGTGCGCCCGAGGGCACTGCTGGGGTCCAGGGCCC
ACCCAGTGTGTCAACTGCAGCCAGTTCCTTCGGGGCCAGGAGTGCGTGGAGGAATGCCGAGTACTGCAGGGGCTC
CCCAGGGAGTATGTGAATGCCAGGCACTGTTTGCCGTGCCACCCCTGAGTGTCAGCCCCAGAATGGCTCAGTGACC
TGTTTTGGACCGGAGGCTGACCAGTGTGTGTGGCCTGTGCCCACTATAAGGACCCTCCCTTCTGCGTGGCCCGCTGC
CCCAGCGGTGTGAAACCTGACCTCTCCTACATGCCCATCTGGAAGTTTCCAGATGAGGAGGGCGCATGCCAGCCT
TGCCCCATCAACTGCACCCACTCCTGTGTGGACCTGGATGACAAGGGCTGCCCCGCCGAGCAGAGAGCCAGCCCT
CTGACGTCCATCATCTCTGCGGTGGTTGGCATTCTGCTGGTCGTGGTCTTGGGGGTGGTCTTTGGGATCCTCATC
AAGCGACGGCAGCAGAAGATCCGGAAGTACACGATGCGGAGACTGCTGCAGGAAACGGAGCTGGTGGAGCCGCTG
ACACCTAGCGGAGCGATGCCCAACCAGGCGCAGATGCGGATCCTGAAAGAGACGGAGCTGAGGAAGGTGAAGGTG
CTTGGATCTGGCGCTTTTGGCACAGTCTACAAGGGCATCTGGATCCCTGATGGGGAGAATGTGAAAATTCCAGTG
GCCATCAAAGTGTTGAGGGAAAACACATCCCCCAAAGCCAACAAAGAAATCTTAGACGAAGCATACGTGATGGCT
GGTGTGGGCTCCCCATATGTCTCCCGCCTTCTGGGCATCTGCCTGACATCCACGGTGCAGCTGGTGACACAGCTT
ATGCCCTATGGCTGCCTCTTAGACCATGTCCGGGAAAACCGCGGACGCCTGGGCTCCCAGGACCTGCTGAACTGG
TGTATGCAGATTGCCAAGGGGATGAGCTACCTGGAGGATGTGCGGCTCGTACACAGGGACTTGGCCGCTCGGAAC
GTGCTGGTCAAGAGTCCCAACCATGTCAAAATTACAGACTTCGGGCTGGCTCGGCTGCTGGACATTGACGAGACA
GAGTACCATGCAGATGGGGGCAAGGTGCCCATCAAGTGGATGGCGCTGGAGTCCATTCTCCGCCGGCGGTTCACC
CACCAGAGTGATGTGTGGAGTTATGGTGTGACTGTGTGGGAGCTGATGACTTTTGGGCCAAACCTTACGATGGG
ATCCCAGCCCGGGAGATCCCTGACCTGCTGGAAAAGGGGGAGCGGCTGCCCCAGCCCCCCATCTGCACCATTGAT
GTCTACATGATCATGGTCAAATGTTGGATGATTGACTCTGAATGTCGGCCCAAGATTCCGGGAGTTGGTGTCTGAA
TTCTCCCGCATGGCCAGGGACCCCCAGCGCTTTGTGGTCATCCAGAATGAGGACTTGGGCCCAGCCAGTCCCTTG
GACACCACCTTCTACCGCTCACTGCTGGAGGACGATGACATGGGGGACCTGGTGGATGCTGAGGAGTATCTGGTA
CCCCAGCAGGGCTTCTTCTGTCCAGACCCTGCCCCGGGCGCTGGGGGCATGGTCCACCACAGGCACCGCAGCTCA
TCTACCAGGAGTGGCGGTGGGGACCTGACACTAGGGCTGGAGCCCTCTGAAGAGGAGGCCCCCAGGTCTCCACTG
GCACCCTCCGAAGGGGCTGGCTCCGATGTATTTGATGGTGACCTGGGAATGGGGGCAGCCAAGGGGCTGCAAAGC
CTCCCCACACATGACCCCAGCCCTCTACAGCGGTACAGTGAGGACCCCACAGTACCCCTGCCCTCTGAGACTGAT
GGCTACGTTGCCCCCCTGACCTGCAGCCCCAGCCTGAATATGTGAACCAGCCAGATGTTCGGCCCCAGCCCCCT
TCGCCCCGAGAGGGCCCTCTGCCTGCTGCCCGACCTGCTGGTGCCACTCTGGAAAGGCCCAAGACTCTCTCCCCA
GGGAAGAATGGGGTCGTCAAAGACGTTTTTGCCTTTGGGGGTGCCGTGGAGAACCCCGAGTACTTGACACCCCAG
GGAGGAGCTGCCCCTCAGCCCCACCCTCCTCCTGCCTTCAGCCCAGCCTTCGACAACCTCTATTACTGGGACCAG
GACCCACCAGAGCGGGGGGCTCCACCCAGCACCTTCAAAGGGACACCTACGGCAGAGAACCCAGAGTACCTGGGT
CTGGACGTGCCAGTGTGA
```

Fig. 5

```
ATGGAGCTGGCCGCCCTGTGCCGGTGGGGCCTGCTGCTCGCGCTGCTGCCCCCGGGGGCCGCCAGCACCCAGGTG
TGCACCGGCACGGACATGAAGCTCCCGCCTGCCCGCCTCCCCCGAGACCCACCTGGACATGCTCCGGCACCTGTAC
CAGGGGTGCCAGGTCGTGCAGGGCAACCTGGAGCTCACCTACCTCCCCACCAACCGCCAGCCTGTCCTTCCTCCAG
GACATCCAGGAGGTGCAGGGGTACGTCCTGATCGCGCACAACCAGGTGCGGCAGGTGCCGCTGCAGCGGCTCCGC
ATCGTCCGGGGCACGCAGCTGTTCGAGGACAACTACGCCCTGGCCGTGCTCGACAACGGCGACCCCCTGAACAAC
ACCACCCCGTGACCGGGGCCAGCCCGGCGGGCTGCGCGAGCTCCAGCTGCGGTCCCTGACGGAGATCCTCAAG
GGCGGGGTCCTGATCCAGCGCAACCCGCAGCTGTGCTACCAGGACACCATCCTCTGGAAGGACATCTTCCACAAG
AACAACCAGCTGGCGCTGACCCTCATCGACACCAACCGGAGCCGCGCCTGCCACCCCTGCTCCCCCATGTGCAAG
GGCAGCCGGTGCTGGGGCGAGTCCAGCGAGGACTGCCAGTCCCTGACGCGCACCGTGTGCGCCGGGGCTGCGCC
CGGTGCAAGGGCCCCTGCCGACCGACTGCTGCCACGGACAGTGCGCCGCGGGCTGCACCGGCCCAAGCACAGC
GACTGCCTCGCCTGCCTGCACTTCAACCACTCCGGGATCTGCGAGCTGCACTGCCCCGCCCTCGTGACGTACAAC
ACCGACACCTTCGAGAGCATGCCCAACCCGGAGGGCCGCTACACCTTCGGGCCTCCTGCGTCACGGCCTGCCCC
TACAACTACCTGAGCACCGACGTGGGCTCCTGCACCCTGGTGTGCCCCCTCCACAACCAGGAGGTCACCGCGGAG
GACGGGACGCAGCCGGTGCGAGAAGTGCAGCAAGCCCTGCGCCCGCGTGTGCTACGGCCTGGGCATGGAGCACCTG
CGGGAGGTGCGCGCCGTCACCTCCGCCAACATCCAGGAGTTCGCCGGGTGCAAGAAGATCTTCGGCAGCCTCGCG
TTCCTGCCGGAGAGCTTCGACGGGGACCCCGCCTCCAACACCGCCCCCCTGCAGCCCGAGCAGCTGCAGGTGTTC
GAGACCCTCGAGGAGATCACGGGCTACCTGTACATCAGCGCCTGGCCGGACTCCCTGCCCGACCTCAGCGTGTTC
CAGAACCTGCAGGTCATCCGGGGGCGCATCCTGCACAACGGCGCCCTACTCCCTCACCCTGCAGGGCCTGGGGATC
AGCTGGCTCGGCCTGCGGTCCCTGCGGGAGCTCGGGAGCGGCCTGGCGCTGATCCACCACAACACCCACCTCTGC
TTCGTGCACACCGTGCCCTGGGACCAGCTGTTCCGCAACCCCCACCAGGCCCTGCTCCACACGGCCAACCGGCCG
CAGGACGAGTGCGTCGGGGAGGGCCTGGCCTGCCACCAGCTGTGCGCGCGCGGCCACTGCTGGGGCCCGGCCCC
ACCCAGTGCGTGAACTGCTCCCAGTTCCTCCGGGGGCAGGAGTGCGTCGAGGAGTGCCGCGTGCTGCAGGGCCTG
CCGCGGGAGTACGTGAACGCCCGCCACTGCCTCCCCTGCCACCCCGAGTGCCAGCCCCAGAACGGCAGCGTCACC
TGCTTCGGGCCGGAGGCCGACCAGTCCGTGGCCCTGCGCCCACTACAAGGACCCGCCCTTCTGCGTGGCGCGGTGC
CCCTCCGGCGTCAAGCCGGACGTGAGCTACATGCCCATCTGGAAGTTCCCCGACGAGGAGGGGCCTGCCAGCCC
TGCCCGATCAACTGCACCCACTCCTGCGTGGACCTGGACGACAAGGGCTGCCCCGCCGAGCAGCGCGCCAGCCCC
CTCACGTCCATCATCAGCGCCGTGGTCGGGATCCTGCTGGTGGTGGTCCTCGGCGTGGTGTTCGGCATCCTGATC
AAGCGGCGCCAGCAGAAGATCCGGAAGTACACCATGCGCCGGCTGCTCCAGGAGACCGAGCTGGTCGAGCCCCTG
ACCCCGTCCGGGGCGATGCCCAACCAGGCCCAGATGCGCATCCTCAAGGAGACCGAGCTGCGGAAGGTGAAGGTG
CTGGGCAGCGGGGCCTTCGGCACGGTCTACAAGGGGATCTGGATCCCCGACGGCGAGAACGTGAAGATCCCCGTG
GCCATCAAGGTCCTCCGCGAGAACACCTCCCCGAAGGCCAACAAGGAGATCCTGGACGAGGCGTACGTGATGGCC
GGCGTGGGGAGCCCCTACGTCAGCCGGCTGCTCGGCATCTGCCTGACCTCCACCGTGCAGCTGGTGACGCAGCTC
ATGCCCTACGGGTGCCTGCTGGACCACGTCCGCGACAACCGGGGCCGGCTCGGGAGCCAGGACCTGCTGAACTGG
TGCATGCAGATCGCCAAGGGCATGTCCTACCTCGAGGACGTGCGCCTGGTGCACCGGGACCTGGCCGCGCGCAAC
GTCCTCGTGAAGAGCCCCAACCACGTGAAGATCACCGACTTCGGCCTGGCCCGGCTGCTCGACATCGACGAGACC
GAGTACCACGCCGACGGGGGCAAGGTCCCGATCAAGTGGATGGCCCTGGAGTCCATCCTGCGCCGGCGCTTCACC
CACCAGAGCGACGTGTGGTCCTACGGGGTGACGGTCTGGGAGCTCATGACCTTCGGCGCCAAGCCCTACGACGGG
ATCCCCGCGCGGGAGATCCCGGACCTGCTGGAGAAGGGCGAGCGCCTCCCCCAGCCCCCCATCTGCACCATCGAC
GTGTACATGATCATGGTGAAGTGCTGGATGATCGACAGCGAGTGCCGGCCGCGCTTCCGGGAGCTGGTCTCCGAG
TTCAGCCGCATGGCCCGGGACCCCCAGCGCTTCGTGGTGATCCAGAACGAGGACCTGGGCCCCGCCTCCCCCTC
GACAGCACCTTCTACCGGTCCCTGCTGGAGGACGACGACATGGGGGACCTCGTCGACGCCGAGGAGTACCTGGTG
CCGCAGCAGGGCTTCTTCTGCCCCGACCCCGCCCCGGGGCGGCGGCATGGTGCACCACCGCCACCGGAGCTCC
AGCACGCGCTCCGGGGGCGGGACCTGACCCTCGGCCTGGAGCCGAGCGAGGAGGAGGCCCGCGGAGCCCCCTG
GCCCCTCCGAGGGGCCGGCAGCGACGTCTTCGACGGCGACCTCGGGATGGGCGCCGCGAAGGGGCTGCAGTCC
CTGCCGACCCACGACCCCAGCCCCCTCCAGCGCTACTCCGAGGACCCCACCGTGCCGCTGCCCAGCGAGACGGAC
GGCTACGTGGCCCCCCTGACCTGCTCCCCGCAGCCGGAGTACGTCAACCAGCCCGACGTGCGGCCCCAGCCCCG
AGCCCCCGGGAGGGGCCCCTCCCGGCCGCCCGCCCGCGGGGCGCCACCCTGGAGCGGCCCAAGACCCTGTCCCCC
GGCAAGAACGGGGTGGTCAAGGACGTCTTCGCCTTCGGCGGGCCGTCGAGAACCCGGAGTACCTCACGCCCCAG
GGCGGGGCCGCGCCCCAGCCCCACCCGCCCCCGGCCTTCAGCCCCGCCTTCGACAACCTGTACTACTGGGACCAG
GACCCCGCCGGAGCGCGGCGCCCCCCCCTCCACCTTCAAGGGCACCCCGACCGCCGAGAACCCCGAGTACCTGGCG
CTCGACGTGCCCGTGTGA
```

Fig. 6

```
atgccgcgcgctcccgctgccgagccgtgcgctccctgctgcgcagccactaccgcgaggtgctgccgctggcc
acgttcgtgcggcgcctgggccccagggctggcggctggtgcagcgcggggacccggcggcttccgcgcgctg
gtggccagtgctggtgtgcgtgccctgggacgcacggccgcccccgccgcccctccttccgccaggtgtcc
tgcctgaaggagctggtggcccgagtgctgcagaggctgtgcgagcgcggcgcgaagaacgtgctggccttcggc
ttcgcgctgctggacgggacccgcggggcccccccgaggccttcaccaccagcgtgcgcagctacctgcccaac
acggtgaccgacgcactgcgggggagcgggggcgtgggggctgctgctgcgccgcgtgggcgacgacgtgctggtt
cacctgctggcacgctgcgcgctctttgtgctggtggctcccagctgcgcctaccaggtgtgcgggccgccgctg
taccagctggcgctgccactcaggcccggccccgccacacgctagtggaccccgaaggcgtctgggatgcgaa
cgggcctggaaccatagcgtcagggaggccggggtcccctgggcctgccagcccgggtgcgaggaggcgcggg
ggcagtgccagccgaagtctgccgttgcccaagaggcccaggcgtggcgctgccctgagccggagcggacgccc
gttggcaggggtcctgggccacccgggcaggacgcgtggaccgagtgacgtggtttctgtgtggtgtcacct
gccagcccgccgaagaagccacctctttgagggtgcgctctctggcacgcgccactccacccatccgtgggc
cgccagcaccacgcgggccccccatccacatcgcggccaccacgtccctgggacacgccttgtccccggtgtac
gccgagaccaagcacttcctctactcctcaggcgacaaggagcagctgcggcccctcctcctactcagctctctg
aggcccagcctgactggcgctcggaggctcgtggagaccatctttctgggttccaggccctggatgccagggact
cccgcaggttgccccgcctgccccagacgcactggcaaatgcggccccctgttctgagctgcttgggaaccac
gcgcagtgcccctacgggtgctcctcaagacgcactgcccgctgcgagctgcggtcacccagcagccggtgtc
tgtgcccggagaagcccagggctctgtgcggccccgaggaggaggacacagacccccgtcgcctggtgcag
ctgctccgcagcacagcagccctggcaggtgtacggcttcgtgcgggcctgcctgcgccggctggtgccccca
ggcctctggggctccaggcacaacgaacgccgcttcctcaggaacaccaagaagttcatctccctgggggaagcat
gccaagctctcgctgcaggagctgacgtggaagatgagcgtgcgggactgcgcttggctgcgcaggagcccaggg
gttggctgtgttccggccgcagagcaccgtctgcgtgaggagatcctggccaagttcctgcactggctgatgagt
gtgtacgtcgtcgagctgctcaggtctttcttttatgtcacggagaccacgtttcaaaagaacaggctcttttc
taccggaagagtgtctggagcaagttgcaaagcattggaatcagacagcacttgaagagggtgcagctgcgggag
ctgtcggaagcagaggtcaggcagcatcgggaagccaggccgccctgctgacgtccagactccgcttcatcccc
aagcctgacgggctgcggccgattgtgaacatggactacgtcgtgggagccagaacgttccgcagagaaagagg
gccgagcgtctcacctcgagggtgaaggcactgttcagcgtgctcaactacgagcgggcgggcgccccggcctc
ctgggcgcctctgtgctgggcctggacgatatccacagggcctggcgcaccttgtgctgcgtgtgcgggcccag
gaccccgccgctgagctgtactttgtcaaggtggatgtgacgggcgcgtacgacaccatccccaggacaggctc
acggaggtcatcgccagcatcatcaaaccccagaacacgtactgcgtgcgtcggtatgccgtggtccagaaggcc
gccatgggcacgtccgcaaggccttcaagagccacgtctctaccttgacagacctccagccgtacatgcgacag
ttcgtggctcacctgcaggagaccagcccgctgagggatgccgtcgtcatcgagcagagctcctccctgaatgag
gccagcagtggcctcttcgacgtcttcctacgcttcatgtgccaccacgccgtgcgcatcagggcaagtcctac
gtccagtgccaggggatcccgcagggctccatcctctccacgctgctctgcagcctgtgctacggcgacatggag
aacaagctgtttgcggggattcggcggacgggctgctcctgcgtttggtggatgatttcttgttggtgacacct
cacctcacccacgcgcaaaaccttcctcaggacgcgaggtggtccgaggtgtccctgagtatgctgcgtggtgaacttg
cggaagacagtggtgaacttccctgtagagccgaggccctgggtggcacggcttttgttcagatgccggcccac
ggcctattccctggtgcggcctgctgctggataccggaccctggaggtgcagagcgactactccagctatgcc
cggacctccatcagagccagtctcaccttcaaccgcggcttcaaggctggggaggaacatgcgtcgcaaactcttt
ggggtcttgcggctgaagtgtcacagcctgtttctggatttgcaggtgaacagcctccagacggtgtgcaccaac
atctacaagatcctcctgctgcaggcgtacaggtttcacgcatgtgtgctgcagctcccatttcatcagcaagtt
tggaagaaccccacattttcctgcgcgtcatctctgacacggcctccctctgctactccatcctgaaagccaag
aacgcagggatgtcgctgggggccaagggcgccgccggccctctgccctcgaggccgtgcagtggctgtgccac
caagccattcctgctcaagctgactcgacaccgtgtcacctacgtgccactcctggggtcactcaggacagccag
acgcagctgagtcggaagctcccggggacgacgctgactgccctggaggccgcagccaacccggcactgccctca
gacttcaagaccatcctggactga
```

Fig. 7

```
ATGCCCCGGCCCCGCGCTGCCCGGCCGTGCGCAGCCTGCTCCGGTCCCACTACCGCGAGGTCCTGCCCCTGGCG
ACCTTCGTGCGGCGCCTCGGCCCCCAGGGGTGGCGGCTGGTGCAGCGCGGCGACCCCGCCGCCTTCCGGCCCTG
GTCGCCCAGTGCCTCGTGTGCGTGCCCGTGGACGCGCGCCCCCCGCCCGCCGCCCCGAGCTTCCGGCAGGTCTCC
TGCCTGAAGGAGCTGGTGGCCCGCGTGCTCCAGCGGCTGTGCGAGCGCGGGGCGAAGAACGTCCTGGCCTTCGGC
TTCGCCCTCCTGGACGGGGCCCGGGGCGGCCCCCCGAGGCCTTCACCACGAGCGTGCGCTCCTACCTGCCCAAC
ACCGTGACCGACGCGCTCCGGGGAGCGGCGCCTGGGGCTGCTGCTCCGCCGGGTCGGCGACGACGTGCTGGTG
CACCTGCTCGCCCGCTGCGCCCTGTTCGTCCTGGTGGCCCCGTCCTGCGCGTACCAGGTGTGCGGGCCCCGCTC
TACCAGCTGGGCGCCGCCACCCAGGCCCGGCCCCCGCCCACGCCAGCGGCCCCCGGCGCCGGCTGGGGTGCGAG
CGGCGCGTGGAACCACTCCGTCCGGGAGGCCGGCGTGCCCCTCGGGCTGCCGGCCCCGGCGCCCGCCGGCGCGGC
GGGAGCGCCTCCCGGAGCCTGCCCCTCCCCAAGCGCCCGCGGCGCGGCGCGGCCCCCGAGCCCGAGCGGACGCCC
GTGGGGCAGGGCTCCTGGGCCCACCCGGGGCGCACCCGGGCCCCAGCGACCGCGGCTTCTGCGTCGTGTCCCCC
GCCCGGCCGGCGGAGGAGGCCACCAGCCTGGAGGGGGCCCTGTCCGGCACCCGCCACAGCCACCCCTCCGTGGGG
CGGCAGCACCACGCCGGCCCCCCAGCACGAGCCGCCCGCCCCGGCCCTGGGACACCCCTGCCCGCCCGTCTAC
GCCGAGACCAAGCACTTCCTCTACTCCAGCGGGGACAAGGAGCAGCTGCGGCCCTCCTTCCTGCTCAGCTCCCTG
CGCCCCAGCCTGACCGGCGCGCGGCGCCTCGTGGAGACGATCTTCCTGGGCTCCCGGCCGTGGATGCCCGGGACC
CCGCGCCGGCTGCCCCGCCTCCCGCAGCGGGTACTGGCAGATGCGGCCCCTGTTCCTGGAGCTCCTGGGCAACCAC
GCCCAGTGCCCCTACGGGGTCCTGCTGAAGACCCACTGCCCCCTCCGGGCCGCCGTGACCCCGGCCGCGGGCGTG
TGCGCCCGCGAGAAGCCCCAGGGGAGCGTCGCCGCCCCCGAGGAGGAGGACACGGACCCCCGGCGCCTGGTGCAG
CTGCTCCGGCAGCACTCCAGCCCGTGGCAGGTGTACGGCTTCGTCCGCGCCTGCCTGCGGCGCCTGGTGCCCCC
GGCCTCTGGGGGTCCCGGCACAACGAGCGCCGGTTCCTGCGCAACACCAAGAAGTTCATCAGCCTGGGCAAGCAC
GCGAAGCTCTCCCTGCAGGAGCTGACCTGGAAGATGAGCGTGCGGGACTGCGCCTGGCTCCGGCGCTCCCCGGGG
GTCGGCTGCGTGCCCGCCGCCGAGCACCGGCTGCGCGAGGAGATCCTGGCGAAGTTCCTCCACTGGCTGATGAGC
GTGTACGTCGTGGAGCTGCTCCGGTCCTTCTTCTACGTGACCGAGACGACCTTCCAGAAGAACCGCCTGTTCTTC
TACCGGAAGAGCGTCTGGTCCAAGCTGCAGAGCATCGGCATCCGCCAGCACCTCAAGCGGGTGCAGCTGCGCGAG
CTGAGCGAGGCCGAGGTGCGGCGACACCGCCAGCACCTAGGACCGGCCCCTCCTGACCTCCCGCCTGCCGGTTCATCCCC
AAGCCGGACCGGGCTCCGCCCCATCGTCAACATGGACTACGTGGTGGGCGCCCCGGACCTTCCGCCGGGAGAAGCGC
GCGGAGCGGCTGACGAGCCGGGTCAAGGCCCTGTTCTCCGTGCTCAACTACGAGCGCGCCCGGCGCCCCGGGCTG
CTGGGCGCCAGCGTGCTCGGGCTGGACGACATCCACCTGGGCTGGCGCACCTTCGTCCTGCGGGGTGCGCGCGCAG
GACCCCCCGCCCGAGCTCTACTTCGTGAAGGTCGACGTGACCGGCGCCTACGACACCATCCCCCAGGACCGGCTG
ACGGAGGTGATCGCCTCCATCATCAAGCCCCAGAACACCTACTGCGTCCGCCGGTACGCCGTGGTGCAGAAGGCC
GCGCACGGCCACGTCCGCAAGGCCTTCAAGAGCCACGTGTCCACCCTGACCGACCTCCAGCCGTACATGCGGCAG
TTCGTGGCCCACCTGCAGGAGACGAGCCCCCTGCGCGACGCCGTCGTGATCGAGCAGTCCAGCTCCCTCAACGAG
GCGAGCTCCGGCTGTTCGACGTGTTCCTGCGGTTCATGTGCCACCACGCCGTCCGCATCCGGGGCAAGAGCTAC
GTCCAGTGCCAGGGGATCCCCCAGGGCTCCATCCTCAGCACCCTGCTGTGCTCCCTCTGCTACGGGGACATGGAG
AACAAGCTGTTCGCCCGGCATCCGCCGGGACGGCCTGCTCCTGCGCCTGGTGGACGACTTCCTCCTGGTCACCCCG
CACCTGACCCACGCCAAGACGTTCCTCCGGACCCTGGTGCGCGGGGTGCCGGAGTACGGCTGCGTCGTGAACCTG
CGGAAGACCGTGGTCAACTTCCCCGTGGAGGACGAGGCCCTCGGGGGCACCGCGTTCGTGCAGATGCCCGCCCAC
GGGCTGTTCCCCTGGTGCGGCCTGCTCCTGGACACCCGGACGCTGGAGGTCCAGAGCGACTACAGCTCCTACGCC
CGCACCAGCATCCGGGCCTCCCTCACCTTCAACCGCGGCTTCAAGGCCGGGCGGAACATGCGCCGGAAGCTGTTC
GGCGTGCTGCGCCTCAAGTGCCACAGCCTGTTCCTGGACCTCCAGGTCAACTCCCTGCAGACCGTGTGCACGAAC
ATCTACAAGATCCTGCTCCTGCAGGCGTACCGGTTCCACGCCTGCGTGCTGCAGCTCCGTTCCACCAGCAGGTC
TGGAAGAACCCCACCTTCTTCCTGCGCGTGATCAGCGACACCGCCTCCCTGTGCTACAGCATCCTCAAGGCCAAG
AACGCCGGGATGTCCCTGGGCGCGAAGGGGCCGCCGGCCCCTGCCCAGCGAGGCCGTGCAGTGGCTCTGCCAC
CAGCCCTTCCTGCTGAAGCTCACCCGGCACCGCGTCACGTACGTGCCGCTGCTGGGCTCCCTCCGGACCGCGCAG
ACCCAGCTGAGCCGCAAGCTGCCCGGGACCACGCTCACCGCCCTGGAGGCCGCCGCGAACCCCGCCCTGCCCTCC
GACTTCAAGACCATCCTCGACTGA
```

Fig. 8 ctgcaggacccggcttccacgtgtgtcccggagccggcgtctcagcacacgctccgctccgggcctgggtgccta
cagcagccagagcagcagggagtccgggacccgggcggcatctgggccaagttaggcgccgccgaggccagcgct
gaacgtctccagggccggaggagccgcggggcgtccggtctgagccgcagcaaatgggctccgacgtgcgggac
ctgaacgcgctgctcccgccgtccctccctgggtggcggcggcggctgtgccctgctgtgagcggcgcggcg
cagtggcgccggtgctggactttgcgccccggggcgcttcggcttacgggtcgttgggcggccccgcgccgcca
ccggctccgccgccacccccgccgccgccgcctcactccttcatcaaacaggagccgagctgggcggcgcggag
ccgcacgaggagcagtgcctgagcgccttcactgtccacttttccggccagttcactggcacagccggagcctgt
cgctacgggcccttcggtcctcctccgccagccaggcgtcatccggccaggccaggatgtttcctaacgcgccc
tacctgccagctgcctcgagagccagcccgctattcgcaatcagggttacagcacggtcaccttcgacgggacg
cccagctacggtcacacgccctcgcaccatgcgggcgcagttccccaaccactcattcaagcatgaggatcccatg
ggccagcagggctgctgggtgagcagcagtactcggtgccgcccccggtctatggctgccacacccccaccgac
agctgcaccggcagccaggctttgctgctgaggacgccctacagcagtgacaatttataccaaatgacatcccag
cttgaatgcatgacctggaatcagatgaacttaggagccaccttaaagggagttgctgctgggagctccagctca
gtgaaatggacagaagggcagagcaaccacacagggtacgagagcgataaccacacaacgcccatcctctgc
ggagcccaatacagaatacacacgcacggtgtcttcagaggcattcaggatgtgcgacgtgtgcctggagtagcc
ccgactcttgtacggtcggcatctgagaccagtgagaaacgcccttcatgtgtgcttacccaggctgcaataag
agatatttaagctgtcccacttacagatgcacagcaggaagcacactggtgagaaaccataccagtgtgacttc
aaggactgtgaacgaaggttttctcgttcagaccagctcaaagacaccaaggagacatacaggtgtgaaacca
ttccagtgtaaaacttgtcagcgaaagttctcccggtccgaccacctgaagacccacaccaggactcatacaggt
aaaacaagtgaaaagcccttcagctgtcggtggccaagttgtcagaaaaagtttgcccggtcagatgaattagtc
cgccatcacaacatgcatcagagaaacatgaccaaactccagctggcgctttga

Fig. 9

A)

```
ATGCAGGACCCCGCCAGCACCTGCGTGCCGGAGCCCGCCTCCCAGCACACCCTCCGGAGCGGCCCGGGGTGCCTG
CAGCAGCCCGAGCAGCAGGGCGTCCGCGACCCGGGCGGGATCTGGGCGAAGCTGGGGGCCGCCGAGGCCTCCGCC
GAGCGGCTCCAGGGCCGCCGGAGCCGCGGCGCGTCCGGGAGCGAGCCCCAGCAGATGGGCTCCGACGTGCGGGAC
CTGAACGCCCTGCTCCCCGCCGTGCCCAGCCTGGGCGGCGGGGGCGGGTGCGCCCTGCCGGTCTCCGGGGCGGCC
CAGTGGGCCCCCGTGCTCGACTTCGCTCCTCCAGGAGCTAGCGCTTACGGATCTCTGGGAGGACCTGCTCCTCCA
CCCGGCTCCGCCACCTCCTCCACCACCTCCACCTCACAGCTTCATCAAGCAGGAGCCCTCCTGGGGCGGCGCCGAG
CCCCACGAGGAGCAGTGCCTGAGCGCCTTCACGGTGCACTTCTCCGGGCAGTTCACGGGACCGCGGGGCCTGC
CGCTACGGCCCCTTCGGGCCGCCCCCCGAGCCAGGCCTCCAGCGGGCAGGCCCGGATGTTCCCCAACGCCCCC
TACCTCCCCTCCTGCCTGGAGAGCCAGCCGGCGATCCGCAACCAGGGCTACAGCACCGTCACGTTCGACGGGACC
CCCTCCTACGGCCACACCCCCAGCCACCAGCCGCCCAGTTCCCCAACCACTCCTTCAAGCACGAGGACCCGATG
GGGCAGCAGGGCAGCCTGGGCGAGCAGCAGTACTCCGTGCCCCCGCCGGTGTACGGGTGCCACACCCCGACGGAC
AGCTGCACCGGCTCCCAGGCCCTCCTGCTGCCGGACCCCCTACAGCTCCGACAACCTCTACCAGATGACCAGCCAG
CTGGAGTGCATGACGTGGAACCAGATGAACCTGGGGGCCACCCTCAAGGGCGTCGCGGCCGGGTCCAGCTCCAGC
GTGAAGTGGACCGAGGGCCAGTCCAACCACAGCACCGGCTACGAGTCCGACAACCACACGACCCCCATCCTGTGC
GGGGCCAGTACCGCATCCACACCCACGGCGTGTTCCGGGGGATCCAGGACGTCCGCCGGGTGCCCGGCGTGGCC
CCGACCCTGGTCCGCAGCGCGTCCGAGACGAGCGAGAAGCGGCCCTTCATGTGCGCCTACCCCGGCTGCAACAAG
CGCTACTTCAAGCTCAGCCACCTGCAGATGCACTCCCGGAAGCACACCGGGGAGAAGCCCTACCAGTGCGACTTC
AAGGACTGCGAGCGCCGGTTCAGCCGCTCCGACCAGCTGAAGCGGCACCAGCGGCCCACACCGGCGTGAAGCCG
TTCCAGTGCAAGACCTGCCAGCGGAAGTTCAGCCGCTCCGACCACCTCAAGACGCACACCCGGACCCACACCGGG
AAGACGAGCGAGAAGCCCTTCTCCTGCCCGCTGGCCCAGCTGCCAGAAGAAGTTCGCCCGGTCCGACGAGCTGGTG
CGCCACCACAACATGCACCAGCGGAACATGACCAAGCTGCAGCTCGCCCTGTGA
```

B)

GCG CCC CCG GGC GCT TCG GCT TAC GGG TCG TTG GGC GGC CCC
GCG CCG CCA CCG GCT CCG CCG CCA CCC CCG CCG CCG CCG CCT

C)

GCC CCC CCC GGC GCC AGC GCG TAC GGG TCC CTG GGC GGC CCG
Ala Pro Pro Gly Ala Ser Ala Tyr Gly Ser Leu Gly Gly Pro

GCC CCG CCC CCC GCC CCG CCC CCC CCG CCG CCC CCC CCG CCG
Ala Pro Pro Pro Ala Pro Pro Pro Pro Pro Pro Pro Pro Pro

D)

GCT CCT CCA GGA GCT AGC GCT TAC GGA TCT CTG GGA GGA CCT
Ala Pro Pro Gly Ala Ser Ala Tyr Gly Ser Leu Gly Gly Pro

GCT CCT CCA CCC GCT CCG CCA CCT CCT CCA CCA CCT CCA CCT
Ala Pro Pro Pro Ala Pro Pro Pro Pro Pro Pro Pro Pro Pro

Fig. 10

```
ATGCAGGACCCCGCCAGCACCTGCGTGCCGGAGCCCGCCTCCCAGCACACCCTCCGGAGCGGCCCCGGGTGCCTG
CAGCAGCCCGAGCAGCAGGGCGTCCGCGACCGGGCGGGATCTGGGCGAAGCTGGGGCCGCCGAGGCCTCCGCC
GAGCGGCTCCAGGGCCGCCGGAGCCGCGGCGCGTCCGGAGCGAGCCCCAGCAGATGGGCTCCGACGTGCGGGAC
CTGAACGCCCTGCTCCCCGCCGTGCCCAGCCTGGGCGGCGGGGGCGGGTGCGCCCTGCCGGTCTCCGGGGCGGCC
CAGTGGGCCCCCGTGCTCGACTTCGCCCCCCCCGGCGCCAGCGCGTACGGGTCCCTGGGCGGCCCGGCCCCGCCC
CCCGCCCCGCCCCCCCGCCGCCCCCCCGCCGCACAGCTTCATCAAGCAGGAGCCCTCCTGGGGCGGCGCCGAG
CCCCACGAGGAGCAGTGCCTGAGCGCCTTCACGGTGCACTTCTCCGGGCAGTTCACCGGGACCGCGGGGGCCTGC
CGCTACGGGCCCTTCGGCCCGCCCCCGCCGAGCCAGGCCTCCAGCGGGCAGGCCCGGATGTTCCCCAACGCCCCC
TACCTCCCCTCCTGCCTGGAGAGCCAGCCGGCGATCCGCAACCAGGGCTACAGCACCGTCACGTTCGACGGGACC
CCCTCCTACGGCCACACCCCAGCCACCACGCCGCCCAGTTCCCCAACCACTCCTTCAAGCACGAGGACCCGATG
GGGCAGCAGGGCAGCCTGGGCGAGCAGCAGTACTCCGTGCCCCCGCCCGTGTACGGGTGCCACACCCCGACGGAC
AGCTGCACCGGCTCCCAGGCCCTCCTGCTGCGGACCCCCTACAGCTCCGACAACCCTCTACCAGATGACCAGCCAG
CTGGAGTGCATGACGTGGAACCAGATGAACCTGGGGGCCACCCTCAAGGGCGTCGCGGCCGGGTCCAGCTCCAGC
GTGAAGTGGACCGAGGGCCAGTCCAACCACAGCACCGGCTACGAGTCCGACAACCACACGACCCCCATCCTGTGC
GGGGCCCAGTACCGCATCCACACCCACGGCGTGTTCCGGGGGATCCAGGACGTCCGCCGGGTGCCCGGCGTGGCC
CCGACCCTGGTCCGCAGCGCGTCCGAGACGAGCGAGAAGCGGCCCTTCATGTGCGCCTACCCCGGCTGCAACAAG
CGCTACTTCAAGCTCAGCCACCTGCAGATGCACTCCCGGAAGCACACCGGGGAGAAGCCCTACCAGTGCGACTTC
AAGGACTGCGAGCGCCGGTTCAGCCGCTCCGACCAGCTGAAGCGGCACCAGCGGCGCCACACCGGCGTGAAGCCG
TTCCAGTGCAAGACCTGCCAGCGGAAGTTCAGCCGCTCCGACCACCTCAAGACGCACACCCGGACCCACACCGGG
AAGACGAGCGAGAAGCCCTTCTCCTGCCGCTGGCCCAGCTGCCAGAAGAAGTTCGCCCGGTCCGACGAGCTGGTG
CGCCACCACAACATGCACCAGCGGAACATGACCAAGCTGCAGCTCGCCCTGTGA
```

Fig. 11

```
ATGGAGTCTCCCTCGGCCCCTCCCCACAGATGGTGCATCCCCTGGCAGAGGCTCCTGCTCACAGCCTCACTTCTA
ACCTTCTGGAACCCGCCCACCACTGCCAAGCTCACTATTGAATCCACGCCGTTCAATGTCGCAGAGGGGAAGGAG
GTGCTTCTACTTGTCCACAATCTGCCCCAGCATCTTTTTGGCTACAGCTGGTACAAAGGTGAAAGAGTGGATGGC
AACCGTCAAATTATAGGATATGTAATAGGAACTCAACAAGCTACCCCAGGGCCCGCATACAGTGGTCGAGAGATA
ATATACCCCAATGCATCCCTGCTGATCCAGAACATCATCCAGAATGACACAGGATTCTACACCCTACACGTCATA
AAGTCAGATCTTGTGAATGAAGAAGCAACTGGCCAGTTCCGGGTATACCCGGAGCTGCCCAAGCCCTCCATCTCC
AGCAACAACTCCAAACCCGTGGAGGACAAGGATGCTGTGGCCTTCACCTGTGAACCTGAGACTCAGGACGCAACC
TACCTGTGGTGGGTAAACAATCAGAGCCTCCCGGTCAGTCCCAGGCTGCAGCTGTCCAATGGCAACAGGACCCTC
ACTCTATTCAATGTCACAAGAAATGACACAGCAAGCTACAAATGTGAAACCCAGAACCCAGTGAGTGCCAGGCGC
AGTGATTCAGTCATCCTGAATGTCCTCTATGGCCCGGATGCCCCCACCATTTCCCCTCTAAACACATCTTACAGA
TCAGGGGAAAATCTGAACCTCTCCTGCCACGCAGCCTCTAACCCACCTGCACAGTACTCTTGGTTTGTCAATGGG
ACTTTCCAGCAATCCACCCAAGAGCTCTTTATCCCCAACATCACTGTGAATAATAGTGGATCCTATACGTGCCAA
GCCCATAACTCAGACACTGGCCTCAATAGGACCACAGTCACGACGATCACAGTCTATGCAGAGCCACCCAAACCC
TTCATCACCAGCAACAACTCCAACCCCGTGGAGGATGAGGATGCTGTAGCCTTAACCTGTGAACCTGAGATTCAG
AACACAACCTACCTGTGGTGGGTAAATAATCAGAGCCTCCCGGTCAGTCCCAGGCTGCAGCTGTCCAATGACAAC
AGGACCCTCACTCTACTCAGTGTCACAAGGAATGATGTAGGACCCTATGAGTGTGGAATCCAGAACAAATTAAGT
GTTGACCACAGCGACCCAGTCATCCTGAATGTCCTCTATGGCCCAGACGACCCCACCATTCCCCCTCATACACC
TATTACCGTCCAGGGGTGAACCTCAGCCTCTCCTGCCATGCAGCCTCTAACCCACCTGCACAGTATTCTTGGCTG
ATTGATGGGAACATCCAGCAACACACACAAGAGCTCTTTATCTCCAACATCACTGAGAAGAACAGCGGACTCTAT
ACCTGCCAGGCCAATAACTCAGCCAGTGGCCACAGCAGGACTACAGTCAAGACAATCACAGTCTCTGCGGAGCTG
CCCAAGCCCTCCATCTCCAGCAACAACTCCAAACCCGTGGAGGACAAGGATGCTGTGGCCTTCACCTGTGAACCT
GAGGCTCAGAACACAACCTACCTGTGGTGGGTAAATGGTCAGAGCCTCCCAGTCAGTCCCAGGCTGCAGCTGTCC
AATGGCAACAGGACCCTCACTCTATTCAATGTCACAAGAAATGACGCAAGAGCCTATGTATGTGGAATCCAGAAC
TCAGTGAGTGCAAACCGCAGTGACCCAGTCACCCTGGATGTCCTCTATGGGCCGGACACCCCATCATTTCCCCC
CCAGACTCGTCTTACCTTTCGGGAGCGAACCTCAACCTCTCCTGCCACTCGGCCTCTAACCCATCCCCGCAGTAT
TCTTGGCGTATCAATGGGATACCGCAGCAACACACACAAGTTCTCTTTATCGCCAAAATCACGCCAAATAATAAC
GGGACCTATGCCTGTTTTGTCTCTAACTTGGCTACTGGCCGCAATAATTCCATAGTCAAGAGCATCACAGTCTCT
GCATCTGGAACTTCTCCTGGTCTCTCAGCTGGGGCCACTGTCGGCATCATGATTGGAGTGCTGGTTGGGGTTGCT
CTGATATAG
```

Fig. 12

```
ATGGAGAGCCCGTCGGCCCCGCCGCACCGGTGGTGCATCCCCTGGCAGCGCCTGCTCCTGACCGCGAGCCTGCTG
ACGTTCTGGAACCCGCCGACCACCGCCAAGCTGACCATCGAGAGCACCCCGTTCAACGTGGCCGAGGGCAAGGAG
GTCCTGCTCCTGGTGCACAACCTGCCCCAGCACCTGTTCGGGTACAGCTGGTACAAGGGCGAGCGGGTGGACGGC
AACCGGCAGATCATCGGCTACGTGATCGGCACCCAGCAGGCCACGCCGGGCCCGCCTACAGCGGGCGGGAGATC
ATCTACCCGAACGCCAGCCTGCTGATCCAGAACATCATCCAGAACGACACCGGCTTCTACACCCTCCACGTGATC
AAGTCGGACCTGGTGAACGAGGAGGCGACCGGCCAGTTCCGGGTCTACCCGGAGCTGCCGAAGCCCAGCATCAGC
AGCAACAACAGCAAGCCGGTGGAGGACAAGGACGCCGTGGCCTTCACCTGCGAGCCGGAGACCCAGGACGCCACG
TACCTGTGGTGGGTGAACAACCAGAGCCTGCCGGTGTCGCCGCGGCTGCAGCTCAGCAACGGCAACCGCACCCTG
ACCCTGTTCAACGTGACCCGGAACGACACCGCCAGCTACAAGTGCGAGACCCAGAACCCGGTCAGCGCCCGGCGG
AGCGACAGCGTGATCCTGAACGTGCTGTACGGCCCCGACGCGCCGACGATCTCGCCGCTGAACACCAGCTACCGG
AGCGGCGAGAACCTCAACCTGAGCTGCCACGCCGCCAGCAACCCGCCGGCCCAGTACAGCTGGTTCGTGAACGGG
ACCTTCCAGCAGTCGACCCAGGAGCTGTTCATCCCGAACATCACCGTGAACAACAGCGGCAGCTACACCTGCCAG
GCCCACAACAGCGACACGGGCCTGAACCGGACCACCGTGACCACCATCACCGTCTACGCCGAGCCCCCGAAGCCG
TTCATCACGAGCAACAACAGCAACCCGGTGGAGGACGAGGACGCGGTGGCCCTGACCTGCGAGCCGGAGATCCAG
AACACCACCTACCTGTGGTGGGTGAACAACCAGTCGCTCCCGGTGAGCCCCCGCCTGCAGCTGAGCAACGACAAC
CGGACCCTGACCCTGCTGAGCGTGACGCGGAACGACGTCGGCCCGTACGAGTGCGGCATCCAGAACGAGCTCAGC
GTGGACCACAGCGACCCGGTGATCCTGAACGTGCTGTACGGCCCGGACGACCCGACCATCTCGCCGAGCTACACC
TACTACCGGCCCGGGGTGAACCTGAGCCTGAGCTGCCACGCCGCCAGCAACCCGCCGGCCCAGTACAGCTGGCTG
ATCGACGGCAACATCCAGCAGCACACCCAGGAGCTCTTCATCTCGAACATCACCGAGAAGAACAGCGGCCTGTAC
ACCTGCCAGGCCAACAACAGCGCGAGCGGCCACAGCCGGACGACCGTGAAGACCATCACCGTCAGCGCCGAGCTG
CCGAAGCCGTCGATCAGCAGCAACAACAGCAAGCCGGTGGAGGACAAGGACGCCGTGGCCTTCACCTGCGAGCCC
GAGGCCCAGAACACCACGTACCTGTGGTGGGTGAACGGCCAGAGCCTGCCGGTGAGCCCGCGGCTGCAGCTCTCG
AACGGCAACCGCACCCTGACCCTGTTCAACGTGACCCGGAACGACGCCCGGGCGTACGTCTGCGGGATCCAGAAC
AGCGTGAGCGCCAACCGGAGCGACCCGGTGACCCTGGACGTGCTGTACGGCCCGGACACCCCGATCATCAGCCCC
CCGGACAGCTCGTACCTGAGCGGCGCCAACCTCAACCTGAGCTGCCACAGCGCCAGCAACCCGAGCCCGCAGTAC
TCGTGGCGGATCAACGGCATCCCGCAGCAGCACACGCAGGTGCTGTTCATCGCCAAGATCACCCCGAACAACAAC
GGCACCTACGCCTGCTTCGTGAGCAACCTGGCGACCGGCCGGAACAACAGCATCGTCAAGAGCATCACCGTGAGC
GCCAGCGGGACCTCGCCCGGCCTGAGCGCCGGCGCCACGGTGGGCATCATGATCGGCGTGCTGGTGGGCGTGGCC
CTCATCTGA
```

Fig. 13

```
ATGCCTCTTGAGCAGAGGAGTCAGCACTGCAAGCCTGAAGAAGGCCTTGAGGCCCGAGGAGAGGCCCTGGGCCTG
GTGGGTGCGCAGGCTCCTGCTACTGAGGAGCAGCAGACCGCTTCTTCCTCTTCTACTCTAGTGGAAGTTACCCTG
GGGGAGGTGCCTGCTGCCGACTCACCGAGTCCTCCCCACAGTCCTCAGGGAGCCTCCAGCTTCTCGACTACCATC
AACTACACTCTTTGGAGACAATCCGATGAGGGCTCCAGCAACCAAGAAGAGGAGGGGCCAAGAATGTTTCCCGAC
CTGGAGTCCGAGTTCCAAGCAGCAATCAGTAGGAAGATGGTTGAGTTGGTTCATTTTCTGCTCCTCAAGTATCGA
GCCAGGGAGCCGGTCACAAAGGCAGAAATGCTGGAGAGTGTCCTCAGAAATTGCCAGGACTTCTTTCCCGTGATC
TTCAGCAAAGCCTCCGAGTACTTGCAGCTGGTCTTTGGCATCGAGGTGGTGGAAGTGGTCCCCATCAGCCACTTG
TACATCCTTGTCACCTGCCTGGGCCTCTCCTACGATGGCCTGCTGGGCGACAATCAGGTCATGCCCAAGACAGGC
CTCCTGATAATCGTCCTGGCCATAATCGCAATAGAGGGCGACTGTGCCCCTGAGGAGAAAATCTGGGAGGAGCTG
AGTATGTTGGAGGTGTTTGAGGGAGGGAGGACAGTGTCTTCGCACATCCCAGGAAGCTGCTCATGCAAGATCTG
GTGCAGGAAAACTACCTGGAGTACCGGCAGGTGCCCGGCAGTGATCCTGCATGCTACGAGTTCCTGTGGGGTCCA
AGGGCCCTCATTGAAACCAGCTATGTGAAAGTCCTGCACCATACACTAAAGATCGGTGGAGAACCTCACATTTCC
TACCCACCCCTGCATGAACGGGCTTTGAGAGAGGGAGAAGAGTGA
```

Fig. 14

```
ATGCCCCTGGAGCAGCGGAGCCAGCACTGCAAGCCGGAGGAGGGCCTCGAGGCCCGCGGGGAGGCCCTGGGCCTG
GTGGGGGCGCAGGCCCCCGCCACCGAGGAGCAGCAGACCGCCTCCAGCTCCAGCACGCTCGTCGAGGTGACCCTG
GGCGAGGTGCCCGCCGCGGACTCCCCCAGCCCGCCCCACTCCCCCAGGGGGCCAGCTCCTTCAGCACCACCATC
AACTACACGCTGTGGCGGCAGTCCGACGAGGGCAGCTCCAACCAGGAGGAGGAGGGCCCCCGCATGTTCCCGGAC
CTCGAGAGCGAGTTCCAGGCCGCCATCTCCCGGAAGATGGTCGAGCTGGTGCACTTCCTGCTCCTGAAGTACCGC
GCGCGGGAGCCCGTGACCAAGGCCGAGATGCTGGAGAGCGTCCTCCGCAACTGCCAGGACTTCTTCCCCGTGATC
TTCTCCAAGGCCAGCGAGTACCTGCAGCTGGTGTTCGGGATCGAGGTCGTGGAGGTGGTCCCCATCTCCCACCTC
TACATCCTGGTGACCTGCCTGGGCCTCAGCTACGACGGGCTGCTGGGCGACAACCAGGTGATGCCGAAGACCGGG
CTCCTGATCATCGTCCTGGCCATCATCGCCATCGAGGGCGACTGCGCGCCCGAGGAGAAGATCTGGGAGGAGCTC
AGCATGCTGGAGGTGTTCGAGGGCCGGGAGGACTCCGTGTTCGCCCACCCCCGCAAGCTGCTCATGCAGGACCTG
GTCCAGGAGAACTACCTGGAGTACCGGCAGGTGCCCGGGAGCGACCCGGCCTGCTACGAGTTCCTCTGGGGCCCC
CGCGCCCTGATCGAGACGTCCTACGTGAAGGTCCTGCACCACACCCTCAAGATCGGGGGCGAGCCCCACATCAGC
TACCCGCCGCTGCACGAGCGGGCCCTGCGCGAGGGCGAGGAGTGA
```

Fig. 15 atgcctcttgagcagaggagtcagcactgcaagcctgaagaaggccttgaggcccgaggagaggccctgggcctg
gtgggtgcgcaggctcctgctactgaggagcaggaggctgcctcctcctcttctactctagttgaagtcaccctg
ggggaggtgcctgctgccgagtcaccagatcctcccagagtcctcagggagcctcagcctcccactaccatg
aactaccctctctggagccaatcctatgaggactccagcaaccaagaagaggagggccaagcaccttccctgac
ctggagtccgagttccaagcagcactcagtaggaaggtggccgagttggttcattttctgctcctcaagtatcga
gccagggagccggtcacaaaggcagaaatgctggggagtgtcgtcggaaattggcagtatttctttcctgtgatc
ttcagcaaagcttccagttccttgcagctggtctttggcatcgagctgatggaagtggacccatcggccacttg
tacatctttgccacctgcctgggcctctcctacgatggcctgctgggtgacaatcagatcatgcccaaggcaggc
ctcctgataatcgtcctggccataatcgcaagagagggcgactgtgccctgaggagaaaatctgggaggagctg
agtgtgttagaggtgtttgaggggagggaagacagtatcttggggatcccaagaagctgctcacccaacatttc
gtgcaggaaaactacctggagtaccggcaggtccccggcagtgatcctgcatgttatgaattcctgtgggtcca
agggccctcgttgaaaccagctatgtgaaagtcctgcaccatatggtaaagatcagtggaggacctcacatttcc
tacccaccctgcatgagtgggttttgagagagggggaagagtga

```
ATGCCCCTGGAGCAGCGCTCGCAGCACTGCAAGCCGGAGGAGGGCCTCGAGGCCCGGGGGCGAGGCCCTGGGCCTG
GTGGGCGCGCAGGCCCCGGCCACCGAGGAGCAGGAGGCCGCCAGCAGCAGCAGCACCCTGGTGGAGGTGACCCTG
GGCGAGGTGCCGGCCGCGGAGAGCCCGGACCCGCCCCAGTCGCCGCAGGGGGCCAGCAGCCTGCCGACCACGATG
AACTACCCGCTCTGGAGCCAGAGCTACGAGGACAGCTCGAACCAGGAGGAGGAGGGCCCGAGCACCTTCCCGGAC
CTGGAGAGCGAGTTCCAGGCCGCCCTGAGCCGGAAGGTGGCCGAGCTGGTCCACTTCCTGCTGCTCAAGTACCGG
GCCCGGGAGCCCGTGACCAAGGCGGAGATGCTGGGCAGCGTGGTGGGCAACTGGCAGTACTTCTTCCCGGTGATC
TTCAGCAAGGCCTCGAGCAGCCTGCAGCTGGTGTTCGGCATCGAGCTGATGGAGGTCGACCCGATCGGCCACCTG
TACATCTTCGCCACCTGCCTCGGGCTGAGCTACGACGGCCTGCTGGGCGACAACCAGATCATGCCGAAGGCCGGC
CTGCTGATCATCGTGCTCGCCATCATCGCCCGGGAGGGCGACTGCGCGCCGGAGGAGAAGATCTGGGAGGAGCTG
AGCGTGCTGGAGGTGTTCGAGGGCCGCGAGGACAGCATCCTGGGGGACCCGAAGAAGCTGCTGACCCAGCACTTC
GTGCAGGAGAACTACCTCGAGTACCGGCAGGTGCCCGGCTCGGACCCGGCCTGCTACGAGTTCCTGTGGGGCCCG
CGGGCCCTGGTCGAGACCAGCTACGTGAAGGTGCTGCACCACATGGTGAAGATCAGCGGCGGCCCGCACATCAGC
TACCCGCCGCTGCACGACTGGGTGCTGCGGGAGGGCGAGGAGTGA
```

Fig. 17

```
ATGGGTGCCCCGACGTTGCCCCCTGCCTGGCAGCCCTTTCTCAAGGACCACCGCATCTCTACATTCAAGAACTGGC
CCTTCTTGGAGGGCTGCGCCTGCACCCCGGAGCGGATGGCCGAGGCTGGCTTCATCCACTGCCCCACTGAGAACGA
GCCAGACTTGGCCCAGTGTTTCTTCTGCTTCAAGGAGCTGGAAGGCTGGGAGCCAGATGACGACCCCATAGAGGAA
CATAAAAAGCATTCGTCCGGTTGCGCTTTCCTTTCTGTCAAGAAGCAGTTTGAAGAATTAACCCTTGGTGAATTTT
TGAAACTGGACAGAGAAAGAGCCAAGAACAAAATTGCAAAGGAAACCAACAATAAGAAGAAAGAATTTGAGGAAAC
TGCGAAGAAAGTGCGCCGTGCCATCGAGCAGCTGGCTGCCATGGATTGA
```

Fig. 18

ATGGGCGCCCCCACCCTGCCGCCGGCCTGGCAGCCGTTCCTCAAGGACCACCGCATCTCGACCTTCAAGAACTGCC
CGTTCCTGGAGGGCTGCGCGTGCACCCCGGAGCGGATGGCCGAGGCCGGCTTCATCCACTGCCCCACCGAGAACGA
GCCGGACCTGGCCCAGTGCTTCTTCTGCTTCAAGGAGCTGGAGGGCTGGGAGCCGGACGACGACCCGATCGAGGAG
CACAAGAAGCACAGCAGCGGCTGCGCCTTCCTGAGCGTGAAGAAGCAGTTCGAGGAGCTGACGCTCGGGGAGTTCC
TGAAGCTGGACCGGGAGCGGGCCAAGAACAAGATCGCGAAGGAGACCAACAACAAGAAGAAGGAGTTCGAGGAGAC
CGCCAAGAAGGTGCGGCGGGCCATCGAGCAGCTGGCCGCCATGGACTGA

Fig. 19

```
ATGCAGGCCGAAGGCCGGGGCACAGGGGGTTCGACGGGCGATGCTGATGGCCCAGGAGGCCCTGGCATTCCTGAT
GGCCCAGGGGGCAATGCTGGCGGCCCAGGAGAGGCGGGTGCCACGGGCGGCAGAGGTCCCCGGGGCGCAGGGGCA
GCAAGGGCCTCGGGGCCGGCAGGAGGCGCCCCGCGGGGTCCGCATGGCGGCGCGGCTTCAGGGCTGAATGGATGC
TGCAGATGCGGGCCAGGGGGCCGGAGAGCCGCCTGCTTGAGTTCTACCTCGCCATGCCTTTCGCGACACCCATG
GAAGCAGAGCTGGCCCGCAGGAGCCTGGCCCAGGATGCCCCACCGCTTCCCGTGCCAGGGGTGCTTCTGAAGGAG
TTCACTGTGTCCGGCAACATACTGACTATCCGACTGACTGCTGCAGACCACCGCCAACTGCAGCTCTCCATCAGC
TCCTGTCTCCAGCAGCTTTCCCTGTTGATGTGGATCACGCAGTGCTTTCTGCCCGTGTTTTTGGCTCAGCCTCCC
TCAGGGCAGAGGCGCTAA
```

Fig. 20

ATGCAGGCCGAGGGCCGCGGCACCGGCGGCTCGACCGGCGACGCCGACGGGCCCGGCGGCCCGGGCATCCCGGAC
GGCCCGGGCGGGAACGCGGGCGGCCCGGGCGAGGCCGGCGCCACCGGCGGGCGGGGCCCGCGGGGCGCCGGCGCC
GCCCGGGCGAGCGGCCCCGGCGGGGGCGCCCCGCGGGGCCCGCACGGCGGCGCCGCCAGCGGCCTGAACGGGTGC
TGCCGGTGCGGCGCCCGCGGCCCGGAGAGCCGGCTCCTGGAGTTCTACCTGGCCATGCCGTTCGCGACCCCGATG
GAGGCCGAGCTGGCCCGGCGGAGCCTGGCCCAGGACGCCCCGCCGCTGCCCGTGCCGGGCGTGCTCCTGAAGGAG
TTCACGGTGAGCGGCAACATCCTGACCATCCGGCTGACCGCCGCGGACCACCGGCAGCTGCAGCTGTCGATCAGC
AGCTGCCTCCAGCAGCTGAGCCTGCTGATGTGGATCACCCAGTGCTTCCTGCCGGTGTTCCTGGCCCAGCCGCCC
AGCGGCCAGCGCCGGTGA

Fig. 21

```
ATGGGGGACAAGGATATGCCTACTGCTGGGATGCCGAGTCTTCTCCAGAGTTCCTCTGAGAGTCCTCAGAGTTGT
CCTGAGGGGAGGACTCCCAGTCTCCTCTCCAGATTCCCCAGAGTTCTCCTGAGAGCGACGACACCCTGTATCCT
CTCCAGAGTCCTCAGAGTCGTTCTGAGGGGGAGGACTCCTCGGATCCTCTCCAGAGACCTCCTGAGGGGAAGGAC
TCCCAGTCTCCTCTCCAGATTCCCCAGAGTTCTCCTGAGGGCGACGACACCCAGTCTCCTCTCCAGAATTCTCAG
AGTTCTCCTGAGGGGAAGGACTCCCTGTCTCCTCTAGAGATTTCTCAGAGCCCTCCTGAGGGTGAGGATGTCCAG
TCTCCTCTGCAGAATCCTGCGAGTTCCTTCTTCTCCTCTGCTTTATTGAGTATTTTCCAGAGTTCCCCTGAGAGT
ACTCAAAGTCCTTTTGAGGGTTTTCCCCAGTCTGTTCTCCAGATTCCTGTGAGCGCCGCCTCCTCCTCCACTTTA
GTGAGTATTTTCCAGAGTTCCCCTGAGAGTACTCAAAGTCCTTTTGAGGGTTTTCCCCAGTCTCCACTCCAGATT
CCTGTGAGCCGCTCCTTCTCCTCCACTTTATTGAGTATTTTCCAGAGTTCCCCTCCACTTTACTGAGTACTTTT
GAGGGTTTTGCCCAGTCTCCTCTCCAGATTCCTGTGAGCCCCTCCTCCTCCACTTTACTGAGTCTTTTCCAG
AGTTTCTCTGAGAGAACTCAGAGTACTTTTGAGGGTTTTGCCCAGTCTTCTCTCCAGATTCCTGTGAGCCCCTCC
TTCTCCTCCACTTTAGTGAGTCTTTTCCAGAGTTCCCTGAGAGAACTCAGAGTACTTTTGAGGGTTTTCCCCAG
TCTCCTCTCCAGATTCCTGTGAGCTCCTCCTCCTCCTCCACTTTATTGAGTCTTTTCCAGAGTTCCCTGAGAGA
ACTCACAGTACTTTTGAGGGTTTTCCCCAGTCTCTTCTCCAGATTCCTATGACCTCCTCCTTCTCCTCTACTTTA
TTGAGTATTTTCCAGAGTTCTCCTGAGAGTGCTCAAAGTACTTTTGAGGGTTTTCCCCAGTCTCCTCTCCAGATT
CCTGGGAGCCCCTCCTTCTCCTCCACTTTACTGAGTCTTTTCCAGAGTTCCCTGAGAGAACTCACAGTACTTTT
GAGGGTTTTCCCCAGTCTCCTCTCCAGATTCCTATGACCTCCTCCTTCTCCTACTTTATTGAGTATTTTACAG
AGTTCTCCTGAGAGTGCTCAAAGTGCTTTTGAGGGTTTTCCCCAGTCTCCTCTCCAGATTCCTGTGAGCTCCTCT
TTCTCCTACACTTTATTGAGTCTTTTCCAGAGTTCCCTGAGAGAACTCACAGTACTTTTGAGGGTTTTCCCCAG
TCTCCTCTCCAGATTCCTGTGAGCTCCTCCTCCTCCTCCACTTTATTGAGTCTTTTCCAGAGTTCCCTGAG
TGTACTCAAAGTACTTTTGAGGGTTTTCCCCAGTCTCCTCTCCAGATTCCTCAGAGTCCTCCTGAAGGGAGAAT
ACCCATTCTCCTCTCCAGATTGTTCCAAGTCTTCCTGAGTGGGAGGACTCCCTGTCTCCTCACTACTTTCCTCAG
AGCCCTCCTCAGGGGGAGGACTCCCTATCTCCTCACTACTTTCCTCAGAGCCCTCCTCAGGGGGAGGACTCCCTG
TCTCCTCACTACTTTCCTCAGAGCCCTCAGGGGGAGGACTCCCTGTCTCCTCACTACTTTCCTCAGAGCCCTCCT
CAGGGGGAGGACTCCATGTCTCCTCTCTACTTTCCTCAGAGTCCTCTTCAGGGGGAGGAATTCCAGTCTTCTCTC
CAGAGCCCTGTGAGCATCTGCTCCTCCTCCACTCCATCCAGTCTTCCCCAGAGTTTCCCTGAGAGTTCTCAGAGT
CCTCCTGAGGGCCTGTCCAGTCTCCTCTCCATAGTCCTCAGAGCCCTCCTGAGGGGATGCACTCCCAATCTCCT
CTCCAGAGTCCTGAGAGTGCTCCTGAGGGGGAGGATTCCCTGTCTCCTCTCCAAATTCCTCAGAGTCCTCTTGAG
GGACAGGACTCCCTGTCTTCTCTCCATTTTCCTCAGAGTCCTCCTGAGTGGGAGGACTCCCTCTCTCCTCTCCAC
TTTCCTCAGTTTCCTCCTCAGGGGGAGGACTTCCAGTCTTCTCTCCAGAGTCCTGTGAGTATCTGCTCCTCCTCC
ACTTCTTTGAGTCTTCCCCAGAGTTTCCCTGAGAGTCCTCAGAGTCCTCCTGAGGGGCCTGCTCAGTCTCCTCTC
CAGAGACCTGTCAGCTCCTTCTTCTCCTACACTTTAGCGAGTCTTCTCCAAAGTTCCCATGAGAGTCCTCAGAGT
CCTCCTGAGGGGCCTGCCCAGTCTCCTCTCCAGAGTCCTGTGAGCTCCTTCCCCTCCTCCACTTCATCGAGTCTT
TCCCAGAGTTCTCCTGTGAGCTCCTTCCCCTCCTCCACTTCATCGAGTCTTTCCAAGAGTTCCCCTGAGAGTCCT
CTCCAGAGTCCTGTGATCTCCTTCTCCTCCTCCACTTCATTGAGCCCATTCAGTGAAGAGTCCAGCAGCCCAGTA
GATGAATATACAAGTTCCTCAGACACCTTGCTAGAGAGTGATTCCTTGACAGACAGCGAGTCCTTGATAGAGAGC
GAGCCCTTGTTCACTTATACACTGGATGAAAAGGCTGGACGAGTTGGCGCGGTTCTTCTCCTCAAATATCAAGTG
AAGCAGCCTATCACAAAGGCAGAGATGCTGACGAATGTCATCAGCAGGTACACGGGCTACTTTCCTGTGATCTTC
AGGAAAGCCCGTGAGTTCATAGAGATACTTTTTGGCATTTCCCTGAGAGAAGTGGACCCTGATGACTCCTATGTC
TTTGTAAACACATTAGACCTCACCTCTGAGGGGTGTCTGAGTGATGAGCAGGGCATGTCCCAGAACCGCCTCCTG
ATTCTTATTCTGAGTATCATCTTCATAAAGGGCACCTATGCCTCTGAGGAGGTCATCTGGGATGTGCTGAGTGGA
ATAGGGGTGCGTGCTGGGAGGGAGCACTTTGCCTTTGGGGAGCCCAGGGAGCTCCTCACTAAAGTTTGGGTGCAG
GAACATTACCTAGAGTACCGGAGGTGCCCAACTCTTCTCCTCCTCGTTACGAATTCCTGTGGGTCCAAGAGCT
CATTCAGAAGTCATTAAGAGGAAAGTAGTAGAGTTTTTGGCCATGCTAAAGAATACCGTCCCTATTACCTTTCCA
TCCTCTTACAAGGATGCTTTGAAAGATGTGGAAGAGAGAGCCCAGGCCATAATTGACACCACAGATGATTCGACT
GCCACAGAAAGTGCAAGCTCCAGTGTCATGTCCCCCAGCTTCTCTTCTGAGTGA
```

Fig. 22

```
ATGGGCGACAAGGACATGCCCACCGCCGGGATGCCGAGCCTGCTCCAGTCCAGCTCCGAGAGCCCCCAGTCCTGC
CCCGAGGGCGAGGACAGCCAGTCCCCCTGCAGATCCCGCAGAGCTCCCCCGAGAGCGACGACACCCTGTACCCC
CTCCAGTCCCCGCAGAGCCGGTCCGAGGGGGAGGACAGCCTCCGACCCGCTGCAGCGCCCCCCCGAGGGCAAGGAC
AGCCAGTCCCCGCTGCAGATCCCGCACAGCTCCCCCGAGGGGGACGACACGCAGAGCCCGCTCCAGAACAGCCAG
TCCAGCCCCGAGGGCAAGGACTCCCTGAGCCCGCTGGAGATCTCCCAGAGCCCCCCGAGGGCGAGGACGTGCAG
TCCCCGCTCCAGAACCCGGCCAGCTCCTTCTTCAGCTCCGCGCTGCTGAGCATCTTCCAGTCCAGCCCCGAGTCC
ACCCAGAGCCCCTTCGAGGGGTTCCCCCAGTCCGTCCTCCAGATCCCGGTGAGCGCCGCCTCCAGCAGCACCCTG
GTGTCCATCTTCCAGAGCTCCCCCGAGAGCACCCAGTCCCCCTTCGAGGGCTTCCCCCAGAGCCCGCTGCAGATC
CCCGTGTCCCCGAGCTTCTCCAGCACGCTCCTGTCCATCTTCCAGAGCTCCCCCGAGCGCACCCAGAGCACCTTC
GAGGGGTTCGCCCAGTCCCCGCTGCAGATCCCCGTGAGCCCCTCCAGCAGCTCCACCCTCCTGAGCCTGTTCCAG
TCCTTCAGCGAGCGGACGCAGTCCACCTTCGAGGGCTTCGCCCAGAGCTCCCTCCAGATCCCCGTGAGCCCGTCC
TTCAGCTCCACCCTGGTCAGCCTGTTCCAGTCCAGCCCCGAGCGCACCCAGTCCACGTTCGAGGGGTTCCCCCAG
AGCCCCCTCCAGATCCCGGTGTCCAGCTCCAGCAGCTCCACCCTGCTGAGCCTCTTCCAGTCCAGCCCCGAGCGG
ACCCACTCCACCTTCGAGGGCTTCCCCCAGAGCCTGCTGCAGATCCCCATGACGTCCAGCTTCTCCAGCACCCTC
CTGTCCATCTTCCAGAGCTCCCCGGAGAGCGCGCAGTCCACCTTCGAGGGCTTCCCCCAGAGCCCCCTGCAGATC
CCCGGGTCCCCGAGCTTCTCCAGCACCCTCCTGAGCCTGTTCCAGTCCAGCCCCGAGCGCACCCACTCCACCTTC
GAGGGCTTCCCCCAGAGAGCCCCCTCCAGATCCCGATGACCTCCAGCTTCTCCAGCACCCTGCTGTCCATCCTCCAG
AGCTCCCCCGAGAGCGCCCAGTCCGCCTCCGAGGGGTTCCCCCAGAGCCCCCTGCAGATCCCGGTGTCCAGCTCC
TTCAGCTACACGCTGCTCTCCCTGTTCCAGAGCAGCCCCGAGCGGACCCACTCCACCTTCGAGGGCTTCCCCCAG
AGCCCCGCTGCAGATCCCCGTGTCCAGCTCCAGCTCCAGCTCCACCCTCCTGAGCCTGTTCCAGTCCAGCCCCGAG
TGCACGCAGTCCACCTTCGAGGGCTTCCCCCAGAGCCCGCTGCAGATCCCCAGTCCCCCCCGAGGGGAGAAC
ACCCACAGCCCGCTCCAGATCGTGCCCTCCCTGCCCGAGTGGGAGGACAGCCTGTCCCCGCACTACTTCCCGCAG
AGCCCCCGCAGGGCGAGGACAGCCTCTCCCCCACTACTTCCCGCAGAGCCCGCCCCAGGGGGAGGACTCCCTG
AGCCCCCACTACTTCCCGCAGTCCCCCAGGGCGAGGACAGCCTGTCCCCGCACTACTTCCCCAGAGCCCGCCC
CAGGGGGAGGACTCCATGAGCCCCCTCTACTTCCCCCAGTCCCCGCTGCAGGGCGAGGAGTTCCAGAGCTCCCTG
CAGAGCCCCGTGTCCATCTGCAGCTCCAGCACCCCCTCCAGCCTCCCGCAGAGCTTCCCGGAGTCCAGCCAGTCC
CCCCCGAGGGCCCGGTCCAGAGCCCCCTGCACTCCCCGCAGAGCCCCCCGGAGGGGATGCACTCCCAGAGCCCC
CTGCAGTCCCCCGAGAGCGCCCCCGAGGGCGAGGACTCCCTCAGCCCGCTGCAGATCCCCCAGTCCCCGCTGGAG
GGGGAGGACAGCCTCTCCAGCCTGCACTTCCCCCAGTCCCCGCCCGAGTGGGAGGACAGCCTGAGCCCCCTCCAC
TTCCCCCAGTTCCCGCCCCAGGGCGAGGACTTCCAGTCCAGCCTGCAGTCCCCCGTGAGCATCTGCTCCAGCTCC
ACGAGCCTGTCCCTCCCCAGAGCTTCCCGGAGTCCCCCGCCGGCGAGGAGGGCCGGCCAGTCCCCCCTG
CAGCGCCCCGTGAGCCTCCTTCTTCAGCTACACCCTGGCCCTCCCTCCTGCAGAGCTCCCAGCGAGAGCCCGCAGAGC
CCGCCCGAGGGCCCGCCCAGTCCCCGCTGCAGAGCCCCGTGTCCAGCTTCCCCTCCAGCACCTCCAGCTCCCTC
AGCCAGTCCAGCCCGTGTCCAGCTTCCCGTCCAGCACCTCCAGCTCCCTGAGCAAGAGCTCCCCGAGAGCCCC
CTGCAGTCCCCCGTGATCAGCTTCTCCAGCTCCACGAGCCTCTCCCCGTTCAGCGAGGAGTCCAGCTCCCCCGTC
GACGAGTACACCAGCTCCAGCGACACCCTGCTGGAGTCCGACAGCCTCACCGACTCCGAGAGCCTGATCGAGAGC
GAGCCCCTGTTCACCTACACGCTCGACGAGAAGGTGGACGAGCTGGCCGGGTTCCTGCTCCTGAAGTACCAGGTG
AAGCAGCCCATCACCAAGGCCGAGATGCTGACCAACGTCATCTCCCGCTACACCGGCTACTTCCCGGTGATCTTC
CGGAAGGCGCGCGAGTTCATCGAGATCCTCTTCGGGATCAGCCTGCGGGAGGTGGACCCCGACGACTCCTACGTC
TTCGTGAACACGCTGGACCTCACCAGCGAGGGCTGCCTGTCCGACGAGCAGGGGATGAGCCAGAACCGCCTGCTC
ATCCTGATCCTGTCCATCATCTTCATCAAGGGCACCTACGCCAGCGAGGAGGTCATCTGGGACGTGCTCTCCGGG
ATCGGCGTGCGGGCCGGCCGCGAGCACTTCGCCTTCGGGGAGCCCCGGGAGCTGCTGACCAAGGTCTGGGTGCAG
GAGCACTACCTCGAGTACCGCGAGGTGCCCAACAGCTCCCCGCCCCGGTACGAGTTCCTGTGGGGCCCCCGCGCC
CACAGCGAGGTCATCAAGCGGAAGGTGGTGGAGTTCCTGGCGATGCTCAAGAACACGGTCCCCATCACCTTCCCG
TCCAGCTACAAGGACGCCCTGAAGGACGTGGAGGAGCGGGCCCAGGCCATCATCGACACCACCGACGACTCCACG
GCCACCGAGAGCGCCTCCAGCTCCGTGATGAGCCCCAGCTTCTCCAGCGAGTGA
```

Fig. 23

```
ATGCAGTCCCCGCTGCAGGGCGAGGAGTTCCAGAGCTCCCTGCAGAGCCCCGTGTCCATCTGCAGCTCCAGCACC
CCCTCCAGCCTCCCGCAGAGCTTCCCCGAGTCCAGCCAGTCCCCCCCGAGGGCCCGGTCCAGAGCCCCCTGCAC
TCCCCGCAGAGCCCCCCGGAGGGGATGCACTCCCAGAGCCCCCTGCAGTCCCCCGAGAGCGCCCCCGAGGGCGAG
GACTCCCTCAGCCCGCTGCAGATCCCCCAGTCCCCGCTGGAGGGGAGGACAGCCTCTCCAGCCTGCACTTCCCC
CAGTCCCCGCCCGAGTGGGAGGACAGCCTGAGCCCCTCCACTTCCCCCAGTTCCCGCCCCAGGGCGAGGACTTC
CAGTCCAGCCTGCAGTCCCCCGTGAGCATCTGCTCCAGCTCCACGAGCCTGTCCCTCCCCAGAGCTTCCCGGAG
TCCCCCAGAGCCCGCCCGAGGGGCCGGCGCAGTCCCCCCTGCAGCGCCCCGTGAGCTCCTTCTTCAGCTACACC
CTGGCCTCCCTCCTGCAGAGCTCCCACGAGGAGCCCAGCGAGCCCGCCCGAGGGCCCCGCCCAGTCCCCGCTGCAG
AGCCCCGTGTCCAGCTTCCCCTCCAGCACCTCCAGCTCCCTCAGCCAGTCCAGCCCGGTGTCCAGCTTCCCGTCC
AGCACCTCCAGCTCCCTGAGCAAGAGCTCCCCGAGAGCCCCCTGCAGTCCCCGTGATCAGCTTCTCCAGCTCC
ACGAGCCTCTCCCCGTTCAGCGAGGAGTCCAGCTCCCCCGTCGACGAGTACACCAGCTCCAGCGACACCCTGCTG
GAGTCCGACAGCCTCACCGACTCCGAGAGCCTGATCGAGAGCGAGCCCCTGTTCACCTACACGCTCGACGAGAAG
GTGGACGAGCTGGCCCGGTTCCTGCTCCTGAAGTACCAGGTGAAGCAGCCCATCACCAAGGCCGAGATGCTGACC
AACGTCATCTCCCGCTACACCGGCTACTTCCCCGGTGATCTTCCGGAAGGCGCGCGAGTTCATCGAGATCCTCTTC
GGGATCAGCCTGCGGGAGGTGGACCCCGACGACTCCTACGTCTTCGTGAACACGCTGGACCTCACCAGCGAGGGC
TGCCTGTCCGACGAGCAGGGCATGAGCCAGAACCGCCTGCTCATCCTGATCCTGTCCATCATCTTCATCAAGGGC
ACCTACGCCAGCGAGGAGGTCATCTGGGACGTGCTCTCCGGGATCGGCGTGCGGGCCGGCCGCGAGCACTTCGCC
TTCGGGGAGCCCCGGGAGCTGCTGACCAAGGTCTGGGTGCAGGAGCACTACCTCGAGTACCGCGAGGTGCCCAAC
AGCTCCCGCCCCGGTACGAGTTCCTGTGGGGCCCCCGCGCCCACAGCGAGGTCATCAAGCGGAAGGTGGTGGAG
TTCCTGGCGATGCTCAAGAACACGGTCCCCATCACCTTCCCGTCCAGCTACAAGGACGCCCTGAAGGACGTGGAG
GAGCGGGCCCAGGCCATCATCGACACCACCGACGACTCCACGGCCACCGAGAGCGCGTCCAGCTCCGTGATGAGC
CCCAGCTTCTCCAGCGAGTGA
```

Fig. 24

ATGCCTCCCGTTCCAGGCGTTCCATTCCGCAACGTTGACAACGACTCCCCGACCTCAGTTGAGTTAGAAGACTGG
GTAGATGCACAGCATCCCACAGATGAGGAAGAGGAGGAAGCCTCCTCCGCCTCTTCCACTTTGTACTTAGTATTT
TCCCCCTCTTCTTTCTCCACATCCTCTTCTCTGATTCTTGGTGGTCCTGAGGAGGAGGAGGTGCCCTCTGGTGTG
ATACCAAATCTTACCGAGAGCATTCCAGTAGTCCTCCACAGGGTCCTCCACAGGGTCCTTCCCAGAGTCCTCTG
AGCTCCTGCTGCTCCTCTTTTTCATGGAGCTCATTCAGTGAGGAGTCCAGCAGCCAGAAAGGGGAGGATACAGGC
ACCTGTCAGGGCCTGCCAGACAGTGAGTCCTCTTTCACATATACACTAGATGAAAAGGTGGCCGAGTTAGTGGAG
TTCCTGCTCCTCAAATACGAAGCAGAGGAGCCTGTAACAGAGGCAGAGATGCTGATGATTGTCATCAAGTACAAA
GATTACTTTCCTGTGATACTCAAGAGAGCCCGTGAGTTCATGGAGCTTCTTTTTGGCCTTGCCCTGATAGAAGTG
GGCCCTGACCACTTCTGTGTGTTTGCAAACACAGTAGGCCTCACCGATGAGGGTAGTGATGATGAGGGCATGCCC
GAGAACAGCCTCCTGATTATTATTCTGAGTGTGATCTTCATAAAGGGCAACTGTGCCTCTGAGGAGGTCATCTGG
GAAGTGCTGAATGCAGTAGGGGTATATGCTGGGAGGGAGCACTTCGTCTATGGGGAGCCTAGGGAGCTCCTCACT
AAAGTTTGGGTGCAGGGACATTACCTGGAGTATCGGGAGGTGCCCCACAGTTCTCCTCCATATTATGAATTCCTG
TGGGGTCCAAGAGCCCATTCAGAAAGCATCAAGAAGAAAGTACTAGAGTTTTTAGCCAAGCTGAACAACACTGTT
CCTAGTTCCTTTCCATCCTGGTACAAGGATGCTTTGAAAGATGTGGAAGAGAGAGTCCAGGCCACAATTGATACC
GCAGATGATGCCACTGTCATGGCCAGTGAAAGCCTCAGTGTCATGTCCAGCAACGTCTCCTTTTCTGAGTGA

Fig. 25

ATGCCCCCGGTGCCCGGCGTCCCCTTCCGGAACGTGGACAACGACAGCCCCACCTCCGTGGAGCTGGAGGACTGG
GTCGACGCCCAGCACCCGACCGACGAGGAGGAGGAGGAGGCCAGCTCCGCGAGCTCCACGCTCTACCTGGTGTTC
AGCCCCTCCAGCTTCTCCACCAGCTCCAGCCTGATCCTCGGGGGCCCCGAGGAGGAGGAGGTGCCCTCCGGGGTC
ATCCCGAACCTGACCGAGAGCATCCCCTCCAGCCCCCCGCAGGGCCCGCCCCAGGGGCCCTCCCAGAGCCCCCTG
TCCAGCTGCTGCAGCTCCTTCAGCTGGTCCAGCTTCTCCGAGGAGAGCTCCAGCCAGAAGGGCGAGGACACCGGC
ACGTGCCAGGGGCTCCCGGACTCCGAGAGCTCCTTCACCTACACCCTGGACGAGAAGGTGGCCGAGCTGGTGGAG
TTCCTCCTGCTGAAGTACGAGGCCGAGGAGCCCGTCACCGAGGCCGAGATGCTCATGATCGTGATCAAGTACAAG
GACTACTTCCCCGTGATCCTGAAGCGCGCCCGGGAGTTCATGGAGCTGCTCTTCGGCCTGGCGCTGATCGAGGTC
GGGCCCGACCACTTCTGCGTGTTCGCCAACACGGTGGGCCTCACCGACGAGGGGAGCGACGACGAGGGCATGCCG
GAGAACTCCCTGCTGATCATCATCCTCAGCGTCATCTTCATCAAGGGCAACTGCGCCTCCCAGGAGGTGATCTGG
GAGGTGCTGAACGCCGTCGGGGTGTACGCGGGCCGCGAGCACTTCGTGTACGGGGAGCCCCGGGAGCTGCTCACC
AAGGTCTGGGTGCAGGGCCACTACCTGGAGTACCGCGAGGTGCCGCACAGCTCCCCCCCGTACTACGAGTTCCTG
TGGGGCCCCCGGGCCCACAGCGAGTCCATCAAGAAGAAGGTCCTCGAGTTCCTGGCCAAGCTGAACAACACCGTG
CCCAGCAGCTTCCCCTCCTGGTACAAGGACGCCCTCAAGGACGTCGAGGACGCGCGTGCAGGCCACGATCGACACC
GCGGACGACGCCACCGTGATGGCCAGCGAGTCCCTGAGCGTCATGTCCAGCAACGTGTCCTTCAGCGAGTGA

Fig. 26

SEQUENCE LISTING

```
<160> NUMBER OF SEQ ID NOS: 57

<210> SEQ ID NO 1
<211> LENGTH: 1668
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
atgacaccgg gcacccagtc tcctttcttc ctgctgctgc tcctcacagt gcttacagtt      60
gttacaggtt ctggtcatgc aagctctacc ccaggtggag aaaaggagac ttcggctacc     120
cagagaagtt cagtgcccag ctctactgag aagaatgctg tgagtatgac cagcagcgta     180
ctctccagcc acagcccggg ttcaggctcc tccaccactc agggacagga tgtcactctg     240 gcccggcca cggaaccagc ttcaggttca gctgccacct ggggacagga tgtcacctcg     300
gtcccagtca ccaggccagc cctgggctcc accaccccgc cagcccacga tgtcacctca     360
```

```
gccccggaca acaagccagc cccgggctcc accgcccccc cagcccacgg tgtcacctcg    420
gccccggaca ccaggccggc cccgggctcc accgcccccc cagcccacgg tgtcacctcg    480
gccccggaca ccaggccggc cccgggctcc accgcccccc cagcccacgg tgtcacctcg    540
gccccggaca ccaggccggc cccgggctcc accgcccccc cagcccacgg tgtcacctcg    600
gccccggaca ccaggccggc cccgggctcc accgcccccc cagcccacgg tgtcacctcg    660
gccccggaca ccaggccggc cccgggctcc accgcccccc cagcccacgg tgtcacctcg    720
gccccggaca acaggcccgc cttgggctcc accgcccctc cagtccacaa tgtcacctcg    780
gcctcaggct ctgcatcagg ctcagcttct actctggtgc acaacggcac ctctgccagg    840
gctaccacaa ccccagccag caagagcact ccattctcaa ttcccagcca ccactctgat    900
actcctacca cccttgccag ccatagcacc aagactgatg ccagtagcac tcaccatagc    960
tcggtacctc ctctcacctc ctccaatcac agcacttctc cccagttgtc tactggggtc    1020
tctttctttt tcctgtcttt tcacatttca aacctccagt ttaattcctc tctggaagat    1080
cccagcaccg actactacca agagctgcag agagacattt ctgaaatgtt tttgcagatt    1140
tataaacaag ggggtttttct ggcctctcc aatattaagt tcaggccagg atctgtggtg    1200
gtacaattga ctctggcctt ccgagaaggt accatcaatg tccacgacgt ggagacacag    1260
ttcaatcagt ataaaacgga agcagcctct cgatataacc tgacgatctc agacgtcagc    1320
gtgagtgatg tgccatttcc tttctctgcc cagtctgggg ctggggtgcc aggctggggc    1380
atcgcgctgc tggtgctggt ctgtgttctg gttgcgctgg ccattgtcta tctcattgcc    1440
ttggctgtct gtcagtgccg ccgaaagaac tacgggcagc tggacatctt ccagcccgg    1500 gatacctacc atcctatgag cgagtacccc acctaccaca ccatgggcg ctatgtgccc    1560 cctagcagta ccgatcgtag cccctatgag aaggtttctg caggtaacgg tggcagcagc    1620
ctctcttaca caaacccagc agtggcagcc gcttctgcca acttgtag    1668

<210> SEQ ID NO 2
<211> LENGTH: 1668
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2 atgaccccg gcacccagag cccgttcttc ctgctcctgc tgctcacggt gctgaccgtc    60
gtgaccgggt ccggccacgc cagctccacc cccgggggcg agaaggagac gagcgccacc    120
cagcggtcca gcgtgccctc agcaccgag aagaacgcgg tctccatgac cagctccgtg    180
ctgagctccc acagccccgg gtccggcagc tccacgaccc agggccagga cgtgaccctc    240 gcccggcca ccgagcccgc cagcgggtcc gccgcgacgt ggggccagga cgtcaccagc    300
gtgcccgtga cccgccccgc cctggggagc accacgccgc ccgcccacga cgtcacctcc    360 gccccgaca acaagcccgc gccgggcagc accgcccccc cgcccacgg ggtgacctcc    420 gccccgaca cgcggccggc cccggcagc accgcgcccc cgcccacgg cgtgacctcc    480 gccccggaca cccgccccgc cccggggagc acggcccgc ggcgcacgg cgtcacctcc    540 gccccggaca cccgccccgc cccggggagc accgcccgc cgcccacgg cgtgacgtcc    600 gcgcccgaca cccgccccgc cccggcagc accgcccccc cgcccacgg ggtgacctcc    660 gccccggaca cgcggccgc gcccggcagc accgcccgc cggcccacgg ggtcacctcc    720
```

```
gcccccgaca accgcccgc gctgggcagc accgcccccc cggtgcacaa cgtgacgtcc      780
gccagcgggt ccgccagcgg ctccgccagc accctcgtcc acaacggcac cagcgcgcgg      840
gccaccacca cgcccgcctc aagagcacc cccttctcca tccccagcca ccactccgac       900
accccgacca cgctggccag ccactccacc aagaccgacg ccagctccac ccaccacagc      960
tccgtgccgc cgctgacgag ctccaaccac agcacctccc cccagctcag caccggggtg     1020
tccttcttct tcctgagctt ccacatcagc aacctgcagt tcaactccag cctcgaggac     1080
ccgtccaccg actactacca ggagctgcag cgcgacatca gcgagatgtt cctgcagatc     1140
tacaagcagg gcgggttcct cggcctgtcc aacatcaagt tccggcccgg gagcgtcgtg     1200
gtgcagctga cgctcgcgtt ccgcgagggc accatcaacg tccacgacgt ggagacccag     1260
ttcaaccagt acaagaccga ggccgcctcc cggtacaacc tgacgatcag cgacgtctcc     1320
gtgagcgacg tgcccttccc cttctccgcc cagagcggcg ccggggtccc gggctggggg     1380
atcgcgctgc tcgtgctggt gtgcgtcctg gtggccctcg ccatcgtgta cctgatcgcc     1440
ctggcggtct gccagtgccg ccggaagaac tacggccagc tcgacatctt ccccgcccgc     1500
gacacctacc accccatgtc cgagtacccg acctaccaca cccacgggcg gtacgtgccc     1560
cccagctcca cggaccgcag cccctacgag aaggtgtccg ccggcaacgg cgggagctcc     1620
ctgagctaca ccaaccccgg cgtcgccgcg ccagcgcca acctgtga                   1668
```

<210> SEQ ID NO 3
<211> LENGTH: 1263
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

```
atgcctgggg ggtgctcccg gggccccgcc gccggggacg ggcgtctgcg gctggcgcga       60
ctagcgctgg tactcctggg ctgggtctcc tcgtcttctc ccacctcctc ggcatcctcc      120
ttctcctcct cggcgccgtt cctggcttcc gccgtgtccg cccagccccc gctgccggac      180
cagtgccccg cgctgtgcga gtgctccgag gcagcgcgca cagtcaagtg cgttaaccgc      240
aatctgaccg aggtgcccac ggacctgccc gcctacgtgc gcaacctctt ccttaccggc      300
aaccagctgg ccgtgctccc tgccggcgcc ttcgcccgcc ggccgccgct ggcggagctg      360
gccgcgctca acctcagcgg cagcgcctg gacgaggtgc gcgcgggcgc cttcgagcat      420
ctgcccagcc tgcgccagct cgacctcagc cacaacccac tggccgacct cagtcccttc      480
gctttctcgg gcagcaatgc cagcgtctcg gcccccagtc cccttgtgga actgatcctg      540
aaccacatcg tgcccctga agatgagcgg cagaaccgga gcttcgaggg catggtggtg      600
gcggccctgc tggcgggccg tgcactgcag gggctccgcc gcttggagct ggccagcaac      660
cacttccttt acctgccgcg ggatgtgctg gcccaactgc cagcctcag gcacctggac       720
ttaagtaata attcgctggt gagcctgacc tacgtgtcct tccgcaacct gacacatcta     780
gaaagcctcc acctggagga caatgccctc aaggtcttca caatggcac cctggctgag      840
ttgcaaggtc taccccacat tagggttttc ctggacaaca tccctgggt ctgcgactgc      900
cacatggcag acatggtgac ctggctcaag gaaacagagg tagtgcaggg caaagaccgg      960
ctcacctgtg catatccgga aaaaatgagg aatcgggtcc tcttggaact caacagtgct     1020
gacctggact gtgacccgat cttcccccca tccctgcaaa cctcttatgt cttcctgggt     1080
```

```
attgttttag ccctgatagg cgctattttc ctcctggttt tgtatttgaa ccgcaagggg    1140
ataaaaaagt ggatgcataa catcagagat gcctgcaggg atcacatgga agggtatcat    1200
tacagatatg aaatcaatgc ggaccccaga ttaacgaacc tcagttctaa ctcggatgtc    1260
tga                                                                  1263

<210> SEQ ID NO 4
<211> LENGTH: 1263
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
atgcccggcg ggtgcagccg ggcccggcc gcggggacg gccgcctgcg gctcgcgcgc        60
ctggccctgg tgctcctggg gtgggtctcc agctccagcc ccacctccag cgcctccagc    120
ttctccagct ccgcccctt cctggccagc gcggtgtccg cccagccccc gctccccgac    180
cagtgccccg ccctgtgcga gtgcagcgag gccgcgcgga ccgtgaagtg cgtcaaccgc    240
aacctgacgg aggtgcccac cgacctcccg gcctacgtgc ggaacctgtt cctgaccggc    300
aaccagctcg ccgtcctgcc cgccggcgcc ttcgcgcgcc ggccgcccct ggccgagctc    360
gccgccctga acctgtccgg gagccgcctc gacgaggtgc gggccggcgc gttcgagcac    420
ctgccgtccc tgcgccagct cgacctgagc cacaaccccc tggccgacct ctccccttc    480 gccttcagcg ggagcaacgc ctccgtgagc gcccctccc cgctggtcga gctgatcctc    540
aaccacatcg tgccccccga ggacgagcgg cagaaccgca gcttcgaggg catggtggtc    600
gcggccctgc tggccgggcg ggcccctcag ggctgcgcc ggctgagct cgcctccaac    660 cacttcctgt acctgccccg cgacgtgctc gcgcagctgc cgagcctgcg gcacctcgac    720
ctgtccaaca cagcctggt gtccctcacc tacgtcagct tccgcaacct gacgcacctg    780
gagtccctcc acctggagga caacgccctg aaggtgctgc acaacggcac cctcgccgag    840
ctgcaggggc tgcccacat ccgggtgttc ctcgacaaca cccctgggt ctgcgactgc    900 cacatggccg acatggtgac ctggctgaag gagaccgagg tggtccaggg caaggaccgc    960
ctgacgtgcg cgtaccccga gaagatgcgg aaccgggtgc tcctggagct gaacagcgcc   1020
gacctcgact gcgacccgat cctgccccc tccctgcaga ccagctacgt gttcctcggg   1080
atcgtcctgg ccctgatcgg cgccatcttc ctcctggtgc tgtacctcaa ccgcaagggc   1140
atcaagaagt ggatgcacaa catccgggac gcctgccgcg accacatgga ggggtaccac   1200
taccggtacg agatcaacgc ggaccccgc ctgaccaacc tgtccagcaa ctccgacgtc   1260
tga                                                                  1263

<210> SEQ ID NO 5
<211> LENGTH: 3768
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
atggagctgg cggccttgtg ccgctggggg ctcctcctcg cctcttgcc ccccggagcc      60 gcgagcaccc aagtgtgcac cggcacagac atgaagctgc ggctccctgc cagtcccgag   120
```

```
acccacctgg acatgctccg ccacctctac cagggctgcc aggtggtgca gggaaacctg    180
gaactcacct acctgcccac caatgccagc ctgtccttcc tgcaggatat ccaggaggtg    240
cagggctacg tgctcatcgc tcacaaccaa gtgaggcagg tcccactgca gaggctgcgg    300
attgtgcgag gcacccagct ctttgaggac aactatgccc tggccgtgct agacaatgga    360
gacccgctga acaataccac ccctgtcaca ggggcctccc caggaggcct gcgggagctg    420
cagcttcgaa gcctcacaga gatcttgaaa ggaggggtct tgatccagcg gaaccccag    480 ctctgctacc aggacacgat tttgtggaag acatcttcc acaagaacaa ccagctggct    540
ctcacactga tagacaccaa ccgctctcgg gcctgccacc cctgttctcc gatgtgtaag    600
ggctcccgct gctggggaga gagttctgag gattgtcaga gctgacgcg cactgtctgt    660 gccggtggct gtgcccgctg caaggggcca ctgcccactg actgctgcca tgagcagtgt    720
gctgccggct gcacgggccc caagcactct gactgcctgg cctgcctcca cttcaaccac    780
agtggcatct gtgagctgca ctgcccagcc ctggtcacct acaacacaga cacgtttgag    840
tccatgccca atcccgaggg ccggtataca ttcgcgcca gctgtgtgac tgcctgtccc    900
tacaactacc tttctacgga cgtgggatcc tgcaccctcg tctgccccct gcacaaccaa    960
gaggtgacag cagaggatgg aacacagcgg tgtgagaagt gcagcaagcc ctgtgcccga   1020
gtgtgctatg gtctgggcat ggagcacttg cgagaggtga gggcagttac cagtgccaat   1080
atccaggagt ttgctggctg caagaagatc tttgggagcc tggcatttct gccggagagc   1140
tttgatgggg acccagcctc caacactgcc ccgctccagc cagagcagct ccaagtgttt   1200
gagactctgg aagagatcac aggttaccta tacatctcag catggccgga cagcctgcct   1260
gacctcagcg tcttccagaa cctgcaagta atccggggac gaattctgca caatggcgcc   1320
tactcgctga ccctgcaagg gctgggcatc agctggctgg gctgcgctc actgagggaa   1380 ctgggcagtg gactggccct catccaccat aacacccacc tctgcttcgt gcacacggtg   1440
ccctgggacc agctctttcg gaacccgcac caagctctgc tccacactgc caaccggcca   1500
gaggacgagt gtgtgggcga gggcctggcc tgccaccagc tgtgcgcccg agggcactgc   1560
tggggtccag gcccacccca gtgtgtcaac tgcagccagt tccttcgggg ccaggagtgc   1620
gtggaggaat gccgagtact gcaggggctc cccaggagt atgtgaatgc caggcactgt   1680
ttgccgtgcc accctgagtg tcagcccag aatggctcag tgacctgttt tggaccggag   1740
gctgaccagt gtgtggcctg tgcccactat aaggaccctc ccttctgcgt ggcccgctgc   1800
cccagcggtg tgaaacctga cctctcctac atgcccatct ggaagttcc agatgaggag   1860 ggcgcatgcc agccttgccc catcaactgc acccactcct gtgtggacct ggatgacaag   1920
ggctgccccg ccgagcagag agccagccct ctgacgtcca tcatctctgc ggtggttggc   1980
attctgctgg tcgtggtctt gggggtggtc tttgggatcc tcatcaagcg acggcagcag   2040
aagatccgga gtacacgat gcggagactg ctgcaggaaa cggagctggt ggagccgctg   2100
acacctagcg gagcgatgcc caaccaggcg cagatgcgga tcctgaaaga gacggagctg   2160
aggaaggtga aggtgcttgg atctggcgct tttggcacag tctacaaggg catctggatc   2220
cctgatgggg agaatgtgaa aattccagtg gccatcaaag tgttgaggga aaacacatcc   2280
cccaaagcca acaaagaaat cttagacgaa gcatacgtga tggctggtgt gggctcccca   2340
tatgtctccc gccttctggg catctgcctg acatccacgg tgcagctggt gacacagctt   2400 atgcccatg gctgcctctt agaccatgtc cgggaaaacc gcggacgcct gggctcccag   2460
gacctgctga actggtgtat gcagattgcc aaggggatga gctacctgga ggatgtgcgg   2520
```

```
ctcgtacaca gggacttggc cgctcggaac gtgctggtca agagtcccaa ccatgtcaaa    2580
attacagact tcgggctggc tcggctgctg acattgacg agacagagta ccatgcagat    2640
gggggcaagg tgcccatcaa gtggatggcg ctggagtcca ttctccgccg gcggttcacc    2700
caccagagtg atgtgtggag ttatggtgtg actgtgtggg agctgatgac ttttggggcc    2760
aaaccttacg atgggatccc agcccgggag atccctgacc tgctggaaaa ggggagcgg    2820 ctgccccagc cccccatctg caccattgat gtctacatga tcatggtcaa atgttggatg    2880
attgactctg aatgtcggcc aagattccgg gagttggtgt ctgaattctc ccgcatggcc    2940 agggacccc agcgctttgt ggtcatccag aatgaggact tgggcccagc cagtcccttg    3000
gacagcacct tctaccgctc actgctggag gacgatgaca tggggggacct ggtggatgct    3060 gaggagtatc tggtacccca gcagggcttc ttctgtccag accctgcccc gggcgctggg    3120
ggcatggtcc accacaggca ccgcagctca tctaccagga gtggcggtgg ggacctgaca    3180
ctagggctgg agccctctga agaggaggcc cccaggtctc cactggcacc ctccgaaggg    3240
gctggctccg atgtatttga tggtgacctg ggaatggggg cagccaaggg gctgcaaagc    3300
ctccccacac atgaccccag ccctctacag cggtacagtg aggaccccac agtacccctg    3360
ccctctgaga ctgatggcta cgttgccccc ctgacctgca gcccccagcc tgaatatgtg    3420
aaccagccag atgttcggcc ccagccccct tcgccccgag agggccctct gcctgctgcc    3480
cgacctgctg gtgccactct ggaaaggccc aagactctct cccagggaa gaatgggggtc    3540 gtcaaagacg tttttgcctt tgggggtgcc gtggagaacc ccgagtactt gacaccccag    3600
ggaggagctg cccctcagcc ccaccctcct cctgccttca gccagccttt cgacaacctc    3660
tattactggg accaggaccc accagagcgg ggggctccac ccagcacctt caaagggaca    3720
cctacggcag agaacccaga gtacctgggt ctggacgtgc cagtgtga                3768

<210> SEQ ID NO 6
<211> LENGTH: 3768
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
atggagctgg ccgccctctg ccggtggggc ctgctgctcg cgctgctgcc cccgggggcc     60
gccagcaccc aggtgtgcac cggcacggac atgaagctcc gcctgccgc ctcccccgag    120 acccacctgg acatgctccg gcacctgtac cagggggtgcc aggtcgtgca gggcaacctg    180
gagctcacct acctgcccac caacgccagc ctgtccttcc tccaggacat ccaggaggtg    240
caggggtacg tcctgatcgc gcacaaccag gtgcgccagg tgccgctgca gcggctccgc    300
atcgtccggg gcacgcagct gttcgaggac aactacgccc tggccgtgct cgacaacggc    360 gacccctga caacaccac ccccgtgacc ggggccagcc ccggcgggct gcgcgagctc    420
cagctgcggt ccctgacgga gatcctcaag ggcggggtcc tgatccagcg caacccgcag    480
ctgtgctacc aggacaccat cctctggaag gacatcttcc acaagaacaa ccagctggcg    540
ctgaccctca tcgacaccaa ccggagccgc gcctgccacc cctgctcccc catgtgcaag    600
ggcagccggg gctggggcga gtccagcgag gactgccagt ccctgacgcg caccgtgtgc    660
gccgggggct gcgcccggtg caaggggccc ctgccgaccg actgctgcca cgagcagtgc    720
gccgcgggct gcaccggccc caagcacagc gactgcctcg cctgcctgca cttcaaccac    780
```

```
tccgggatct gcgagctgca ctgccccgcc ctcgtgacgt acaacaccga caccttcgag      840
agcatgccca acccggaggg ccgctacacc ttcggggcct cctgcgtcac ggcctgcccc      900
tacaactacc tgagcaccga cgtgggctcc tgcaccctgg tgtgcccect ccacaaccag      960 gaggtcaccg cggaggacgg gacgcagcgg tgcgagaagt gcagcaagcc ctgcgcccgc     1020
gtgtgctacg gcctgggcat ggagcacctg cggaggtgc gcgccgtcac ctccgccaac     1080
atccaggagt cgccgggtg caagaagatc ttcggcagcc tcgcgttcct gccggagagc     1140
ttcgacgggg accccgcctc caacaccgcc ccctgcagc ccgagcagct gcaggtgttc     1200
gagaccctcg aggagatcac gggctacctg tacatcagcg cctggccgga ctccctgccc     1260
gacctcagcg tgttccagaa cctgcaggtc atccgggggc gcatcctgca acggcgcc     1320 tactccctca ccctgcaggg cctggggatc agctggctcg gcctgcggtc cctgcgggag     1380
ctcgggagcg gcctggcgct gatccaccac aacacccacc tctgcttcgt gcacaccgtg     1440
ccctgggacc agctgttccg caaccccac caggccctgc tccacacggc caaccggccg     1500
gaggacgagt gcgtcgggga gggcctggcc tgccaccagc tgtgcgcgcg cggccactgc     1560
tgggggcccg gccccaccca gtgcgtgaac tgctcccagt tcctccgggg gcaggagtgc     1620
gtcgaggagt gccgcgtgct gcagggcctg ccgcgggagt acgtgaacgc ccgccactgc     1680
ctcccctgcc accccgagtg ccagcccag aacggcagcg tcacctgctt cgggccggag     1740
gccgaccagt gcgtggcctg cgcccactac aaggaccgc ccttctgcgt ggcgcggtgc     1800
ccctccggcg tcaagccgga cctgagctac atgcccatct ggaagttccc cgacgaggag     1860
ggggcctgcc agccctgccc gatcaactgc acccactcct gcgtggacct ggacgacaag     1920
ggctgccccg ccgagcagcg cgccagcccc ctcacgtcca tcatcagcgc cgtggtcggg     1980
atcctgctgg tggtggtcct cggcgtggtg ttcggcatcc tgatcaagcg cgccagcag     2040 aagatccgga gtacaccat cgccggctg ctccaggaga ccgagctggt cgagcccctg     2100
accccgtccg gggcgatgcc caaccaggcc cagatgcgca tcctcaagga gaccgagctg     2160
cggaaggtga aggtgctggg cagcggggcc ttcggcacgg tctacaaggg gatctggatc     2220
cccgacggcg agaacgtgaa gatccccgtg gccatcaagg tcctccgcga gaacacctcc     2280
ccgaaggcca acaaggagat cctggacgag gcgtacgtga tggccggcgt ggggagcccc     2340
tacgtcagcc ggctgctcgg catctgcctg acctccaccg tgcagctggt gacgcagctc     2400
atgccctacg ggtgcctgct ggaccacgtc cgcgagaacc ggggccggct cgggagccag     2460
gacctgctga actggtgcat gcagatcgcc aagggcatgt cctacctcga ggacgtgcgc     2520
ctggtgcacc gggacctggc cgcgcgcaac gtcctcgtga agagcccaa ccacgtgaag     2580 atcaccgact cggcctggc ccggctgctc gacatcgacg agaccgagta ccacgccgac     2640
gggggcaagg tcccgatcaa gtggatggcc ctggagtcca tcctgcgccg cgcttcacc     2700 caccagagcg acgtgtggtc ctacgggtg acggtctggg agctcatgac cttcggcgcc     2760
aagccctacg acgggatccc cgcgcgggag atcccggacc tgctggagaa gggcgagcgc     2820
ctcccccagc cccccatctg caccatcgac gtgtacatga tcatggtgaa gtgctggatg     2880
atcgacagcg agtgccggcc gcgcttccgg gagctggtct ccgagttcag ccgcatggcc     2940
cgggaccccc agcgcttcgt ggtgatccag aacgaggacc tgggccccgc ctccccctc     3000 gacagcacct tctaccggtc cctgctggag gacgacgaca tggggacct cgtcgacgcc     3060 gaggagtacc tggtgccgca gcagggcttc ttctgccccg accccgcccc cggggcgggc     3120
```

| | |
|---|---|
| ggcatggtgc accaccgcca ccggagctcc agcacgcgct ccgggggcgg ggacctgacc | 3180 |
| ctcggcctgg agccgagcga ggaggaggcc ccgcggagcc ccctggcccc ctccgagggg | 3240 |
| gccggcagcg acgtcttcga cggcgacctc gggatgggcg ccgcgaaggg gctgcagtcc | 3300 |
| ctgccgaccc acgaccccag cccccctccag cgctactccg aggacccac cgtgccgctg | 3360 |
| cccagcgaga cggacggcta cgtggccccc ctgacctgct ccccgcagcc ggagtacgtc | 3420 |
| aaccagcccg acgtgcggcc ccagcccccg agccccgggg aggggcccct ccggccgcc | 3480 |
| cgccccgcgg gcgccaccct ggagcggccc aagaccctgt cccccggcaa gaacggggtg | 3540 |
| gtcaaggacg tgttcgcctt cggcggggcc gtcgagaacc cggagtacct cacgccccag | 3600 |
| ggcggggccg cgcccagcc ccacccgccc cccgccttca gccccgcctt cgacaacctg | 3660 |
| tactactggg accaggaccc gccggagcgc ggcgcccccc cctccaccctt caagggcacc | 3720 |
| ccgaccgccg agaaccccga gtacctgggg ctcgacgtgc ccgtgtga | 3768 |

<210> SEQ ID NO 7
<211> LENGTH: 3399
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7

| | |
|---|---|
| atgccgcgcg ctcccgctg ccgagccgtg cgctccctgc tgcgcagcca ctaccgcgag | 60 |
| gtgctgccgc tggccacgtt cgtgcggcgc ctggggcccc agggctggcg gctggtgcag | 120 |
| cgcggggacc cggcggcttt ccgcgcgctg gtggcccagt gcctggtgtg cgtgccctgg | 180 |
| gacgcacggc cgcccccgc cgcccctcc ttccgccagg tgtcctgcct gaaggagctg | 240 |
| gtggcccgag tgctgcagag gctgtgcgag cgcgcgcgca agaacgtgct ggccttcggc | 300 |
| ttcgcgctgc tggacggggc ccgcggggcc cccccgagg ccttcaccac cagcgtgcgc | 360 |
| agctacctgc ccaacacggt gaccgacgca ctgcggggga gcggggcgtg ggggctgctg | 420 |
| ctgcgccgcg tgggcgacga cgtgctggtt cacctgctgg cacgctgcgc gctcttgtg | 480 |
| ctggtggctc ccagctgcgc ctaccaggtg tgcgggccgc cgctgtacca gctcggcgct | 540 |
| gccactcagg cccggccccc gccacacgct agtggacccc gaaggcgtct gggatgcgaa | 600 |
| cgggcctgga accatagcgt cagggaggcc ggggtccccc tgggcctgcc agccccgggt | 660 |
| gcgaggaggc gcgggggcag tgccagccga agtctgccgt tgcccaagag gcccaggcgt | 720 |
| ggcgctgccc ctgagccgga gcggacgccc gttgggcagg gtcctgggc ccacccgggc | 780 |
| aggacgcgtg gaccgagtga ccgtggtttc tgtgtggtgt cacctgccag acccgccgaa | 840 |
| gaagccacct ctttggaggg tgcgctctct ggcacgcgcc actcccaccc atccgtgggc | 900 |
| cgccagcacc acgcgggccc ccatccaca tcgcggccac cacgtccctg gacacgcct | 960 |
| tgtcccccgt gtacgccga gaccaagcac ttcctctact cctcaggcga caaggagcag | 1020 |
| ctgcggccct ccttcctact cagctctctg aggcccagcc tgactggcgc tcggaggctc | 1080 |
| gtggagacca tctttctggg ttccaggccc tggatgccag ggactccccg caggttgccc | 1140 |
| cgcctgcccc agcgctactg gcaaatgcgg ccctgtttc tggagctgct tgggaaccac | 1200 |
| gcgcagtgcc cctacggggt gctcctcaag acgcactgcc cgctgcgagc tgcggtcacc | 1260 |
| ccagcagccg tgtctgtgc ccgggagaag cccagggct ctgtggcggc ccccgaggag | 1320 |
| gaggacacag acccccgtcg cctggtgcag ctgctccgcc agcacagcag cccctggcag | 1380 |

| | |
|---|---|
| gtgtacggct tcgtgcgggc ctgcctgcgc cggctggtgc ccccaggcct ctggggctcc | 1440 |
| aggcacaacg aacgccgctt cctcaggaac accaagaagt tcatctccct ggggaagcat | 1500 |
| gccaagctct cgctgcagga gctgacgtgg aagatgagcg tgcgggactg cgcttggctg | 1560 |
| cgcaggagcc caggggttgg ctgtgttccg gccgcagagc accgtctgcg tgaggagatc | 1620 |
| ctggccaagt tcctgcactg gctgatgagt gtgtacgtcg tcgagctgct caggtctttc | 1680 |
| ttttatgtca cggagaccac gtttcaaaag aacaggctct ttttctaccg gaagagtgtc | 1740 |
| tggagcaagt tgcaaagcat tggaatcaga cagcacttga agagggtgca gctgcgggag | 1800 |
| ctgtcggaag cagaggtcag gcagcatcgg gaagccaggc ccgccctgct gacgtccaga | 1860 |
| ctccgcttca tccccaagcc tgacgggctg cggccgattg tgaacatgga ctacgtcgtg | 1920 |
| ggagccagaa cgttccgcag agaaaagagg gccgagcgtc tcacctcgag ggtgaaggca | 1980 |
| ctgttcagcg tgctcaacta cgagcgggcg cggcgccccg gcctcctggg cgcctctgtg | 2040 |
| ctgggcctgg acgatatcca cagggcctgg cgcaccttcg tgctgcgtgt gcgggcccag | 2100 |
| gacccgccgc ctgagctgta ctttgtcaag gtggatgtga cgggcgcgta cgacaccatc | 2160 |
| ccccaggaca ggctcacgga ggtcatcgcc agcatcatca aocccagaa cacgtactgc | 2220 |
| gtgcgtcggt atgccgtggt ccagaaggcc gcccatgggc acgtccgcaa ggccttcaag | 2280 |
| agccacgtct ctaccttgac agacctccag ccgtacatgc gacagttcgt ggctcacctg | 2340 |
| caggagacca gcccgctgag ggatgccgtc gtcatcgagc agagctcctc cctgaatgag | 2400 |
| gccagcagtg gcctcttcga cgtcttccta cgcttcatgt gccaccacgc cgtgcgcatc | 2460 |
| aggggcaagt cctacgtcca gtgccagggg atcccgcagg gctccatcct ctccacgctg | 2520 |
| ctctgcagcc tgtgctacgg cgacatggag aacaagctgt tgcgggat cggcgggac | 2580 |
| gggctgctcc tgcgtttggt ggatgatttc ttgttggtga cacctcacct cacccacgcg | 2640 |
| aaaaccttcc tcaggaccct ggtccgaggt gtccctgagt atggctgcgt ggtgaacttg | 2700 |
| cggaagacag tggtgaactt ccctgtagaa gacgaggccc tgggtggcac ggcttttgtt | 2760 |
| cagatgccgg cccacggcct attcccctgg tgcggcctgc tgctggatac ccggacctg | 2820 |
| gaggtgcaga gcgactactc cagctatgcc cggacctcca tcagagccag tctcaccttc | 2880 |
| aaccgcggct tcaaggctgg gaggaacatg cgtcgcaaac tctttggggt cttgcggctg | 2940 |
| aagtgtcaca gcctgtttct ggatttgcag gtgaacagcc tccagacggt gtgcaccaac | 3000 |
| atctacaaga tcctcctgct gcaggcgtac aggtttcacg catgtgtgct gcagctccca | 3060 |
| tttcatcagc aagtttggaa gaaccccaca ttttcctgc gcgtcatctc tgacacggcc | 3120 |
| tccctctgct actccatcct gaaagccaag aacgcaggga tgtcgctggg ggccaagggc | 3180 |
| gccgccggcc ctctgccctc cgaggccgtg cagtggctgt gccaccaagc attcctgctc | 3240 |
| aagctgactc gacaccgtgt cacctacgtg ccactcctgg ggtcactcag gacagcccag | 3300 |
| acgcagctga gtcggaagct cccggggacg acgctgactg ccctggaggc cgcagccaac | 3360 |
| ccggcactgc cctcagactt caagaccatc ctggactga | 3399 |

<210> SEQ ID NO 8
<211> LENGTH: 3399
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 8

```
atgccccggg ccccgcgctg ccgggccgtg cgcagcctgc tccggtccca ctaccgcgag     60
gtcctgcccc tggcgacctt cgtgcggcgc ctcggccccc aggggtggcg gctggtgcag    120
cgcggcgacc ccgccgcctt ccgggccctg gtcgcccagt gcctcgtgtg cgtgccgtgg    180
gacgcgcgcc ccccgcccgc cgccccgagc ttccggcagg tctcctgcct gaaggagctg    240
gtggcccgcg tgctccagcg gctgtgcgag cgcggggcga agaacgtcct ggccttcggc    300
ttcgccctcc tggacggggc ccggggcggc cccccgaggc cttcaccacg agcgtgcgc    360
tcctacctgc ccaacaccgt gaccgacgcg ctccggggga gcggcgcctg ggggctgctg    420
ctccgccggg tcggcgacga cgtgctggtg cacctgctcg cccgctgcgc cctgttcgtc    480
ctggtggccc cgtcctgcgc gtaccaggtg tgcgggcccc cgctctacca gctgggcgcc    540
gccacccagg cccggccccc gcccacgcc agcggccccc ggcgccggct ggggtgcgag    600
cgcgcgtgga accactccgt ccgggaggcc ggcgtgcccc tcgggctgcc ggccccggc    660
gcccgccggc gcggcgggag cgcctcccgg agcctgcccc tcccaagcg ccgcggcgc    720
ggcgcggccc ccgagcccga gcggacgccc gtggggcagg gctcctgggc ccacccgggg    780
cgcacccggg gccccagcga ccgcggcttc tgcgtcgtgt ccccccgccg gccggcggag    840
gaggccacca gcctggaggg ggccctgtcc ggcacccgcc acagccaccc ctccgtgggg    900
cggcagcacc acgccggccc cccagcacg agccgcccgc ccggccctg ggacaccccc    960
tgcccgcccg tctacgccga gaccaagcac ttcctctact ccagcgggga caaggagcag   1020
ctgcggccct ccttcctgct cagctccctg cgcccagcc tgaccggcgc gcggcgcctc   1080
gtggagacga tcttcctggg ctcccggccg tggatgcccg gaccccgcg ccggctgccc   1140
cgcctcccgc agcggtactg gcagatgcgc cccctgttcc tggagctcct gggcaaccac   1200
gcccagtgcc cctacggggt cctgctgaag acccactgcc cctccgggc cgccgtgacc   1260
ccggccgcgg gcgtgtgcgc ccgcgagaag ccccagggga cgtcgccgc ccccgaggag   1320
gaggacacgg accccggcg cctggtgcag ctgctccggc agcactccag cccgtggcag   1380
gtgtacggct tcgtccgcgc ctgcctgcgg cgcctggtgc ccccggcct tgggggtcc   1440
cggcacaacg agcgccggtt cctgcgcaac accaagaagt catcagcct gggcaagcac   1500
gcgaagctct ccctgcagga gctgacctgg aagatgagcg tgcgggactg cgcctggctc   1560
cggcgctccc cggggggtcgg ctgcgtgccc gccgccgagc accggctgcg cgaggagatc   1620
ctggcgaagt tcctccactg gctgatgagc gtgtacgtcg tggagctgct ccggtccttc   1680
ttctacgtga ccgagacgac cttccagaag aaccgcctgt tcttctaccg gaagagcgtc   1740
tggtccaagc tgcagagcat cggcatccgc cagcacctca gcgggtgca gctgcgcgag   1800
ctgagcgagg ccgaggtgcg gcagcaccgc gaggcccggc ccgccctcct gacctcccgc   1860
ctgcggttca tccccaagcc ggacgggctc cgccccatcg tcaacatgga ctacgtggtg   1920
ggcgcccgga ccttccgccg ggagaagcgc cggagcggc tgacgagccg ggtcaaggcc   1980
ctgttctccg tgctcaacta cgagcgcgcc cggcgccccg gctgctggg cgccagcgtg   2040
ctcgggctgg acgacatcca ccgggcctgg cgcaccttcg tcctgcgggt gcgcgcgcag   2100
gacccccgc ccgagctcta cttcgtgaag gtcgacgtga ccggcgccta cgacaccatc   2160
ccccaggacc ggctgacgga ggtgatcgcc tccatcatca gccccagaa cacctactgc   2220
gtccgccggt acgccgtggt gcagaaggcc gcgcacggcc acgtccgcaa ggccttcaag   2280
agccacgtgt ccaccctgac cgacctccag ccgtacatgc ggcagttcgt ggcccacctg   2340
caggagacga gccccctgcg cgacgccgtc gtgatcgagc agtccagctc cctcaacgag   2400
```

```
gcgagctccg ggctgttcga cgtgttcctg cggttcatgt gccaccacgc cgtccgcatc      2460
cggggcaaga gctacgtgca gtgccagggg atcccccagg gctccatcct cagcaccctg      2520
ctgtgctccc tctgctacgg ggacatggag aacaagctgt cgccggcat ccgccgggac       2580 ggcctgctcc tgcgcctggt ggacgacttc ctcctggtca ccccgcacct gacccacgcc      2640
aagacgttcc tccggaccct ggtgcgcggg gtgccggagt acggctgcgt cgtgaacctg      2700
cggaagaccg tggtcaactt ccccgtggag gacgaggccc tcgggggcac cgcgttcgtg      2760
cagatgcccg cccacgggct gttccctgg tgcggcctgc tcctggacac ccggacgctg       2820
gaggtccaga gcgactacag ctcctacgcc cgcaccagca tccgggcctc cctcaccttc      2880
aaccgcggct tcaaggccgg gcggaacatg cgccggaagc tgttcggcgt gctgcgcctc      2940
aagtgccaca gctgttcct ggacctccag gtcaactccc tgcagaccgt gtgcacgaac       3000
atctacaaga tcctgctcct gcaggcgtac cggttccacg cctgcgtgct gcagctcccg      3060
ttccaccagc aggtctggaa gaacccccacc ttcttcctgc gcgtgatcag cgacaccgcc    3120
tccctgtgct acagcatcct caaggccaag aacgccggga tgtccctggg cgcgaagggg     3180
gccgccggcc cctgcccag cgaggccgtg cagtggctct gccaccaggc cttcctgctg      3240
aagctcaccc ggcaccgcgt cacgtacgtg ccgctgctgg gctccctccg gaccgcgcag     3300
acccagctga gccgcaagct gcccgggacc acgctcaccg ccctggaggc cgccgcgaac     3360
cccgccctgc cctccgactt caagaccatc ctcgactga                            3399

<210> SEQ ID NO 9
<211> LENGTH: 1554
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
ctgcaggacc cggcttccac gtgtgtcccg gagccggcgt ctcagcacac gctccgctcc        60
gggcctgggt gcctacagca gccagagcag cagggagtcc gggacccggg cggcatctgg      120
gccaagttag gcgccgccga ggccagcgct gaacgtctcc agggccggag gagccgcggg      180
gcgtccgggt ctgagccgca gcaaatgggc tccgacgtgc gggacctgaa cgcgctgctg      240
cccgccgtcc cctccctggg tggcggcggc ggctgtgccc tgcctgtgag cggcgcggcg      300
cagtgggcgc cggtgctgga cttgcgccc ccgggcgctt cggcttacgg gtcgttgggc       360
ggccccgcgc cgccaccggc tccgccgcca ccccgccgc cgccgcctca ctccttcatc       420
aaacaggagc cgagctgggg cggcgcggag ccgcacgagg agcagtgcct gagcgccttc      480
actgtccact tttccggcca gttcactggc acagccggag cctgtcgcta cgggccccttc    540 ggtcctcctc cgcccagcca ggcgtcatcc ggccaggcca ggatgtttcc taacgcgccc     600
tacctgccca gctgcctcga gagccagccc gctattcgca atcagggtta cagcacggtc     660
accttcgacg ggacgcccag ctacggtcac acgccctcgc accatgcggc gcagttcccc    720
aaccactcat tcaagcatga ggatcccatg ggccagcagg gctcgctggg tgagcagcag    780
tactcggtgc cgcccccggt ctatggctgc cacaccccca ccgacagctg caccggcagc    840
caggctttgc tgctgaggac gccctacagc agtgacaatt tataccaaat gacatcccag    900
cttgaatgca tgacctggaa tcagatgaac ttaggagcca ccttaaaggg agttgctgct    960
gggagctcca gctcagtgaa atggacagaa gggcagagca accacagcac agggtacgag  1020
```

| | |
|---|---|
| agcgataacc acacaacgcc catcctctgc ggagcccaat acagaataca cacgcacggt | 1080 |
| gtcttcagag gcattcagga tgtgcgacgt gtgcctggag tagccccgac tcttgtacgg | 1140 |
| tcggcatctg agaccagtga gaaacgcccc ttcatgtgtg cttacccagg ctgcaataag | 1200 |
| agatatttta agctgtccca cttacagatg cacagcagga agcacactgg tgagaaacca | 1260 |
| taccagtgtg acttcaagga ctgtgaacga aggttttctc gttcagacca gctcaaaaga | 1320 |
| caccaaagga gacatacagg tgtgaaacca ttccagtgta aaacttgtca gcgaaagttc | 1380 |
| tcccggtccg accacctgaa gacccacacc aggactcata caggtaaaac aagtgaaaag | 1440 |
| cccttcagct gtcggtggcc aagttgtcag aaaaagtttg cccggtcaga tgaattagtc | 1500 |
| cgccatcaca acatgcatca gagaaacatg accaaactcc agctggcgct ttga | 1554 |

<210> SEQ ID NO 10
<211> LENGTH: 1554
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10

| | |
|---|---|
| atgcaggacc ccgccagcac ctgcgtgccg gagcccgcct cccagcacac cctccggagc | 60 |
| ggccccgggt gcctgcagca gcccgagcag cagggcgtcc gcgacccggg cgggatctgg | 120 |
| gcgaagctgg gggccgccga ggcctccgcc gagcggctcc agggccgccg gagccgcggc | 180 |
| gcgtccggga gcgagcccca gcagatgggc tccgacgtgc gggacctgaa cgccctgctc | 240 |
| cccgccgtgc ccagcctggg cggcgggggc gggtgcgccc tgccggtctc cggggcggcc | 300 |
| cagtgggccc ccgtgctcga cttcgctcct ccaggagcta gcgcttacgg atctctggga | 360 |
| ggacctgctc ctccaccggc tccgccacct cctccaccac ctccacctca gcttcatc | 420 |
| aagcaggagc cctcctgggg cggcgccgag ccccacgagg agcagtgcct gagcgccttc | 480 |
| acggtgcact tctccgggca gttcaccggg accgcggggg cctgccgcta cggccccttc | 540 |
| ggcccgcccc cccgagcca ggcctccagc gggcaggccc ggatgttccc caacgccccc | 600 |
| tacctcccct cctgcctgga gagccagccg gcgatccgca accagggcta cagcaccgtc | 660 |
| acgttcgacg ggaccccctc ctacggccac acccccagcc accacgccgc ccagttcccc | 720 |
| aaccactcct tcaagcacga ggacccgatg gggcagcagg gcagcctggg cgagcagcag | 780 |
| tactccgtgc ccccgcccgt gtacgggtgc acacccccga cggacagctg caccggctcc | 840 |
| caggccctcc tgctgcggac cccctacagc tccgacaacc tctaccagat gaccagccag | 900 |
| ctggagtgca tgacgtggaa ccagatgaac ctggggggcca ccctcaaggg cgtcgcggcc | 960 |
| gggtccagct ccagcgtgaa gtggaccgag gccagtccaa ccacagcac cggctacgag | 1020 |
| tccgacaacc acacgacccc catcctgtgc ggggcccagt accgcatcca cccacggc | 1080 |
| gtgttccggg ggatccagga cgtccgccgg gtgcccggcg tggccccgac cctggtccgc | 1140 |
| agcgcgtccg agacgagcga gaagcggccc ttcatgtgcg cctaccccgg ctgcaacaag | 1200 |
| cgctacttca gctcagcca cctgcagatg cactcccgga gcacaccgg ggagaagccc | 1260 |
| taccagtgcg acttcaagga ctgcgagcgc cggttcagcc gctccgacca gctgaagcgg | 1320 |
| caccagcggc gccacaccgg cgtgaagccg ttccagtgca gacctgcca gcggaagttc | 1380 |
| agccgctccg accacctcaa gacgcacacc cggacccaca ccgggaagac gagcgagaag | 1440 |
| cccttctcct gccgctggcc cagctgccag aagaagttcg cccggtccga cgagctggtg | 1500 |

```
cgccaccaca acatgcacca gcggaacatg accaagctgc agctcgccct gtga        1554
```

<210> SEQ ID NO 11
<211> LENGTH: 1554
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11

```
atgcaggacc ccgccagcac ctgcgtgccg gagcccgcct cccagcacac cctccggagc   60
ggccccgggt gcctgcagca gcccgagcag cagggcgtcc gcgacccggg cgggatctgg   120
gcgaagctgg gggccgccga ggcctccgcc gagcggctcc agggccgccg gagccgcggc   180
gcgtccggga gcgagcccca gcagatgggc tccgacgtgc gggacctgaa cgccctgctc   240
cccgccgtgc ccagcctggg cggcgggggc gggtgcgccc tgccggtctc cggggcggcc   300
cagtgggccc ccgtgctcga cttcgccccc cccgcgcca gcgcgtacgg gtccctgggc   360
ggcccggccc cgccccccgc cccgccccc ccgccgcccc cccgccgca cagcttcatc    420
aagcaggagc cctcctgggg cggcgccgag ccccacgagg agcagtgcct gagcgccttc   480
acggtgcact tctccgggca gttcaccggg accgcggggg cctgccgcta cggccccttc   540
ggcccgcccc cccgagcca ggcctccagc gggcaggccc ggatgttccc caacgccccc    600
tacctccccct cctgcctgga gagccagccg gcgatccgca accagggcta cagcaccgtc   660
acgttcgacg ggaccccctc ctacggccac accccagcc accgccgc ccagttcccc     720
aaccactcct tcaagcacga ggacccgatg gggcagcagg cagcctggg cgagcagcag    780
tactccgtgc cccgcccgt gtacgggtgc acacccccga cggacagctg caccggctcc   840
caggccctcc tgctgcggac ccctacagc tccgacaacc tctaccagat gaccagccag    900
ctggagtgca tgacgtggaa ccagatgaac ctggggggcca ccctcaaggg cgtcgcggcc   960
gggtccagct ccagcgtgaa gtggaccgag gccagtcca accacagcac cggctacgag   1020
tccgacaacc acacgacccc catcctgtgc gggccccagt accgcatcca cccacggg   1080
gtgttccggg ggatccagga cgtccgccgg gtgccggcg tggccccgac cctggtccgc   1140
agcgcgtccg agacgagcga gaagcggccc ttcatgtgcg cctacccgg ctgcaacaag   1200
cgctacttca agctcagcca cctgcagatg cactcccgga agcacaccgg ggagaagccc   1260
taccagtgcg acttcaagga ctgcgagcgc cggttcagcc gctccgacca gctgaagcgg   1320
caccagcggc gccacaccgg cgtgaagccg ttccagtgca gacctgcca gcggaagttc   1380
agccgctccg accacctcaa gacgcacacc cggacccaca ccgggaagac gagcgagaag   1440
cccttctcct gccgctggcc cagctgccag aagaagttcg cccggtccga cgagctggtg   1500
cgccaccaca acatgcacca gcggaacatg accaagctgc agctcgccct gtga        1554
```

<210> SEQ ID NO 12
<211> LENGTH: 2109
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12

```
atggagtctc cctcggcccc tccccacaga tggtgcatcc cctggcagag gctcctgctc   60
```

| | |
|---|---|
| acagcctcac ttctaacctt ctggaacccg cccaccactg ccaagctcac tattgaatcc | 120 |
| acgccgttca atgtcgcaga ggggaaggag gtgcttctac ttgtccacaa tctgccccag | 180 |
| catcttttg gctacagctg gtacaaaggt gaaagagtgg atggcaaccg tcaaattata | 240 |
| ggatatgtaa taggaactca acaagctacc ccagggcccg catacagtgg tcgagagata | 300 |
| atatacccca atgcatccct gctgatccag aacatcatcc agaatgacac aggattctac | 360 |
| accctacacg tcataaagtc agatcttgtg aatgaagaag caactggcca gttccgggta | 420 |
| tacccggagc tgcccaagcc ctccatctcc agcaacaact ccaaacccgt ggaggacaag | 480 |
| gatgctgtgg ccttcacctg tgaacctgag actcaggacg caacctacct gtggtgggta | 540 |
| aacaatcaga gcctcccggt cagtcccagg ctgcagctgt ccaatggcaa caggaccctc | 600 |
| actctattca atgtcacaag aaatgacaca gcaagctaca atgtgaaaac ccagaaccca | 660 |
| gtgagtgcca ggcgcagtga ttcagtcatc ctgaatgtcc tctatggccc ggatgccccc | 720 |
| accatttccc ctctaaacac atcttacaga tcagggggaaa atctgaacct ctcctgccac | 780 |
| gcagcctcta acccacctgc acagtactct tggtttgtca atgggacttt ccagcaatcc | 840 |
| acccaagagc tctttatccc caacatcact gtgaataata gtggatccta tacgtgccaa | 900 |
| gcccataact cagacactgg cctcaatagg accacagtca cgacgatcac agtctatgca | 960 |
| gagccaccca accccttcat caccagcaac aactccaacc ccgtggagga tgaggatgct | 1020 |
| gtagccttaa cctgtgaacc tgagattcag aacacaacct acctgtggtg ggtaaataat | 1080 |
| cagagcctcc cggtcagtcc caggctgcag ctgtccaatg acaacaggac cctcactcta | 1140 |
| ctcagtgtca caaggaatga tgtaggaccc tatgagtgtg gaatccagaa caaattaagt | 1200 |
| gttgaccaca gcgacccagt catcctgaat gtcctctatg gcccagacga ccccaccatt | 1260 |
| tcccctcat acacctatta ccgtccaggg gtgaacctca gcctctcctg ccatgcagcc | 1320 |
| tctaacccac ctgcacagta ttcttggctg attgatggga acatccagca acacacacaa | 1380 |
| gagctcttta tctccaacat cactgagaag acagcggac tctataccctg ccaggccaat | 1440 |
| aactcagcca gtggccacag caggactaca gtcaagacaa tcacagtctc tgcggagctg | 1500 |
| cccaagccct ccatctccag caacaactcc aaacccgtgg aggacaagga tgctgtggcc | 1560 |
| ttcacctgtg aacctgaggc tcagaacaca acctacctgt ggtgggtaaa tggtcagagc | 1620 |
| ctcccagtca gtcccaggct gcagctgtcc aatggcaaca ggaccctcac tctattcaat | 1680 |
| gtcacaagaa atgacgcaag agcctatgta tgtggaatcc agaactcagt gagtgcaaac | 1740 |
| cgcagtgacc cagtcaccct ggatgtcctc tatgggccgg acacccccat catttccccc | 1800 |
| ccagactcgt cttacctttc gggagcgaac ctcaacctct cctgccactc ggcctctaac | 1860 |
| ccatccccgc agtattcttg gcgtatcaat gggataccgc agcaacacac acaagttctc | 1920 |
| tttatcgcca aaatcacgcc aaataataac gggacctatg cctgttttgt ctctaacttg | 1980 |
| gctactggcc gcaataattc catagtcaag agcatcacag tctctgcatc tggaacttct | 2040 |
| cctggtctct cagctggggc cactgtcggc atcatgattg gagtgctggt tggggttgct | 2100 |
| ctgatatag | 2109 |

<210> SEQ ID NO 13
<211> LENGTH: 2109
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13

```
atggagagcc cgtcggcccc gccgcaccgg tggtgcatcc cctggcagcg cctgctcctg     60
accgcgagcc tgctgacgtt ctggaacccg ccgaccaccg ccaagctgac catcgagagc    120
accccgttca acgtggccga gggcaaggag gtcctgctcc tggtgcacaa cctgccccag    180
cacctgttcg ggtacagctg gtacaagggc gagcgggtgg acggcaaccg gcagatcatc    240
ggctacgtga tcggcaccca gcaggccacg ccgggcccgg cctacagcgg gcgggagatc    300
atctacccga cgccagcct gctgatccag aacatcatcc agaacgacac cggcttctac    360
accctccacg tgatcaagtc ggacctggtg aacgaggagg cgaccggcca gttccgggtc    420
tacccggagc tgccgaagcc cagcatcagc agcaacaaca gcaagccggt ggaggacaag    480
gacgccgtgg ccttcacctg cgagccgag acccaggacg ccacgtacct gtggtgggtg    540
aacaaccaga gcctgccggt gtcgccgcgg ctgcagctca gcaacggcaa ccgcaccctg    600
accctgttca acgtgacccg gaacgacacc gccagctaca gtgcgagac ccagaacccg    660
gtcagcgccc ggcggagcga cagcgtgatc ctgaacgtgc tgtacggccc cgacgcgccg    720
acgatctcgc cgctgaacac cagctaccgg agcggcgaga acctcaacct gagctgccac    780
gccgccagca cccgccggc ccagtacagc tggttcgtga acgggacctt ccagcagtcg    840
acccaggagc tgttcatccc gaacatcacc gtgaacaaca gcggcagcta cacctgccag    900
gcccacaaca gcgacacggg cctgaaccgg accaccgtga ccaccatcac cgtctacgcc    960
gagcccccga agccgttcat cacgagcaac aacagcaacc cggtggagga cgaggacgcg   1020
gtggccctga cctgcgagcc ggagatccag aacaccacct acctgtggtg ggtgaacaac   1080
cagtcgctcc cggtgagccc ccgcctgcag ctgagcaacg acaaccggac cctgaccctg   1140
ctgagcgtga cgcggaacga cgtcggcccg tacgagtgcg gcatccagaa cgagctcagc   1200
gtggaccaca gcgacccggt gatcctgaac gtgctgtacg gcccggacga cccgaccatc   1260
tcgccgagct acacctacta ccggcccggg gtgaacctga gcctgagctg ccacgccgcc   1320
agcaacccgc cggcccagta cagctggctg atcgacggca acatccagca gcacacccag   1380
gagctcttca tctcgaacat caccgagaag aacagcggcc tgtacacctg ccaggccaac   1440
aacagcgcga gcggccacag ccggacgacc gtgaagacca tcaccgtcag cgccgagctg   1500
ccgaagccgt cgatcagcag caacaacagc aagccggtgg aggacaagga cgccgtggcc   1560
ttcacctgcg agcccgaggc ccagaacacc acgtacctgt ggtgggtgaa cggccagagc   1620
ctgccggtga cccgcggct gcagctctcg aacggcaacc gcaccctgac cctgttcaac   1680
gtgacccgga acgacgcccg ggcgtacgtc tgcgggatcc agaacagcgt gagcgccaac   1740
cggagcgacc cggtgaccct ggacgtgctg tacggcccgg acaccccgat catcagcccc   1800
ccggacagct cgtacctgag cggcgccaac ctcaacctga gctgccacag cgccagcaac   1860
ccgagcccgc agtactcgtg gcggatcaac ggcatcccgc agcagcacac gcaggtgctg   1920
ttcatcgcca agatcacccc gaacaacaac ggcacctacg cctgcttcgt gagcaacctg   1980
gcgaccggcc ggaacaacag catcgtcaag agcatcaccg tgagcgccag cgggacctcg   2040
cccgcctga cgccggcgc cacggtgggc atcatgatcg gcgtgctggt gggcgtggcc   2100
ctcatctga                                                           2109
```

<210> SEQ ID NO 14
<211> LENGTH: 945
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 14

```
atgcctcttg agcagaggag tcagcactgc aagcctgaag aaggccttga ggcccgagga      60
gaggccctgg gcctggtggg tgcgcaggct cctgctactg aggagcagca gaccgcttct     120
tcctcttcta ctctagtgga agttaccctg ggggaggtgc ctgctgccga ctcaccgagt     180
cctccccaca gtcctcaggg agcctccagc ttctcgacta ccatcaacta cactctttgg     240
agacaatccg atgagggctc cagcaaccaa gaagaggagg ggccaagaat gtttcccgac     300
ctggagtccg agttccaagc agcaatcagt aggaagatgg ttgagttggt tcattttctg     360
ctcctcaagt atcgagccag ggagccggtc acaaaggcag aaatgctgga gagtgtcctc     420
agaaaattgc caggacttct tcccgtgatc ttcagcaaag cctccgagta cttgcagctg     480
gtctttggca tcgaggtggt ggaagtggtc cccatcagcc acttgtacat ccttgtcacc     540
tgcctgggcc tctcctacga tggcctgctg ggcgacaatc aggtcatgcc aagacaggc     600
ctcctgataa tcgtcctggc cataatcgca atagagggcg actgtgcccc tgaggagaaa     660
atctgggagg agctgagtat gttggaggtg tttgagggga gggaggacag tgtcttcgca     720
catcccagga agctgctcat gcaagatctg gtgcaggaaa actacctgga gtaccggcag     780
gtgcccggca gtgatcctgc atgctacgag ttcctgtggg gtccaagggc cctcattgaa     840
accagctatg tgaaagtcct gcaccataca ctaaagatcg gtggagaacc tcacatttcc     900
tacccacccc tgcatgaacg ggctttgaga gagggagaag agtga                     945
```

<210> SEQ ID NO 15
<211> LENGTH: 945
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 15

```
atgcccctgg agcagcggag ccagcactgc aagccggagg agggcctcga ggcccgcggg      60
gaggccctgg gcctggtggg ggcgcaggcc cccgccaccg aggagcagca gaccgcctcc     120
agctccagca cgctcgtcga ggtgaccctg ggcgaggtgc cgccgccgga ctcccccagc     180
ccgcccccact cccccaggg ggccagctcc ttcagcacca ccatcaacta cacgctgtgg     240
cggcagtccg acgagggcag ctccaaccag gaggaggagg ccccccgcat gttcccggac     300
ctcgagagcg agttccaggc cgccatctcc cggaagatgg tcgagctggt gcacttcctg     360
ctcctgaagt accgcgcgcg ggagcccgtg accaaggccg agatgctgga gagcgtcctc     420
cgcaactgcc aggacttctt ccccgtgatc ttctccaagg ccagcgagta cctgcagctg     480
gtgttcggga tcgaggtcgt ggaggtggtc cccatctccc acctctacat cctggtgacc     540
tgcctgggcc tcagctacga cgggctgctg ggcgacaacc aggtgatgcc gaagaccggg     600
ctcctgatca tcgtcctggc catcatcgcc atcgagggcg actgcgcgcc cgaggagaag     660
atctgggagg agctcagcat gctggaggtg ttcgagggcc gggaggactc cgtgttcgcc     720
caccccgca agctgctcat gcaggacctg gtccaggaga actacctgga gtaccggcag     780
gtgcccggga gcgacccggc ctgctacgag ttcctctggg gccccgcgc cctgatcgag     840
acgtcctacg tgaaggtcct gcaccacacc ctcaagatcg ggggcgagcc ccacatcagc     900
```

```
tacccgccgc tgcacgagcg ggccctgcgc gagggcgagg agtga              945
```

<210> SEQ ID NO 16
<211> LENGTH: 945
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16

```
atgcctcttg agcagaggag tcagcactgc aagcctgaag aaggccttga ggcccgagga    60
gaggccctgg gcctggtggg tgcgcaggct cctgctactg aggagcagga ggctgcctcc   120
tcctcttcta ctctagttga agtcaccctg ggggaggtgc ctgctgccga gtcaccagat   180
cctcccagtt gtcctcaggg agcctccagc ctccccacta ccatgaacta ccctctctgg   240
agccaatcct atgaggactc cagcaaccaa gaagaggagg ggccaagcac cttccctgac   300
ctggagtccg agttccaagc agcactcagt aggaaggtgg ccgagttggt tcattttctg   360
ctcctcaagt atcgagccag ggagccggtc acaaaggcag aaatgctggg gagtgtcgtc   420
ggaaattggc agtatttctt tcctgtgatc ttcagcaaag cttccagttc cttgcagctg   480
gtctttggca tcgagctgat ggaagtggac cccatcggcc acttgtacat ctttgccacc   540
tgcctgggcc tctcctacga tggcctgctg ggtgacaatc agatcatgcc caaggcaggc   600
ctcctgataa tcgtcctggc cataatcgca agagagggcg actgtgcccc tgaggagaaa   660
atctgggagg agctgagtgt gttagaggtg tttgagggga gggaagacag tatcttgggg   720
gatcccaaga agctgctcac ccaacatttc gtgcaggaaa actacctgga gtaccggcag   780
gtccccggca gtgatcctgc atgttatgaa ttcctgtggg gtccaagggc cctcgttgaa   840
accagctatg tgaaagtcct gcaccatatg gtaaagatca gtggaggacc tcacatttcc   900
tacccacccc tgcatgagtg ggttttgaga gagggggaag agtga               945
```

<210> SEQ ID NO 17
<211> LENGTH: 945
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17

```
atgcccctgg agcagcgctc gcagcactgc aagccggagg agggcctcga ggcccggggc    60
gaggccctgg gcctggtggg cgcgcaggcc ccggccaccg aggagcagga ggccgccagc   120
agcagcagca ccctggtgga ggtgaccctg ggcgaggtgc cggccgcgga gagcccggac   180 ccgcccccagt cgccgcaggg ggccagcagc ctgccgacca cgatgaacta cccgctctgg   240
agccagagct acgaggacag ctcgaaccag gaggaggagg gcccgagcac cttcccggac   300
ctggagagcg agttccaggc cgccctgagc cggaaggtgg ccgagctggt ccacttcctg   360
ctgctcaagt accgggcccg ggagcccgtg accaaggcgg agatgctggg cagcgtggtg   420
ggcaactggc agtacttctt cccggtgatc ttcagcaagg cctcgagcag cctgcagctg   480
gtgttcggca tcgagctgat ggaggtcgac ccgatcggcc acctgtacat cttcgccacc   540
tgcctgggcc tgagctacga cggcctgctg ggcgacaacc agatcatgcc gaaggccggc   600
ctgctgatca tcgtgctcgc catcatcgcc cgggagggcg actgcgcgcc ggaggagaag   660
atctgggagg agctgagcgt gctggaggtg ttcgagggcc gcgaggacag catcctgggg   720
```

```
gacccgaaga agctgctgac ccagcacttc gtgcaggaga actacctcga gtaccggcag    780
gtgcccggct cggacccggc ctgctacgag ttcctgtggg gcccgcgggc cctggtcgag    840
accagctacg tgaaggtgct gcaccacatg gtgaagatca gcggcggccc gcacatcagc    900
tacccgccgc tgcacgagtg ggtgctgcgg gagggcgagg agtga                    945

<210> SEQ ID NO 18
<211> LENGTH: 429
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
atgggtgccc cgacgttgcc ccctgcctgg cagcccttc tcaaggacca ccgcatctct     60
acattcaaga actggccctt cttggagggc tgcgcctgca ccccggagcg gatggccgag   120
gctggcttca tccactgccc cactgagaac gagccagact tggcccagtg tttcttctgc   180
ttcaaggagc tggaaggctg ggagccagat gacgacccca tagaggaaca taaaaagcat   240
tcgtccggtt gcgcttttcct ttctgtcaag aagcagtttg aagaattaac ccttggtgaa   300
tttttgaaac tggacagaga aagagccaag aacaaaattg caaaggaaac caacaataag   360
aagaaagaat tgaggaaac tgcgaagaaa gtgcgccgtg ccatcgagca gctggctgcc    420
atggattga                                                            429

<210> SEQ ID NO 19
<211> LENGTH: 429
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
atgggcgccc ccaccctgcc gccggcctgg cagccgttcc tcaaggacca ccgcatctcg    60
accttcaaga actggccgtt cctggagggc tgcgcgtgca ccccggagcg gatggccgag   120
gccggcttca tccactgccc caccgagaac gagccggacc tggcccagtg cttcttctgc   180
ttcaaggagc tggagggctg ggagccggac gacgacccga tcgaggagca caagaagcac   240
agcagcggct gcgccttcct gagcgtgaag aagcagttcg aggagctgac gctcggggag   300
ttcctgaagc tggaccggga gcgggccaag aacaagatcg cgaaggagac caacaacaag   360
aagaaggagt cgaggagac cgccaagaag gtgcggcggg ccatcgagca gctggccgcc    420
atggactga                                                            429

<210> SEQ ID NO 20
<211> LENGTH: 543
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
atgcaggccg aaggccgggg cacagggggt tcgacgggcg atgctgatgg cccaggaggc    60
cctggcattc ctgatggccc aggggcaat gctggcggcc caggagaggc gggtgccacg   120
ggcggcagag gtccccgggg cgcaggggca gcaagggcct cggggccggg aggaggcgcc   180
```

```
ccgcggggtc cgcatggcgg cgcggcttca gggctgaatg gatgctgcag atgcggggcc    240
agggggccgg agagccgcct gcttgagttc tacctcgcca tgcctttcgc gacacccatg    300
gaagcagagc tggcccgcag gagcctggcc caggatgccc accgcttcc cgtgccaggg     360 gtgcttctga aggagttcac tgtgtccggc aacatactga ctatccgact gactgctgca    420
gaccaccgcc aactgcagct ctccatcagc tcctgtctcc agcagctttc cctgttgatg    480
tggatcacgc agtgctttct gcccgtgttt ttggctcagc ctccctcagg gcagaggcgc    540
taa                                                                  543

<210> SEQ ID NO 21
<211> LENGTH: 543
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
atgcaggccg agggccgcgg caccggcggc tcgaccggcg acgccgacgg gccggcggc     60 ccgggcatcc cggacggccc gggcgggaac gcgggcggcc cgggcgaggc cggcgccacc    120
ggcgggcggg gccgcgggg cgccggcgcc gccgggcga gcggccccgg cggggcgcc      180 ccgcggggcc cgcacggcgg cgccgccagc ggcctgaacg ggtgctgccg gtgcggcgcc    240
cgcggcccgg agagccggct cctggagttc tacctggcca tgccgttcgc gaccccgatg    300
gaggccgagc tggcccggcg gagcctggcc caggacgccc cgccgctgcc cgtgccgggc    360
gtgctcctga aggagttcac ggtgagcggc aacatcctga ccatccggct gaccgccgcg    420
gaccaccggc agctgcagct gtcgatcagc agctgcctcc agcagctgag cctgctgatg    480
tggatcaccc agtgcttcct gccggtgttc ctggcccagc cgcccagcgg ccagcgccgg    540
tga                                                                  543

<210> SEQ ID NO 22
<211> LENGTH: 3429
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
atgggggaca aggatatgcc tactgctggg atgccgagtc ttctccagag ttcctctgag    60
agtcctcaga gttgtcctga gggggaggac tcccagtctc ctctccagat tccccagagt    120
tctcctgaga gcgacgacac cctgtatcct tccagagtc ctcagagtcg ttctgagggg    180
gaggactcct cggatcctct ccagagacct cctgagggga aggactccca gtctcctctc    240
cagattcccc agagttctcc tgagggcgac gacacccagt ctcctctcca gaattctcag    300
agttctcctg aggggaagga ctccctgtct cctctagaga tttctcagag ccctcctgag    360
ggtgaggatg tccagtctcc tctgcagaat cctgcgagtt ccttcttctc ctctgcttta    420
ttgagtattt tccagagttc ccctgagagt actcaaagtc cttttgaggg ttttccccag    480
tctgttctcc agattcctgt gagcgccgcc tcctcctcca ctttagtgag tatttttccag   540 agttccctg agagtactca aagtcctttt gagggttttc cccagtctcc actccagatt    600
cctgtgagcc gctccttctc ctccactttta ttgagtattt tccagagttc ccctgagaga   660
```

```
actcagagta ctttttgaggg ttttgcccag tctcctctcc agattcctgt gagcccctcc    720
tcctcctcca ctttactgag tcttttccag agtttctctg agagaactca gagtactttt    780
gagggttttg cccagtcttc tctccagatt cctgtgagcc cctccttctc ctccacttta    840
gtgagtcttt tccagagttc ccctgagaga actcagagta ctttttgaggg ttttccccag   900
tctcctctcc agattcctgt gagctcctcc tcctcctcca ctttattgag tcttttccag    960
agttccctg agagaactca cagtactttt gagggttttc cccagtctct tctccagatt    1020
cctatgacct cctccttctc ctctacttta ttgagtattt tccagagttc tcctgagagt   1080
gctcaaagta ctttttgaggg ttttccccag tctcctctcc agattcctgg gagcccctcc   1140
ttctcctcca ctttactgag tcttttccag agttccctg agagaactca cagtactttt   1200
gagggttttc cccagtctcc tctccagatt cctatgacct cctccttctc ctctacttta   1260
ttgagtattt tacagagttc tcctgagagt gctcaaagtg ctttttgaggg ttttccccag  1320
tctcctctcc agattcctgt gagctcctct ttctcctaca ctttattgag tcttttccag   1380
agttccctg agagaactca cagtactttt gagggttttc cccagtctcc tctccagatt   1440
cctgtgagct cctcctcctc ctcctccact ttattgagtc ttttccagag ttccctgag   1500
tgtactcaaa gtactttga gggttttccc cagtctcctc tccagattcc tcagagtcct   1560
cctgaagggg agaataccca ttctcctctc cagattgttc caagtcttcc tgagtgggag   1620
gactccctgt ctcctcacta ctttcctcag agccctcctc aggggagga ctccctatct   1680
cctcactact ttcctcagag ccctcctcag ggggaggact cccctgtctcc tcactacttt   1740
cctcagagcc ctcagggga ggactccctg tctcctcact actttcctca gagccctcct   1800
caggggagg actccatgtc tcctctctac tttcctcaga gtcctcttca gggggaggaa   1860
ttccagtctt ctctccagag ccctgtgagc atctgctcct cctccactcc atccagtctt   1920
ccccagagtt tccctgagag ttctcagagt cctcctgagg ggcctgtcca gtctcctctc   1980
catagtcctc agagccctcc tgaggggatg cactcccaat ctcctctcca gagtcctgag   2040
agtgctcctg aggggagga ttccctgtct cctctccaaa ttcctcagag tcctcttgag   2100
ggagaggact ccctgtcttc tctccatttt cctcagagtc ctcctgagtg ggaggactcc   2160
ctctctcctc tccactttcc tcagtttcct cctcaggggg aggacttcca gtcttctctc   2220
cagagtcctg tgagtatctg ctcctcctcc acttctttga gtcttcccca gagtttccct   2280
gagagtcctc agagtcctcc tgaggggcct gctcagtctc ctctccagag acctgtcagc   2340
tccttcttct cctacacttt agcgagtctt ctccaaagtt cccatgagag tcctcagagt   2400
cctcctgagg ggcctgccca gtctcctctc cagagtcctg tgagctcctt cccctcctcc   2460
acttcatcga gtctttccca gagttctcct gtgagctcct tccccctcctc acttcatcg   2520
agtctttcca agagttcccc tgagagtcct ctccagagtc ctgtgatctc cttctcctcc   2580
tccacttcat tgagcccatt cagtgaagag tccagcagcc cagtagatga atatacaagt   2640
tcctcagaca ccttgctaga gagtgattcc ttgacagaca gcgagtcctt gatagagagc   2700
gagcccttgt tcacttatac actggatgaa aaggtggacg agttggcgcg gtttcttctc   2760
ctcaaatatc aagtgaagca gcctatcaca aaggcagaga tgctgacgaa tgtcatcagc   2820
aggtacacgg gctactttcc tgtgatcttc aggaaagccc gtgagttcat agagatactt   2880
tttggcattt ccctgagaga agtggacct gatgactcct atgtctttgt aaacacatta   2940
gacctcacct ctgaggggtg tctgagtgat gagcagggca tgtcccagaa ccgcctcctg   3000
attcttattc tgagtatcat cttcataaag ggcacctatg cctctgagga ggtcatctgg   3060
```

```
gatgtgctga gtggaatagg ggtgcgtgct gggagggagc actttgcctt tggggagccc    3120
agggagctcc tcactaaagt ttgggtgcag gaacattacc tagagtaccg ggaggtgccc    3180
aactcttctc ctcctcgtta cgaattcctg tggggtccaa gagctcattc agaagtcatt    3240
aagaggaaag tagtagagtt tttggccatg ctaaagaata ccgtccctat tacctttcca    3300
tcctcttaca aggatgcttt gaaagatgtg gaagagagag cccaggccat aattgacacc    3360
acagatgatt cgactgccac agaaagtgca agctccagtg tcatgtcccc cagcttctct    3420
tctgagtga                                                             3429
```

<210> SEQ ID NO 23
<211> LENGTH: 3429
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23

```
atgggcgaca aggacatgcc caccgccggg atgccgagcc tgctccagtc cagctccgag      60
agcccccagt cctgccccga gggcgaggac agccagtccc cctgcagat cccgcagagc      120 tcccccgaga gcgacgacac cctgtacccc ctccagtccc cgcagagccg gtccgagggg     180
gaggacagct ccgacccgct gcagcgcccc ccgagggca aggacagcca gtccccgctg     240
cagatcccgc agagctcccc cgaggggac gacacgcaga gccccctcca gaacagccag      300
tccagccccg agggcaagga ctccctgagc ccgctggaga tctcccagag ccccccgag      360 ggcgaggacg tgcagtcccc gctccagaac ccggccagct ccttcttcag ctccgcgctg     420
ctgagcatct tccagtccag ccccgagtcc acccagagcc ccttcgaggg gttcccccag     480
tccgtcctcc agatcccggt gagcgccgcc tccagcagca cctggtgtc catcttccag      540 agctcccccg agagcaccca gtccccccttc gagggcttcc cccagagccc gctgcagatc    600
cccgtgtccc ggagcttctc cagcacgctc ctgtccatct tccagagctc cccgagcgc     660 acccagagca ccttcgaggg gttcgcccag tccccgctgc agatccccgt gagcccctcc    720
agcagctcca ccctcctgag cctgttccag tccttcagcg agcggacgca gtccaccttc    780
gagggcttcg cccagagctc cctccagatc ccgtgagcc cgtccttcag ctccacccctg    840 gtcagcctgt tccagtccag ccccgagcgc acccagtcca cgttcgaggg gttcccccag    900
agccccctcc agatcccggt gtccagctcc agcagctcca cctgctgag cctcttccag    960 tccagccccg agcggaccca ctccaccttc gagggcttcc cccagagcct gctgcagatc   1020
cccatgacgt ccagcttctc cagcaccctc ctgtccatct tccagagctc cccggagagc   1080
gcgcagtcca ccttcgaggg cttcccccag agcccctgc agatcccgg tccccgagc      1140 ttctccagca ccctcctgag cctgttccag tccagccccg agcgcacgca ctccaccttc   1200
gagggcttcc cccagagccc cctccagatc ccgatgacct ccagcttctc cagcaccctg   1260
ctgtccatcc tccagagctc ccccgagagc gcccagtccg ccttcgaggg gttcccccag   1320
agccccctgc agatcccggt gtccagctcc ttcagctaca cgctgctctc cctgttccag   1380
agcagccccg agcggaccca ctccaccttc gagggcttcc cccagagccc gctgcagatc   1440
cccgtgtcca gctccagctc cagctccacc ctcctgagcc tgttccagtc cagccccgag   1500
tgcacgcagt ccaccttcga gggcttcccc cagagcccgc tgcagatccc ccagtccccc   1560 cccgagggg agaacaccca gcccgctc cagatcgtgc cctccctgcc cgagtgggag      1620
```

```
gacagcctgt ccccgcacta cttcccgcag agccccccgc agggcgagga cagcctctcc    1680
ccccactact tcccgcagag cccgcccag ggggaggact ccctgagccc ccactacttc    1740
ccgcagtccc cccagggcga ggacagcctg tccccgcact acttcccca gagcccgccc    1800 caggggagg actccatgag cccctctac ttccccagt ccccgctgca gggcgaggag    1860
ttccagagct ccctgcagag ccccgtgtcc atctgcagct ccagcacccc ctccagcctc    1920
ccgcagagct tccccgagtc cagccagtcc ccccccgagg gccggtcca gagcccctg     1980 cactccccgc agagcccccc ggaggggatg cactcccaga gccccctgca gtccccgag     2040 agcgcccccg agggcgagga ctccctcagc ccgctgcaga tccccagtc cccgctggag    2100 ggggaggaca gcctctccag cctgcacttc ccccagtccc cgcccgagtg ggaggacagc    2160 ctgagcccc tccacttccc ccagttcccg ccccagggcg aggacttcca gtccagcctg    2220 cagtccccccg tgagcatctg ctccagctcc acagcctgt ccctccccca gagcttcccg    2280
gagtcccccc agagcccgcc cgaggggcg gcgcagtccc cctgcagcg cccgtgagc     2340 tccttcttca gctacaccct ggcctccctc ctgcagagct cccacgagag cccgcagagc    2400
ccgcccgagg gccccgccca gtcccgctg cagagcccg tgtccagctt ccctccagc     2460 acctccagct ccctcagcca gtccagcccc gtgtccagct cccgtccag cacctccagc    2520 tccctgagca gagctcccc cgagagcccc ctgcagtccc ccgtgatcag cttctccagc    2580
tccacgagcc tctccccgtt cagcgaggag tccagctccc ccgtcgacga gtacaccagc    2640
tccagcgaca ccctgctgga gtccgacagc ctcaccgact ccgagagcct gatcgagagc    2700
gagcccctgt tcacctacac gctcgacgag aaggtggacg agctggcccg gttcctgctc    2760
ctgaagtacc aggtgaagca gcccatcacc aaggccgaga tgctgaccaa cgtcatctcc    2820
cgctacaccg gctacttccc ggtgatcttc cggaaggcgc gcgagttcat cgagatcctc    2880
ttcgggatca gcctgcggga ggtggacccc gacgactcct acgtcttcgt gaacacgctg    2940
gacctcacca gcgagggctg cctgtccgac gagcagggga tgagccagaa ccgcctgctc    3000
atcctgatcc tgtccatcat cttcatcaag ggcacctacg ccagcgagga ggtcatctgg    3060
gacgtgctct ccgggatcgg cgtgcgggcc ggccgcgagc acttcgcctt cggggagccc    3120
cgggagctgc tgaccaaggt ctgggtgcag gagcactacc tcgagtaccg cgaggtgccc    3180
aacagctccc cgccccggta cgagttcctg tggggccccc gcgccacag cgaggtcatc    3240 aagcggaagg tggtggagtt cctggcgatg ctcaagaaca cggtccccat caccttcccg    3300
tccagctaca aggacgccct gaaggacgtg gaggagcggg cccaggccat catcgacacc    3360
accgacgact ccacggccac cgagagcgcg tccagctccg tgatgagccc cagcttctcc    3420
agcgagtga                                                            3429
```

<210> SEQ ID NO 24
<211> LENGTH: 1596
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 24

```
atgcagtccc cgctgcaggg cgaggagttc cagagctccc tgcagagccc cgtgtccatc      60
tgcagctcca gcaccccctc cagcctcccg cagagcttcc ccgagtccag ccagtccccc     120
cccgagggcc cggtccagag ccccctgcac tccccgcaga gccccccgga ggggatgcac     180
```

```
tcccagagcc ccctgcagtc ccccgagagc gccccgagg gcgaggactc cctcagcccg      240
ctgcagatcc cccagtcccc gctggagggg gaggacagcc tctccagcct gcacttcccc      300
cagtccccgc ccgagtggga ggacagcctg agccccctcc acttccccca gttcccgccc      360
cagggcgagg acttccagtc cagcctgcag tccccgtga gcatctgctc cagctccacg      420
agcctgtccc tccccagag cttcccggag tccccaga gcccgccga ggggccggcg      480 cagtccccc tgcagcgccc cgtgagctcc ttcttcagct acaccctggc ctccctcctg      540
cagagctccc acgagagccc gcagagcccg cccgagggcc ccgcccagtc ccgctgcag      600 agccccgtgt ccagcttccc ctccagcacc tccagctccc tcagccagtc cagccccgtg      660
tccagcttcc cgtccagcac ctccagctcc ctgagcaaga gctcccccga gaccccctg      720 cagtcccccg tgatcagctt ctccagctcc acgagcctct ccccgttcag cgaggagtcc      780
agctcccccg tcgacgagta caccagctcc agcgacaccc tgctggagtc cgacagcctc      840
accgactccg agagcctgat cgagagcgag cccctgttca cctacacgct cgacgagaag      900
gtggacgagc tggcccggtt cctgctcctg aagtaccagg tgaagcagcc catcaccaag      960
gccgagatgt gaccaacgt catctcccgc tacaccggct acttcccggt gatcttccgg     1020
aaggcgcgcg agttcatcga gatcctcttc gggatcagcc tgcgggaggt ggaccccgac     1080
gactcctacg tcttcgtgaa cacgctggac ctcaccagcg agggctgcct gtccgacgag     1140
caggggatga gccagaaccg cctgctcatc ctgatcctgt ccatcatctt catcaagggc     1200
acctacgcca gcgaggaggt catctgggac gtgctctccg ggatcggcgt gcgggccggc     1260
cgcgagcact tcgccttcgg ggagccccgg gagctgctga ccaaggtctg ggtgcaggag     1320
cactacctcg agtaccgcga ggtgcccaac agctccccgc ccggtacga gttcctgtgg     1380 ggccccgcg cccacagcga ggtcatcaag cggaaggtgg tggagttcct ggcgatgctc     1440
aagaacacgg tccccatcac cttcccgtcc agctacaagg acgccctgaa ggacgtggag     1500
gagcgggccc aggccatcat cgacaccacc gacgactcca cggccaccga gagcgcgtcc     1560
agctccgtga tgagccccag cttctccagc gagtga                             1596
```

<210> SEQ ID NO 25
<211> LENGTH: 1122
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 25

```
atgcctcccg ttccaggcgt tccattccgc aacgttgaca cgactccccc gacctcagtt       60
gagttagaag actgggtaga tgcacagcat cccacagatg aggaagagga ggaagcctcc      120
tccgcctctt ccactttgta cttagtattt tccccctctt cttcctccac atcctcttct      180
ctgattcttg gtggtcctga ggaggaggag gtgccctctg tgtgatacc aaatcttacc      240 gagagcattc ccagtagtcc tccacagggt cctccacagg gtccttccca gagtcctctg      300
agctcctgct gctcctcttt ttcatggagc tcattcagtg aggagtccag cagccagaaa      360
ggggaggata caggcacctg tcagggcctg ccagacagtg agtcctcttt cacatataca      420
ctagatgaaa aggtggccga gttagtggag ttcctgctcc tcaaatacga agcagaggag      480
cctgtaacag aggcagagat gctgatgatt gtcatcaagt acaaagatta ctttcctgtg      540
atactcaaga gagcccgtga gttcatggag cttctttttg gccttgccct gatagaagtg      600
```

```
ggccctgacc acttctgtgt gtttgcaaac acagtaggcc tcaccgatga gggtagtgat    660
gatgagggca tgcccgagaa cagcctcctg attattattc tgagtgtgat cttcataaag    720
ggcaactgtg cctctgagga ggtcatctgg gaagtgctga atgcagtagg ggtatatgct    780
gggagggagc acttcgtcta tggggagcct agggagctcc tcactaaagt ttgggtgcag    840
ggacattacc tggagtatcg ggaggtgccc cacagttctc ctccatatta tgaattcctg    900
tggggtccaa gagcccattc agaaagcatc aagaagaaag tactagagtt tttagccaag    960
ctgaacaaca ctgttcctag ttcctttcca tcctggtaca aggatgcttt gaaagatgtg    1020
gaagagagag tccaggccac aattgatacc gcagatgatg ccactgtcat ggccagtgaa    1080
agcctcagtg tcatgtccag caacgtctcc ttttctgagt ga    1122
```

<210> SEQ ID NO 26
<211> LENGTH: 1122
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 26

```
atgccccegg tgcccggcgt ccccttccgg aacgtggaca cgacagccc cacctccgtg    60 gagctggagg actgggtcga cgcccagcac ccgaccgacg aggaggagga ggaggccagc    120
tccgcgagct ccacgctcta cctggtgttc agcccctcca gcttctccac cagctccagc    180
ctgatcctcg gggcccccga ggaggaggag gtgcctccg gggtcatccc gaacctgacc    240
gagagcatcc cctccagccc ccgcagggc ccgcccagg ggccctccca gagcccctg    300 tccagctgct gcagctcctt cagctggtcc agcttctccg aggagagctc cagccagaag    360
ggcgaggaca ccggcacgtg ccaggggctc ccggactccg agagctcctt cacctacacc    420
ctggacgaga aggtggccga gctggtggag ttcctcctgc tgaagtacga ggccgaggag    480
cccgtcaccg aggccgagat gctcatgatc gtgatcaagt acaaggacta cttccccgtg    540
atcctgaagc gcgcccggga gttcatggag ctgctcttcg gcctggcgct gatcgaggtc    600
gggcccgacc acttctgcgt gttcgccaac acggtgggcc tcaccgacga ggggagcgac    660
gacgagggca tgccggagaa ctcccctgctg atcatcatcc tcagcgtcat cttcatcaag    720
ggcaactgcg cctccgagga ggtgatctgg gaggtgctga acgccgtcgg ggtgtacgcg    780
ggccgcgagc acttcgtgta cggggagccc cgggagctgc tcaccaaggt ctgggtgcag    840
ggccactacc tggagtaccg cgaggtgccg cacagctccc ccccgtacta cgagttcctg    900
tggggccccc gggcccacag cgagtccatc aagaagaagg tcctcgagtt cctggccaag    960
ctgaacaaca ccgtgcccag cagcttcccc tcctggtaca aggacgccct caaggacgtc    1020
gaggagcgcg tgcaggccac gatcgacacc gcggacgacg ccaccgtgat ggccagcgag    1080
tccctgagcg tcatgtccag caacgtgtcc ttcagcgagt ga    1122
```

<210> SEQ ID NO 27
<211> LENGTH: 13
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 27
gccgccacca ugg                                                    13

<210> SEQ ID NO 28
<211> LENGTH: 14
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: c or u
<220> FEATURE:
<221> NAME/KEY: modified_base
<222> LOCATION: (5)..(5)
<223> OTHER INFORMATION: a, c, u, g, unknown or other
<220> FEATURE:
<221> NAME/KEY: modified_base
<222> LOCATION: (9)..(9)
<223> OTHER INFORMATION: u or a
<220> FEATURE:
<221> NAME/KEY: modified_base
<222> LOCATION: (12)..(12)
<223> OTHER INFORMATION: c or u

<400> SEQUENCE: 28
nccancccnu cncc                                                   14

<210> SEQ ID NO 29
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29
aaaaaaaaaa aaaaaaaaaa aaaaaaaaaa aaaaaaaaaa aaaaaaaaaa aaaaaaaaaa     60
aaaaaaaaaa aaaaaaaaaa aaaaaaaaaa aaaaaaaaaa aaaaaaaaaa aaaaaaaaaa    120
aaaaaaaaaa aaaaaaaaaa aaaaaaaaaa aaaaaaaaaa aaaaaaaaaa aaaaaaaaaa    180
aaaaaaaaaa aaaaaaaaaa                                                200

<210> SEQ ID NO 30
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(200)
<223> OTHER INFORMATION: This region may encompass 10 to 200 nucleotides

<400> SEQUENCE: 30
aaaaaaaaaa aaaaaaaaaa aaaaaaaaaa aaaaaaaaaa aaaaaaaaaa aaaaaaaaaa     60
aaaaaaaaaa aaaaaaaaaa aaaaaaaaaa aaaaaaaaaa aaaaaaaaaa aaaaaaaaaa    120
aaaaaaaaaa aaaaaaaaaa aaaaaaaaaa aaaaaaaaaa aaaaaaaaaa aaaaaaaaaa    180
aaaaaaaaaa aaaaaaaaaa                                                200

<210> SEQ ID NO 31
<211> LENGTH: 100
<212> TYPE: DNA
<213> ORGANISM: Artificial Sequence
<220> FEATURE:

```
<223> OTHER INFORMATION: Description of Artificial Sequence: Synthetic
      polynucleotide
<220> FEATURE:
<221> NAME/KEY: misc_feature
<222> LOCATION: (1)..(100)
<223> OTHER INFORMATION: This region may encompass 10 to 100 nucleotides

<400> SEQUENCE: 31
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa                           100

<210> SEQ ID NO 32
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(100)
<223> OTHER INFORMATION: This region may encompass 20 to 100 nucleotides

<400> SEQUENCE: 32
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa                           100

<210> SEQ ID NO 33
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(80)
<223> OTHER INFORMATION: This region may encompass 40 to 80 nucleotides

<400> SEQUENCE: 33
aaaaaaaaaa aaaaaaaaaa aaaaaaaaaa aaaaaaaaaa aaaaaaaaaa aaaaaaaaaa      60
aaaaaaaaaa aaaaaaaaaa                                                  80

<210> SEQ ID NO 34
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(200)
<223> OTHER INFORMATION: This region may encompass 10 to 200 nucleotides

<400> SEQUENCE: 34
cccccccccc cccccccccc cccccccccc cccccccccc cccccccccc cccccccccc      60
cccccccccc cccccccccc cccccccccc cccccccccc cccccccccc cccccccccc     120
cccccccccc cccccccccc cccccccccc cccccccccc cccccccccc cccccccccc     180
cccccccccc cccccccccc                                                 200

<210> SEQ ID NO 35
<211> LENGTH: 100
<212> TYPE: DNA
<213> ORGANISM: Artificial Sequence
```

```
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(100)
<223> OTHER INFORMATION: This region may encompass 10 to 100 nucleotides

<400> SEQUENCE: 35
cccccccccc cccccccccc cccccccccc cccccccccc cccccccccc cccccccccc      60
cccccccccc cccccccccc cccccccccc cccccccccc                           100

<210> SEQ ID NO 36
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(70)
<223> OTHER INFORMATION: This region may encompass 20 to 70 nucleotides

<400> SEQUENCE: 36
cccccccccc cccccccccc cccccccccc cccccccccc cccccccccc cccccccccc      60
cccccccccc                                                             70

<210> SEQ ID NO 37
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(60)
<223> OTHER INFORMATION: This region may encompass 20 to 60 nucleotides

<400> SEQUENCE: 37
cccccccccc cccccccccc cccccccccc cccccccccc cccccccccc cccccccccc      60

<210> SEQ ID NO 38
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(40)
<223> OTHER INFORMATION: This region may encompass 10 to 40 nucleotides

<400> SEQUENCE: 38
cccccccccc cccccccccc cccccccccc cccccccccc                            40

<210> SEQ ID NO 39
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(15)
<223> OTHER INFORMATION: This region may encompass 0 to 15 residues
```

```
<220> FEATURE:
<223> OTHER INFORMATION: see specification as filed for detailed
      description of substitutions and preferred embodiments

<400> SEQUENCE: 39

Arg Arg Arg Arg Arg Arg Arg Arg Arg Arg Arg Arg Arg Arg Arg
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(15)
<223> OTHER INFORMATION: This region may encompass 0 to 15 residues
<220> FEATURE:
<223> OTHER INFORMATION: see specification as filed for detailed
      description of substitutions and preferred embodiments

<400> SEQUENCE: 40

Lys Lys Lys Lys Lys Lys Lys Lys Lys Lys Lys Lys Lys Lys Lys
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(15)
<223> OTHER INFORMATION: This region may encompass 0 to 15 residues
<220> FEATURE:
<223> OTHER INFORMATION: see specification as filed for detailed
      description of substitutions and preferred embodiments

<400> SEQUENCE: 41

His His His His His His His His His His His His His His His
1               5                   10                  15

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Arg Arg Arg Arg Arg Arg Arg
1               5

<210> SEQ ID NO 43
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Arg Arg Arg Arg Arg Arg Arg Arg
1               5
```

<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Arg Arg Arg Arg Arg Arg Arg Arg Arg
1               5

<210> SEQ ID NO 45
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

His His His Arg Arg Arg Arg Arg Arg Arg Arg Arg
1               5                   10

<210> SEQ ID NO 46
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Arg Arg Arg Arg Arg Arg Arg Arg Arg His His His
1               5                   10

<210> SEQ ID NO 47
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

His His His Arg Arg Arg Arg Arg Arg Arg Arg Arg His His His
1               5                   10                  15

<210> SEQ ID NO 48
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Tyr Ser Ser Arg Arg Arg Arg Arg Arg Arg Arg Ser Ser Tyr
1               5                   10                  15

<210> SEQ ID NO 49
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 49

Arg Lys His Arg Lys His Arg Lys His Arg Lys His
1               5                   10

<210> SEQ ID NO 50
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Tyr Arg Lys His Arg Lys His Arg
1               5

<210> SEQ ID NO 51
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(40)
<223> OTHER INFORMATION: Guanosine, uracil or an analogue of guanosine
      or uracil
<220> FEATURE:
<221> NAME/KEY: misc_feature
<222> LOCATION: (1)..(40)
<223> OTHER INFORMATION: This region may encompass 1 to 40 nucleotides
<220> FEATURE:
<221> NAME/KEY: modified_base
<222> LOCATION: (41)..(43)
<223> OTHER INFORMATION: Guanosine, uracil, adenosine, thymidine,
      cytosine or an analogue of guanosine or uracil
<220> FEATURE:
<221> NAME/KEY: modified_base
<222> LOCATION: (44)..(83)
<223> OTHER INFORMATION: Guanosine, uracil or an analogue of guanosine
      or uracil
<220> FEATURE:
<221> NAME/KEY: misc_feature
<222> LOCATION: (44)..(83)
<223> OTHER INFORMATION: This region may encompass 1 to 40 nucleotides
<220> FEATURE:
<223> OTHER INFORMATION: see specification as filed for detailed
      description of substitutions and preferred embodiments

<400> SEQUENCE: 51
nnnnnnnnnn nnnnnnnnnn nnnnnnnnnn nnnnnnnnnn nnnnnnnnnn nnnnnnnnnn    60
nnnnnnnnnn nnnnnnnnnn nnn                                            83

<210> SEQ ID NO 52
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(40)
<223> OTHER INFORMATION: Cytosine, uracil or an analogue of cytosine or
      uracil
<220> FEATURE:
<221> NAME/KEY: misc_feature
<222> LOCATION: (1)..(40)
<223> OTHER INFORMATION: This region may encompass 1 to 40 nucleotides
<220> FEATURE:
<221> NAME/KEY: modified_base
```

```
<222> LOCATION: (41)..(43)
<223> OTHER INFORMATION: Guanosine, uracil, adenosine, thymidine,
      cytosine or an analogue of cytosine or uracil
<220> FEATURE:
<221> NAME/KEY: modified_base
<222> LOCATION: (44)..(83)
<223> OTHER INFORMATION: Cytosine, uracil or an analogue of cytosine or
      uracil
<220> FEATURE:
<221> NAME/KEY: misc_feature
<222> LOCATION: (44)..(83)
<223> OTHER INFORMATION: This region may encompass 1 to 40 nucleotides
<220> FEATURE:
<223> OTHER INFORMATION: see specification as filed for detailed
      description of substitutions and preferred embodiments

<400> SEQUENCE: 52
nnnnnnnnnn nnnnnnnnnn nnnnnnnnnn nnnnnnnnnn nnnnnnnnnn nnnnnnnnnn    60
nnnnnnnnnn nnnnnnnnnn nnn                                            83

<210> SEQ ID NO 53
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53 gcgccccgg gcgcttcggc ttacgggtcg ttgggcggcc ccgcgccgcc accggctccg      60
ccgccacccc cgccgccgcc gcct                                           84

<210> SEQ ID NO 54
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(84)

<400> SEQUENCE: 54 gcc ccc ccc ggc gcc agc gcg tac ggg tcc ctg ggc ggc ccg gcc ccg       48
Ala Pro Pro Gly Ala Ser Ala Tyr Gly Ser Leu Gly Gly Pro Ala Pro
1               5                   10                  15 ccc ccc gcc ccg ccc ccc ccg ccg ccc ccc ccg ccg                       84
Pro Pro Ala Pro Pro Pro Pro Pro Pro Pro Pro Pro
            20                  25

<210> SEQ ID NO 55
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ala Pro Pro Gly Ala Ser Ala Tyr Gly Ser Leu Gly Gly Pro Ala Pro
1               5                   10                  15

Pro Pro Ala Pro Pro Pro Pro Pro Pro Pro Pro Pro
            20                  25

<210> SEQ ID NO 56
<211> LENGTH: 84
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(84)

<400> SEQUENCE: 56 gct cct cca gga gct agc gct tac gga tct ctg gga gga cct gct cct         48
Ala Pro Pro Gly Ala Ser Ala Tyr Gly Ser Leu Gly Gly Pro Ala Pro
1               5                   10                  15 cca ccc gct ccg cca cct cct cca cca cct cca cct                         84
Pro Pro Ala Pro Pro Pro Pro Pro Pro Pro
            20                  25

<210> SEQ ID NO 57
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Ala Pro Pro Gly Ala Ser Ala Tyr Gly Ser Leu Gly Gly Pro Ala Pro
1               5                   10                  15

Pro Pro Ala Pro Pro Pro Pro Pro Pro Pro Pro
            20                  25
```

COMPOSITION FOR TREATING LUNG CANCER, PARTICULARLY OF NON-SMALL LUNG CANCERS (NSCLC)

This application is a Continuation of U.S. Ser. No. 12/682,213, filed Jul. 9, 2010 now abandoned, which is a National Stage of PCT/EP2008/008503, filed Oct. 8, 2008 which claims foreign priority to PCT Application No, PCT/EP2007/008770, filed Oct. 9, 2007, the disclosures of which are incorporated herein by reference in their entirety.

The instant application contains a Sequence Listing which has been submitted in ASCII format via EFS-Web and is hereby incorporated by reference in its entirety. Said ASCII copy, created on Apr. 1, 2013, is named $067802_{13}CU14_{13}$US2_Sequence_isting.txt and is 77,865 bytes in size.

The present invention relates to an active (immunostimulatory) composition comprising at least one RNA, preferably a mRNA, encoding at least two (preferably different) antigens capable of eliciting an (adaptive) immune response in a mammal. The invention furthermore relates to a vaccine comprising said active (immunostimulatory) composition, and to the use of said active (immunostimulatory) composition (for the preparation of a vaccine) and/or of the vaccine for eliciting an (adaptive) immune response for the treatment of lung cancer, particularly of non-small cell lung cancers (NSCLC), preferably selected from the three main sub-types squamous cell lung carcinoma, adenocarcinoma and large cell lung carcinoma, or of disorders related thereto. Finally, the invention relates to kits, particularly to kits of parts, containing the active (immunostimulatory) composition and/or the vaccine.

Of all malignant tumors 25% are bronchial carcinoma (carcinoma of the lung). Worldwide, it is the most common cause of cancer-related death in men and the second most common in women. In Germany it is the third most abundant sort of carcinoma following carcinoma of the prostata and the colorectal carcinoma. It is responsible for 1.3 million deaths worldwide annually. In Central Europe the incidence is approximately 60 per 100,000 inhabitants and the number of newly people diagnosed with lung cancer is steadily on the rise (in Germany currently being at approximately 50,000 per year). When diagnosed with lung cancer the average overall fife-year survival rate is a mere 5 percent. Nevertheless, the life expectancy of each single patient is wholly dependent on the disease stage (TMN classification) and the subtype of carcinoma (lung cancer) encountered (see below).

The main sub-types of lung cancer categorized by the size and appearance of the malignant cells identified under microscope are small cell lung cancer (20%) and non-small cell lung cancer (NSCLC) (80%). This classification, although based on simple histological criteria, has very important implications for clinical management and prognosis of the disease, with small cell lung cancer usually being treated by chemotherapy, while non-small cell lung cancer is mostly subject to surgery as a first-line treatment.

The non-small cell lung cancers (NSCLC) are grouped together because their prognosis and management are roughly identical. There are three main sub-types: squamous cell lung carcinoma, adenocarcinoma and large cell lung carcinoma. Surgery is the mainstay of treatment; however, only a quarter of the patients undergo successful resection, with a recurrence rate of 50%. Therapeutic approaches in advanced disease involve—following surgery—both adjuvant chemotherapy and/or adjuvant radiotherapy, whereas chemotherapy as monotherapy (first-line therapy) seems to be an approach associated with relatively poor results. In a comparison of four commonly used combination chemotherapy regimens, none was superior. Response rates varied from 15% to 22%, with 1-year survival rates of 31% to 36% (see e.g. O'Mahony, D., S. Kummar, et al. (2005). "Non-small-cell lung cancer vaccine therapy: a concise review." J Clin Oncol 23(35): 9022-8). Thus, even though preoperative chemotherapy seems to have not resulted in a prolongation of life expectancy, adjuvant chemotherapy—also if combined with radiotherapy—did show a significant increase in life expectancy.

One of the chemotherapeutic approaches used today are combinations of platin-based substances with e.g. Gemcitabin even as first-line-therapy, whereas e.g. Pemetrexed is used as second-line therapy.

Another option used for the treatment of NSCLC is the so-called "Targeted Therapy" trying to enhance success of classical cytotoxic chemotherapy by influencing tumor specific target structures on a molecular level. Substances used include Bevacizumab (an angiogenesis inhibitor) or Erlotinib, which is aimed at the tyrosine kinases of the epidermal growth factor receptor (EGFR).

Even though doubtless there is some improvement in the current therapeutic approaches treatment of lung cancer, especially of NSCLC, is still an uphill-struggle with—given the high mortality rates—a strong need for further, alternative or improved ways of treatment.

Thus, it is suggested here to use the immune system in an approach for the treatment of the NSCLC. The immune system plays an important role in the treatment and prevention of numerous diseases. According to the present stage of knowledge, various mechanisms are provided by mammalians to protect the organism by identifying and killing e.g. tumor cells. These tumor cells have to be detected and distinguished from the organism's normal cells and tissues.

The immune system of vertebrates such as humans consists of many types of proteins, cells, organs, and tissues, which interact in an elaborate and dynamic network. As part of this more complex immune response, the vertebrate system adapts over time to recognize particular pathogens or tumor cells more efficiently. The adaptation process creates immunological memories and allows even more effective protection during future encounters. This process of adaptive or acquired immunity forms the basis for vaccination strategies.

The adaptive immune system is antigen-specific and requires the recognition of specific "self" or "non-self" antigens during a process called antigen presentation. Antigen specificity allows for the generation of responses that are tailored to specific pathogens or pathogen-infected cells or tumor cells. The ability to mount these tailored responses is maintained in the body by so called "memory cells". Should a pathogen infect the body more than once, these specific memory cells are used to quickly eliminate it. The adaptive immune system thus allows for a stronger immune response as well as for an immunological memory, where each pathogen or tumor cell is "remembered" by one or more signature antigens.

The major components of the adaptive immune system in vertebrates predominantly include lymphocytes on the cellular level and antibodies on the molecular level. Lymphocytes as cellular components of the adaptive immune system include B cells and T cells which are derived from hematopoietic stem cells in the bone marrow. B cells are involved in the humoral response, whereas T cells are involved in cell mediated immune response. Both B cells and T cells carry receptor molecules that recognize specific targets. T cells recognize a "non-self" target, such as a pathogenic target structure, only after antigens (e.g. small fragments of a pathogen) have been processed and presented in combination with a "self" receptor called a major histocompatibility complex (MHC) molecule. In contrast, the B cell antigen-specific receptor is an antibody molecule on the B cell surface, and recognizes pathogens as such when antibodies on its surface bind to a specific foreign antigen. This antigen/antibody complex is taken up by the B cell and processed by proteolysis into peptides. The B cell then displays these antigenic peptides on its surface MHC class II molecules. This combination of MHC and antigen attracts a matching helper T cell, which releases lymphokines and activates the B cell. As the activated B cell then begins to divide, its offspring secretes millions of copies of the antibody that recognizes this antigen. These antibodies circulate in blood plasma and lymph, bind to pathogens or tumor cells expressing the antigen and mark them for destruction by complement activation or for uptake and destruction by phagocytes.

As a cellular component of the adaptive immune system cytotoxic T cells (CD8$^+$) may form a CTL-response. Cytotoxic T cells (CD8$^+$) can recognize peptides from endogenous pathogens and self-antigens bound by MHC type I molecules. CD8$^+$-T cells carry out their killing function by releasing cytotoxic proteins in the cell.

Mechanisms of the immune system form targets for curative treatments. Appropriate methods are typically based on the administration of adjuvants to elicit an innate immune response or on the administration of antigens or immunogens in order to evoke an adaptive immune response. As antigens are typically based on specific components of pathogens (e.g. surface proteins) or fragments thereof, administration of nucleic acids to the patient which is followed by the expression of desired polypeptides, proteins or antigens is envisaged as well.

Hitherto conventional methods for eliciting the immune response, immunization or vaccination are based on the use of DNA molecules in order to incorporate the required genetic information into the cell. Various methods have been developed for introducing DNA into cells, such as calcium phosphate transfection, polyprene transfection, protoplast fusion, electroporation, microinjection and lipofection, lipofection having in particular proven to be a suitable method. DNA viruses may likewise be used as a DNA vehicle. Because of their infectious properties, such viruses achieve a very high transfection rate. The viruses used are genetically modified in such a manner that no functional infectious particles are formed in the transfected cell. Despite these precautions, however, it is not possible to rule out the risk of uncontrolled propagation of the introduced gene and viral genes, for example due to potential recombination events. This also entails the risk of the DNA being inserted into an intact gene of the host cell's genome by e.g. recombination, with the consequence that this gene may be mutated and thus completely or partially inactivated or may give rise to misinformation. In other words, synthesis of a gene product which is vital to the cell may be completely suppressed or alternatively a modified or incorrect gene product is expressed. One particular risk occurs if the DNA is integrated into a gene which is involved in the regulation of cell growth. In this case, the host cell may become degenerate and lead to cancer or tumor formation. Furthermore, if the DNA introduced into the cell is to be expressed, it is necessary for the corresponding DNA vehicle to contain a strong promoter, such as the viral CMV promoter. The integration of such promoters into the genome of the treated cell may result in unwanted alterations of the regulation of gene expression in the cell. Another risk of using DNA as an agent to induce an immune response (e.g. as a vaccine) is the induction of pathogenic anti-DNA antibodies in the patient into whom the foreign DNA has been introduced, so bringing about a (possibly fatal) immune response.

Thus overall, there is room and a need for an efficient system, which may be used to effectively stimulate the immune system to allow treatment of lung cancer, especially of non-small cell lung cancer (NSCLC), while avoiding the problems of uncontrolled propagation of an introduced gene due to DNA based compositions.

It is thus an object of the present invention to provide a composition, which a) allows treatment of lung cancer by stimulating the immune system, while b) avoiding the above mentioned disadvantages.

This object is solved by the subject matter of the present invention, particularly by an active (immunostimulatory) composition comprising at least one RNA, encoding at least two (preferably different) antigens selected from the group comprising the antigens:
hTERT,
WT1,
MAGE-A2,
5T4,
MAGE-A3,
MUC1,
Her-2/neu,
NY-ESO-1,
CEA,
Survivin,
MAGE-C1, and/or
MAGE-C2.

Surprisingly, it has been found that a specific combination of at least two antigens, antigenic proteins or antigenic peptides of the afore mentioned group, as contained in an active (immunostimulatory) composition according to the present invention, is capable to effectively stimulate the (adaptive) immune system to allow treatment of lung cancer, especially of non-small cell lung cancer (NSCLC). Herein, the terms antigens, antigenic proteins or antigenic peptides may be used synonymously. In the context of the present invention, an active (immunostimulatory) composition according to the present invention shall be further understood as a composition, which is able to elicit an immune response, preferably an adaptive immune response as defined herein, due to one of the component(s) contained or encoded by the components of the active (immunostimulatory) composition, preferably by the at least one RNA, preferably (m)RNA, encoding the at least two (preferably different) antigens.

The at least one RNA of the active (immunostimulatory) composition may encode hTERT. In the context of this invention "hTERT" is human telomerase reverse transcriptase and the preferred sequence of the RNA, preferably of the mRNA, encoding "hTERT"—if being used in the active (immunostimulatory) composition according to the invention—is shown in FIG. 7 (SEQ ID NO: 7), and—even more preferably, in FIG. 8 (SEQ ID NO: 8). Minev, Hipp et al. (2000) described that telomerase is a ribonucleoprotein enzyme which has been linked to malignant transformation in human cells (Minev, B., J. Hipp, et al. (2000). "Cytotoxic T cell immunity against telomerase reverse transcriptase in humans." Proc Natl Acad Sci USA 97(9): 4796-801). Telomerase activity is increased in the vast majority of human tumors, making its gene product the first molecule common to all human tumors. The generation of endogenously processed telomerase peptides bound to Class I MHC molecules could therefore target cytotoxic T lymphocytes (CTL) to tumors of different origins. Thus, according to them this could advance vaccine therapy against cancer provided that precursor CTL recognizing telomerase peptides in normal adults and cancer patients can be expanded through immunization. They further demonstrated that the majority of normal individuals and patients with prostate cancer immunized in vitro against two HLA-A2.1 restricted peptides from telomerase reverse transcriptase (hTRT) developed hTRT-specific CTL. Carpenter and Vonderheide (2006) (Carpenter, E. L. and R. H. Vonderheide (2006); "Telomerase-based immunotherapy of cancer." Expert Opin Biol Ther 6(10): 1031-9) reported that the progression from the cloning of human telomerase reverse transcriptase (hTERT) in 1997 to the first clinical trials of hTERT as an antitumor immunotherapy target has been swift. hTERT is overexpressed in the vast majority of human cancers whereas it has limited expression in normal adult tissue. It plays a critical role in oncogenesis and may be expressed by cancer stem cells. However, despite being a self antigen, hTERT is immunogenic both in vitro and in vivo. Several Phase I studies of hTERT immunotherapy have been completed in patients with breast, prostate, lung and other cancers, and clinical and immunological results are encouraging. Immunotherapy induced functional, antitumor T cells in patients in the absence of clinical toxicity. The opportunity for vaccinating individuals as an immunoprevention strategy can also be envisioned for hTERT-based therapies. Nair, S. K. and Heiser et al. (2000) described the induction of anti-murine TERT immunity in mice vaccinated with dendritic cells transduced with murine TERT RNA (see Nair, S. K., A. Heiser, et al. (2000). "Induction of cytotoxic T cell responses and tumor immunity against unrelated tumors using telomerase reverse transcriptase RNA transfected dendritic cells." Nat Med 6(9): 1011-7). According to a preferred embodiment, the at least one RNA of the active (immunostimulatory) composition may thus encode an hTERT antigen selected from the sequence as shown in FIG. 7 (SEQ ID NO: 7), and—more preferably, in FIG. 8 (SEQ ID NO: 8). According to a further preferred embodiment, the at least one RNA of the active (immunostimulatory) composition may alternatively or additionally encode an hTERT antigen selected from a fragment, a variant or an epitope of an hTERT sequence as shown in FIG. 7 (SEQ ID NO: 7), and—more preferably, as shown in FIG. 8 (SEQ ID NO: 8).

The at least one RNA of the active (immunostimulatory) composition may furthermore encode WT1. In the context of this invention "WT1" is Wilms tumor 1 and the preferred sequence of the RNA, preferably of the mRNA, encoding "WT1"—if being used in the active (immunostimulatory) composition according to the invention—is shown in FIG. 9 (SEQ ID NO: 9), more preferably in FIG. 10 (SEQ ID NO: 10), and—even more preferably—in FIG. 11 (SEQ ID NO: 11). Oka, Y. A. and Tsuboi et al., (2004) found that Wilm's tumor protein is overexpressed in lung cancer (see Oka, Y., A. Tsuboi, et al. (2004). "Induction of WT1 (Wilms' tumor gene)-specific cytotoxic T lymphocytes by WT1 peptide vaccine and the resultant cancer regression." Proc Natl Acad Sci USA 101(38): 13885-90). Oka et al. (2004, supra) vaccinated 10 patients with lung cancer with a peptide derived from WT1. They could show that clinical response correlated with anti-tumor CD8+ T cell activity. The Wilms' tumor gene WT1 is overexpressed in leukemias and various types of solid tumors, and the WT1 protein was demonstrated to be an attractive target antigen for immunotherapy against these malignancies. Oka et al. (2004, supra) reported the outcome of a phase I clinical study of WT1 peptide-based immunotherapy for patients with breast or lung cancer, myelodysplastic syndrome, or acute myeloid leukemia. Twelve of the 20 patients for whom the efficacy of WT1 vaccination could be assessed showed clinical responses such as reduction in leukemic blast cells or tumor sizes and/or tumor markers. A clear correlation was observed between an increase in the frequencies of WT1-specific cytotoxic T lymphocytes after WT1 vaccination and clinical responses. It was therefore demonstrated that WT1 vaccination could induce WT1-specific cytotoxic T lymphocytes and resulted in cancer regression without damage to normal tissues. According to a preferred embodiment, the at least one RNA of the active (immunostimulatory) composition may thus encode an WT1 antigen selected from the sequence as shown in FIG. 9 (SEQ ID NO: 9), and—more preferably, as shown in FIG. 10 (SEQ ID NO: 10) and even more preferably as shown in FIG. 11 (SEQ ID NO: 11). According to a further preferred embodiment, the at least one RNA of the active (immunostimulatory) composition may alternatively or additionally encode an WT1 antigen selected from a fragment, a variant or an epitope of an WT1 sequence as shown in FIG. 9 (SEQ ID NO: 9), and—more preferably, as shown in FIG. 10 (SEQ ID NO; 10) and even more preferably as shown in FIG. 11 (SEQ ID NO: 11).

The at least one RNA of the active (immunostimulatory) composition may furthermore encode MAGE-A2. In the context of this invention "MAGE-A2" is the melanoma antigen family A, 28 and the preferred sequence of the RNA, preferably of the mRNA, encoding "MAGE-A2"—if being used in the active (immunostimulatory) composition according to the invention—is shown in FIG. 14 (SEQ ID NO: 14), and—even more preferably—in FIG. 15 (SEQ ID NO: 15). Gillespie and Coleman (1999) (Gillespie, A. M. and R. E. Coleman (1999). "The potential of melanoma antigen expression in cancer therapy." Cancer Treat Rev 25(4): 219-27) reported expression in bladder cancer, breast cancer, colorectal cancer, gastric cancer, head and neck cancer, lung cancer, maxillary cancer, melanoma, oesophagus cancer, osteosarcoma and ovary cancer. According to a preferred embodiment, the at least one RNA of the active (immunostimulatory) composition may thus encode an MAGE-A2 antigen selected from the sequence as shown in FIG. 14 (SEQ ID NO: 14), and—more preferably, as shown in FIG. 15 (SEQ ID NO: 15). According to a further preferred embodiment, the at least one RNA of the active (immunostimulatory) composition may alternatively or additionally encode an MAGE-A2 antigen selected from a fragment, a variant or an epitope of an MAGE-A2 sequence as shown in FIG. 14 (SEQ ID NO: 14), and—more preferably, as shown in FIG. 15 (SEQ ID NO: 15).

The at least one RNA of the active (immunostimulatory) composition may furthermore encode 5T4. In the context of this invention "5T4" is trophoblast glycoprotein and the preferred sequence of the RNA, preferably of the mRNA, encoding "5T4"—if being used in the active (immunostimulatory) composition according to the invention—is shown in FIG. 3 (SEQ ID NO: 3), and—even more preferably—in FIG. 4 (SEQ ID NO: 4). Harrop, Connolly et al. (2006) reported that the human oncofetal antigen 5T4 is a 72-kDa leucine-rich membrane glycoprotein which is expressed at high levels on the placenta and also on a wide range of human carcinomas including colorectal, gastric, renal, and ovarian cancers but rarely on normal tissues (see Harrop, R., N. Connolly, et al. (2006). "Vaccination of colorectal cancer patients with modified Vaccinia Ankara delivering the tumor antigen 5T4 (TroVax) induces immune responses which correlate with disease control: a phase VII trial." Clin Cancer Res 12(11 Pt 1): 3416-24). Overexpression of 5T4 is associated with poor prognosis in patients with colorectal, gastric, and ovarian carcinoma. Despite such compounding factors, 5T4-specific cellular and/or humoral immune responses were induced in the majority of patients (16 of 17; 94%) following TroVax immunization, which was considered encouraging compared with many other cancer immunotherapy trials. In summary, they showed safety and immunogenicity of TroVax delivered via i.m. and i.d. routes of administration. Zhao and Wang (2007) (Zhao, Y. and Y. Wang (2007). "5T4 oncotrophoblast glycoprotein: janus molecule in life and a novel potential target against tumors." Cell Mol Immunol 4(2): 99-104) reported that 5T4 oncotrophoblast glycoprotein is a transmembrane protein expressed on the embryonic tissue and various malignant tumor cell surfaces. It plays a vital role in the multiple biological and pathological processes including massive cellular migration during the embryogenesis, cell invasion associated with implantation, and neoplastic metastasis in the progression of tumorigenesis. According to Kopreski, Benko et al. (2001) 5T4 is a trophoblast glycoprotein frequently overexpressed in epithelial malignancies that provides a potential target for cancer therapeutics (see Kopreski, M. S., F. A. Benko, et al. (2001). "Circulating RNA as a tumor marker: detection of 5T4 mRNA in breast and lung cancer patient serum." Ann N Y Acad Sci 945: 172-8). Serum was collected from 19 patients with advanced breast cancer (5 patients) or non-small-cell lung cancer (14 patients), and from 25 normal control volunteers having amplifiable RNA. RNA extracted from the serum was RT-PCR amplified using heminested, two-stage reactions, with products detected by gel electrophoresis. 5T4 mRNA was reproducibly detected in 8/19 (42%) cancer patient sera, including 2/5 breast cancer patient sera and 6/14 lung cancer patient sera, but in only 3/25 (12%) normal control sera (p=0.035). According to a preferred embodiment, the at least one RNA of the active (immunostimulatory) composition may thus encode an 5T4 antigen selected from the sequence as shown in FIG. 3 (SEQ ID NO: 3), and—more preferably, as shown in FIG. 4 (SEQ ID NO: 4). According to a further preferred embodiment, the at least one RNA of the active (immunostimulatory) composition may alternatively or additionally encode an 5T4 antigen selected from a fragment, a variant or an epitope of an 5T4 sequence as shown in FIG. 3 (SEQ ID NO: 3), and—more preferably, as shown in FIG. 4 (SEQ ID NO: 4).

The at least one RNA of the active (immunostimulatory) composition may furthermore encode MAGE-A3. In the context of this invention "MAGE-A3" is the melanoma antigen family A, 3 and the preferred sequence of the RNA, preferably of the mRNA, encoding "MAGE-A3"—if being used in the active (immunostimulatory) composition according to the invention—is shown in FIG. 16 (SEQ ID NO: 16), and—even more preferably—in FIG. 17 (SEQ ID NO: 17). Gillespie and Coleman (1999) (Gillespie, A. M. and R. E. Coleman (1999). "The potential of melanoma antigen expression in cancer therapy." Cancer Treat Rev 25(4): 219-27) reported expression in bladder cancer, breast cancer, colorectal cancer, gastric cancer, glioma, head and neck cancer, lung, maxillary cancer, melanoma, neuroblastoma, oesophagus cancer and ovary cancer. Sienel, Varwark et al. (2004) described a study performed to determine the rate of MAGE-A3 expression in early-stage non-small cell lung cancer (NSCLC) (see Sienel, W., C. Varwerk, et al (2004). "Melanoma associated antigen (MAGE)-A3 expression in Stages I and II non-small cell lung cancer: results of a multi-center study." Eur J Cardiothorac Surg 25(1): 131-4). Primary tumor samples from 204 patients with operable clinical stages I or II NSCLC were collected and the pathological stage determined. MAGE-A3 expression was analyzed from tissue samples by detection of MAGE-A3 transcripts using reverse-transcriptase polymerase chain reaction. MAGE-A3 expression was observed in 80 out of the 204 (39.2%) examined stages I-II primary tumors. Atanackovic, Altorki et al. (2004) described that MAGE-A3a tumor-associated antigen originally identified in melanoma, was also found in non-small cell lung tumors (see Atanackovic, D., N. K. Altorki, et al. (2004). "Vaccine-induced CD4+ T cell responses to MAGE-3 protein in lung cancer patients." J Immunol 172(5): 3289-96). In a clinical trial nine NSCLC patients were vaccinated with the protein; 3 developed antibody responses. Seven of 8 patients who received MAGE-A3 combined with adjuvant ASO2B generated antibodies against MAGE-A3. Several of these patients also developed T cell responses to the protein. According to a preferred embodiment, the at least one RNA of the active (immunostimulatory) composition may thus encode an MAGE-A3 antigen selected from the sequence as shown in FIG. 16 (SEQ ID NO: 16), and—more preferably, as shown in FIG. 17 (SEQ ID NO: 17). According to a further preferred embodiment, the at least one RNA of the active (immunostimulatory) composition may alternatively or additionally encode an MAGE-A3 antigen selected from a fragment, a variant or an epitope of an MAGE-A3 sequence as shown in FIG. 16 (SEQ ID NO: 16), and—more preferably, as shown in FIG. 17 (SEQ ID NO: 17).

The at least one RNA of the active (immunostimulatory) composition may furthermore encode MUC1. In the context of this invention "MUC1" is mucin 1 and the preferred sequence of the RNA, preferably of the mRNA, encoding "MUC1"—if being used in the active (immunostimulatory) composition according to the invention—is shown in FIG. 1 (SEQ ID NO: 1), and—even more preferably—in FIG. 2 (SEQ ID NO: 2). Cancer-associated mucins are a potential target for immunotherapy. These molecules are thought to promote metastases by facilitating adhesion of malignant cells to the endothelial cell surface. According to Denda-Nagai and Irimura (2000) (Denda-Nagai, K. and T. Irimura (2000). "MUC1 in carcinoma-host interactions." Glycoconj J 17(7-9): 649-58) MUC-1 is overexpressed in 90% of all adenocarcinomas, including breast, lung, pancreas, prostate, stomach, colon and ovary. Kontani, Taguchi et al. (2001) found that MUC-1 has been found to be expressed in 60% of lung cancers (see Kontani, K., O. Taguchi, et al (2001). "Modulation of MUC1 mucin as an escape mechanism of breast cancer cells from autologous cytotoxic T-lymphocytes." Br J Cancer 84(9): 1258-64), whereas Kontani, Taguchi et al. (2003) found in a study analyzing the use of pulsed DCs with MUC1 antigens to elicit cellular immunity in MUC1 positive cancers, that clinically seven of nine MUC-1 positive patients responded to the treatment with either a reduction in tumor marker levels or disappearance of malignant pleural effusion (see Kontani, K., O. Taguchi, et al. (2003). "Dendritic cell vaccine immunotherapy of cancer targeting MUC1 mucin." Int J Mol Med 12(4): 493-502). Three of these responding patients had NSCLC. Palmer, Parker et al. (2001) reported that in a phase I clinical trial using MUC1 peptide in stage III/IV NSCLC, safety and tolerability of this agent was established (see Palmer, M., J. Parker, et al (2001). "Phase I study of the BLP25 (MUC1 peptide) liposomal vaccine for active specific immunotherapy in stage IIIB/IV non-small-cell lung cancer." Clin Lung Cancer 3(1): 49-57; discussion 58). Five of 12 patients (42%) had immunologic responses, and 4 of 12 patients (33%) achieved stable disease. Wierecky, Mueller et al (2006) further identified two HLA-A2 binding novel 9-mer peptides of the TAA MUC1, which is overexpressed on various hematological and epithelial malignancies (see Wierecky, J., M. Mueller, et al. (2006). "Dendritic cell-based cancer immunotherapy targeting MUC-1." Cancer Immunol Immunother 55(1): 63-7). Cytotoxic T cells generated after pulsing DC with these peptides were able to induce lysis of tumor cells expressing MUC1 in an antigen-specific and HLA-restricted fashion. Within two clinical studies, it was demonstrated that vaccination of patients with advanced cancer using DCs pulsed with MUC1 derived peptides was well tolerated without serious side effects and was able to induce immunological responses. Of 20 patients with metastatic renal cell carcinoma, 6 patients showed regression of metastases with 3 objective responses (1 CR, 2 PR). According to a preferred embodiment, the at least one RNA of the active (immunostimulatory) composition may thus encode an MUC antigen selected from the sequence as shown in FIG. 1 (SEQ ID NO: 1), and—more preferably, as shown in FIG. 2 (SEQ ID NO: 2). According to a further preferred embodiment, the at least one RNA of the active (immunostimulatory) composition may alternatively or additionally encode an MUC1 antigen selected from a fragment, a variant or an epitope of an MUC1 sequence as shown in FIG. 1 (SEQ ID NO: 1), and—more preferably, as shown in FIG. 2 (SEQ ID NO: 2).

The at least one RNA of the active (immunostimulatory) composition may furthermore encode Her-2/neu. In the context of this invention "Her-2/neu" is v-erb-b2 erythroblastic leukemia viral oncogene homolog 2 and the preferred sequence of the RNA, preferably of the mRNA, encoding "Her-2/neu"—if being used in the active (immunostimulatory) composition according to the invention—is shown in FIG. 5 (SEQ ID NO: 5), and—even more preferably—in FIG. 6 (SEQ ID NO: 6). According to Baxevanis, Sotiropolou et al., (2004) HER-2/neu (also known as HER2 or c-erb-82) is a 185-kDa protein receptor with tyrosine kinase activity and extensive homology to the epidermal growth factor (EGF) receptor (see Baxevanis, C. N., P. A. Sotiropoulou, et al. (2004). "Immunobiology of HER-2/neu oncoprotein and its potential application in cancer immunotherapy." Cancer Immunol Immunother 53(3): 166-75). HER-2/neu is expressed in many epithelial tumors and known to be overexpressed in approximately 20-25% of all ovarian and breast cancers, 35-45% of all pancreatic adenocarcinomas, and up to 90% of colorectal carcinomas. HER-2/neu overexpression represents a marker of poor prognosis. Overexpression of Her-2 has been observed in malignant tumors of the breast, ovary, pancreas, colon, lung and other tissues. Her-2 is normally expressed at low levels in variety of human tissues (skin, digestive tract epithelium, breast, ovary, hepatocytes). Bernhard, Salazar (2002) report in their conclusion that early results of clinical trials actively immunizing cancer patients against HER-2/neu demonstrated that immunity could be generated and that immune responses persisted over a period of time (see Bernhard, H., Salazar L., et al. (2002). "Vaccination against the HER-2/neu oncogenic protein." Endocr Relat Cancer 9(1): 33-44). Current vaccine trials were focused solely on the use of epitope- or peptide-based vaccines, largely due to the observation that peptide vaccine strategies could circumvent neu-specific tolerance in rodent models. The next generation of vaccine approaches according to Bernhard et al. (2002, supra) will likely include protein-based vaccines, HER-2/neu antigen preparations loaded onto DC, and nucleic acid based formulations. Studies in rodent models exploring these strategies at a pre-clinical level were promising. Expansion of HER-2/neu-specific T-cell ex vivo following active immunization or in vitro culture with HER-2/neu-expressing DC was thus considered as being a therapeutic option for treating advanced stage HER-2/neu-overexpressing tumors. Baxevanis, Sotiridou et al. (2006) found that in humans, although immunological responses have been detected against the peptides used for vaccination no clinical responses have been described (see Baxevanis, C. N., N. N. Sotiriadou, et al. (2006). "Immunogenic HER-2/neu peptides as tumor vaccines." Cancer Immunol Immunother 55(1): 85-95). According to Disis, Gooley et al. (2002) Her-2/neu is a member of the EGFR family (see Disis, M. L., T. A. Gooley, et al. (2002). "Generation of T-cell immunity to the HER-2/ neu protein after active immunization with HER-2/neu peptide-based vaccines." J Clin Oncol 20(11): 2624-32). It is frequently overexpressed in breast, ovary, prostate, colon and lung cancers. In a phase I clinical trial 38 patients (2 with NSCLC) were vaccinated with a Her-2/neu peptide. 92% of the patients developed T-cell immunity to Her-2/neu. According to a preferred embodiment, the at least one RNA of the active (immunostimulatory) composition may thus encode an Her-2/neu antigen selected from the sequence as shown in FIG. 5 (SEQ ID NO: 5), and—more preferably, as shown in FIG. 6 (SEQ ID NO: 6). According to a further preferred embodiment, the at least one RNA of the active (immunostimulatory) composition may alternatively or additionally encode an Her-2/neu antigen selected from a fragment, a variant or an epitope of an Her-2/neu sequence as shown in FIG. 5 (SEQ ID NO: 5), and—more preferably, as shown in FIG. 6 (SEQ ID NO: 6).

The at least one RNA of the active (immunostimulatory) composition may furthermore encode NY-ESO-1. In the context of this invention "NY-ESO-1" is cancer/testis antigen 18 and the preferred sequence of the RNA, preferably of the mRNA, encoding "NY-ESO-1"—if being used in the active (immunostimulatory) composition according to the invention—is shown in FIG. 20 (SEQ ID NO: 20), and—even more preferably—in FIG. 21 (SEQ ID NO: 21). Chen, Scanlan et al. (1997) reported the mRNA expression of NY-ESO-1 in various human tumors by RT-PCR finding Melanoma 23/67, Ovarian cancer 2/8, Breast cancer 10/33, Thyroid cancer 2/5, Prostate cancer 4/16, Bladder cancer 4/5, Colon cancer 0/16, Burkitt lymphoma 1/2, Glioma 0/15, Basal cell carcinoma 0/2, Gastric cancer 0/12, Leiomyosarcoma 0/2, Lung cancer 2/12, Other sarcomas 0/2, Renal cancer 0/10, Pancreatic cancer 0/2, Lymphoma 0/10, Seminoma 0/1, Hepatoma 2/7, Spinal cord tumor 0/1 (see Chen, Y. T., M. J. Scanlan, et al., (1997). "A testicular antigen aberrantly expressed in human cancers detected by autologous antibody screening." Proc Natl Acad Sci USA 94(5): 1914-8). Jager, Karbach et al. (2006) reported that NY-ESO-1 is a cancer/testis antigen expressed in a range of human malignancies, and that a number of vaccine strategies targeting NY-ESO-1 were being developed (see Jager, E., J. Karbach, et al. (2006). "Recombinant vaccinia/fowlpox NY-ESO-1 vaccines induce both humoral and cellular NY-ESO-1-specific immune responses in cancer patients." Proc Natl Acad Sci USA 103(39): 14453-8). In the presented study, the safety and immunogenicity of recombinant vaccinia-NY-ESO-1 and recombinant fowlpox-NY-ESO-1 were analyzed in a series of 36 patients with a range of different tumor types. Each construct was first tested individually at two different dose levels and then in a prime-boost setting with recombinant vaccinia-NY-ESO-1 followed by recombinant fowlpox-NY-ESO-1. The vaccines were well tolerated either individually or together. NY-ESO-1-specific antibody responses and/or specific CD8 and CD4 T cell responses directed against a broad range of NY-ESO-1 epitopes were induced by a course of at least four vaccinations at monthly intervals in a high proportion of patients. CD8 T cell clones derived from five vaccinated patients were shown to lyse NY-ESO-1-expressing melanoma target cells. In several patients with melanoma, there was a strong impression that the natural course of the disease was favorably influenced by vaccination. Davis, Chen et al. (2004) reported that HLA-A2-restricted NY-ESO-1 peptides injected intradermally were shown to be safe and immunogenic (Davis, I. D., W. Chen, et al. (2004). "Recombinant NY-ESO-1 protein with ISCOMATRIX adjuvant induces broad integrated antibody and CD4(+) and CD8(+) T cell responses in humans."

Proc Natl Acad Sci USA 101(29): 10697-702). Although these trials were designed only to determine safety and immunogenicity, some patients showed tumor regression or stabilization of disease. It was further expressed by Jager, Gnjatic et al. (2000) that a broad NY-ESO-1-specific immune response including antibody and CD4 and CD8 T cell responses was seen after immunization with recombinant NY-ESO-1 protein combined with ISCOMATRIX adjuvant (CSL Ltd., Parkville, Victoria, Australia) in patients with resected NY-ESO-1-expressing melanoma (see lager, E., S. Gnjatic, et al. (2000). "Induction of primary NY-ESO-1 immunity: CD8+ T lymphocyte and antibody responses in peptide-vaccinated patients with NY-ESO-1+ cancers." Proc Natl Acad Sci USA 97(22): 12198-203). This immune response to the vaccine appeared to be associated with long disease-free survival. Furthermore Odunsi, Qian e al (2007) reported that vaccination with an NY-ESO-1 peptide induces integrated humoral and T cell responses in ovarian cancer (see Odunsi, K., F. Qian, et al. (2007). "Vaccination with an NY-ESO-1 peptide of HLA class I/II specificities induces integrated humoral and T cell responses in ovarian cancer." Proc Natl Acad Sci USA 104(31): 12837-42). According to a preferred embodiment, the at least one RNA of the active (immunostimulatory) composition may thus encode an NY-ESO-1 antigen selected from the sequence as shown in FIG. 20 (SEQ ID NO: 20), and—more preferably, as shown in FIG. 21 (SEQ ID NO: 21). According to a further preferred embodiment, the at least one RNA of the active (immunostimulatory) composition may alternatively or additionally encode an NY-ESO-1 antigen selected from a fragment, a variant or an epitope of an NY-ESO-1 sequence as shown in FIG. 20 (SEQ ID NO: 20), and—more preferably, as shown in FIG. 21 (SEQ ID NO: 21).

The at least one RNA of the active (immunostimulatory) composition may furthermore encode CEA. In the context of this invention "CEA" is carcinoembryonic antigen (CECAMS=carcinoembryonic antigen-related cell adhesion molecule 5) and the preferred sequence of the RNA, preferably of the mRNA, encoding "CEA"—if being used in the active (immunostimulatory) composition according to the invention—is shown in FIG. 12 (SEQ ID NO: 12), and—even more preferably—in FIG. 13 (SEQ ID NO: 13). According to Hammarstrom (1999) CEA is a 180 kDa onco-fetal glycoprotein that acts as an adhesion molecule, and is overexpressed in 70% of NSCLC (Hammarstrom, S. (1999). "The carcinoembryonic antigen (CEA) family: structures, suggested functions and expression in normal and malignant tissues." Semin Cancer Biol 9(2): 67-81). Berinstein (2002) reported that CEA has many attractive features as a target for active vaccination approaches against cancer (Berinstein, N. L. (2002). "Carcinoembryonic antigen as a target for therapeutic anticancer vaccines: a review." J Clin Oncol 20(8): 2197-207). It has a favorable expression pattern and is expressed in more than 50% of all human cancers. It may play a role in the tumorigenesis process itself, and thus its expression may be selected and conserved throughout cancer progression. It has been well documented that CEA is processed and presented on various MHC class 1 molecules. Moreover, immunologic tolerance to CEA is not absolute. There are extensive data demonstrating that human T cells can recognize, become activated to, and lyse cancer cells that are expressing CEA. Several different therapeutic vaccination approaches using CEA as a target antigen have been assessed. The safety of these approaches has been established. In addition, humoral and/or cellular responses to CEA have been documented. Although for the most part the patients chosen for these studies presented by Berinstein (2002, supra) had very advanced and refractory metastatic colon cancer, some evidence of clinical activity has been documented, with disease stabilization and even objective responses occurring in some patients. Dendritic cells pulsed with an agonist CEA MHC class I binding peptide (CAP1-6D) and poxvirus-based vectors incorporating CEA, with or without costimulatory molecules, seemed most active in activating CD8 T-cell responses. Unfortunately, dendritic cell approaches may be limited by the logistical difficulty of obtaining patient-specific preparations of dendritic cells. Four phase I studies using the canarypox vector system to target CEA were reported. These trials showed that such approaches were safe, with mild grade 1 and grade 2 toxicities limited primarily to the site of injection. Moreover, the trials showed that specific cellular T-cell responses can be activated to CEA in the majority of patients. These responses may be enhanced by the inclusion of the B7.1 costimulatory molecule in the vector or by the addition of recombinant GM-CSF at the injection site. Although no objective clinical responses were reported, a significant proportion of patients in these phase I studies have experienced disease stabilization. Vaccination strategies to further enhance the frequency of T cells recognizing CEA where considered to further augment the clinical activity of these vaccines. There are data that suggest that at least some vaccines may be more effective in minimal disease states. Ueda, Itoh et al (2004) described one study, in which 18 patients with metastatic gastrointestinal or lung cancer were treated with autologous dendritic cells pulsed with CEA-derived peptide (see Ueda, Y., T. Itoh, et al. (2004). "Dendritic cell-based immunotherapy of cancer with carcinoembryonic antigen-derived, HLA-A24-restricted CTL epitope: Clinical outcomes of 18 patients with metastatic gastrointestinal or lung adenocarcinomas." Int J Oncol 24(4): 909-17). Immune reactions measured by skin testing and in vitro T cell assays were observed in most of the patients. Although no objective clinical responses were reported, some patients had stable disease while receiving this immunotherapy. According to a preferred embodiment, the at least one RNA of the active (immunostimulatory) composition may thus encode an CEA antigen selected from the sequence as shown in FIG. 12 (SEQ ID NO: 12), and—more preferably, as shown in FIG. 13 (SEQ ID NO: 13). According to a further preferred embodiment, the at least one RNA of the active (immunostimulatory) composition may alternatively or additionally encode an CEA antigen selected from a fragment a variant or an epitope of an CEA sequence as shown in FIG. 12 (SEQ ID NO: 12), and—more preferably, as shown in FIG. 13 (SEQ ID NO: 13).

The at least one RNA of the active (immunostimulatory) composition may furthermore encode Survivin. In the context of this invention "Survivin" is baculoviral IAP repeat-containing 5 (survivin) and the preferred sequence of the RNA, preferably of the mRNA, encoding "survivin"—if being used in the active (immunostimulatory) composition according to the invention—is shown in FIG. 18 (SEQ ID NO: 18), and—even more preferably—in FIG. 19 (SEQ ID NO: 19). Grube, Moritz et al (2007) described Survivin (see Grube, M., S. Moritz, et al. (2007). "CD8+ T cells reactive to survivin antigen in patients with multiple myeloma." Clin Cancer Res 13(3): 1053-60). Survivin is a member of the inhibitors of apoptosis family and is overexpressed in different types of malignancies. Cytotoxic T cells recognizing survivin epitopes can be elicited in vitro and by vaccination in patients with leukemia, breast cancer, and melanoma. It was investigated whether survivin-specific CD8+ T cells occur in patients with multiple myeloma and T cells recognizing HLA-A2.1-binding survivin peptide were detected in 9 of 23 patients and in 1 of 21 healthy volunteers. Survivin-reactive T cells were identified as terminally differentiated effector T cells (CD8+, CD45RA+, and CCR7−). Positive survivin expression of myeloma cells in bone marrow specimens was shown in 7 of 11 patients. Survivin is highly expressed in most human cancer cells of epithelial and hematopoietic origin, and overexpression is associated with cancer progression, poor prognosis, resistance, and short patient survival. Duffy, O'Donovan (2007) described that Survivin is a 16.5 kDa protein overexpressed in almost all malignancies but rarely detected in normal differentiated adult tissues (see Duffy, M. J., N. O'Donovan, et al (2007). "Survivin: a promising tumor biomarker." Cancer Lett 249(1): 49-60). Functionally, survivin has been shown to inhibit apoptosis, promote cell proliferation and enhance angiogenesis. Consistent with its role in these processes, survivin was described as playing a key role in cancer progression. Because of the large difference in expression between normal and malignant tissue and its causal role in cancer progression, survivin is currently undergoing intensive investigation as a potential tumor marker. Emerging data suggests that measurement of survivin can aid the early diagnosis of bladder cancer, determine prognosis in multiple cancer types and predict response to diverse anticancer therapies. Zeis, Siegel et al. (2003) demonstrated that human survivin-specific CTLs generated from PBMC by stimulation with autologous dendritic cells transfected with survivin-RNA were cytotoxic for a range of hemopoietic malignant cell lines and primary tumor cells isolated from patients with acute myeloid leukemia (see Zeis, M., S. Siegel, et al. (2003). "Generation of cytotoxic responses in mice and human individuals against hematological malignancies using survivin-RNA-transfected dendritic cells." J Immunol 170 (11): 5391-7). It was also shown that vaccination of mice with survivin-RNA-transfected dendritic cells lead to long term resistance to challenge by a survivin-expressing lymphoma, demonstrating the potential of survivin as a tumor rejection Ag. Evidence for the use of survivin as a target structure for immunotherapeutic strategies against hematological neoplasms was provided. According to a preferred embodiment, the at least one RNA of the active (immunostimulatory) composition may thus encode an Survivin antigen selected from the sequence as shown in FIG. 18 (SEQ ID NO: 18), and—more preferably, as shown in FIG. 19 (SEQ ID NO: 19). According to a further preferred embodiment, the at least one RNA of the active (immunostimulatory) composition may alternatively or additionally encode an Survivin antigen selected from a fragment, a variant or an epitope of an Survivin sequence as shown in FIG. 18 (SEQ ID NO: 18), and—more preferably as shown in FIG. 19 (SEQ ID NO: 19).

The at least one RNA of the active (immunostimulatory) composition may furthermore encode MAGE-C1. In the context of this invention "MAGE-C1" is the melanoma antigen family C, 1 and the preferred sequence of the RNA, preferably of the mRNA, encoding "MAGE-C1"—if being used in the active (immunostimulatory) composition according to the invention—is shown in FIG. 22 (SEQ ID NO: 22), more preferably in FIG. 23 (SEQ ID NO: 23), and—even more preferably—in FIG. 24 (SEQ ID NO: 24). Lucas, De Smet et al. (1998) recently identified MAGE-C1 by performing RDA (see Lucas, S., C. De Smet, et al. (1998). "Identification of a new MAGE gene with tumor-specific expression by representational difference analysis." Cancer Res 58(4): 743-52). MAGE-C1 was not expressed in a panel of normal tissues tested with the exception of testis. Among tumoral samples, MAGE-C1 was frequently expressed in seminomas, melanomas, and bladder carcinomas. It was also expressed in a significant fraction of head and neck carcinomas, breast carcinomas, non-small lung carcinomas, prostate adenocarcinomas and sarcomas. Jungbluth, Chen et al. (2002) described expression in breast cancer, ovary cancer, liver cancer, testis cancer, bladder cancer, melanoma and non-small cell lung cancer (39%) (see Jungbluth, A. A., Y. T. Chen, et al. (2002). "CT7 (MAGE-C1) antigen expression in normal and neoplastic tissues." Int J Cancer 99(6): 839-45). Gure, Chua et al. (2005) analyzed tumors from 523 non-small-cell lung cancer (NSCLC) patients for the expression of cancer-testis antigens (see Gure, A. O., R. Chua, et al. (2005). "Cancer-testis genes are coordinately expressed and are markers of poor outcome in non-small cell lung cancer." Clin Cancer Res 11(22): 8055-62). MAGE-C1 was present in 18.8%. Scanlan, Altorki et al. (2000) furthermore reported expression of CT antigens in 33 non-small cell lung cancers: MAGE-C1: 30% (see Scanlan, M. J., N. K. Altorki, et al. (2000). "Expression of cancer-testis antigens in lung cancer: definition of bromodomain testis-specific gene (BRDT) as a new CT gene, CT9." Cancer Lett 150(2): 155-64). According to a preferred embodiment, the at least one RNA of the active (immunostimulatory) composition may thus encode an MAGE-C1 antigen selected from the sequence as shown in FIG. 22 (SEQ ID NO: 22), and—mote preferably, as shown in FIG. 23 (SEQ ID NO: 23) and even more preferably as shown in FIG. 24 (SEQ ID NO: 24). According to a further preferred embodiment, the at least one RNA of the active (immunostimulatory) composition may alternatively or additionally encode an MAGE-C1 antigen selected from a fragment, a variant or an epitope of an MAGE-C1 sequence as shown in FIG. 22 (SEQ ID NO: 22), and—more preferably, as shown in FIG. 23 (SEQ ID NO: 23) and even more preferably as shown in FIG. 24 (SEQ ID NO: 24).

The at least one RNA of the active (immunostimulatory) composition may furthermore encode MAGE-C2. In the context of this invention "MAGE-C2" is the melanoma antigen family C2 and the preferred sequence of the RNA, preferably of the mRNA, encoding "MAGE-C2"—if being used in the active (immunostimulatory) composition according to the invention—is shown in FIG. 25 (SEQ ID NO: 25), and—even more preferably—in FIG. 26 (SEQ ID NO: 26). Lucas, De Plaen et al (2000) recently identified MAGE-C2 by performing RDA on a melanoma cell line (see Lucas, S., E. De Plaen, et al. (2000). "MAGE-B5, MAGE-86, MAGE-C2, and MAGE-C3: four new members of the MAGE family with tumor-specific expression." Int J Cancer 87(1): 55-60). MAGE-C2 was not expressed in a panel of normal tissues tested with the exception of testis. Among tumoral samples, MAGE-C2 was frequently expressed in seminomas, melanomas, and bladder carcinomas. It was also expressed in a significant fraction of head and neck carcinomas, breast carcinomas, non-small lung carcinomas and sarcomas. Scanlan, Altorki et al (2000) reported expression of CT antigens in 33 non-small cell lung cancers: MAGE-C2: 30% (see Scanlan, M. J., N. K. Altorki, et al. (2000). "Expression of cancer-testis antigens in lung cancer: definition of bromodomain testis-specific gene (BRDT) as a new CT gene, CT9." Cancer Lett 150(2): 155-64). According to a preferred embodiment, the at least one RNA of the active (immunostimulatory) composition may thus encode an MAGE-C2 antigen selected from the sequence as shown in FIG. 25 (SEQ ID NO: 25), and—more preferably, as shown in FIG. 26 (SEQ ID NO: 26). According to a further preferred embodiment, the at least one RNA of the active (immunostimulatory) composition may alternatively or additionally encode an MAGE-C2 antigen selected from a fragment, a variant or an epitope of an MAGE-C2 sequence as shown in FIG. 25 (SEQ ID NO: 25), and—more preferably, as shown in FIG. 26 (SEQ ID NO: 26).

Antigens, antigenic proteins or antigenic peptides as defined above which may be encoded by the at least one RNA of the active (immunostimulatory) composition according to the present invention, may comprise fragments or variants of those sequences. Such fragments or variants may typically comprise a sequence having a sequence homology with one of the above mentioned antigens, antigenic proteins or antigenic peptides or sequences or their encoding nucleic acid sequences of at least 5%, 10%, 20%, 30%, 40%, 50%, 60%, preferably at least 70%, more preferably at least 80%, equally more preferably at least 85%, even more preferably at least 90% and most preferably at least 95% or even 97%, to the entire wild-type sequence, either on nucleic acid level or on amino acid level.

"Fragments" of antigens, antigenic proteins or antigenic peptides in the context of the present invention may comprise a sequence of an antigen, antigenic protein or antigenic peptide as defined above, which is, with regard to its amino acid sequence (or its encoded nucleic acid sequence), N-terminally, C-terminally and/or intrasequentially truncated compared to the amino acid sequence of the original (native) protein (or its encoded nucleic acid sequence). Such truncation may thus occur either on the amino acid level or correspondingly on the nucleic acid level. A sequence homology with respect to such a fragment as defined above may therefore preferably refer to the entire antigen, antigenic protein or antigenic peptide as defined above or to the entire (coding) nucleic acid sequence of such an antigen, antigenic protein or antigenic peptide.

Fragments of antigens, antigenic proteins or antigenic peptides in the context of the present invention may furthermore comprise a sequence of an antigen, antigenic protein or antigenic peptide as defined above, which has a length of about 6 to about 20 or even more amino acids, e.g. fragments as processed and presented by MHC class I molecules, preferably having a length of about 8 to about 10 amino acids, e.g. 8, 9, or 10, (or even 6, 7, 11, or 12 amino acids), or fragments as processed and presented by MHC class II molecules, preferably having a length of about 13 or more amino acids, e.g. 13, 14, 15, 16, 17, 18, 19, 20 or even more amino acids, wherein these fragments may be selected from any part of the amino acid sequence. These fragments are typically recognized by T-cells in form of a complex consisting of the peptide fragment and an MHC molecule, i.e. the fragments are typically not recognized in their native form.

Fragments of antigens, antigenic proteins or antigenic peptides as defined herein may also comprise epitopes of those antigens, antigenic proteins or antigenic peptides. Epitopes (also called "antigen determinants") in the context of the present invention are typically fragments located on the outer surface of (native) antigens, antigenic proteins or antigenic peptides as defined herein, preferably having 5 to 15 amino acids, more preferably having 5 to 12 amino acids, even more preferably having 6 to 9 amino acids, which may be recognized by antibodies or B-cell receptors, i.e. in their native form. Such epitopes of antigens, antigenic proteins or antigenic peptides may furthermore be selected from any of the herein mentioned variants of such antigens, antigenic proteins or antigenic peptides. In this context antigenic determinants can be conformational or discontinous epitopes which are composed of segments of the antigens, antigenic proteins or antigenic peptides as defined herein that are discontinuous in the amino acid sequence of the antigens, antigenic proteins or antigenic peptides as defined herein but are brought together in the three-dimensional structure or continuous or linear epitopes which are composed of a single polypeptide chain.

"Variants" of antigens, antigenic proteins or antigenic peptides as defined above may be encoded by the at least one RNA of the active (immunostimulatory) composition according to the present invention, wherein nucleic acids of the at least one (m)RNA, encoding the antigen, antigenic protein or antigenic peptide as defined above, are exchanged. Thereby, an antigen, antigenic protein or antigenic peptide may be generated, having an amino acid sequence which differs from the original sequence in one or more mutation(s), such as one or more substituted, inserted and/or deleted amino acid(s). Preferably, these fragments and/or variants have the same biological function or specific activity compared to the full-length native antigen or antigenic protein, e.g. its specific antigenic property.

The at least one RNA of the active (immunostimulatory) composition according to the present invention may also encode an antigen or an antigenic protein as defined above, wherein the encoded amino acid sequence comprises conservative amino acid substitution(s) compared to its physiological sequence. Those encoded amino acid sequences as well as their encoding nucleotide sequences in particular fall under the term variants as defined above. Substitutions in which amino acids which originate from the same class are exchanged for one another are called conservative substitutions. In particular, these are amino acids having aliphatic side chains, positively or negatively charged side chains, aromatic groups in the side chains or amino acids, the side chains of which can enter into hydrogen bridges, e.g. side chains which have a hydroxyl function. This means that e.g. an amino acid having a polar side chain is replaced by another amino acid having a likewise polar side chain, or, for example, an amino acid characterized by a hydrophobic side chain is substituted by another amino acid having a likewise hydrophobic side chain (e.g. serine (threonine) by threonine (serine) or leucine (isoleucine) by isoleucine (leucine)). Insertions and substitutions are possible, in particular, at those sequence positions which cause no modification to the three-dimensional structure or do not affect the binding region. Modifications to a three-dimensional structure by insertion(s) or deletion(s) can easily be determined e.g. using CD spectra (circular dichroism spectra) (Urry, 1985, Absorption, Circular Dichroism and ORD of Polypeptides, in: Modern Physical Methods in Biochemistry, Neuberger et al. (ed.), Elsevier, Amsterdam).

Furthermore, variants of antigens, antigenic proteins or antigenic peptides as defined above, which may be encoded by the at least one RNA of the active (immunostimulatory) composition according to the present invention, may also comprise those sequences, wherein nucleic acids of the at least one (m)RNA are exchanged according to the degeneration of the genetic code, without leading to an alteration of respective amino acid sequence of the antigen, antigenic protein or antigenic peptide, i.e. the amino acid sequence or at least part thereof may not differ from the original sequence in one or more mutation(s) within the above meaning.

In order to determine the percentage to which two sequences (nucleic acid sequences, e.g. RNA or mRNA sequences as defined herein, or amino acid sequences, preferably their encoded amino acid sequences, e.g. the amino acid sequences of the antigens, antigenic proteins or antigenic peptides as defined above) are identical, the sequences can be aligned in order to be subsequently compared to one another. Therefore, e.g. gaps can be inserted into the sequence of the first sequence and the component at the corresponding position of the second sequence can be compared. If a position in the first sequence is occupied by the same component as is the case at a position in the second sequence, the two sequences are identical at this position. The percentage to which two sequences are identical is a function of the number of identical positions divided by the total number of positions. The percentage to which two sequences are identical can be determined using a mathematical algorithm. A preferred, but not limiting, example of a mathematical algorithm which can be used is the algorithm of Karlin et al. (1993), PNAS USA, 90:5873-5877 or Altschul et al. (1997), Nucleic Acids Res., 25:3389-3402. Such an algorithm is integrated in the BLAST program. Sequences which are identical to the sequences of the present invention to a certain extent can be identified by this program.

The active (immunostimulatory) composition according to the present invention comprises, as defined above, at least one RNA, encoding least two (preferably different) antigens selected from any of the antigens of the above group, since according to the invention a specific combination of at least two (preferably different) antigens of the afore mentioned group is capable to effectively stimulate the (adaptive) immune system to allow treatment of lung cancer, especially of non-small cell lung cancer (NSCLC). However, the present invention may also provide such active (immunostimulatory) compositions, comprising at least one RNA, encoding three, four, five, six, seven, eight, nine, ten, eleven or even twelve (preferably different) antigens selected from any of the antigens of the above group, wherein any combination of these antigens is possible and envisaged.

According to a particularly preferred embodiment, the at least one RNA of the active (immunostimulatory) composition according to the present invention, may encode at least two (preferably different) antigens selected from any of the antigens of a subgroup comprising the following antigens:
  hTERT,
  WT1,
  5T4,
  NY-ESO-1,
  Survivin, and/or
  MAGE-C2.

More preferably, the present invention may also provide an active (immunostimulatory) composition, comprising at least one RNA, encoding at least three, four, five or six (preferably different) antigens selected from any of the antigens of the above group or subgroup, wherein any combination of these antigens is possible.

Accordingly, due to another particularly preferred embodiment, the at least one RNA of the active (immunostimulatory) composition of the present invention, may encode at least two (preferably different) antigens selected from any of the antigens of the above mentioned group(s) or subgroup(s) comprising (at least) any one of the following combinations of antigens:
  hTERT and WT1, or
  hTERT and 5T4, or
  hTERT and NY-ESO-1, or
  hTERT and Survivin, or
  hTERT and MAGE-C2, or
  WT1 and 5T4, or
  WT1 and NY-ESO-1, or
  WT1 and Survivin, or
  WT1 and MAGE-C2, or
  5T4 and NY-ESO-1, or
  5T4 and Survivin, or
  5T4 and MAGE-C2, or
  NY-ESO-1 and Survivin, or
  NY-ESO-1 and MAGE-C2, or
  Survivin and MAGE-C2,
  or
  hTERT, WT1 and 5T4, or
  hTERT, WT1 and NY-ESO-1, or
  hTERT, WT1 and Survivin, or
  hTERT, WT1 and MAGE-C2, or
  hTERT, 5T4, and NY-ESO-1, or
  hTERT, 5T4, and Survivin, or
  hTERT, 5T4, and MAGE-C2, or
  hTERT, NY-ESO-1 and Survivin, or
  hTERT, NY-ESO-1 and MAGE-C2, or
  hTERT, Survivin and MAGE-C2, or
  WT1, 5T4 and NY-ESO-1, or
  WT1, 5T4 and Survivin, or
  WT1, 5T4 and MAGE-C2, or
  WT1, NY-ESO-1 and Survivin, or
  WT1, NY-ESO-1 and MAGE-C2, or
  WT1, Survivin and MAGE-C2, or
  5T4, NY-ESO-1 and Survivin, or
  5T4, NY-ESO-1 and MAGE-C2, or
  5T4, Survivin and MAGE-C2, or
  NY-ESO-1, Survivin, and MAGE-C2,
  or
  hTERT, WT1, 5T4 and NY-ESO-1, or
  hTERT, WT1, 5T4 and Survivin, or
  hTERT, WT1, 5T4 and MAGE-C2, or
  hTERT, 5T4, NY-ESO-1 and Survivin, or
  hTERT, 5T4, NY-ESO-1 and MAGE-C2, or
  hTERT, NY-ESO-1, Survivin and MAGE-C2, or
  WT1, 5T4, NY-ESO-1, and Survivin, or
  WT1, 5T4, NY-ESO-1, and MAGE-C2, or
  WT1, 5T4, Survivin, and MAGE-C2, or
  5T4, NY-ESO-1, Survivin, and MAGE-C2,
  or
  hTERT, WT1, 5T4, NY-ESO-1 and Survivin, or
  hTERT, WT1, 5T4, NY-ESO-1 and MAGE-C2, or
  WT1, 5T4, NY-ESO-1, Survivin and MAGE-C2,
  or
  hTERT, WT1, 5T4, NY-ESO-1, Survivin, and MAGE-C2.

More preferably, the at least one RNA of the active (immunostimulatory) composition of the present invention, may encode at least two (preferably different) antigens exclusively selected from any of the antigens of the above mentioned group(s) or subgroup(s) comprising (at least) any one of the following combinations of antigens:
  hTERT and WT1, or
  hTERT and 5T4, or
  hTERT and NY-ESO-1, or
  hTERT and Survivin, or
  hTERT and MAGE-C2, or
  WT1 and 5T4, or
  WT1 and NY-ESO-1, or
  WT1 and Survivin, or
  WT1 and MAGE-C2, or
  5T4 and NY-ESO-1, or
  5T4 and Survivin, or
  5T4 and MAGE-C2, or
  NY-ESO-1 and Survivin, or
  NY-ESO-1 and MAGE-C2, or
  Survivin and MAGE-C2,
  or
  hTERT, WT1 and 5T4, or
  hTERT, WT1 and NY-ESO-1, or
  hTERT, WT1 and Survivin, or
  hTERT, WT1 and MAGE-C2, or
  hTERT, 5T4, and NY-ESO-1, or
  hTERT, 5T4, and Survivin, or
  hTERT, 5T4, and MAGE-C2, or
  hTERT, NY-ESO-1 and Survivin, or
  hTERT, NY-ESO-1 and MAGE-C2, or
  hTERT, Survivin and MAGE-C2, or
  WT1, 5T4 and NY-ESO-1, or WT1, 5T4 and Survivin, or
WT1, 5T4 and MAGE-C2, or
WT1, NY-ESO-1 and Survivin, or
WT1, NY-ESO-1 and MAGE-C2, or
WT1, Survivin and MAGE-C2, or
5T4, NY-ESO-1 and Survivin, or
5T4, NY-ESO-1 and MAGE-C2, or
5T4, Survivin and MAGE-C2, or
NY-ESO-1, Survivin, and MAGE-C2, or
hTERT, WT1, 5T4 and NY-ESO-1, or
hTERT, WT1, 5T4 and Survivin, or
hTERT, WT1, 5T4 and MAGE-C2, or
hTERT, 5T4, NY-ESO-1 and Survivin, or
hTERT, 5T4, NY-ESO-1 and MAGE-C2, or
hTERT, NY-ESO-1, Survivin and MAGE-C2, or
WT1, 5T4, NY-ESO-1, and Survivin, or
WT1, 5T4, NY-ESO-1, and MAGE-C2, or
WT1, 5T4, Survivin, and MAGE-C2, or
5T4, NY-ESO-1, Survivin, and MAGE-C2, or
hTERT, WT1, 5T4, NY-ESO-1 and Survivin, or
hTERT, WT1, 5T4, NY-ESO-1 and MAGE-C2, or
WT1, 5T4, NY-ESO-1, Survivin and MAGE-C2, or
hTERT, WT1, 5T4, NY-ESO-1, Survivin, and MAGE-C2.

According to a further preferred embodiment, the present invention provides an active (immunostimulatory) composition comprising at least one RNA, encoding at least two (preferably different) antigens,
a) wherein at least one, preferably at least two, three, four, five or even six, of these at least two antigens is (are) selected from:
   5T4
   NY-ESO-1,
   MAGE-A2,
   MAGE-A3,
   MAGE-C1, and/or
   MAGE-C2, and
b) wherein the further antigen(s) is (are) selected from at least one antigen as defined herein, preferably in any of the herein mentioned combinations, groups or subgroups of antigens, e.g. the further antigen(s) is (are) selected from, e.g.:
   hTERT,
   WT1,
   MAGE-A2,
   5T4,
   MAGE-A3,
   MUC1,
   Her-2/neu,
   NY-ESO-1,
   CEA,
   Survivin,
   MAGE-C1, and/or
   MAGE-C2.

According to a further preferred embodiment, the at least one antigen(s) according to a) is (are) selected from:
   NY-ESO-1,
   MAGE-C1, and/or
   MAGE-C2.

According to another preferred embodiment, the at least one antigen(s) according to a) is (are) selected from:
   MAGE-C1, and/or
   MAGE-C2.

According to another preferred embodiment, the at least one antigen(s) according to b) is (are) selected from an antigen (antigens) as defined in one of the following combinations:
   hTERT and WT1; or
   hTERT and MAGE-A2; or
   hTERT and 5T4; or
   hTERT and MAGE-A3; or
   hTERT and MUC1; or
   hTERT and Her-2/neu; or
   hTERT and NY-ESO-1; or
   hTERT and CEA; or
   hTERT and Survivin; or
   hTERT and MAGE-C1; or
   hTERT and MAGE-C2; or
   WT1 and MAGE-A2; or
   WT1 and 5T4; or
   WT1 and MAGE-A3; or
   WT1 and MUC1; or
   WT1 and Her-2/neu; or
   WT1 and NY-ESO-1; or
   WT1 and CEA; or
   WT1 and Survivin; or
   WT1 and MAGE-C1; or
   WT1 and MAGE-C2; or
   MAGE-A2 and 5T4; or
   MAGE-A2 and MAGE-A3; or
   MAGE-A2 and MUC1; or
   MAGE-A2 and Her-2/neu; or
   MAGE-A2 and NY-ESO-1; or
   MAGE-A2 and CEA; or
   MAGE-A2 and Survivin; or
   MAGE-A2 and MAGE-C1; or
   MAGE-A2 and MAGE-C2; or
   5T4 and MAGE-A3; or
   5T4 and MUC1; or
   5T4 and Her-2/neu; or
   5T4 and NY-ESO-1; or
   5T4 and CEA; or
   5T4 and Survivin; or
   5T4 and MAGE-C1; or
   5T4 and MAGE-C2; or
   MAGE-A3 and MUC1; or
   MAGE-A3 and Her-2/neu; or
   MAGE-A3 and NY-ESO-1; or
   MAGE-A3 and CEA; or
   MAGE-A3 and Survivin; or
   MAGE-A3 and MAGE-C1
   MAGE-A3 and MAGE-C2
   MUC1 and Her-2/neu; or
   MUC1 and NY-ESO-1; or
   MUC1 and CEA; or
   MUC1 and Survivin; or
   MUC1 and MAGE-C1; or
   MUC1 and MAGE-C2; or
   HER-2/NEU and NY-ESO-1; or
   HER-2/NEU and CEA; or
   HER-2/NEU and Survivin; or
   HER-2/NEU and MAGE-C1; or
   HER-2/NEU and MAGE-C2; or
   NY-ESO-1 and CEA; or
   NY-ESO-1 and Survivin; or
   NY-ESO-1 and MAGE-C1; or
   NY-ESO-1 and MAGE-C2; or
   CEA and Survivin; or
   CEA and MAGE-C1; or
   CEA and MAGE-C2; or Survivin and MAGE-C1; or
Survivin and MAGE-C2; or
MAGE-C1 and MAGE-C2;
or
hTERT, WT1 and MAGE-A2; or
hTERT, WT1 and 5T4; or
hTERT, WT1 and MAGE-A3; or
hTERT, WT1 and MUC1; or
hTERT, WT1 and Her-2/neu; or
hTERT, WT1 and NY-ESO-1; or
hTERT, WT1 and CEA; or
hTERT, WT1 and Survivin; or
hTERT, WT1 and MAGE-C1; or
hTERT, WT1 and MAGE-C2; or
WT1, MAGE-A2 and 5T4; or
WT1, MAGE-A2 and MAGE-A3; or
WT1, MAGE-A2 and MUC1; or
WT1, MAGE-A2 and Her-2/neu; or
WT1, MAGE-A2 and NY-ESO-1; or
WT, MAGE-A2 and CEA; or
WT1, MAGE-A2 and Survivin; or
WT1, MAGE-A2 and MAGE-C1; or
WT1, MAGE-A2 and MAGE-C2; or
MAGE-A2, 5T4 and MAGE-A3; or
MAGE-A2, 5T4 and MUC1; or
MAGE-A2, 5T4 and Her-2/neu; or
MAGE-A2, 5T4 and NY-ESO-1; or
MAGE-A2, 5T4 and CEA; or
MAGE-A2, 5T4 and Survivin; or
MAGE-A2, 5T4 and MAGE-C1; or
MAGE-A2, 5T4 and MAGE-C2; or
5T4, MAGE-A3 and MUC1; or
5T4, MAGE-A3 and Her-2/neu; or
5T4, MAGE-A3 and NY-ESO-1; or
5T4, MAGE-A3 and CEA; or
5T4, MAGE-A3 and Survivin; or
5T4, MAGE-A3 and MAGE-C1; or
5T4, MAGE-A3 and MAGE-C2; or
MAGE-A3, MUC1 and Her-2/neu; or
MAGE-A3, MUC1 and NY-ESO-1; or
MAGE-A3, MUC1 and CEA; or
MAGE-A3, MUC1 and Survivin; or
MAGE-A3, MUC1 and MAGE-C1; or
MAGE-A3, MUC1 and MAGE-C2; or
MUC1, Her-2/neu and NY-ESO-1; or
MUC1, Her-2/neu and CEA; or
MUC1, Her-2/neu and Survivin; or
MUC1, Her-2/neu and MAGE-C1; or
MUC1, Her-2/neu and MAGE-C2; or
HER-2/NEU, NY-ESO-1 and CEA; or
HER-2/NEU, NY-ESO-1 and Survivin; or
HER-2/NEU, NY-ESO-1 and MAGE-C1; or
HER-2/NEU, NY-ESO-1 and MAGE-C2; or
NY-ESO-1, CEA and Survivin; or
NY-ESO-1, CEA and MAGE-C1; or
NY-ESO-1, CEA and MAGE-C2; or
CEA, Survivin and MAGE-C1; or
CEA, Survivin and MAGE-C2; or
Survivin, MAGE-C1 and MAGE-C2;
or
hTERT, WT1, MAGE-A2 and 5T4; or
hTERT, WT1, MAGE-A2 and MAGE-A3; or
hTERT, WT1, MAGE-A2 and MUC1; or
hTERT, WT1, MAGE-A2 and Her-2/neu; or
hTERT, WT1, MAGE-A2 and NY-ESO-1; or
hTERT, WT1, MAGE-A2 and CEA; or
hTERT, WT1, MAGE-A2 and Survivin; or
hTERT, WT1, MAGE-A2 and MAGE-C1; or
hTERT, WT1, MAGE-A2 and MAGE-C2; or
WT1, MAGE-A2, 5T4 and MAGE-A3; or
WT1, MAGE-A2, 5T4 and MUC1; or
WT1, MAGE-A2, 5T4 and Her-2/neu; or
WT1, MAGE-A2, 5T4 and NY-ESO-1; or
WT1, MAGE-A2, 5T4 and CEA; or
WT1, MAGE-A2, 5T4 and Survivin; or
WT1, MAGE-A2, 5T4 and MAGE-C1; or
WT1, MAGE-A2, 5T4 and MAGE-C2; or
MAGE-A2, 5T4, MAGE-A3 and MUC1; or
MAGE-A2, 5T4, MAGE-A3 and Her-2/neu; or
MAGE-A2, 5T4, MAGE-A3 and NY-ESO-1; or
MAGE-A2, 5T4, MAGE-A3 and CEA; or
MAGE-A2, 5T4, MAGE-A3 and Survivin; or
MAGE-A2, 5T4, MAGE-A3 and MAGE-C1; or
MAGE-A2, 5T4, MAGE-A3 and MAGE-C2; or
5T4, MAGE-A3, MUC1, and Her-2/neu; or
5T4, MAGE-A3, MUC1 and NY-ESO-1; or
5T4, MAGE-A3, MUC1 and CEA; or
5T4, MAGE-A3, MUC1 and Survivin; or
5T4, MAGE-A3, MUC1 and MAGE-C1; or
5T4, MAGE-A3, MUC1 and MAGE-C2; or
MAGE-A3, MUC1, Her-2/neu and NY-ESO-1; or
MAGE-A3, MUC1, Her-2/neu and CEA; or
MAGE-A3, MUC1, Her-2/neu and Survivin; or
MAGE-A3, MUC1, Her-2/neu and MAGE-C1; or
MAGE-A3, MUC1, Her-2/neu and MAGE-C2; or
MUC1, Her-2/neu, NY-ESO-1 and CEA; or
MUC1, Her-2/neu, NY-ESO-1 and Survivin; or
MUC1, Her-2/neu, NY-ESO-1 and MAGE-C1; or
MUC, Her-2/neu, NY-ESO-1 and MAGE-C2; or
HER-2/NEU, NY-ESO-1, CEA and Survivin; or
HER-2/NEU, NY-ESO-1, CEA and MAGE-C1; or
HER-2/NEU, NY-ESO-1, CEA and MAGE-C2; or
NY-ESO-1, CEA, Survivin and MAGE-C1; or
NY-ESO-1, CEA, Survivin and MAGE-C2; or
CEA, Survivin, MAGE-C1 and MAGE-C2;
or
hTERT, WT1, MAGE-A2, 5T4 and MAGE-A3; or
hTERT, WT1, MAGE-A2, 5T4 and MUC; or
hTERT, WT1, MAGE-A2, 5T4 and Her-2/neu; or
hTERT, WT1, MAGE-A2, 5T4 and NY-ESO-1; or
hTERT, WT1, MAGE-A2, 5T4 and CEA; or
hTERT, WT1. MAGE-A2, 5T4 and Survivin; or
hTERT, WT1, MAGE-A2, 5T4 and MAGE-C1; or
hTERT, WT1, MAGE-A2, 5T4 and MAGE-C2; or
WT1, MAGE-A2, 5T4, MAGE-A3 and MUC1; or
WT1, MAGE-A2, 5T4, MAGE-A3 and Her-2/neu; or
WT1, MAGE-A2, 5T4, MAGE-A3 and NY-ESO-1; or
WT1, MAGE-A2, 5T4, MAGE-A3 and CEA; or
WT1, MAGE-A2, 5T4, MAGE-A3 and Survivin; or
WT1, MAGE-A2, 5T4, MAGE-A3 and MAGE-C1; or
WT1, MAGE-A2, 5T4, MAGE-A3 and MAGE-C2; or
MAGE-A2, 5T4, MAGE-A3, MUC1 and Her-2/neu; or
MAGE-A2, 5T4, MAGE-A3, MUC1 and NY-ESO-1; or
MAGE-A2, 5T4, MAGE-A3, MUC1 and CEA; or
MAGE-A2, 5T4, MAGE-A3, MUC1 and Survivin; or
MAGE-A2, 5T4, MAGE-A3, MUC1 and MAGE-C1; or
MAGE-A2, 5T4, MAGE-A3, MUC1 and MAGE-C2; or
5T4, MAGE-A3, MUC1, Her-2/neu and NY-ESO-1; or
5T4, MAGE-A3, MUC1, Her-2/neu and CEA; or
5T4, MAGE-A3, MUC1, Her-2/neu and Survivin; or
5T4, MAGE-A3, MUC1, Her-2/neu and MAGE-C1; or
5T4, MAGE-A3, MUC1, Her-2/neu and MAGE-C2; or
MAGE-A3, MUC1, Her-2/neu, NY-ESO-1 and CEA; or MAGE-A3, MUC1, Her-2/neu, NY-ESO-1 and Survivin; or MAGE-A3, MUC1, Her-2/neu, NY-ESO-1 and MAGE-C1; or MAGE-A3, MUC1, Her-2/neu, NY-ESO-1 and MAGE-C2; or MUC1, Her-2/neu, NY-ESO-1, CEA and Survivin; or MUC1, Her-2/neu, NY-ESO-1, CEA and MAGE-C1; or MUC1, Her-2/neu, NY-ESO-1, CEA and MAGE-C2; or HER-2/NEU, NY-ESO-1, CEA, Survivin and MAGE-C1; or HER-2/NEU, NY-ESO-1, CEA, Survivin and MAGE-C2; or NY-ESO-1, CEA, Survivin, MAGE-C1 and MAGE-C2; or hTERT, WT1, MAGE-A2, 5T4, MAGE-A3 and MUC1; or hTERT, WT1. MAGE-A2, 5T4, MAGE-A3 and Her-2/neu; or hTERT, WT1, MAGE-A2, 5T4, MAGE-A3 and NY-ESO-1; or hTERT, WT1, MAGE-A2, 5T4, MAGE-A3 and CEA; or hTERT, WT1, MAGE-A2, 5T4, MAGE-A3 and Survivin; or hTERT, WT1, MAGE-A2, 5T4, MAGE-A3 and MAGE-C1; or hTERT, WT1, MAGE-A2, 5T4, MAGE-A3 and MAGE-C2; or WT1, MAGE-A2, 5T4, MAGE-A3, MUC1 and Her-2/neu; or WT1, MAGE-A2, 5T4, MAGE-A3, MUC1 and NY-ESO-1; or WT1, MAGE-A2, 5T4, MAGE-A3, MUC1 and CEA; or WT1, MAGE-A2, 5T4, MAGE-A3, MUC1 and Survivin; or WT1, MAGE-A2, 5T4, MAGE-A3, MUC1 and MAGE-C1; or WT1, MAGE-A2, 5T4, MAGE-A3, MUC1 and MAGE-C2; or MAGE-A2, 5T4, MAGE-A3, MUC1, Her-2/neu and NY-ESO-1; or MAGE-A2, 5T4, MAGE-A3, MUC1, Her-2/neu and CEA; or MAGE-A2, 5T4. MAGE-A3, MUC1, Her-2/neu and Survivin; or MAGE-A2, 5T4, MAGE-A3, MUC1, Her-2/neu and MAGE-C1; or MAGE-A2, 5T4, MAGE-A3, MUC1, Her-2/neu and MAGE-C2; or 5T4, MAGE-A3, MUC1, Her-2/neu, NY-ESO-1 and CEA; or 5T4, MAGE-A3, MUC1, Her-2/neu, NY-ESO-1 and Survivin; or 5T4, MAGE-A3, MUC1, Her-2/neu, NY-ESO-1 and MAGE-C1; or 5T4, MAGE-A3, MUC1, Her-2/neu, NY-ESO-1 and MAGE-C2; or MAGE-A3, MUC1, Her-2/neu, NY-ESO-1, CEA and Survivin; or MAGE-A3, MUC1, Her-2/neu, NY-ESO-1, CEA and MAGE-C1; or MAGE-A3, MUC1, Her-2/neu, NY-ESO-1, CEA and MAGE-C2; or MUC1, Her-2/neu, NY-ESO-1. CEA, Survivin and MAGE-C1; or MUC1, Her-2/neu, NY-ESO-1, CEA, Survivin and MAGE-C2; or HER-2/NEU, NY-ESO-1, CEA, Survivin, MAGE-C1 and MAGE-C2; or hTERT, WT1, MAGE-A2, 5T4, MAGE-A3, MUC1 and Her-2/neu; or hTERT, WT1, MAGE-A2, 5T4, MAGE-A3, MUC1 and NY-ESO-1; or hTERT, WT1, MAGE-A2, 5T4, MAGE-A3, MUC1 and CEA; or hTERT, WT1, MAGE-A2, 5T41, MAGE-A3, MUC1 and Survivin; or hTERT, WT1, MAGE-A2, 5T4, MAGE-A3, MUC1 and MAGE-C1; or hTERT, WT1, MAGE-A2, 5T4, MAGE-A3, MUC1 and MAGE-C2; or WT1, MAGE-A2, 5T4, MAGE-A3, MUC1, Her-2/neu and NY-ESO-1; or WT1, MAGE-A2, 5T4, MAGE-A3, MUC1, Her-2/neu and CEA; or WI, MAGE-A2, 5T4, MAGE-A3, MUC1, Her-2/neu and Survivin; or WT1, MAGE-A2, 5T4, MAGE-A3, MUC1, Her-2/neu and MAGE-C1; or WT1, MAGE-A2, 5T4, MAGE-A3, MUC1, Her-2/neu and MAGE-C2; or MAGE-A2, 5T4, MAGE-A3, MUC1, Her-2/neu, NY-ESO-1 and CEA; or MAGE-A2, 5T4, MAGE-A3, MUC1, Her-2/neu, NY-ESO-1 and Survivin; or MAGE-A2, 5T4, MAGE-A3, MUC1, Her-2/neu, NY-ESO-1 and MAGE-C1; or MAGE-A2, 5T4, MAGE-A3, MUC1, Her-2/neu, NY-ESO-1 and MAGE-C2; or 5T4, MAGE-A3, MUC1, Her-2/neu, NY-ESO-1, CEA and Survivin; or 5T4, MAGE-A3, MUC1, Her-2/neu, NY-ESO-1, CEA and MAGE-C1; or 5T4, MAGE-A3, MUC1, Her-2/neu, NY-ESO-1, CEA and MAGE-C2; or MAGE-A3, MUC1, Her-2/neu, NY-ESO-1, CEA, Survivin and MAGE-C1; or MAGE-A3, MUC1, Her-2/neu, NY-ESO-1, CEA, Survivin and MAGE-C2; or MUC1, Her-2/neu, NY-ESO-1, CEA, Survivin, MAGE-C1 and MAGE-C2; or hTERT, WT1, MAGE-A2, 5T4, MAGE-A3, MUC1, Her-2/neu and NY-ESO-1; or hTERT, WT1, MAGE-A2, 5T4, MAGE-A3, MUC1, Her-2/neu and CEA; or hTERT, WT1, MAGE-A2, 5T4, MAGE-A3, MUC1, Her-2/neu and Survivin; or hTERT, WT1, MAGE-A2, 5T4, MAGE-A3, MUC1, Her-2/neu and MAGE-C1; or hTERT, WT1, MAGE-A2, 5T4, MAGE-A3, MUC1, Her-2/neu and MAGE-C2; or WT1, MAGE-A2, 5T4, MAGE-A3, MUC1, Her-2/neu, NY-ESO-1 and CEA; or WT1, MAGE-A2, 5T4, MAGE-A3, MUC1, Her-2/neu, NY-ESO-1 and Survivin; or WT1, MAGE-A2, 5T4, MAGE-A3, MUC1, Her-2/neu, NY-ESO-1 and MAGE-C1; or WT1, MAGE-A2, 5T4, MAGE-A3, MUC1, Her-2/neu, NY-ESO-1 and MAGE-C2; or MAGE-A2, 5T4, MAGE-A3, MUC1, Her-2/neu, NY-ESO-1, CEA and Survivin; or MAGE-A2, 5T4, MAGE-A3, MUC1, Her-2/neu, NY-ESO-1, CEA and MAGE-C1; or MAGE-A2, 5T4, MAGE-A3, MUC1, Her-2/neu, NY-ESO-1, CEA and MAGE-C2; or 5T4, MAGE-A3, MUC1, Her-2/neu, NY-ESO-1, CEA, Survivin and MAGE-C1; or 5T4, MAGE-A3, MUC1, Her-2/neu, NY-ESO-1, CEA, Survivin and MAGE-C2; or MAGE-A3, MUC1, Her-2/neu, NY-ESO-1, CEA, Survivin, MAGE-C1 and MAGE-C2;

or hTERT, WT1, MAGE-A2, 5T4, MAGE-A3, MUC1, Her-2/neu, NY-ESO-1 and CEA or hTERT, WT1, MAGE-A2, 5T4, MAGE-A3, MUC1, Her-2/neu, NY-ESO-1 and Survivin; or hTERT, WT1, MAGE-A2, 5T4, MAGE-A3, MUC1, Her-2/neu, NY-ESO-1 and MAGE-C1; or hTERT, WT1, MAGE-A2, 5T4, MAGE-A3, MUC1, Her-2/neu, NY-ESO-1 and MAGE-C2; or WT1, MAGE-A2, 5T4, MAGE-A3, MUC1, Her-2/neu, NY-ESO-1, CEA and Survivin; or WT1, MAGE-A2, 5T4, MAGE-A3, MUC1, Her-2/neu, NY-ESO-1, CEA and MAGE-C1; or WT1, MAGE-A2, 5T4, MAGE-A3, MUC1, Her-2/neu, NY-ESO-1, CEA and MAGE-C2; or MAGE-A2, 5T4, MAGE-A3, MUC1, Her-2/neu, NY-ESO-1, CEA, Survivin and MAGE-C1; or MAGE-A2, 5T4, MAGE-A3, MUC1, Her-2/neu, NY-ESO-1, CEA, Survivin and MAGE-C2; or 5T4, MAGE-A3, MUC1, Her-2/neu, NY-ESO-1, CEA, Survivin, MAGE-C1 and MAGE-C2;

or hTERT, WT1, MAGE-A2, 5T4, MAGE-A3, MUC1, Her-2/neu, NY-ESO-1, CEA and Survivin; or hTERT, WT1, MAGE-A2, 5T4, MAGE-A3, MUC1, Her-2/neu, NY-ESO-1, CEA and MAGE-C1; or hTERT, WT1, MAGE-A2, 5T4, MAGE-A3, MUC1, Her-2/neu, NY-ESO-1, CEA and MAGE-C2; or WT1, MAGE-A2, 5T4, MAGE-A3, MUC1, Her-2/neu, NY-ESO-1, CEA, Survivin and MAGE-C1; or WT1, MAGE-A2, 5T4, MAGE-A3, MUC1, Her-2/neu, NY-ESO-1, CEA, Survivin and MAGE-C2; or MAGE-A2, 5T4, MAGE-A3, MUC1, Her-2/neu, NY-ESO-1, CEA. Survivin, MAGE-C1 and MAGE-C2;

or hTERT, WT1, MAGE-A2, 5T4, MAGE-A3, MUC1, Her-2/neu, NY-ESO-1, CEA, Survivin and MAGE-C1; or hTERT, WT1, MAGE-A2, 5T4, MAGE-A3, MUC1, Her-2/neu, NY-ESO-1, CEA, Survivin and MAGE-C2; or WT1, MAGE-A2, 5T4. MAGE-A3, MUC1, Her-2/neu, NY-ESO-1, CEA, Survivin, MAGE-C1 and MAGE-C2;

or hTERT, WT1, MAGE-A2, 5T4, MAGE-A3, MUC1, Her-2/neu, NY-ESO-1, CEA, Survivin, MAGE-C1 and MAGE-C2.

According to another particularly preferred embodiment, the at least one antigen(s) according to b) is (are) selected from the following specific combination of antigens as defined above:

Survivin and 5T4

The at least one RNA of the active (immunostimulatory) composition according to the present invention is typically any RNA, preferably, without being limited thereto, a coding RNA, a circular or linear RNA, a single- or a double-stranded RNA (which may also be regarded as a RNA due to non-covalent association of two single-stranded RNA) or a partially double-stranded or partially single stranded RNA, which are at least partially self complementary (both of these partially double-stranded or partially single stranded RNA molecules are typically formed by a longer and a shorter single-stranded RNA molecule or by two single stranded RNA-molecules, which are about equal in length, wherein one single-stranded RNA molecule is in part complementary to the other single-stranded RNA molecule and both thus form a double-stranded RNA in this region, i.e. a partially double-stranded or partially single stranded RNA with respect to the entire RNA sequence). More preferably, the at least one RNA of the active (immunostimulatory) composition according to the present invention is a single-stranded RNA, even more preferably a linear RNA. Most preferably, the at least RNA of the active (immunostimulatory) composition according to the present invention is a messenger RNA (mRNA). In this context, a messenger RNA (mRNA) is typically a RNA, which is composed of (at least) several structural elements, e.g. an optional 5'-UTR region, an upstream positioned ribosomal binding site followed by a coding region, an optional 3'-UTR region, which may be followed by a poly-A tail (and/or a poly-C-tail).

Due to one particularly preferred embodiment, each of the at least two (preferably different) antigens of the active (immunostimulatory) composition of the present invention, may be encoded by one (monocistronic) RNA, preferably one (monocistronic) mRNA. In other words, the active (immunostimulatory) composition of the present invention may contain at least two (monocistronic) RNAs, preferably mRNAs, wherein each of these at least two (monocistronic) RNAs, preferably mRNAs, may encode just one (preferably different) antigen, selected from one of the above mentioned groups or subgroups, preferably in one of the above mentioned combinations.

According to another particularly preferred embodiment, the active (immunostimulatory) composition of the present invention, may comprise (at least) one bi- or even multicistronic RNA, preferably mRNA, i.e. (at least) one RNA which carries two or even more of the coding sequences of at the least two (preferably different) antigens, selected from one of the above mentioned groups or subgroups, preferably in one of the above mentioned combinations. Such coding sequences of the at least two (preferably different) antigens of the (at least) one bi- or even multicistronic RNA may be separated by at least one IRES (internal ribosomal entry site) sequence, as defined below. Thus, the term "encoding at least two (preferably different) antigens" may mean, without being limited thereto, that the (at least) one (bi- or even multicistronic) RNA, preferably a mRNA, may encode e.g. at least two, three, four, five, six, seven, eight, nine, ten, eleven or twelve (preferably different) antigens of the above mentioned group(s) of antigens or their fragments or variants within the above definitions. More preferably, without being limited thereto, the (at least) one (bi- or even multicistronic) RNA, preferably mRNA, may encode e.g. at least two, three, four, five or six (preferably different) antigens of the above mentioned subgroup(s) of antigens or their fragments or variants within the above definitions. In this context, a so-called IRES (internal ribosomal entry site) sequence as defined above can function as a sole ribosome binding site, but it can also serve to provide a bi- or even multicistronic RNA as defined above which codes for several proteins, which are to be translated by the ribosomes independently of one another. Examples of IRES sequences which can be used according to the invention are those from picornaviruses (e.g. FMDV), pestiviruses (CFFV), polioviruses (PV), encephalomyocarditis viruses (ECMV), foot and mouth disease viruses (FMDV), hepatitis C viruses (HCV), classical swine fever viruses (CSFV), mouse leukoma virus (MLV), simian immunodeficiency viruses (SIV) or cricket paralysis viruses (CrPV).

According to a further particularly preferred embodiment, the active (immunostimulatory) composition of the present invention, may comprise a mixture of at least one monocistronic RNA, preferably mRNA, as defined above, and at least one bi- or even multicistronic RNA, preferably mRNA, as defined above. The at least one monocistronic RNA and/or the at least one bi- or even multicistronic RNA preferably encode different antigens or their fragments or variants within the above definitions, the antigens preferably being selected from one of the above mentioned groups or subgroups of antigens, more preferably in one of the above mentioned combinations. However, the at least one monocistronic RNA and the at least one bi- or even multicistronic RNA may preferably also encode (in part) identical antigens selected from one of the above mentioned groups or subgroups of antigens, preferably in one of the above mentioned combinations, provided that the active (immunostimulatory) composition of the present invention as a whole provides at least two (preferably different) antigens as defined above. Such an embodiment may be advantageous e.g. for a staggered, e.g. time dependent, administration of the active (immunostimulatory) composition of the present invention to a patient in need thereof. The components of such an active (immunostimulatory) composition of the present invention, particularly the different RNAs encoding the at least two (preferably different) antigens, may be e.g. contained in (different parts of) a kit of parts composition or may be e.g. administered separately as components of different active (immunostimulatory) compositions according to the present invention.

Preferably, the at least one RNA of the active (immunostimulatory) composition, encoding at least two (preferably different) antigens selected from the above defined group or subgroup of antigens, more preferably in the above combinations, typically comprises a length of about 50 to about 20000, or 100 to about 20000 nucleotides, preferably of about 250 to about 20000 nucleotides, more preferably of about 500 to about 10000, even more preferably of about 500 to about 5000.

According to one embodiment, the at least one RNA of the active (immunostimulatory) composition, encoding at least two (preferably different) antigens selected from the above defined group(s) or subgroup(s) of antigens, more preferably in the above combinations, may be in the form of a modified RNA, wherein any modification, as defined herein, may be introduced into the at least one RNA of the active (immunostimulatory) composition. Modifications as defined herein preferably lead to a stabilized at least one RNA of the active (immunostimulatory) composition of the present invention.

According to a first embodiment, the at least one RNA of the active (immunostimulatory) composition of the present invention may thus be provided as a 'stabilized RNA', preferably a stabilized mRNA, that is to say as an (m)RNA that is essentially resistant to in vivo degradation (e.g. by an exo- or endo-nuclease). Such stabilization can be effected, for example, by a modified phosphate backbone of the at least one (m)RNA of the active (immunostimulatory) composition of the present invention. A backbone modification in connection with the present invention is a modification in which phosphates of the backbone of the nucleotides contained in the RNA are chemically modified. Nucleotides that may be preferably used in this connection contain e.g. a phosphorothioate-modified phosphate backbone, preferably at least one of the phosphate oxygens contained in the phosphate backbone being replaced by a sulfur atom. Stabilized (m)RNAs may further include, for example: non-ionic phosphate analogues, such as, for example, alkyl and aryl phosphonates, in which the charged phosphonate oxygen is replaced by an alkyl or aryl group, or phosphodiesters and alkylphosphotriesters, in which the charged oxygen residue is present in alkylated form. Such backbone modifications typically include, without implying any limitation, modifications from the group consisting of methylphosphonates, phosphoramidates and phosphorothioates (e.g. cytidine-5'-O-(1-thiophosphate)).

The at least one RNA of the active (immunostimulatory) composition of the present invention may additionally or alternatively also contain sugar modifications. A sugar modification in connection with the present invention is a chemical modification of the sugar of the nucleotides of the at least one RNA and typically includes, without implying any limitation, sugar modifications selected from the group consisting of 2'-deoxy-2'-fluoro-oligoribonucleotide (2'-fluoro-2'-deoxycytidine-5'-triphosphate, 2'-fluoro-2'-deoxyuridine-5'-triphosphate), 2'-deoxy-2'-deamine oligoribonucleotide (2'-amino-2'-deoxycytidine-5'-triphosphate, 2'-amino-2'-deoxyuridine-S'-triphosphate), 2'-O-alkyl oligoribonucleotide, 2'-deoxy-2'-C-alkyl oligoribonucleotide (2'-O-methylcytidine-5'-triphosphate, 2'-methyluridine-5'-triphosphate), 2'-C-alkyl oligoribonucleotide, and isomers thereof (2'-aracytidine-5'-triphosphate, 2'-arauridine-S'-triphosphate), or azidotriphosphate (2'-azido-2'-deoxycytidine-5'-triphosphate, 2'-azido-2'-deoxyuridine-5'-triphosphate).

The at least one RNA of the active (immunostimulatory) composition of the present invention may additionally or alternatively also contain at least one base modification, which is preferably suitable for increasing the expression of the protein coded for by the at least one RNA sequence significantly as compared with the unaltered, i.e. natural (=native), RNA sequence. Significant in this case means an increase in the expression of the protein compared with the expression of the native RNA sequence by at least 20%, preferably at least 30%, 40%, 50% or 60%, more preferably by at least 70%, 80%, 90% or even 100% and most preferably by at least 150%, 200% or even 300% or more. In connection with the present invention, a nucleotide having such a base modification is preferably selected from the group of the base-modified nucleotides consisting of 2-amino-6-chloropurineriboside-5'-triphosphate, 2-aminoadenosine-5'-triphosphate, 2-thiocytidine-5'-triphosphate, 2-thiouridine-5'-triphosphate, 4-thiouridine-5'-triphosphate, 5-aminoallylcytidine-5'-triphosphate, 5-aminoallyluridine-5'-triphosphate, 5-bromocytidine-5'-triphosphate, 5-bromouridine-5'-triphosphate, 5-iodocytidine-5'-triphosphate, 5-iodouridine-5'-triphosphate, 5-methykytidine-5'-triphosphate, 5-methyluridine-5'-triphosphate, 6-azacytidine-5'-triphosphate, 6-azauridine-5'-triphosphate, 6-chloropurineriboside-5'-triphosphate, 7-deazaadenosine-5'-triphosphate, 7-deazaguanosine-5'-triphosphate, 8-azaadenosine-5'-triphosphate, 8-azidoadenosine-5'-triphosphate, benzimidazole-riboside-5'-triphosphate, N1-methyladenosine-5'-triphosphate, N1-methylguanosine-5'-triphosphate, N6-methyladenosine-5'-triphosphate, O6-methylguanosine-5'-triphosphate, pseudouridine-5'-triphosphate, or puromycin-5'-triphosphate, xanthosine-5'-triphosphate. Particular preference is given to nucleotides for base modifications selected from the group of base-modified nucleotides consisting of 5-methylcytidine-5'-triphosphate, 7-deazaguanosine-5'-triphosphate, 5-bromocytidine-5'-triphosphate, and pseudouridine-5'-triphosphate.

According to another embodiment, the at least one RNA of the active (immunostimulatory) composition of the present invention can likewise be modified (and preferably stabilized) by introducing further modified nucleotides containing modifications of their ribose or base moieties. Generally, the at least one (m)RNA of the active (immunostimulatory) composition of the present invention may contain any native (=naturally occurring) nucleotide, e.g. guanosine, uracil, adenosine, and/or cytosine or an analogue thereof. In this connection, nucleotide analogues are defined as non-natively occurring variants of naturally occurring nucleotides. Accordingly, analogues are chemically derivatized nucleotides with non-natively occurring functional groups, which are preferably added to or deleted from the naturally occurring nucleotide or which substitute the naturally occurring functional groups of a nucleotide. Accordingly, each component of the naturally occurring nucleotide may be modified, namely the base component, the sugar (ribose) component and/or the phosphate component forming the backbone (see above) of the RNA sequence. Analogues of guanosine, uracil, adenosine, and cytosine include, without implying any limitation, any naturally occurring or non-naturally occurring guanosine, uracil, adenosine, thymidine or cytosine that has been altered chemically, for example by acetylation, methylation, hydroxylation, etc., including 1-methyl-adenosine, 1-methyl-guanosine, 1-methyl-inosine, 2,2-dimethyl-guanosine, 2,6-diaminopurine, 2'-Amino-2'-deoxyadenosine, 2'-Amino-2'-deoxycytidine, 2'-Amino-2'-deoxyguanosine, 2'-Amino-2'-deoxyuridine, 2-Amino-6-chloropurineriboside, 2-Aminopurine-riboside, 2-Araadenosine, 2'-Aracytidine, 2'-Arauridine, 2'-Azido-2'-deoxyadenosine, 2'-Azido-2'-deoxycytidine, 2'-Azido-2'-deoxyguanosine, 2'-Azido-2'-deoxyuridine, 2-Chloroadenosine, 2'-Fluoro-2'-deoxyadenosine, 2'-Fluoro-2'-deoxycytidine, 2'-Fluoro-2'-deoxyguanosine, 2'-Fluoro-2'-deoxyuridine, 2'-Fluorothymidine, 2-methyl-adenosine, 2-methyl-guanosine, 2-methyl-thio-N-6-isopenenyl-adenosine, 2'-O-Methyl-2-aminoadenosine, 2'-O-Methyl-2'-deoxyadenosine, 2'-O-Methyl-2'-deoxycytidine, 2'-O-Methyl-2'-deoxyguanosine, 2'-O-Methyl-2'-deoxyuridine, 2'-O-Methyl-5-methyluridine, 2'-O-Methylinosine, 2'-O-Methylpseudouridine, 2-Thiocytidine, 2-thio-cytosine, 3-methyl-cytosine, 4-acetyl-cytosine, 4-Thiouridine, 5-(carboxyhydroxymethyl)-uracil, 5,6-Dihydrouridine, 5-Aminoallylcytidine, 5-Aminoallyl-deoxy-uridine, 5-Bromouridine, 5-carboxymethylaminomethyl-2-thio-uracil, 5-carboxymethylamonomethyl-uracil, 5-Chloro-Ara-cytosine, 5-Fluoro-uridine, 5-Iodouridine, 5-methoxycarbonylmethyl-uridine, 5-methoxy-uridine, 5-methyl-2-thio-uridine, 6-Azacytidine, 6-Azauridine, 6-Chloro-7-deaza-guanosine, 6-Chloropurineriboside, 6-Mercapto-guanosine, 6-Methyl-mercaptopurine-riboside, 7-Deaza-2'-deoxy-guanosine, 7-Deazaadenosine, 7-methyl-guanosine, 8-Azaadenosine, 8-Bromo-adenosine, 8-Bromo-guanosine, 8-Mercapto-guanosine, 8-Oxoguanosine, Benzimidazole-riboside, Beta-D-mannosyl-queosine, Dihydro-uracil, Inosine, N1-Methyladenosine, N6-([6-Aminohexyl]carbamoylmethyl)-adenosine, N6-isopentenyl-adenosine, N6-methyl-adenosine, N7-Methyl-xanthosine, N-uracil-5-oxyacetic acid methyl ester, Puromycin, Queosine, Uracil-5-oxyacetic acid, Uracil-5-oxyacetic acid methyl ester, Wybutoxosine, Xanthosine, and Xylo-adenosine. The preparation of such analogues is known to a person skilled in the art, for example from U.S. Pat. No. 4,373,071, U.S. Pat. No. 4,401,796, U.S. Pat. No. 4,415,732, U.S. Pat. No. 4,458,066, U.S. Pat. No. 4,500,707, U.S. Pat. No. 4,668,777, U.S. Pat. No. 4,973,679, U.S. Pat. No. 5,047,524, U.S. Pat. No. 5,132,418, U.S. Pat. No. 5,153,319, U.S. Pat. No. 5,262,530 and U.S. Pat. No. 5,700,642. In the case of an analogue as described above, particular preference may be given according to the invention to those analogues that increase the immunogenity of the RNA of the inventive active (immunostimulatory) composition and/or do not interfere with a further modification of the RNA that has been introduced.

According to a particular embodiment, the at least one RNA of the active (immunostimulatory) composition of the present invention can contain a lipid modification. Such a lipid-modified RNA typically comprises a RNA as defined herein, encoding at least two antigens selected from the group or subgroup of antigens as defined above, preferably in the above combinations. Such a lipid-modified RNA typically further comprises at least one linker covalently linked with that RNA, and at least one lipid covalently linked with the respective linker. Alternatively, the lipid-modified RNA comprises an at least one RNA as defined herein and at least one (bifunctional) lipid covalently linked (without a linker) with that RNA. According to a third alternative, the lipid-modified RNA comprises a RNA as defined herein, at least one linker covalently linked with that RNA, and at least one lipid covalently linked with the respective linker, and also at least one (bifunctional) lipid covalently linked (without a linker) with that RNA.

The lipid contained in the at least one RNA of the inventive active (immunostimulatory) composition (complexed or covalently bound thereto) is typically a lipid or a lipophilic residue that preferably is itself biologically active. Such lipids preferably include natural substances or compounds such as, for example, vitamins, e.g. alpha-tocopherol (vitamin E), including RRR-alpha-tocopherol (formerly D-alpha-tocopherol), L-alpha-tocopherol, the racemate D,L-alpha-tocopherol, vitamin E succinate (VES), or vitamin A and its derivatives, e.g. retinoic acid, retinol, vitamin D and its derivatives, e.g. vitamin D and also the ergosterol precursors thereof, vitamin E and its derivatives, vitamin K and its derivatives, e.g. vitamin K and related quinone or phytol compounds, or steroids, such as bile acids, for example cholic acid, deoxycholic acid, dehydrocholic acid, cortisone, digoxygenin, testosterone, cholesterol or thiocholesterol. Further lipids or lipophilic residues within the scope of the present invention include, without implying any limitation, polyalkylene glycols (Oberhauser et al., Nucl. Acids Res., 1992, 20, 533), aliphatic groups such as, for example, C1-C20-alkanes, C1-C20-alkenes or C1-C20-alkanol compounds, etc., such as, for example, dodecanediol, hexadecanol or undecyl residues (Saison-Behmoaras et al., EMBO J, 1991, 10, 111; Kabanov et al., FEBS Lett., 1990, 259, 327; Svinarchuk et al., Biochimie, 1993, 75, 49), phospholipids such as, for example, phosphatidylglycerol, diacylphosphatidylglycerol, phosphatidylcholine, dipalmitoylphosphatidylcholine, distearoylphosphatidylcholine, phosphatidylserine, phosphatidylethanolamine, di-hexadecyl-rac-glycerol, sphingolipids, cerebrosides, gangliosides, or triethylammonium 1,2-di-O-hexadecyl-rac-glycero-3-H-phosphonate (Manoharan et al., Tetrahedron Lett., 1995, 36, 3651; Shea et al., Nucl. Acids Res., 1990, 18, 3777), polyamines or polyalkylene glycols, such as, for example, polyethylene glycol (PEG) (Manoharan et al., Nucleosides & Nucleotides, 1995, 14, 969), hexaethylene glycol (HEG), palmitin or palmityl residues (Mishra et al., Biochim. Biophys. Acta, 1995, 1264, 229), octadecylamines or hexylamino-carbonyl-oxycholesterol residues (Crooke et al., J. Pharmacol. Exp. Ther., 1996, 277, 923), and also waxes, terpenes, alicyclic hydrocarbons, saturated and mono- or poly-unsaturated fatty acid residues, etc.

The at least one RNA of the active (immunostimulatory) composition of the present invention may likewise be stabilized in order to prevent degradation of the RNA in vivo by various approaches. It is known in the art that instability and (fast) degradation of mRNA or of RNA in vivo in general may represent a serious problem in the application of RNA based compositions. This instability of RNA is typically due to RNA-degradin enzymes, "RNAases" (ribonucleases), wherein contamination with such ribonucleases may sometimes completely degrade RNA in solution. Accordingly, the natural degradation of mRNA in the cytoplasm of cells is very finely regulated and RNase contaminations may be generally removed by special treatment prior to use of said compositions, in particular with diethyl pyrocarbonate (DEPC). A number of mechanisms of natural degradation are known in this connection in the prior art, which may be utilized as well. E.g., the terminal structure is typically of critical importance for a mRNA in vivo. As an example, at the 5'end of naturally occurring mRNAs there is usually a so-called "cap structure" (a modified guanosine nucleotide), and at the 3'end is typically a sequence of up to 200 adenosine nucleotides (the so-called poly-A tail) (SEQ ID NO: 29).

The at least one RNA of the active (immunostimulatory) composition of the present invention, particularly if provided as a mRNA, can therefore be stabilized against degradation by RNases by the addition of a so-called "5' cap" structure. Particular preference is given in this connection to an m7G (5')ppp (5'(A,G(5')ppp(5')A or G(5')ppp(5')G as the 5' cap" structure. However, such a modification is introduced only if a modification, for example a lipid modification, has not already been introduced at the 5' end of the (m)RNA of the inventive immunostimulatory composition or if the modification does not interfere with the immunogenic properties of the (unmodified or chemically modified) (m)RNA.

According to a further preferred embodiment, the at least one RNA. of the active (immunostimulatory) composition of the present invention may contain, especially if the RNA is in the form of a mRNA, a poly-A tail on the 3' terminus of typically about 10 to 200 adenosine nucleotides (SEQ ID NO: 30), preferably about 10 to 100 adenosine nucleotides(SEQ. ID NO: 31 more preferably about 20 to 100 adenosine nucleotides (SEQ ID NO: 32) or even more preferably about 40 to 80 adenosine nucleotides (SEQ ID NO: 33).

According to a further preferred embodiment, the at least one RNA of the active (immunostimulatory) composition of the present invention may contain, especially if the RNA is in the form of a mRNA, a poly-C tail on the 3' terminus of typically about 10 to 200 cytosine nucleotides (SEQ ID NO: 34), preferably about 10 to 100 cytosine nucleotides (SEQ ID NO: 35), more preferably about 20 to 70 cytosine nucleotides SEQ ID NO: 36 ) or even more preferably about 2.0 to 60 (SEQ ID NO: 37) or even 10 to 40 cytosine nucleotides ( SEQ ID NO: 38).

According to another embodiment, the at least one RNA of the active (immunostimulatory) composition of the present invention may be modified, and thus stabilized, especially if the RNA is in the form of a mRNA, by modifying the G/C content of the RNA, preferably of the coding region of the at least one RNA.

In a particularly preferred embodiment of the present invention, the G/C content of the coding region of the at least one (m)RNA of the active (immunostimulatory) composition of the present invention is modified, particularly increased, compared to the G/C content of the coding region of its particular wild-type (m)RNA, i.e. the unmodified (m)RNA. The encoded amino acid sequence of the at least one (m)RNA is preferably not modified compared to the coded amino acid sequence of the particular wild-type (m)RNA.

This modification of the at least one (m)RNA of the active (immunostimulatory) composition of the present invention is based on the fact that the sequence of any (m)RNA region to be translated is important for efficient translation of that (m)RNA. Thus, the composition and the sequence of various nucleotides is important. In particular, sequences having an increased G (guanosine)/C (cytosine) content are more stable than sequences having an increased A (adenosine)/U (uracil) content. According to the invention, the codons of the (m)RNA are therefore varied compared to its wild-type (m)RNA, while retaining the translated amino acid sequence, such that they include an increased amount of G/C nucleotides. In respect to the fact that several codons code for one and the same amino acid (so-called degeneration of the genetic code), the most favorable codons for the stability can be determined (so-called alternative codon usage).

Depending on the amino acid to be encoded by the at least one (m)RNA, there are various possibilities for modification of the at least one (m)RNA sequence, compared to its wild-type sequence. In the case of amino acids which are encoded by codons which contain exclusively G or C nucleotides, no modification of the codon is necessary. Thus, the codons for Pro (CCC or CCG), Arg (CGC or CGG), Ala (GCC or GCG) and Gly (GGC or GGG) require no modification, since no A or U is present.

In contrast, codons which contain A and/or U nucleotides can be modified by substitution of other codons which code for the same amino acids but contain no A and/or U. Examples of these are:
the codons for Pro can be modified from CCU or CCA to CCC or CCG;
the codons for Arg can be modified from CGU or CGA or AGA or AGG to CGC or CGC;
the codons for Ala can be modified from GCU or GCA to GCC or GCG;
the codons for Gly can be modified from GGU or GGA to GGC or GGG.

In other cases, although A or U nucleotides cannot be eliminated from the codons, it is however possible to decrease the A and U content by using codons which contain a lower content of A and/or U nucleotides. Examples of these are:
the codons for Phe can be modified from UUU to UUC;
the codons for Leu can be modified from UUA, UUG, CUU or CUA to CUC or CUG;
the codons for Ser can be modified from UCU or UCA or AGU to UCC, UCG or AGC;
the codon for Tyr can be modified from UAU to UAC;
the codon for Cys can be modified from UGU to UGC;
the codon for His can be modified from CAU to CAC;
the codon for Gln can be modified from CAA to CAG;
the codons for Ile can be modified from AUU or AUA to AUC;
the codons for Thr can be modified from ACU or ACA to ACC or ACG;
the codon for Asn can be modified from AAU to AAC;
the codon for Lys can be modified from AAA to AAG;
the codons for Val can be modified from GUU or GUA to GUC or GUG;
the codon for Asp can be modified from GAU to GAC;
the codon for Glu can be modified from GAA to GAG;
the stop codon UAA can be modified to UAG or UGA.

In the case of the codons for Met (AUG) and Trp (UGG), on the other hand, there is no possibility of sequence modification.

The substitutions listed above can be used either individually or in all possible combinations to increase the G/C content of the at least one (m)RNA of the active (immunostimulatory) composition of the present invention compared to its particular wild-type (m)RNA (i.e. the original sequence). Thus, for example, all codons for Thr occurring in the wild-type sequence can be modified to ACC (or ACG). Preferably, however, for example, combinations of the above substitution possibilities are used: substitution of all codons coding for Thr in the original sequence (wild-type (m)RNA) to ACC (or ACG) and
substitution of all codons originally coding for Ser to UCC (or UCG or AGC);
substitution of all codons coding for Ile in the original sequence to AUC and
substitution of all codons originally coding for Lys to AAG and
substitution of all codons originally coding for Tyr to UAC;
substitution of all codons coding for Val in the original sequence to GUC (or GUG) and
substitution of all codons originally coding for Glu to GAG and
substitution of all codons originally coding for Ala to GCC (or GCG) and
substitution of all codons originally coding for Arg to CGC (or CGG);
substitution of all codons coding for Val in the original sequence to GUC (or GUG) and
substitution of all codons originally coding for Glu to GAG and
substitution of all codons originally coding for Ala to GCC (or GCG) and
substitution of all codons originally coding for Gly to GGC (or GGG) and
substitution of all codons originally coding for Asn to AAC;
substitution of all codons coding for Val in the original sequence to GUC (or GUG) and
substitution of all codons originally coding for Phe to UUC and
substitution of all codons originally coding for Cys to UGC and
substitution of all codons originally coding for Leu to CUG (or CUC) and
substitution of all codons originally coding for Gln to CAG and
substitution of all codons originally coding for Pro to CCC (or CCG): etc.

Preferably, the G/C content of the coding region of the at least one (m)RNA of the active (immunostimulatory) composition of the present invention is increased by at least 7%, more preferably by at least 15%, particularly preferably by at least 20%, compared to the G/C content of the coded region of the wild-type (m)RNA which codes for an antigen, antigenic protein or antigenic peptide as defined herein or its fragment or variant thereof. According to a specific embodiment at least 5%, 10%, 20%, 30%, 40%, 50%, 60%, more preferably at least 70%, even more preferably at least 80% and most preferably at least 90%, 95% or even 100% of the substitutable codons in the region coding for an antigen, antigenic protein or antigenic peptide as defined herein or its fragment or variant thereof or the whole sequence of the wild type (m)RNA sequence are substituted, thereby increasing the GC/content of said sequence.

In this context, it is particularly preferable to increase the G/C content of the at least one (m)RNA of the active (immunostimulatory) composition of the present invention to the maximum (i.e. 100% of the substitutable codons), in particular in the region coding for a protein, compared to the wild-type sequence.

According to the invention, a further preferred modification of the at least one (m)RNA of the active (immunostimulatory) composition of the present invention is based on the finding that the translation efficiency is also determined by a different frequency in the occurrence of tRNAs in cells. Thus, if so-called "rare codons" are present in the at least one (m)RNA of the active (immunostimulatory) composition of the present invention to an increased extent, the corresponding modified at least one (m)RNA sequence is translated to a significantly poorer degree than in the case where codons coding for relatively "frequent" tRNAs are present.

According to the invention, in the modified at least one (m)RNA of the active (immunostimulatory) composition of the present invention, the region which codes for the adjuvant protein is modified compared to the corresponding region of the wild-type (m)RNA such that at least one codon of the wild-type sequence which codes for a tRNA which is relatively rare in the cell is exchanged for a codon which codes for a tRNA which is relatively frequent in the cell and carries the same amino acid as the relatively rare tRNA. By this modification, the sequences of the at least one (m)RNA of the active (immunostimulatory) composition of the present invention is modified such that codons for which frequently occurring tRNAs are available are inserted. In other words, according to the invention, by this modification all codons of the wild-type sequence which code for a tRNA which is relatively rare in the cell can in each case be exchanged for a codon which codes for a tRNA which is relatively frequent in the cell and which, in each case, carries the same amino acid as the relatively rare tRNA.

Which tRNAs occur relatively frequently in the cell and which, in contrast, occur relatively rarely is known to a person skilled in the art; cf. e.g. Akashi, Curr. Opin. Genet. Dev. 2001, 11(6): 660-666. The codons which use for the particular amino acid the tRNA which occurs the most frequently, e.g. the Gly codon, which uses the tRNA which occurs the most frequently in the (human) cell, are particularly preferred.

According to the invention, it is particularly preferable to link the sequential G/C content which is increased, in particular maximized, in the modified at least one (m)RNA of the active (immunostimulatory) composition of the present invention, with the "frequent" codons without modifying the amino acid sequence of the protein encoded by the coding region of the (m)RNA. This preferred embodiment allows provision of a particularly efficiently translated and stabilized (modified) at least one (m)RNA of the active (immunostimulatory) composition of the present invention.

The determination of a modified at least one (m)RNA of the active (immunostimulatory) composition of the present invention as described above (increased G/C content; exchange of tRNAs) can be carried out using the computer program explained in WO 02/098443—the disclosure content of which is included in its full scope in the present invention. Using this computer program, the nucleotide sequence of any desired (m)RNA can be modified with the aid of the genetic code or the degenerative nature thereof such that a maximum G/C content results, in combination with the use of codons which code for tRNAs occurring as frequently as possible in the cell, the amino acid sequence coded by the modified at least one (m)RNA preferably not being modified compared to the non-modified sequence. Alternatively, it is also possible to modify only the G/C content or only the codon usage compared to the original sequence. The source code in Visual Basic 6.0 (development environment used: Microsoft Visual Studio Enterprise 6.0 with Servicepack 3) is also described in WO 02/098443.

In a further preferred embodiment of the present invention, the A/U content in the environment of the ribosome binding site of the at least one (m)RNA of the active (immunostimulatory) composition of the present invention is increased compared to the A/U content in the environment of the ribosome binding site of its particular wild-type (m)RNA. This modification (an increased A/U content around the ribosome binding site) increases the efficiency of ribosome binding to the at least one (m)RNA. An effective binding of the ribosomes to the ribosome binding site (Kozak sequence: GCCGCCAC-CAUGG (SEQ ID NO: 27), the AUG forms the start codon) in turn has the effect of an efficient translation of the at least one (m)RNA.

According to a further embodiment of the present invention the at least one (m)RNA of the active (immunostimulatory) composition of the present invention may be modified with respect to potentially destabilizing sequence elements. Particularly, the coding region and/or the 5' and/or 3' untranslated region of this at least one (m)RNA may be modified compared to the particular wild-type (m)RNA such that is contains no destabilizing sequence elements, the coded amino acid sequence of the modified at least one (m)RNA preferably not being modified compared to its particular wild-type (m)RNA. It is known that, for example, in sequences of eukaryotic RNAs destabilizing sequence elements (DSE) occur, to which signal proteins bind and regulate enzymatic degradation of RNA in vivo. For further stabilization of the modified at least one (m)RNA, optionally in the region which encodes for an antigen, antigenic protein or antigenic peptide as defined herein, one or more such modifications compared to the corresponding region of the wild-type (m)RNA can therefore be carried out, so that no or substantially no destabilizing sequence elements are contained there. According to the invention, DSE present in the untranslated regions (3'- and/or 5'-UTR) can also be eliminated from the at least one (m)RNA of the active (immunostimulatory) composition of the present invention by such modifications.

Such destabilizing sequences are e.g. AU-rich sequences (AURES), which occur in 3'-UTR sections of numerous unstable RNAs (Caput et al., Proc. Natl. Acad. Sci. USA 1986, 83: 1670 to 1674). The at least one (m)RNA of the active (immunostimulatory) composition of the present invention is therefore preferably modified compared to the wild-type (m)RNA such that the at least one (m)RNA contains no such destabilizing sequences. This also applies to those sequence motifs which are recognized by possible endonucleases, e.g. the sequence GAACAAG, which is contained in the 3'-UTR segment of the gene which codes for the transferrin receptor (Binder et al., EMBO J. 1994, 13: 1969 to 1980). These sequence motifs are also preferably removed in the at least one (m)RNA of the active (immunostimulatory) composition of the present invention.

Also preferably according to the invention, the at least one (m)RNA of the active (immunostimulatory) composition of the present invention has, in a modified form, at least one IRES as defined above and/or at least one 5' and/or 3' stabilizing sequence, in a modified form, e.g. to enhance ribosome binding or to allow expression of different encoded antigens located on an at least one (bi- or even multicistronic) RNA of the active (immunostimulatory) composition of the present invention.

According to the invention, the at least one (m)RNA of the active (immunostimulatory) composition of the present invention furthermore preferably has at least one 5' and/or 3' stabilizing sequence. These stabilizing sequences in the 5' and/or 3' untranslated regions have the effect of increasing the half-life of the at least one (m)RNA in the cytosol. These stabilizing sequences can have 100% sequence homology to naturally occurring sequences which occur in viruses, bacteria and eukaryotes, but can also be partly or completely synthetic. The untranslated sequences (UTR) of the globin gene, e.g. from *Homo sapiens* or *Xenopus laevis* may be mentioned as an example of stabilizing sequences which can be used in the present invention for a stabilized RNA. Another example of a stabilizing sequence has the general formula (C/U)CCAN$_x$CCC(U/A)Py$_x$UC(C/U)CC (SEQ ID NO: 28), which is contained in the 3'UTR of the very stable RNA which codes for globin, (I)-collagen, 15-lipoxygenase or for tyrosine hydroxylase (cf. Holcik et al., Proc. Natl. Acad. Sci. USA 1997, 94: 2410 to 2414). Such stabilizing sequences can of course be used individually or in combination with one another and also in combination with other stabilizing sequences known to a person skilled in the art. The at least one (m)RNA of the active (immunostimulatory) composition of the present invention is therefore preferably present as globin UTR (untranslated regions)-stabilized RNA, in particular as globin UTR-stabilized RNA.

Nevertheless, substitutions, additions or eliminations of bases are preferably carried out with the at least one RNA of the active (immunostimulatory) composition of the present invention, using a DNA matrix for preparation of the at least one RNA of the active (immunostimulatory) composition of the present invention by techniques of the well known site directed mutagenesis or with an oligonucleotide ligation strategy (see e.g. Maniatis et al., Molecular Cloning: A Laboratory Manual, Cold Spring Harbor Laboratory Press, 3rd ed., Cold Spring Harbor, N.Y., 2001). In such a process, for preparation of the at least one (m)RNA, a corresponding DNA molecule may be transcribed in vitro. This DNA matrix preferably comprises a suitable promoter, e.g. a T7 or SP6 promoter, for in vitro transcription, which is followed by the desired nucleotide sequence for the at least one RNA to be prepared and a termination signal for in vitro transcription. The DNA molecule, which forms the matrix of an at least one RNA of interest, may be prepared by fermentative proliferation and subsequent isolation as part of a plasmid which can be replicated in bacteria. Plasmids which may be mentioned as suitable for the present invention are e.g. the plasmids pT7Ts (GENBANK®accession number U26404; Lai et al., Development 1995, 121: 2349 to 2360), pGEM® series, e.g. pGEM®-1 (GENBANK®accession number X65300; from Promega) and pSP64 (GENBANK®accession number X65327); cf. also Mezei and Storts, Purification of PCR Products, in: Griffin and Griffin (ed.), PCR Technology: Current Innovation, CRC Press, Boca Raton, Fla., 2001.

The stabilization of the at least one RNA of the active (immunostimulatory) composition of the present invention can likewise by carried out by associating or complexing the at least one RNA with, or binding it to, a cationic compound, in particular a polycationic compound, for example a (poly) cationic peptide or protein. In particular the use of protamine, nucleoline, spermin or spermidine as the polycationic, nucleic-acid-binding protein to the RNA is particularly effective. Furthermore, the use of other cationic peptides or proteins, such as poly-L-lysine or histones, is likewise possible. This procedure for stabilizing RNA is described in EP-A-1083232, the disclosure of which is incorporated by reference into the present invention in its entirety. Further preferred cationic substances which can be used for stabilizing the RNA of the active (immunostimulatory) composition of the present invention include cationic polysaccharides, for example chitosan, polybrene, polyethyleneimine (PEI) or poly-L-lysine (PLL), etc. Association or complexing of the at least one RNA of the inventive active (immunostimulatory) composition with cationic compounds, e.g. cationic proteins or cationic lipids, e.g. oligofectamine as a lipid based complexation reagent) preferably increases the transfer of the at least one RNA present as a pharmaceutically active component into the cells to be treated or into the organism to be treated. It is also referred to the disclosure herein with regard to the stabilizing effect for the at least one RNA of the active (immunostimulatory) composition of the present invention by complexation, which holds for the stabilization of RNA as well.

According to another particularly preferred embodiment, the at least RNA of the active (immunostimulatory) composition may additionally or alternatively encode a secretory signal peptide. Such signal peptides are sequences, which typically exhibit a length of about 15 to 30 amino acids and are preferably located at the N-terminus of the encoded peptide, without being limited thereto. Signal peptides as defined herein preferably allow the transport of the antigen, antigenic protein or antigenic peptide as encoded by the at least one RNA of the active (immunostimulatory) composition into a defined cellular compartment, preferably the cell surface, the endoplasmic reticulum (ER) or the endosomal-lysosomal compartment. Examples of secretory signal peptide sequences as defined herein include, without being limited thereto, signal sequences of classical or non-classical MHC-molecules (e.g. signal sequences of MHC I and II molecules, e.g. of the MHC class I molecule HLA-A*0201), signal sequences of cytokines or immunoglobulines as defined herein, signal sequences of the invariant chain of immunoglobulines or antibodies as defined herein, signal sequences of Lamp1, Tapasin, Erp57, Calretikulin, Calnexin, and further membrane associated proteins or of proteins associated with the endoplasmic reticulum (ER) or the endosomal-lysosomal compartment. Particularly preferably, signal sequences of MHC class I molecule HLA-A*0201 may be used according to the present invention.

Any of the above modifications may be applied to the at least one RNA of the active (immunostimulatory) composition of the present invention, and further to any (m)RNA as used in the context of the present invention and may be, if suitable or necessary, be combined with each other in any combination, provided, these combinations of modifications do not interfere with each other in the respective at least one RNA. A person skilled in the art will be able to take his choice accordingly.

According to another embodiment, the active (immunostimulatory) composition according to the invention may comprise an adjuvant. In this context, an adjuvant may be understood as any compound, which is suitable to support administration and delivery of the active (immunostimulatory) composition according to the invention. Furthermore, such an adjuvant may, without being bound thereto, initiate or increase an immune response of the innate immune system, i.e. a non-specific immune response. With other words, when administered, the active (immunostimulatory) composition according to the invention typically initiates an adaptive immune response due to the at least two antigens encoded by the at least one RNA contained in the inventive active (immunostimulatory) composition. Additionally, the active (immunostimulatory) composition according to the invention may generate an (supportive) innate immune response due to addition of an adjuvant as defined herein to the active (immunostimulatory) composition according to the invention. Such an adjuvant may be selected from any adjuvant known to a skilled person and suitable for the present case, i.e. supporting the induction of an immune response in a mammal. Preferably, the adjuvant may be selected from the group consisting of, without being limited thereto, TDM, MDP, muramyl dipeptide, pluronics, alum solution, aluminium hydroxide, ADJUMER® (polyphosphazene); aluminium phosphate gel; glucans from algae; algammulin; aluminium hydroxide gel (alum); highly protein-adsorbing aluminium hydroxide gel; low viscosity aluminium hydroxide gel; AF or SPT (emulsion of squalane (5%), Tween 80 (0.2%), Pluronic L121 (1.25%), phosphate-buffered saline, pH 7.4); AVRIDINE™ (propanediamine); BAY R1005™ ((N-(2-deoxy-2-L-leucylamino-b-D-glucopyranosyl)-N-octadecyl-dodecanoylamide hydroacetate); CALCITRIOL™ (1-alpha,2S-dihydroxy-vitamin D3); calcium phosphate gel; CAP™ (calcium phosphate nanoparticles); cholera holotoxin, cholera-toxin-A1-protein-A-D-fragment fusion protein, sub-unit B of the cholera toxin; CRL 1005 (block copolymer P1205); cytokine-containing liposomes; DDA (dimethyldioctadecylammonium bromide); DHEA (dehydroepiandrosterone); DMPC (dimyristoylphosphatidylcholine); DMPG (dimyristoylphosphatidylglycerol); DOC/alum complex (deoxycholic acid sodium salt); Freund's complete adjuvant; Freund's incomplete adjuvant; gamma inulin; Gerbu adjuvant (mixture of: i) N-acetylglucosaminyl-(P1-4)-N-acetylmuramyl-L-alanyl-D-glutamine (GMDP), ii) dimethyldioctadecylammonium chloride (DDA), iii) zinc-L-proline salt complex (ZnPro-8); GM-CSF); GMDP (N-acetylglucosaminyl-(b1-4)-N-acetylmuramyl-L-alanyl-D-isoglutamine); imiquimod (1-(2-methylpropyl)-1H-imidazol-4,5-c)quinoline-4-amine); ImmTher™ (N-acetylglucosaminyl-N-acetylmuramyl-L-Ala-D-isoGlu-L-Ala-glycerol dipalmitate); DRVs (immunoliposomes prepared from dehydration-rehydration vesicles); interferon-gamma; interleukin-1beta; interleukin-2; interleukin-7; interleukin-12; ISCOMS™; ISCOPREP 7.0.3.™; liposomes; LOXORIBINE™ (7-allyl-8-oxoguanosine); LT oral adjuvant (*E. coli* labile enterotoxin-protoxin); microspheres and microparticles of any composition; MF59™; (squalene-water emulsion); MONTANIDE ISA 51™ (purified incomplete Freund's adjuvant); MONTANIDE ISA 720™ (metabolisable oil adjuvant); MPL™ (3-Q-desacyl-4'-monophosphoryl lipid A); MTP-PE and MTP-PE liposomes ((N-acetyl-L-alanyl-D-isoglutaminyl-L-alanine-2-(1,2-dipalmitoyl-sn-glycero-3-(hydroxyphosphoryloxy))-ethylamide, monosodium salt); MURAMETIDE™ (Nac-Mur-L-Ala-D-GCn-OCH$_3$); MURAPALMITINE™ and D-MURAPALMITINE™ (Nac-Mur-L-Thr-D-isoCln-sn-glyceroldipalmitoyl); NAGO (neuraminidase-galactose oxidase); nanospheres or nanoparticles of any composition; NISVs (non-ionic surfactant vesicles); PLEURAN™ (β-glucan); PLGA, PGA and PLA (homo- and co-polymers of lactic acid and glycolic acid; microspheres/nanospheres); PLURONIC L121™; PMMA (polymethyl methacrylate); PODDS™ (proteinoid microspheres); polyethylene carbamate derivatives; poly-rA: poly-rU (polyadenylic acid-polyuridylic acid complex); polysorbate 80 (Tween 80); protein cochleates (Avanti Polar Lipids, Inc., Alabaster, Ala.); STIMULON™ (QS-21); Quil-A (Quil-A saponin); S-28463 (4-amino-otec-dimethyl-2-ethoxymethyl-1H-imidazo[4,5-c]quinoline-1-ethanol); SAF-1™ ("Syntex adjuvant formulation"); Sendai proteoliposomes and Sendai-containing lipid matrices; Span-85 (sorbitan trioleate); Specol (emulsion of Marcol 52, Span 85 and Tween 85); squalene or Robane® (2,6,10,15,19,23-hexamethyltetracosan and 2,6,10,15,19,23-hexamethyl-2,6,10,14,18,22-tetracosahexane); stearoyltyrosine (octadecyltyrosine hydrochloride); Theramid® (N-acetylglucosaminyl-N-acetylmuramyl-L-Ala-D-isoGlu-L-Ala-dipalmitoxypropylamide); Theronyl-MDP (Termurtide™ or [thr 1]-MDP; N-acetylmuramyl-L-threonyl-D-isoglutamine); Ty particles (Ty-VLPs or virus-like particles); Walter-Reed liposomes (liposomes containing lipid A adsorbed on aluminium hydroxide), and lipopeptides, including Pam3Cys, in particular aluminium salts, such as Adjuphos, Alhydrogel, Rehydragel; emulsions, including CFA, SAF, IFA, MF59, Provax, TiterMax, Montanide, Vaxfectin; copolymers, including Optivax (CRL1005), L121, Poloaxmer4010), etc.; liposomes, including Stealth, cochleates, including BIORAL; plant derived adjuvants, including QS21, Quil A, Iscomatrix, ISCOM; adjuvants suitable for costimulation including Tomatine, biopolymers, including PLG, PMM, Inulin; microbe derived adjuvants, including Romurtide, DETOX, MPL, CWS, Mannose, CpG nucleic acid sequences, CpG7909, ligands of human TLR 1-10, ligands of murine TLR 1-13, ISS-1018, IC31, Imidazoquinolines, Ampligen, Ribi529, IMOxine, IRIVs, VLPs, cholera toxin, heat-labile toxin, Pam3Cys, Flagellin, GPI anchor, LNFPIII/Lewis X, antimicrobial peptides, UC-1V150, RSV fusion protein, cdiGMP; and adjuvants suitable as antagonists including CGRP neuropeptide.

Suitable adjuvants may also be selected from cationic or polycationic compounds wherein the adjuvant is preferably prepared upon complexing the at least one RNA of the inventive active (immunostimulatory composition) with the cationic or polycationic compound. Association or complexing the RNA of the active (immunostimulatory) composition with cationic or polycationic compounds as defined herein preferably provides adjuvant properties and confers a stabilizing effect to the at least one RNA of the active (immunostimulatory) composition. Particularly such preferred, such cationic or polycationic compounds are selected from cationic or polycationic peptides or proteins, including protamine, nucleoline, spermin or spermidine, or other cationic peptides or proteins, such as poly-L-lysine (PLL), poly-arginine, basic polypeptides, cell penetrating peptides (CPPs), including HIV-binding peptides, Tat, HIV-1 Tat (HIV), Tat-derived peptides, Penetratin, VP22 derived or analog peptides, HSV VP22 (Herpes simplex), MAP, KALA or protein transduction domains (PTDs, PpT620, prolin-rich peptides, arginine-rich peptides, lysine-rich peptides, MPG-peptide(s), Pep-1, L-oligomers, Calcitonin peptide(s), Antennapedia-derived peptides (particularly from *Drosophila antennapedia*), pAntp, plsI, FGF, Lactoferrin, Transportan, Buforin-2, Bac715-24, SynB, SynB(1), pVEC, hCT-derived peptides, SAP, protamine, spermine, spermidine, or histones. Further preferred cationic or polycationic compounds may include cationic polysaccharides, for example chitosan, polybrene, cationic polymers, e.g. polyethyleneimine (PEI), cationic lipids, e.g. DOTMA: [1-(2,3-sioleyloxy)propyl)]-N,N,N-trimethylammonium chloride, DMRIE, di-C14-amidine, DOTIM, SAINT, DC-Chol, BGTC, CTAP, DOPC, DODAP, DOPE: Dioleyl phosphatidylethanolamine, DOSPA, DODAB, DOIC, DMEPC, DOGS: Dioctadecylamidoglicyl-spermin, DIMRI: Dimyristo-oxypropyl dimethyl hydroxyethyl ammonium bromide, DOTAP: dioleoyloxy-3-(trimethylammonio)propane, DC-6-14: O,O-ditetradecanoyl-N-α-trimethylammonioacetyl)diethanolamine chloride, CLIP1: rac-[(2,3-dioctadecyloxypropyl)(2-hydroxyethyl)]-dimethylammonium chloride, CLIP6: rac-[2(2,3-dihexadecyloxypropyl-oxymethyloxy)ethyl]trimethylammonium, CLIP9: rac-[2(2,3-dihexadecyloxypropyl-oxysuccinyloxy)ethyl]-trimethylammonium, oligofectamine, or cationic or polycationic polymers, e.g. modified polyaminoacids, such as β-aminoacid-polymers or reversed polyamides, etc., modified polyethylenes, such as PVP (poly(N-ethyl-4-vinylpyridinium bromide)), etc., modified acrylates, such as pDMAEMA (poly(dimethylaminoethyl methylacrylate)), etc., modified Amidoamines such as pAMAM (poly(amidoamine)), etc., modified polybetaaminoester (PBAE), such as diamine end modified 1,4 butanediol diacrylate-co-5-amino-1-pentanol polymers, etc., dendrimers, such as polypropylamine dendrimers or pAMAM based dendrimers, etc., polyimine(s), such as PEI: poly(ethyleneimine), poly (propyleneimine), etc., polyallylamine, sugar backbone based polymers, such as cyclodextrin based polymers, dextran based polymers, Chitosan, etc., silan backbone based polymers, such as PMOXA-PDMS copolymers, etc., Block-polymers consisting of a combination of one or more cationic blocks (e.g. selected of a cationic polymer as mentioned above) and of one or more hydrophilic- or hydrophobic blocks (e.g polyethyleneglycole); etc.

Additionally, preferred cationic or polycationic proteins or peptides, which can be used as an adjuvant by complexing the at least one RNA of the active (immunostimulatory) composition, may be selected from following proteins or peptides having the following total formula (I): (Arg)t (SEQ ID NO: 39);(Lys)m (SEQ ID NO: 40);(His)n (SEQ ID NO: 41);(Orn) o; (Xaa)x, wherein l+m+n+o+x=8-15, and l, m, n or o independently of each other may be any number selected from 0, 1 , 2, 3 4, 5, 6, 7, 8, 9, 10, 11 , 12, 13, 14 or 15, provided that the overall content of Arg, Lys, His and Orn represents at least 50% of all amino acids of the oligopeptide; and Xaa may he any amino acid selected from native (=naturally occurring) or non-native amino acids except of Arg, Lys, His or Orn; and x may be any number selected from 0, 1 , 2, 3 or 4, provided, that the overall content of Xaa does not exceed 50% of all amino acids of the oligopeptide. Particularly preferred oligoarginines in this context are e.g. $Arg_7$ (SEQ ID NO: 42), $Arg_8$(SEQ ID NO: 43), $Arg_9$(SEQ ID NO: 44), $Arg_7$(SEQ ID NO: 42), $H_3R_9$(SEQ ID NO: 45), $R_9 H_3$ (SEQ ID NO: 46 ), $H_3 R_9 H_3$ (SEQ ID NO: 47 ), $YSSR_9ssy$ (SEQ ID NO: 48), $(RKH)_4$ (SEQ ID NO: 49), $Y(RKJ)_2R$ (SEQ ID NO: 50), etc.

Suitable adjuvants may furthermore be selected from nucleic acids having the formula (II): $G_1X_mG_n$ (SEQ ID NO: 51), wherein: G is guanosine, uracil or an analogue of guanosine or uracil; X is guanosine, uracil, adenosine, thymidine, cytosine or an analogue of the above-mentioned nucleotides; 1 is an integer from 1 to 40, wherein when 1=1 G is guanosine or an analogue thereof, when 1>1 at least 50% of the nucleotides are guanosine or an analogue thereof; m is an integer and is at least 3; wherein when m=3 X is uracil or an analogue thereof, when m>3 at least 3 successive uracils or analogues of uracil occur; n is an integer from 1 to 40, wherein when n=1 G is guanosine or an analogue thereof, when n>1 at least 50% of the nucleotides are guanosine or an analogue thereof.

Other suitable adjuvants may furthermore be selected from nucleic acids having the formula (III): $C_1X_m C_n$(SEQ ID NO:52, wherein: C is cytosine, uracil or an analogue of cytosine or uracil; X is guanosine, uracil, adenosine, thymidine, cytosine or an analogue of the above-mentioned nucleotides; 1 is an integer from 1 to 40, wherein when 1 =1 C is cytosine or an analogue thereof, when 1 >1 at least 50% of the nucleotides are cytosine or an analogue thereof; m is an integer and is at least 3; wherein when m =3 X is uracil or an analogue thereof, when m >3 at least 3 successive uracils or analogues of uracil occur; a is an integer from 1 to 40, wherein when n =1 C is cytosine or an analogue thereof, when n >1 at least 50% of the nucleotides are cytosine or an analogue thereof.

According to one preferred embodiment, the present invention may furthermore provide a vaccine containing the active (immunostimulatory) composition according to the invention. The inventive vaccine may additionally contain a pharmaceutically acceptable carrier and/or further auxiliary substances and additives and/or adjuvants. According to a particularly preferred embodiment, the antigens encoded by the at least one RNA of the active (immunostimulatory) composition, contained in the inventive vaccine, are selected from the above mentioned groups or subgroups. According to an even more preferred embodiment, the protein antigens are selected from any of the antigens of the following subgroup comprising NY-ESO1 [accession number NM_0013271],

[hTERT laccession number NM_198253], survivin [accession number AF077350], 5T4 [accession number NM_006670] and WT1 [accession number NM_000378], and/or from any of the antigens of the following subgroup comprising MAGE-C1 and MAGE-C2, as defined herein, and/or from any of the antigens of the following subgroup comprising MAGE-A2 and MAGE-A3, as defined herein.

The inventive vaccine typically comprises a safe and effective amount of the at least one RNA of the active (immunostimulatory) composition as defined above encoding at least two antigens as defined above, more preferably encoding at least two antigens selected from any of the above groups or subgroups, most preferably in any of the indicated combinations. As used herein, "safe and effective amount" means an amount of the at least one RNA of the active (immunostimulatory) composition in the vaccine as defined above, that is sufficient to significantly induce a positive modification of lung cancer, preferably of a non-small-cell lung cancer (NSCLC) related condition to be treated, more preferably of conditions related to the three main sub-types of non-small-cell lung cancer (NSCLC) including, without being restricted thereto, squamous cell lung carcinoma, adenocarcinoma and large cell lung carcinoma. At the same time, however, a "safe and effective amount" is small enough to avoid serious side-effects, that is to say to permit a sensible relationship between advantage and risk. The determination of these limits typically lies within the scope of sensible medical judgment. In relation to the inventive vaccine, the expression "safe and effective amount" preferably means an amount of the RNA (and thus of the encoded at least two antigens) that is suitable for stimulating the adaptive immune system in such a manner that no excessive or damaging immune reactions are achieved but, preferably, also no such immune reactions below a measurable level. Such a "safe and effective amount" of the at least one RNA of the active (immunostimulatory) composition in the vaccine as defined above may furthermore be selected in dependence of the type of RNA, e.g. monocistronic, bi- or even multicistronic RNA, since a bi- or even multicistronic RNA may lead to a significantly higher expression of the encoded antigen(s) than use of an equal amount of a monocistronic RNA. A "safe and effective amount" of the at least one RNA of the active (immunostimulatory) composition as defined above, which is contained in the inventive vaccine, will furthermore vary in connection with the particular condition to be treated and also with the age and physical condition of the patient to be treated, the severity of the condition, the duration of the treatment, the nature of the accompanying therapy, of the particular pharmaceutically acceptable carrier used, and similar factors, within the knowledge and experience of the accompanying doctor. The vaccine according to the invention can be used according to the invention for human and also for veterinary medical purposes, as a pharmaceutical composition or as a vaccine.

The vaccine according to the invention typically contains a pharmaceutically acceptable carrier. The expression "pharmaceutically acceptable carrier" as used herein preferably includes the liquid or non-liquid basis of the inventive vaccine. If the inventive vaccine is provided in liquid form, the carrier will typically be pyrogen-free water; isotonic saline or buffered (aqueous) solutions, e.g. phosphate-, citrate-buffered solutions, etc. Particularly for injection of the inventive vaccine, water or preferably a buffer, more preferably an aqueous buffer, may be used, containing a sodium salt, preferably at least 50 mM of a sodium salt, a calcium salt, preferably at least 0.01 mM of a calcium salt, and optionally a potassium salt, preferably at least 3 mM of a potassium salt. According to a preferred embodiment, the sodium, calcium and, optionally, potassium salts may occur in the form of their halogenides, e.g. chlorides, iodides, or bromides, in the form of their hydroxides, carbonates, hydrogen carbonates, or sulfates, etc. Without being limited thereto, examples of sodium salts include e.g. NaCl, NaI, NaBr, $Na_2CO_3$, $NaHCO_3$, $Na_2SO_4$, examples of the optional potassium salts include e.g. KCl, KI, KBr, $K_2CO_3$, $KHCO_3$, $K_2SO_4$, and examples of calcium salts include e.g. $CaCl_2$, $CaI_2$, $CaBr_2$, $CaCO_3$, $CaSO_4$, $Ca(OH)_2$. Furthermore, organic anions of the aforementioned cations may be contained in the buffer. According to a more preferred embodiment, the buffer suitable for injection purposes as defined above, may contain salts selected from sodium chloride (NaCl), calcium chloride ($CaC_2$) and optionally potassium chloride (KCl), wherein further anions may be present additional to the chlorides. $CaCl_2$ can also be replaced by another salt like KCl. Typically, the salts in the injection buffer are present in a concentration of at least 50 mM sodium chloride (NaCl), at least 3 mM potassium chloride (KCl) and at least 0.01 mM calcium chloride ($CaCl_2$). The injection buffer may be hypertonic, isotonic or hypotonic with reference to the specific reference medium, i.e. the buffer may have a higher, identical or lower salt content with reference to the specific reference medium, wherein preferably such concentrations of the aforementioned salts may be used, which do not lead to damage of cells due to osmosis or other concentration effects. Reference media are e.g. in "in vivo" methods occurring liquids such as blood, lymph, cytosolic liquids, or other body liquids, or e.g. liquids, which may be used as reference media in "in vitro" methods, such as common buffers or liquids. Such common buffers or liquids are known to a skilled person. Ringer-Lactate solution is particularly preferred as a liquid basis.

However, one or more compatible solid or liquid fillers or diluents or encapsulating compounds may be used as well, which are suitable for administration to a person. The term "compatible" as used herein means that the constituents of the inventive vaccine are capable of being mixed with the at least one RNA of the active (immunostimulatory) composition, encoding at least two antigens as defined above, in such a manner that no interaction occurs which would substantially reduce the pharmaceutical effectiveness of the inventive vaccine under typical use conditions. Pharmaceutically acceptable carriers, fillers and diluents must, of course, have sufficiently high purity and sufficiently low toxicity to make them suitable for administration to a person to be treated. Some examples of compounds which can be used as pharmaceutically acceptable carriers, fillers or constituents thereof are sugars, such as, for example, lactose, glucose and sucrose; starches, such as, for example, corn starch or potato starch; cellulose and its derivatives, such as, for example, sodium carboxymethylcellulose, ethylcellulose, cellulose acetate; powdered tragacanth; malt; gelatin; tallow; solid glidants, such as, for example, stearic acid, magnesium stearate; calcium sulfate; vegetable oils, such as, for example, groundnut oil, cottonseed oil, sesame oil, olive oil, corn oil and oil from theobroma; polyols, such as, for example, polypropylene glycol, glycerol, sorbitol, mannitol and polyethylene glycol; alginic acid.

The choice of a pharmaceutically acceptable carrier is determined in principle by the manner in which the inventive vaccine is administered. The inventive vaccine can be administered, for example, systemically or locally. Routes for systemic administration in general include, for example, transdermal, oral, parenteral routes, including subcutaneous, intravenous, intramuscular, intraarterial, intradermal and intraperitoneal injections and/or intranasal administration routes. Routes for local administration in general include, for example, topical administration routes but also intradermal, transdermal, subcutaneous, or intramuscular injections or intralesional, intracranial, intrapulmonal, intracardial, or sublingual injections. More preferably, vaccines may be administered by an intradermal, subcutaneous, or intramuscular route. Compositions/vaccines are therefore preferably formulated in liquid or solid form. The suitable amount of the inventive vaccine to be administered can be determined by routine experiments with animal models. Such models include, without implying any limitation, rabbit, sheep, mouse, rat, dog and non-human primate models. Preferred unit dose forms for injection include sterile solutions of water, physiological saline or mixtures thereof. The pH of such solutions should be adjusted to about 7.4. Suitable carriers for injection include hydrogels, devices for controlled or delayed release, polylactic acid and collagen matrices. Suitable pharmaceutically acceptable carriers for topical application include those which are suitable for use in lotions, creams, gels and the like. If the inventive vaccine is to be administered perorally, tablets, capsules and the like are the preferred unit dose form. The pharmaceutically acceptable carriers for the preparation of unit dose forms which can be used for oral administration are well known in the prior art. The choice thereof will depend on secondary considerations such as taste, costs and storability, which are not critical for the purposes of the present invention, and can be made without difficulty by a person skilled in the art.

The inventive vaccine can additionally contain one or more auxiliary substances in order to further increase the immunogenicity. A synergistic action of the at least one RNA of the active (immunostimulatory) composition as defined above and of an auxiliary substance, which may be optionally also contained in the inventive vaccine as described above, is preferably achieved thereby. Depending on the various types of auxiliary substances, various mechanisms can come into consideration in this respect. For example, compounds that permit the maturation of dendritic cells (DCs), for example lipopolysaccharides, TNF-alpha or CD40 ligand, form a first class of suitable auxiliary substances. In general, it is possible to use as auxiliary substance any agent that influences the immune system in the manner of a "danger signal" (LPS, GP96, etc.) or cytokines, such as GM-CFS, which allow an immune response produced by the immune-stimulating adjuvant according to the invention to be enhanced and/or influenced in a targeted manner. Particularly preferred auxiliary substances are cytokines, such as monokines, lymphokines, interleukins or chemokines, that—additional to induction of the adaptive immune response by the encoded at least two antigens—promote the innate immune response, such as IL-1, IL-2, IL-3, IL-4, IL-5, IL-6, IL-7, IL-8, IL-9, IL-10, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, INF-alpha, IFN-beta, INF-gamma, GM-CSF, G-CSF, M-CSF, LT-beta or TNF-alpha, growth factors, such as hGH.

Further additives which may be included in the inventive vaccine are emulsifiers, such as, for example, Tween®; wetting agents, such as, for example, sodium lauryl sulfate; colouring agents; taste-imparting agents, pharmaceutical carriers; tablet-forming agents; stabilizers; antioxidants; preservatives.

The inventive vaccine can also additionally contain any further compound, which is known to be immune-stimulating due to its binding affinity (as ligands) to human Toll-like receptors TLR1, TLR2, TLR3, TLR4, TLR5, TLR6, TLR7, TLR8, TLR9, TLR10, or due to its binding affinity (as ligands) to murine Toll-like receptors TLR1, TLR2, TLR3, TLR4, TLR5, TLR6, TLR7, TLR8, TLR9, TLR10, TLR11, TLR12 or TLR13.

Another class of compounds, which may be added to an inventive vaccine in this context, may be CpG nucleic acids, in particular CpG-RNA or CpG-DNA. A CpG-RNA or CpG-DNA can be a single-stranded CpG-DNA (ss CpG-DNA), a double-stranded CpG-DNA (dsDNA), a single-stranded CpG-RNA (ss CpG-RNA) or a double-stranded CpG-RNA (ds CpG-RNA). The CpG nucleic acid is preferably in the form of CpG-RNA, more preferably in the form of single-stranded CpG-RNA (ss CpG-RNA). The CpG nucleic acid preferably contains at least one or more (mitogenic) cytosine/guanine dinucleotide sequence(s) (CpG motif(s)). According to a first preferred alternative, at least one CpG motif contained in these sequences, that is to say the C (cytosine) and the G (guanine) of the CpG motif, is unmethylated. All further cytosines or guanines optionally contained in these sequences can be either methylated or unmethylated. According to a further preferred alternative, however, the C (cytosine) and the G (guanine) of the CpG motif can also be present in methylated form.

According to a further preferred object of the present invention, the inventive active (immunostimulatory) composition or the at least one RNA encoding at least two (preferably) different antigens as defined herein, may be used (for the preparation of a vaccine according to the present invention) for the treatment of lung cancer, preferably of a non-small-cell lung cancer (NSCLC) related condition, more preferably of conditions related to the three main sub-types of non-small-cell lung cancer (NSCLC) including, without being restricted thereto, squamous cell lung carcinoma, adenocarcinoma and large cell lung carcinoma.

According to a further preferred object of the present invention, the inventive vaccine or the at least one RNA encoding at least two (preferably) different antigens as defined herein may be used for the treatment of lung cancer, preferably of a non-small-cell lung cancer (NSCLC) related condition, more preferably of conditions related to the three main sub-types of non-small-cell lung cancer (NSCLC) including, without being restricted thereto, squamous cell lung carcinoma, adenocarcinoma and large cell lung carcinoma.

In this context also included in the present invention are methods of treating lung cancer, preferably of a non-small-cell lung cancer (NSCLC) related condition, more preferably of conditions related to the three main sub-types of non-small-cell lung cancer (NSCLC) including, without being restricted thereto, squamous cell lung carcinoma, adenocarcinoma and large cell lung carcinoma, by administering to a patient in need thereof a pharmaceutically effective amount of an inventive vaccine, or a pharmaceutically effective amount of an inventive active (immunostimulatory) composition. Such a method typically comprises an optional first step of preparing the inventive active (immunostimulatory) composition, or the inventive vaccine, and a second step, comprising administering (a pharmaceutically effective amount of) said inventive active (immunostimulatory) composition or said inventive vaccine to a patient in need thereof. A patient in need thereof will be typically selected from any mammal. In the context of the present invention, a mammal is preferably selected from the group comprising, without being limited thereto, e.g. goat, cattle, swine, dog, cat, donkey, monkey, ape, a rodent such as a mouse, hamster, rabbit and, particularly, human, wherein the mammal typically suffers from lung cancer, preferably of a non-small-cell lung cancer (NSCLC) related condition, more preferably of conditions related to the three main sub-types of non-small-cell lung cancer (NSCLC) including, without being restricted thereto, squamous cell lung carcinoma, adenocarcinoma and large cell lung carcinoma or a condition related thereto.

The invention relates also to the use of the inventive active (immunostimulatory) composition or the at least one RNA encoding at least two (preferably) different antigens as defined herein (for the preparation of an inventive vaccine), preferably for eliciting an immune response in a mammal, preferably for the treatment of lung cancer, more preferably for the treatment of a non-small-cell lung cancer (NSCLC) related condition as defined herein.

Similarly, the invention also relates also to the use of the inventive vaccine per se or the at least one RNA encoding at least two (preferably) different antigens as defined herein for eliciting an adaptive immune response in a mammal, preferably for the treatment of lung cancer, more preferably of a non-small-cell lung cancer (NSCLC) related condition as defined herein.

Prevention or treatment of lung cancer in a patient in need thereof, preferably of a non-small-cell lung cancer (NSCLC) related condition as defined herein, may be carried out by administering the inventive active (immunostimulatory) composition and/or the inventive vaccine at once or in a time staggered manner, e.g. as a kit of parts, each part containing at least one preferably different antigen. For administration, preferably any of the administration mutes may be used as defined above. E.g., one may treat lung cancer, preferably a non-small-cell lung cancer (NSCLC) related condition as defined herein, by inducing or enhancing an adaptive immune response on the basis of at least two (specifically selected) antigens encoded by the at least one RNA of the inventive active (immunostimulatory) composition. Administering of the inventive active (immunostimulatory) composition and/or the inventive vaccine may then occur prior, concurrent and/or subsequent to administering another inventive active (immunostimulatory) composition and/or inventive vaccine as defined herein which may contain another combination of RNAs encoding different antigens, wherein each antigen encoded by the at least one RNA of the inventive active (immunostimulatory) composition may preferably be suitable for the therapy of lung cancer, more preferably for the treatment of a non-small-cell lung cancer (NSCLC) related condition as defined herein. In this context, a therapy as defined herein may also comprise the modulation of a disease associated to lung cancer, preferably a disease associated to non-small-cell lung cancer (NSCLC) as defined herein.

According to one further embodiment, the present invention furthermore comprises the use of the active (immunostimulatory) composition (for the preparation of an (inventive) vaccine) for modulating, preferably to induce or enhance, an immune response in a mammal as defined above, more preferably to support the treatment of lung cancer, especially NSCLC as defined herein. In this context, support of the treatment of lung cancer, especially NSCLC as defined herein, may be any combination of a conventional cancer therapy for lung cancer, especially for NSCLC as defined herein, such as radiation therapy, chemotherapy, proton therapy, hormonal therapy, antibody therapy, adjuvant therapies, therapies including other vaccines than an inventive vaccine, therapies including kinase inhibitors or small nucleotides, etc., or some combination of these, and a therapy using the inventive active (immunostimulatory) composition or the inventive vaccine as defined herein. Support of the treatment of lung cancer, especially NSCLC as defined herein, may be also envisaged in any of the other embodiments defined herein.

Administration of the inventive active (immunostimulatory) composition or the at least one RNA encoding at least two (preferably) different antigens as defined herein or the inventive vaccine may be carried out in a time staggered treatment. A time staggered treatment may be e.g. administration of the inventive active (immunostimulatory) composition or the at least one RNA encoding at least two (preferably) different antigens as defined herein or the inventive vaccine prior, concurrent and/or subsequent to a therapy of lung cancer, especially NSCLC, e.g. by administration of the inventive active (immunostimulatory) composition or vaccine prior, concurrent and/or subsequent to a therapy or an administration of a therapeutic suitable for the treatment of lung cancer, especially of NSCLC as defined herein. Such time staggered treatment may be carried out using e.g. a kit, preferably a kit of parts as defined below.

Time staggered treatment may additionally or alternatively also comprise an administration of the inventive active (immunostimulatory) composition or vaccine, preferably of the at least one RNA encoding at least two (preferably different) antigens as defined above, in a form, wherein the at least one RNA encoding at least two (preferably different) antigens as defined above, preferably forming part of the inventive active (immunostimulatory) composition or vaccine, is administered parallel, prior or subsequent to another at least one RNA encoding at least two (preferably different) antigens as defined above, preferably forming part of the same inventive active (immunostimulatory) composition or vaccine. Preferably, the administration (of all at least one RNAs) occurs within an hour, more preferably within 30 minutes, even more preferably within 15, 10, 5, 4, 3, or 2 minutes or even within 1 minute. Such time staggered treatment may be carried out using e.g. a kit, preferably a kit of parts as defined below.

According to a final embodiment, the present invention also provides kits, particularly kits of parts, comprising the active inventive (immunostimulatory) composition, and/or the inventive vaccine, and optionally technical instructions with information on the administration and dosage of the inventive active (immunostimulatory) composition and/or the inventive vaccine. The technical instructions may contain information about administration and dosage of the inventive active (immunostimulatory) composition, and/or the inventive vaccine. Such kits, preferably kits of parts, may applied e.g. for any of the above mentioned applications or uses, preferably for the use of at least one inventive active (immunostimulatory) composition (for the preparation of an inventive vaccine) for the treatment of lung cancer, especially of NSCLC as defined herein. The kits may also be applied for the use of at least one inventive active (immunostimulatory) composition (for the preparation of an inventive vaccine) for the treatment of lung cancer, preferably NSCLC as defined herein, wherein the inventive active (immunostimulatory) composition) and/or the vaccine due to the encoded at least two antigens may be capable to induce or enhance an immune response in a mammal as defined above. Such kits may further be applied for the use of at least one inventive active (immunostimulatory) composition, (for the preparation of an inventive vaccine) for modulating, preferably for eliciting, e.g. to induce or enhance, an immune response in a mammal as defined above, and preferably to support treatment of lung cancer, especially of NSCLC. Kits of parts, as a special form of kits, may contain one or more identical or different active inventive (immunostimulatory) compositions and/or one or more identical or different inventive vaccines in different parts of the kit. Kits of parts may also contain an (e.g. one) active inventive (immunostimulatory) composition, an (e.g. one) inventive vaccine and/or the at least one RNA encoding at least one antigen as defined above in different parts of the kit, e.g. each part of the kit containing at least one RNA encoding a preferably different antigen. Additionally, a combination of both types of kits of parts is possible. Kits of parts may be used, e.g. when a time staggered treatment is envisaged, e.g. when using different formulations and/or increasing concentrations of the active inventive (immunostimulatory) composition, the inventive vaccine and/or the at least one RNA encoding at least one antigens as defined above during the same treatment in vivo. Kits of parts may also be used when a separated formulation or administration of the different antigens of the inventive active (immunostimulatory) composition (i.e. in parts) is envisaged or necessary (e.g. for technical reasons), but e.g. a combined presence of the different antigens in vivo is still to be achieved. Particularly kits of parts as a special form of kits are envisaged, wherein each part of the kit contains at least one preferably different antigen as defined above, all parts of the kit of parts preferably forming the active inventive (immunostimulatory) composition or the inventive vaccine as defined herein. Such specific kits of parts may particularly be suitable, e.g. if different antigens are formulated separately as different parts of the kits, but are then administered at once together or in a time staggered manner to the mammal in need thereof. In the latter case administration of all of the different parts of such a kit typically occurs within a short time limit, such that all antigens are present in the mammal at about the same time subsequent to administration of the last part of the kit. Any of the above kits may be used in a treatment as defined above.

ADVANTAGES OF THE PRESENT INVENTION

The present invention provides an active (immunostimulatory) composition for the treatment of lung cancer, particularly of non-small lung cancer (NSCLC), wherein the composition comprises at least one RNA, preferably a mRNA, encoding at least two (preferably different) antigens capable of eliciting an (adaptive) immune response in a mammal wherein the antigens are selected from the group consisting of hTERT, WT1, MAGE-A2, 5T4, MAGE-A3, MUC1, Her-2/neu, NY-ESO-1, CEA, Survivin, MAGE-C1, or MAGE-C2. Such an active (immunostimulatory) composition allows efficient treatment of lung cancer, particularly of non-small lung cancer (NSCLC), or supplementary treatment when using conventional therapies. It furthermore avoids the problem of uncontrolled propagation of the introduced DNA sequences by the use of RNA as an approach for curative methods. RNA as used in the inventive active (immunostimulatory) composition has additional considerable advantages over DNA expression systems e.g. in immune response, immunization or vaccination. These advantages include, infer alia, that RNA introduced into a cell is not integrated into the genome. This avoids the risk of mutation of this gene, which otherwise may be completely or partially inactivated or give rise to misinformation. It further avoids other risks of using DNA as an agent to induce an immune response (e.g. as a vaccine) such as the induction of pathogenic anti-DNA antibodies in the patient into whom the foreign DNA has been introduced, so bringing about a (possibly fatal) immune response. In contrast, no anti-RNA antibodies have yet been detected.

FIGURES

The following Figures are intended to illustrate the invention further. They are not intended to limit the subject matter of the invention thereto.

FIG. 1: depicts a RNA sequence (SEQ ID NO: 1) (starting sequence based on the wildtype) encoding MUC1 (HsMUC1-5×VNTR (The wildtype sequence normally shows 40 tandem repeats. These were—for cloning reasons—reduced to 5 tandem repeats). GC content: 61.27%; length: 1668 bp).

FIG. 2: depicts a (GC) stabilized RNA sequence (SEQ ID NO: 2) encoding MUC1 (HsMUC1 GC-5×VNTR, 1. GC maximized, 2. Codon usage) GC content: 73.56%; length 1668 bp. Difference to basic sequence (FIG. 1 (SEQ ID NO: 1)): 398/1668 bases=23.86%.

FIG. 3: depicts a RNA sequence (SEQ ID NO: 3) (starting sequence based on the wildtype) encoding 5T4 (Hs5T4 (trophoblast glycoprotein TPBG); GC content: 61.60%; length: 1263 bp.

FIG. 4: depicts a (GC) stabilized RNA sequence (SEQ ID NO: 4) encoding 5T4 (Hs5T4 GC, 1. GC-maximized, 2. Codon usage); GC content: 70.47%; length 1263 bp. Difference to basic sequence (FIG. 3 (SEQ ID NO: 3)): 247/1263 Bases=19.56%.

FIG. 5: depicts a RNA sequence (SEQ ID NO: 5) (starting sequence based on the wildtype) encoding Her-2/neu (HsHer2/neu (v-erb-b2 erythroblastic leukemia viral oncogene homolog 2)); GC content: 60.78%; length: 3768 bp.

FIG. 6: depicts a (GC) stabilized RNA sequence (SEQ ID NO: 6) encoding Her-2/neu (HsHer2/neu GC, 1. GC-maximized, 2. Codon usage); GC content: 70.54%; length 3768 bp. Difference to basic sequence (FIG. 5 (SEQ ID NO: 5)): 772/3768 Bases=20.49%.

FIG. 7: depicts a RNA sequence (SEQ ID NO: 7) (starting sequence based on the wildtype) encoding hTERT (HsTERT (telomerase reverse transcriptase); GC Content: 66.08%; Length: 3399 bp.

FIG. 8: depicts a (GC) stabilized RNA sequence (SEQ ID NO: 8) encoding hTERT (HsTERT GC, 1. GC-maximized, 2. Codon usage); GC Content: 72.96%; Length 3399 bp, Difference to basic sequence (FIG. 7 (SEQ ID NO: 7)): 566/3399 Bases=16.65%.

FIG. 9: depicts a RNA sequence (SEQ ID NO: 9) (starting sequence based on the wildtype) encoding WT1 (HsWT1 (Wilms tumor 1)); GC Content: 61.78%; Length: 1554 bp.

FIG. 10: FIG. 10 A) depicts a RNA sequence (SEQ ID NO: 10) encoding WT1 (HsWT1 (Wilms tumor 1)) showing a sequence with a reduced GC content in region 325-408 of said sequence compared to the corresponding region of the wildtype sequence.

FIGS. 10 B), C) and D) show a comparison of the corresponding regions 325-408:
 in B) the wildtype sequence according to FIG. 9 (SEQ ID NO: 53),
 in C) the GC-maximized sequence according to FIG. 11 (SEQ ID NOS 54 and 55, respectively, in order of appearance), and
 in D) the GC-reduced sequence according to FIG. 10 (SEQ ID NOS 56 and 57, respectively, in order of appearance), which all show a different GC-pattern.

FIG. 11: depicts a (GC) stabilized RNA sequence (SEQ ID NO: 11) encoding WT1 (HsWT1 GC, 1. GC-maximized, 2. Codon usage); GC Content: 72.59%; Length 1554 bp. Difference to basic sequence (FIG. 9 (SEQ ID NO: 9)): 322/1554 Bases=20.72%.

FIG. 12: depicts a RNA sequence (SEQ ID NO: 12) (starting sequence based on the wildtype) encoding CEA (CEA (carcinoembryonic antigen) HsCEACAM5); GC Content: 52.20%; Length: 2109 bp.

FIG. 13: depicts a (GC) stabilized RNA sequence (SEQ ID NO: 13) encoding CEA (CEACAM5 GC, 1. GC-maximized, 2. Codon usage, already in place); GC Content: 66.24%;

Length 2109 bp. Difference to basic sequence (FIG. 12 (SEQ ID NO: 12)): 495/2109 Bases=23.47%.

FIG. 14: depicts a RNA sequence (SEQ ID NO: 14) (starting sequence based on the wildtype) encoding MAGE-A2 (HsMAGE-A2 (melanoma antigen family A, 2) HsMAGE-A2B). GC Content: 55.87%; Length: 945 bp.

FIG. 15: depicts a (GC) stabilized RNA sequence (SEQ ID NO: 15) encoding MAGE-A2 (HsMAGE-A2B GC, 1. GC-maximized, 2. Codon usage); GC Content: 68.57%; Length 945 bp. Difference to basic sequence (FIG. 14 (SEQ ID NO: 14)): 187/945 Bases=19.79%.

FIG. 16: depicts a RNA sequence (SEQ ID NO: 16) (starting sequence based on the wildtype) encoding MAGE-A3 (MAGE-A3 (melanoma antigen family A, 3) MAGE-A3) GC Content: 56.30%; Length: 945 bp.

FIG. 17: depicts a (GC) stabilized RNA sequence (SEQ ID NO: 17) encoding MAGE-A3 (MAGE-A3 GC, 1. GC-maximized, 2. Codon usage, already known GC-Enrichment); GC Content: 69.00%; Length 945 bp. Difference to basic sequence (FIG. 16 (SEQ ID NO: 16)): 190/945 Bases=20.11%.

FIG. 18: depicts a RNA sequence (SEQ ID NO: 18) (starting sequence based on the wildtype) encoding Survivin (Survivin (baculoviral IAP repeat-containing 5, BIRC5) HsSurvivin(wt)); GC Content: 52.68%; Length: 429 bp.

FIG. 19: depicts a (GC) stabilized RNA sequence (SEQ ID NO: 19) encoding Survivin (HsSurvivin(GC), 1. GC-maximized, 2. Codon Usage, already known GC-Enrichment); GC Content: 65.27%; Length: 429 bp. Difference to basic sequence (FIG. 18 (SEQ ID NO: 18)): 72/429 Bases=16.78%.

FIG. 20: depicts a RNA sequence (SEQ ID NO: 20) (starting sequence based on the wildtype) encoding NY-ESO-1 (*Homo sapiens* NY-ESO-1 (NY-ESO-1 (wt)); GC-Content 67.4%.

FIG. 21: depicts a (GC) stabilized RNA sequence (SEQ ID NO: 21) encoding NY-ESO-1 (NY-ESO-1 (GC), GC-Content 79.56%, (already known GC-Enrichment); Difference to wt (FIG. 20 (SEQ ID NO: 20)): 112/543 Bases, 20.63%.

FIG. 22: depicts a RNA sequence (SEQ ID NO: 22) (starting sequence based on the wildtype) encoding MAGE-C1 (HsMAGEC1 (melanoma antigen family C, 1) HsMAGEC1 (wt)) GC Content: 51.86%; Length: 3429 bp.

FIG. 23: depicts a (GC) stabilized RNA sequence (SEQ ID NO: 23) encoding MAGE-C1 (HsMAGEC1 (GC), 1. GC-maximized, 2. Codon usage). GC Content: 68.73%; Length 3429 bp. Difference to basic sequence (FIG. 22 (SEQ ID NO: 22)): 964/3429 Bases=28.11%

FIG. 24: depicts a (GC) stabilized RNA sequence (SEQ ID NO: 24) encoding a truncated MAGE-C1 (HsMAGEC1 (GC), 1. GC-maximized, 2. Codon usage). In comparison to the basic sequence (FIG. 22 (SEQ ID NO: 22)) the repeat regions were deleted and the sequence according to FIG. 24, following an initial start codon (ATG), starts at aa 613 of the GC-maximized wildtype sequence (FIG. 23 (SEQ ID NO: 23)).

FIG. 25: depicts a RNA sequence (SEQ ID NO: 25) (starting sequence based on the wildtype) encoding MAGE-C2 (HsMAGE-C2 (melanoma antigen family C, 2)HsMAGE-C2); GC Content: 50.81%; Length: 1122 bp.

FIG. 26: depicts a (GC) stabilized RNA sequence (SEQ ID NO: 26) encoding MAGE-C2 (HsMAGE-C2 GC, 1. GC-maximized, 2. Codon usage; GC Content: 66.58%; Length 1122 bp, Difference to basic sequence (FIG. 25 (SEQ ID NO: 25)): 264/1122 Bases=23.53%.

FIG. 27 shows the presence of IgG1 antibodies specific for the tumour antigen NY-ESO-1 in mice which were vaccinated with the mRNA vaccine consisting of components, each containing mRNA coding for one NSCLC related antigen (NY-ESO-1, MAGE-C1, MAGE-C2, Survivin and 5T4) formulated with protamine at a mass ratio of 4:1.

Figure 28:
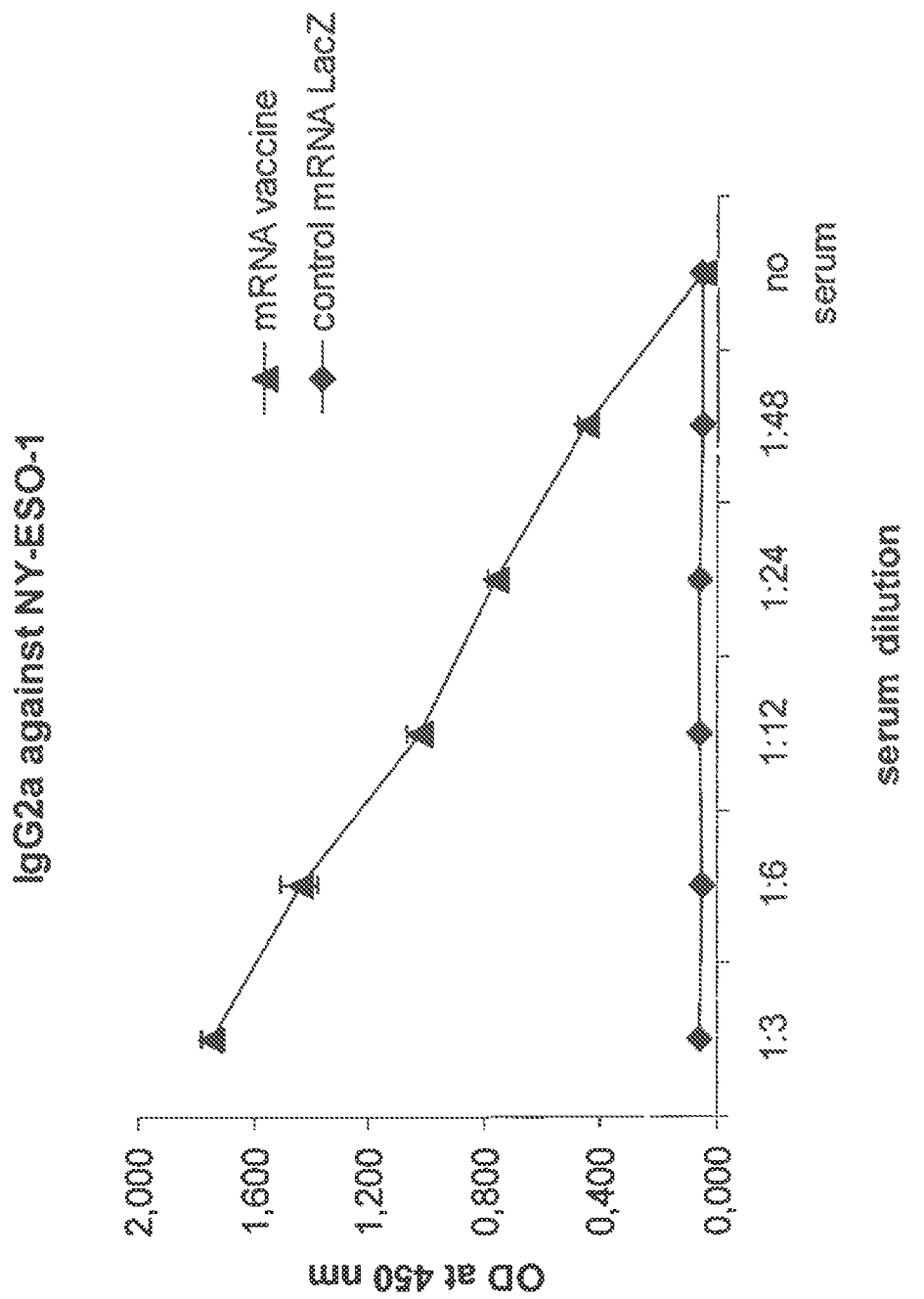

FIG. 28: shows the presence of IgG2a antibodies specific for the tumour antigen NY-ESO-1 in mice which were vaccinated with the mRNA vaccine consisting of components, each containing mRNA coding for one NSCLC related antigen (NY-ESO-1, MAGE-C1, MAGE-C2, Survivin and 5T4) formulated with protamine at a mass ratio of 4:1.

Figure 29:
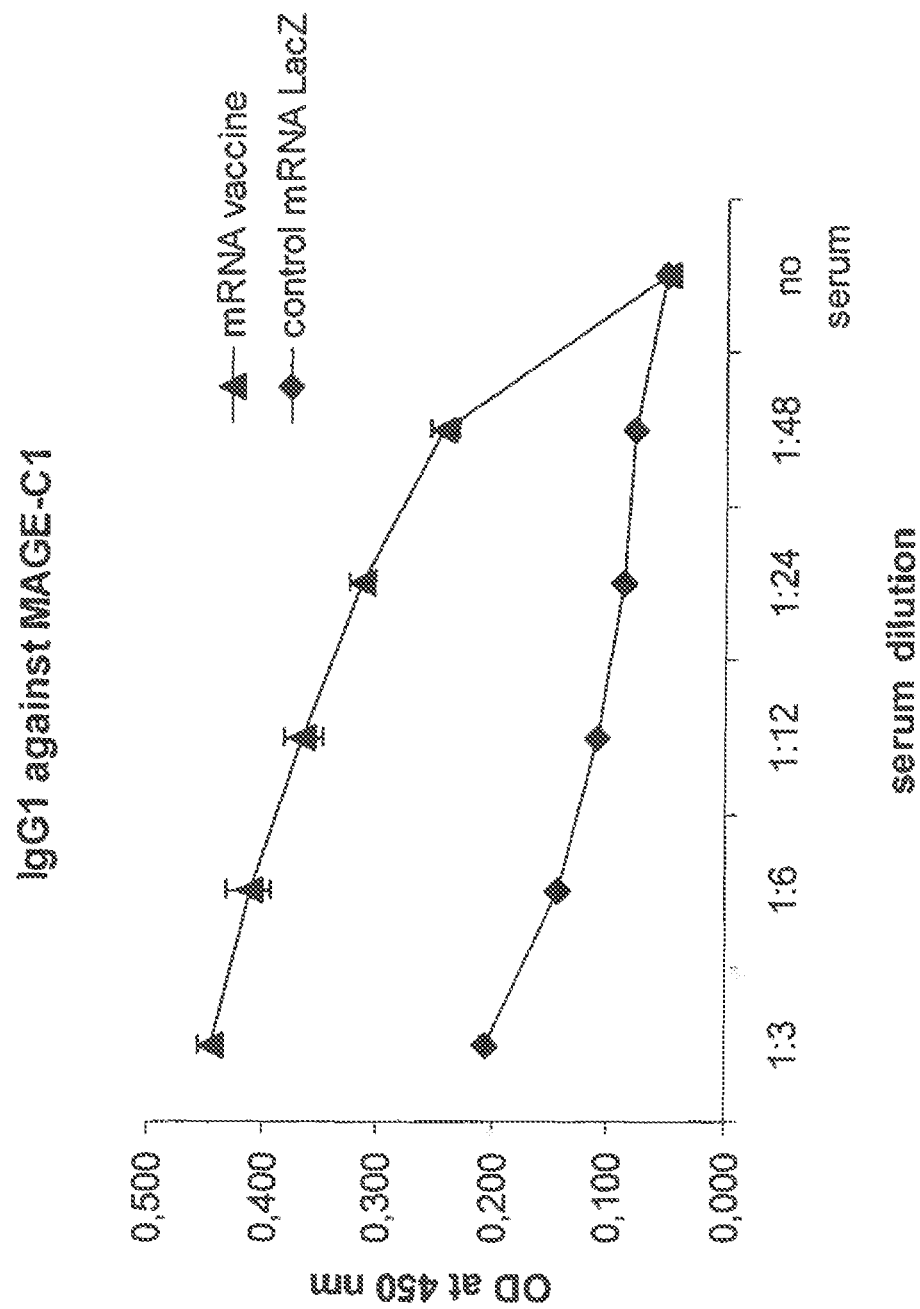

FIG. 29: shows the presence of IgG1 antibodies specific for the tumour antigen MAGE-C1 in mice which were vaccinated with the mRNA vaccine consisting of 5 components, each containing mRNA coding for one NSCLC related antigen (NY-ESO-1, MAGE-C1, MAGE-C2, Survivin and 5T4) formulated with protamine at a mass ratio of 4:1.

Figure 30:
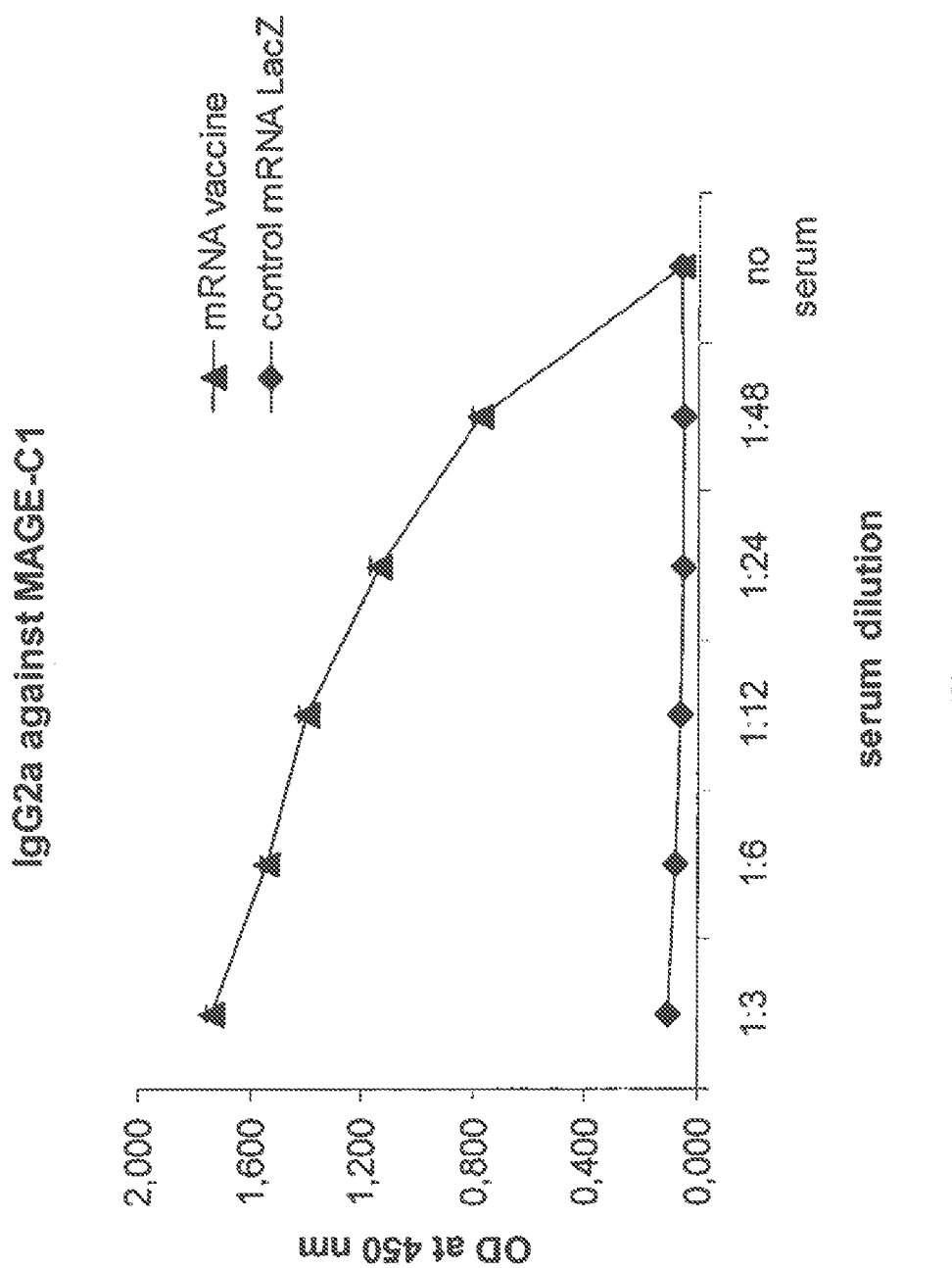

FIG. 30: shows the presence of IgG2a antibodies specific for the tumour antigen MAGE-C1 in mice which were vaccinated with the mRNA vaccine consisting of 5 components, each containing mRNA coding for one NSCLC related antigen (NY-ESO-1, MAGE-C1, MAGE-C2, Survivin and 5T4) formulated with protamine at a mass ratio of 4:1.

Figure 31:
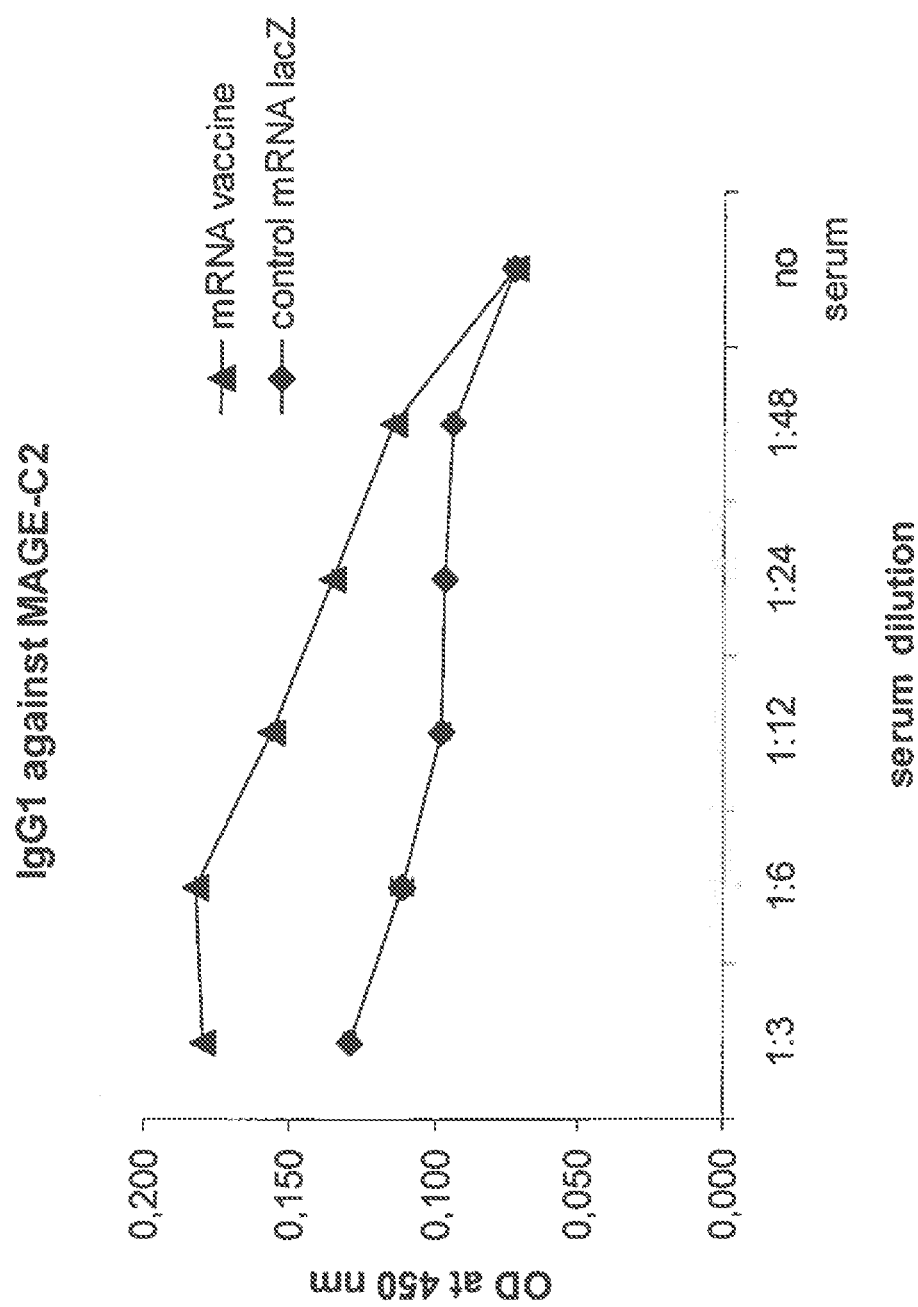

FIG. 31 shows the presence of IgG1 antibodies specific for the tumour antigen MAGE-C2 in mice which were vaccinated with the mRNA vaccine consisting of 5 components, each containing mRNA coding for one NSCLC related antigen (NY-ESO-1, MAGE-C1, MAGE-C2. Survivin and 5T4) formulated with protamine at a mass ratio of 4:1.

Figure 32:
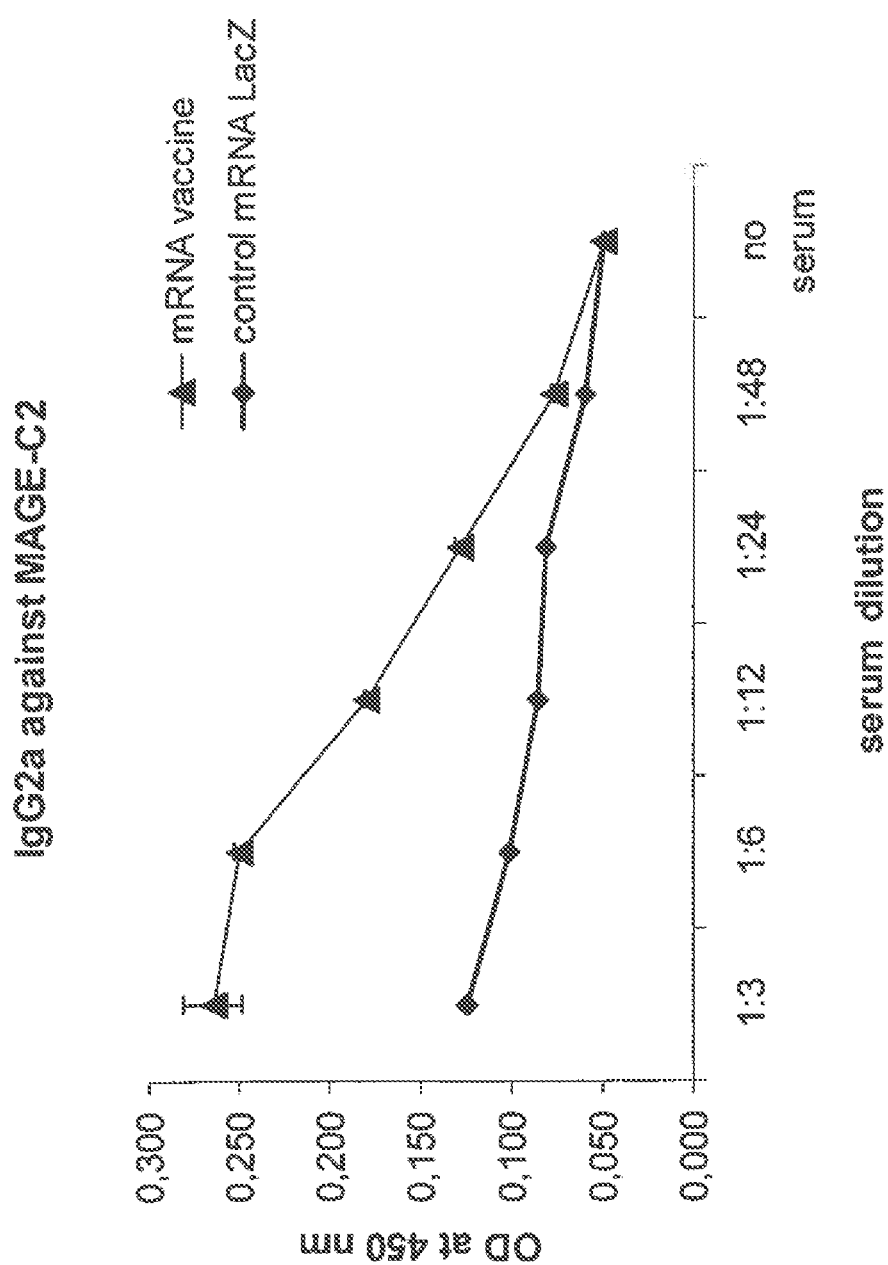

FIG. 32: shows the presence of IgG2a antibodies specific for the tumour antigen MAGE-C2 in mice which were vaccinated with the mRNA vaccine consisting of 5 components, each containing mRNA coding for one NSCLC related antigen (NY-ESO-1, MAGE-C1, MAGE-C2, Survivin and 5T4) formulated with protamine at a mass ratio of 4:1.

Figure 33:
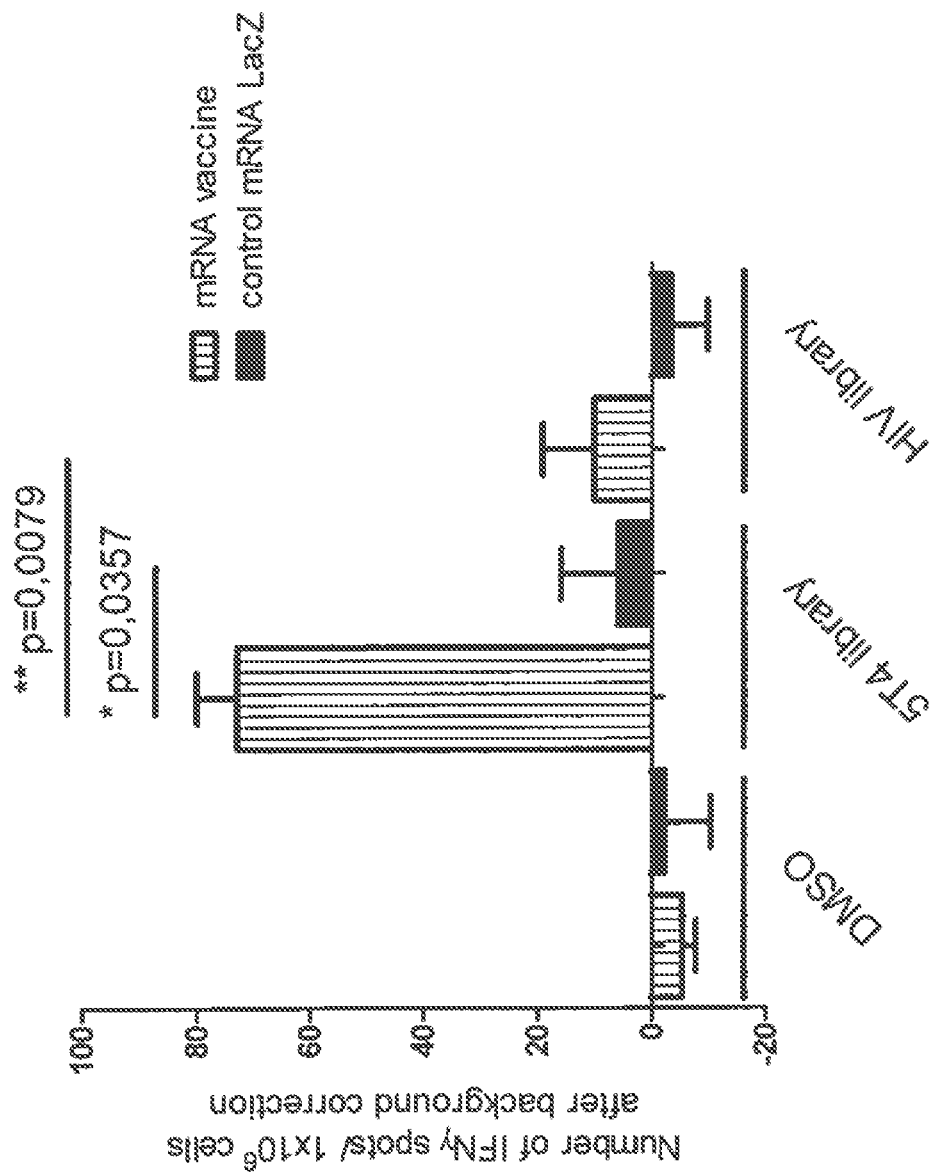

FIG. 33: shows the induction of antigen-specific T-lymphocytes directed against the tumour antigen 5T4 in mice which were vaccinated with the mRNA vaccine consisting of 5 components, each containing mRNA coding for one NSCLC related antigen (NY-ESO-1, MAGE-C1, MAGE-C2, Survivin and 5T4) formulated with protamine at a mass ratio of 4:1.

Figure 34:
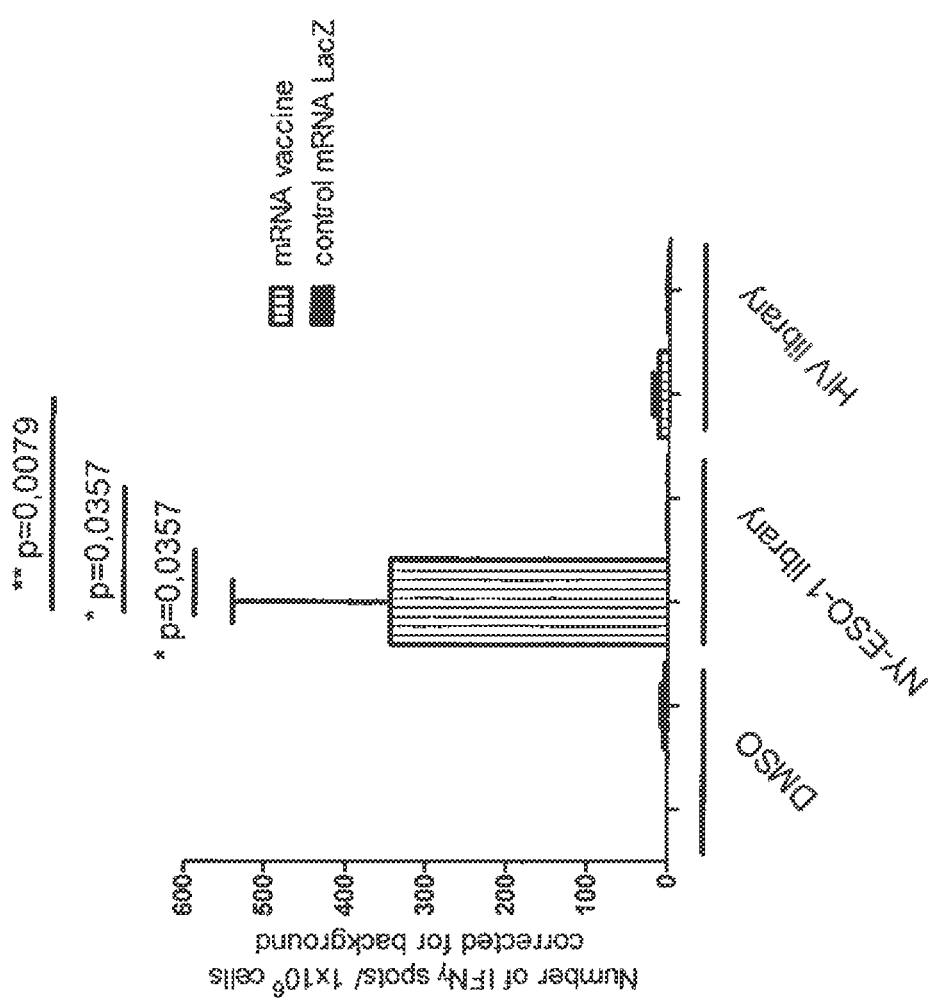

FIG. 34: shows the induction of antigen-specific T-lymphocytes directed against the tumour antigen NY-ESO-1 in mice which were vaccinated with the mRNA vaccine consisting of 5 components, each containing mRNA coding for one NSCLC related antigen (NY-ESO-1, MAGE-C1. MAGE-C2, Survivin and 5T4) formulated with protamine at a mass ratio of 4:1.

EXAMPLES

The following examples are intended to illustrate the invention further. They are not intended to limit the subject matter of the invention thereto.

1. Preparation of Encoding Plasmids:

In the following experiment DNA sequences, corresponding to the respective mRNA sequences end encoding the antigens
  hTERT,
  WT1,
  MAGE-A2,
  5T4,
  MAGE-A3,
  MUC1,
  Her-2/neu,
  NY-ESO-1,
  CEA, Survivin,
MAGE-C1, or
MAGE-C2.
respectively, were prepared and used for in vitro transcription and transfection experiments. Thereby, the DNA sequence corresponding to the native antigen encoding mRNA was increased in GC-content and codon-optimized. Then, the coding sequence was transferred into an RNActive construct (CureVac GmbH, Tübingen, Germany), which has been modified with a poly-A-tag and a poly-C-tag (A70-C30).

2. In Vitro Transcription:

Based on the recombinant plasmid DNA obtained in Example 1 the RNA sequences were prepared by in vitro transcription. Therefore, the recombinant plasmid DNA was linearized and subsequently in vitro transcribed using the T7 RNA polymerase. The DNA template was then degraded by DNase I digestion, and the RNA was recovered by LiCl precipitation and further cleaned by HPLC extraction (PUREMessenger®, CureVac GmbH, Tübingen, Germany).

3. Complexation with Protamine

For transfection of the RNA into cells and organisms the RNA obtained by in vitro transcription was preferably complexed, more preferably with protamine upon mixing the RNA with protamine.

4. Vaccination Experiments

For vaccination the RNA obtained by the in vitro transcription experiment as shown above (see Experiment 2) was transfected into mice (Mice: C57 BL/6), preferably when complexed with protamine (see Experiment 3). Transfection occurred in different groups, wherein 5 mice (C57 BL/6) per group were immunized intradermally 8 times within 3 weeks with the inventive mRNA cocktail, i.e. a mixture of mRNA complexed with protamine, wherein the RNA codes for at least two of the antigens hTERT, WT1, MAGE-A2, 5T4, MAGE-A3, MUC1, Her-2/neu, NY-ESO-1, CEA, Survivin, MAGE-C1, or MAGE-C2.

5. Detection of an Antigen-Specific Immune Response (B-Cell Immune Response):

Detection of an antigen-specific immune response (B-cell immune response) was carried out by detecting antigen-specific antibodies. Therefore, blood samples were taken from the vaccinated mice one week after the last vaccination and sera were prepared. MaxiSorb plates (Nalgene Nunc International) were coated with the antigenic protein as encoded by the mRNA-Cocktail (0.5 µg/well). After blocking with 1×PBS containing 0.05% Tween-20 and 1% BSA the plates were incubated with diluted mouse serum (1:30, 1:90, 1:270, 1:810). Subsequently a biotin-coupled secondary antibody (Anti-mouse-IgG2a Pharmingen) was added. After washing, the plate was incubated with Horseradish peroxidase-streptavidin and subsequently the conversion of the ABTS substrate (2,2'-azino-bis(3-ethyl-benzthiazoline-6-sulfonic acid) was measured.

6. Detection of an Antigen-Specific Cellular Immune Response (T Cell Immune Response) by ELISPOT:

2 weeks after the last vaccination mice were sacrificed, the spleens were removed and the splenocytes were isolated. The splenocytes were restimulated for 7 days in the presence of peptides from the above antigens (peptide library) or coincubated with dendritic cells generated from bone marrow cells of native syngeneic mice, which are electroporated with RNA coding for the antigen. To determine an antigen-specific cellular immune response INFgamma secretion was measured after re-stimulation. For detection of INFgamma a coat multiscreen plate (Millipore) was incubated overnight with coating buffer 0.1 M carbonate-bicarbonate buffer pH 9.6, 10.59 g/l $Na_2CO_3$, 8.4 g/l $NaHCO_3$) comprising antibody against INFγ (BD Pharmingen, Heidelberg, Germany). Stimulators and effector cells were incubated together in the plate in the ratio of 1:20 for 24 h. The plate was washed with 1×PBS and incubated with a biotin-coupled secondary antibody. After washing with 1×PBS/0.05% Tween-20 the substrate (5-Bromo-4-Cloro-3-Indolyl Phosphate/Nitro Blue Tetrazolium Liquid Substrate System from Sigma Aldrich, Taufkirchen, Germany) was added to the plate and the conversion of the substrate could be detected visually.

7. Tumor Challenge:

Immunization:

One week after the last immunization 1 Mio B16 melanoma cells or TRAMP-C1 cells were injected subcutaneously in the mice. Within 2 weeks (B16) or 7 weeks (TRAMP-C1), respectively, tumour volume was determined 8. Preparation of a mRNA Vaccine A particular example of the inventive active (immunostimulatory) composition, comprising a combination of several antigens for the use as a vaccine for the treatment of non-small cell lung cancer (NSCLC) was prepared in the following according to the above disclosure. The exemplary inventive active (immunostimulatory) composition consisted of 5 components, each containing mRNA coding for one NSCLC related antigen (NY-ESO-1, MAGE-C1, MAGE-C2, Survivin and 5T4, according to SEQ ID NOs: 4, 19, 21, 24 and 26 (GC-enriched sequences)) formulated with protamine at a mass ratio of 4:1.

Vaccination

C57BL/6 mice were vaccinated intradermally with the mRNA vaccine consisting of components, each containing mRNA coding for one NSCLC related antigen (NY-ESO-1, MAGE-C1, MAGE-C2, Survivin and 5T4, according to SEQ ID NOs: 4, 19, 21, 24 and 26 (GC-enriched sequences)) formulated with protamine (64 µg per antigen per cycle, divided into 4 injections/cycle). Control vaccination was performed using the corresponding total doses of RNA coding for LacZ (control mRNA lacZ). The vaccination comprised three immunization cycles (week 1, 3, and 5). The groups, number of mice and mouse strains are indicated in the following table:

| Groups | Mouse strain | Number of mice |
|---|---|---|
| mRNA vaccine | C57BL/6 | 10 |
|  |  | 5 for Elispot and 5 for antibody detection in serum by ELISA |
| Control mRNA lacZ | C57BL/6 | 5 |
|  |  | 3 for Elispot and all 5 for antibody detection in serum by ELISA |

Detection of Antigen-Specific Antibodies 6 days after last vaccination blood samples (200 µl) were taken retro-orbitally and serum was analyzed for the presence of antigen specific antibody subtypes IgG1 and IgG2a using ELISA. 96-well ELISA plates were coated with recombinant protein (10 µg/ml in coating buffer, incubation at 37° C. for 4 h) and blocked with 200 µl blocking buffer per well overnight at 4° C. Subsequently, the samples were incubated with serum pooled from each group of mice and titrated in dilutions ranging from 1:3 to 1:48 for 4 hours at room temperature. After incubation with a specific antibody (1:300 in blocking buffer) against mouse IgG1 or IgG2a and incubation with a HRP-coupled secondary antibody (1:500 in blocking buffer), TMB-substrate was added. The colorimetric reaction was measured at 450 nm using an ELISA reader (Tecan Deutschland GmbH, Crailsheim, Germany).

Elispot

For the detection of cytotoxic T-lymphocyte (CTL) responses the analysis of the secretion of the effector cytokine IFN-γ in response to a specific stimulus can be visualized at a single cell level using the ELISPOT technique.

Splenocytes from antigen-vaccinated and control mice were isolated 6 days after last vaccination and then transferred into 96-well ELISPOT plates coated with an anti-IFN-γ capture antibody (10 μg/ml). The cells were then stimulated for 24 hours at 37° C. either with relevant antigen-derived peptide library or with the HIV-derived library or the solvent of the peptides, DMSO, or incubated in pure medium as a control. All libraries were used at a concentration of 1 μg/peptide/ml. After the incubation period the cells were washed out of the plate and the IFN-γ secreted by the cells was detected using a biotinylated secondary antibody against murine IFN-γ (1 μg/ml), followed by streptavidin-AKP. Spots were visualized using BCIP/NBT substrate and counted using an automated ELISPOT reader (Immunospot Analyzer, CTL Analyzers LLC).

Statistical Analysis

Statistical analysis was performed using Graph Pad Prism 5.01 (GraphPad Software, Inc.). All results were expressed as the mean (or median)±standard error of means. For Elispot assays, due to the fact that the basal activation is strongly individual dependent, a background correction was performed individually per mouse by subtraction of the number of spots in medium wells from all other values. Two-tailed Mann-Whitney tests were used to analyze difference between the test groups with a significance level of 5%.

Results and Discussion

Mice were vaccinated with the mRNA vaccine containing five components as defined above, particularly GC-enriched mRNAs coding for the NSCLC-associated antigens NY-ESO-1, MAGE-C2, MAGE-C1, Survivin and 5T4, (according to SEQ ID NOs: 4, 19, 21, 24 and 26 (GC-enriched sequences)) each formulated separately with the cationic peptide protamine at a mass ratio of 4:1. Control mice were treated with irrelevant RNA coding for LacZ formulated with protamine at the same ratio as the mRNA vaccine.

Using serum isolated from blood drawn from the antigen-vaccinated and control mice, we tested the induction of specific antibodies against the antigens. For three of the five analyzed proteins, MAGE-C1, MAGE-C2 and NY-ESO-1, we detected antigen specific antibodies in serum of mice vaccinated with the mRNA vaccine demonstrating that the mRNAs are functional and immunogenic in vivo. Proteins required for detection of antibodies were produced in E. coli. As production of proteins in E. coli can influence post-translational modifications and these are not well described for the used antigens, this could account for the lack of response seen for the remaining proteins.

Next the activation of cytotoxic T-cells in response to the administration of the mRNA vaccine was analyzed. IFN-γ is the main mediator of Th1 responses and secreted by activated CTLs. Therefore the presence of antigen-specific cytotoxic T-cells in splenocytes from vaccinated mice was investigated using the ELISPOT technique. As an antigenic stimulus for splenocytes restricted peptide libraries were used. Because distinct epitopes of the used human antigens for mouse MHC ($H-2K^b$ and $H-2D^b$ in C578B16 mice) are not known, we had to use a hypothetical selection of peptides selected due to potential binding affinity by search of the SYFPEITHI database. Out of peptide libraries (15mers with 11 amino acids overlap) spanning the whole sequences of the proteins, those 15mers containing the hypothetically best epitopes were selected and pooled up to a maximum of 18 peptides. However, these selections might not necessarily contain the correct epitopes so that the detection of immune responses with the help of these tools can easily yield false negative results. Nevertheless, the stimulation with two of these libraries, originating from NY-ESO-1 and 5T4, led to high IFN-γ secretion in splenocytes from mice vaccinated with the mRNA vaccine and not in splenocytes from control mice, vaccinated with mRNA coding for irrelevant protein β-galactosidase. None of the splenocytes reacted to the HIV-derived control peptide library. The number of IFN-γ spots by splenocytes incubated in medium alone represents the basal activation of the freshly isolated cells. Due to the fact that the basal activation is strongly individual dependent, the background correction was performed individually by subtraction of the number of spots in medium wells from all other values.

The results of these experiments are shown in FIGS. 27 to 34.

The invention claimed is:

1. A kit comprising at least five different immunostimulatory compositions, wherein the at least five different immunostimulatory compositions are:
   (a) an immunostimulatory composition comprising an isolated NY-ESO-1 antigen coding RNA complexed with protamine;
   (b) an immunostimulatory composition comprising an isolated MAGE-C1 antigen coding RNA complexed with protamine;
   (c) an immunostimulatory composition comprising an isolated MAGE-C2 antigen coding RNA complexed with protamine;
   (d) an immunostimulatory composition comprising an isolated 5T4 antigen coding RNA complexed with protamine; and
   (e) an immunostimulatory composition comprising an isolated Survivin antigen coding RNA complexed with protamine.

2. The kit according to claim 1, further comprising an immunostimulatory composition comprising an isolated MUC-1 antigen coding RNA complexed with protamine.

3. The kit according to claim 1, wherein at least one of said at least five different immunostimulatory compositions comprises RNA that is mRNA.

4. The kit according to claim 1, wherein at least one of said at least five different immunostimulatory compositions comprises RNA that is monocistronic RNA.

5. The kit according to claim 1, wherein the antigen coding RNA of said at least five different immunostimulatory compositions is monocistronic RNA.

6. The kit according to claim 3, wherein the mRNA comprises a G/C content of the antigen coding region that is increased compared to the G/C content of a wild-type RNA encoding the antigen.

7. The kit according to claim 3, wherein the mRNA comprises a A/U content in the environment of the ribosome binding site that is increased compared with the A/U content of a wild-type RNA encoding the antigen.

8. The kit according to claim 3, wherein the mRNA comprises a 5' untranslated region (5'UTR) and/or 3' untranslated region (3'UTR) that is modified compared to a wild-type RNA encoding the antigen.

9. The kit according to claim 3, wherein the mRNA comprises a 5' cap structure; a poly(A) tail; a poly(C) tail; and/or a globin 3'UTR.

10. The kit according to claim 1, wherein at least one of said at least five different immunostimulatory compositions comprises at least one adjuvant.

11. The kit according to claim 1, wherein at least one of said at least five different immunostimulatory compositions comprises a pharmaceutically acceptable carrier.

12. A method of treating lung cancer in a subject comprising administering an effective amount of said at least five different immunostimulatory compositions of a kit according to claim 1 to the subject.

13. The method according to claim 12, wherein the lung cancer is non-small-cell lung cancer (NSCLC).

14. The kit of claim 1, wherein at least one of said at least five different immunostimulatory compositions comprises RNA that comprises a globin 3' UTR.

15. The kit according to claim 1, wherein each of said different immunostimulatory compositions comprises isolated mRNA complexed with protamine and wherein each of said different immunostimulatory compositions comprises mRNA comprising a 5' cap structure, a poly(A) tail, a globin 3' UTR, and a G/C content of the antigen coding region, which is increased compared to the G/C content of wild-type RNA encoding the antigen.

16. The kit according to claim 2, wherein each of said different immunostimulatory compositions comprises isolated mRNA complexed with protamine and wherein each of said different immunostimulatory compositions comprises mRNA comprising a 5' cap structure, a poly(A) tail, a globin 3' UTR, and a G/C content of the antigen coding region, which is increased compared to the G/C content of wild-type RNA encoding the antigen.

17. The kit according to claim 3, wherein the mRNA comprises a 3'UTR that does not comprise an AU-rich sequence.

18. The kit according to claim 3, wherein at least one of said at least five different immunostimulatory compositions comprises RNA that does not comprise the sequence GAACAAG.

19. A method of treating lung cancer in a subject comprising administering an effective amount of said at least five different immunostimulatory compositions of a kit according to claim 2 to the subject.

20. A kit comprising at least five different immunostimulatory compositions, wherein the at least five different immunostimulatory compositions are:
  (a) an immunostimulatory composition comprising an isolated NY-ESO-1 antigen coding RNA comprising a globin 3' untranslated region (3'UTR);
  (b) an immunostimulatory composition comprising an isolated MAGE-C1 antigen coding RNA comprising a globin 3'UTR;
  (c) an immunostimulatory composition comprising an isolated MAGE-C2 antigen coding RNA comprising a globin 3'UTR;
  (d) an immunostimulatory composition comprising an isolated 5T4 antigen coding RNA comprising a globin 3'UTR; and
  (e) an immunostimulatory composition comprising an isolated Survivin antigen coding RNA comprising a globin 3'UTR.

21. The kit according to claim 20, further comprising an immunostimulatory composition comprising an isolated MUC-1 antigen coding RNA comprising a globin 3'UTR.

22. The kit according to claim 20, wherein at least one of said at least five different immunostimulatory compositions comprises RNA that is mRNA.

23. The kit according to claim 20, wherein at least one of said at least five different immunostimulatory compositions comprises RNA that is monocistronic RNA.

24. The kit according to claim 20, wherein the antigen coding RNA of said at least five different immunostimulatory compositions is monocistronic RNA.

25. The kit according to claim 22, wherein the mRNA comprises a G/C content of the antigen coding region that is increased compared to the G/C content of a wild-type RNA encoding the antigen.

26. The kit according to claim 22, wherein the mRNA comprises a A/U content in the environment of the ribosome binding site that is increased compared with the A/U content of a wild-type RNA encoding the antigen.

27. The kit according to claim 22, wherein the mRNA comprises a 5' untranslated region (5'UTR) that is modified compared to a wild-type RNA encoding the antigen.

28. The kit according to claim 22, wherein the mRNA comprises a 5' cap structure; a poly(A) tail; and/or a poly(C) tail.

29. The kit according to claim 22, wherein at least one of said at least five different immunostimulatory compositions comprises RNA that is complexed with one or more polycationic molecules.

30. The kit of claim 29, wherein the one or more polycationic molecules comprise protamine.

31. The kit according to claim 20, wherein at least one of said at least five different immunostimulatory compositions comprises at least one adjuvant.

32. The kit according to claim 20, wherein at least one of said at least five different immunostimulatory compositions comprises a pharmaceutically acceptable carrier.

33. A method of treating lung cancer in a subject comprising administering an effective amount of said at least five different immunostimulatory compositions of a kit according to claim 20 to the subject.

34. A method of treating lung cancer in a subject comprising administering an effective amount of said at least five different immunostimulatory compositions of a kit according to claim 21 to the subject.

35. The method according to claim 33, wherein the lung cancer is non-small-cell lung cancer (NSCLC).

36. A kit comprising at least five different immunostimulatory compositions, wherein the at least five different immunostimulatory compositions are:
  (a) an immunostimulatory composition comprising an isolated NY-ESO-1 antigen coding RNA comprising a G/C content of the antigen coding region that is increased compared to the G/C content of a wild-type RNA encoding the antigen;
  (b) an immunostimulatory composition comprising an isolated MAGE-C1 antigen coding RNA comprising a G/C content of the antigen coding region that is increased compared to the G/C content of a wild-type RNA encoding the antigen;
  (c) an immunostimulatory composition comprising an isolated MAGE-C2 antigen coding RNA comprising a G/C content of the antigen coding region that is increased compared to the G/C content of a wild-type RNA encoding the antigen;
  (d) an immunostimulatory composition comprising an isolated 5T4 antigen coding RNA comprising a G/C content of the antigen coding region that is increased compared to the G/C content of a wild-type RNA encoding the antigen; and
  (e) an immunostimulatory composition comprising an isolated Survivin antigen coding RNA comprising a G/C content of the antigen coding region that is increased compared to the G/C content of a wild-type RNA encoding the antigen.

37. The kit according to claim 36, further comprising an immunostimulatory composition comprising an isolated MUC-1 antigen coding RNA comprising a G/C content of the antigen coding region that is increased compared to the G/C content of a wild-type RNA encoding the antigen.

38. The kit according to claim 36, wherein at least one of said at least five different immunostimulatory compositions comprises RNA that is mRNA.

39. The kit according to claim 36, wherein at least one of said at least five different immunostimulatory compositions comprises RNA that is monocistronic RNA.

40. The kit according to claim 36, wherein the antigen coding RNA of said at least five different immunostimulatory compositions is monocistronic RNA.

41. The kit according to claim 38, wherein the mRNA comprises a A/U content in the environment of the ribosome binding site that is increased compared with the A/U content of a wild-type RNA encoding the antigen.

42. The kit according to claim 38, wherein the mRNA comprises a 5' untranslated region (5'UTR) and/or 3' untranslated region (3'UTR) that is modified compared to a wild-type RNA encoding the antigen.

43. The kit according to claim 38, wherein the mRNA comprises a 5' cap structure; a poly(A) tail; a poly(C) tail; and/or a globin 3'UTR.

44. The kit according to claim 36, wherein at least one of said at least five different immunostimulatory compositions comprises RNA that is complexed with one or more polycationic molecules.

45. The kit of claim 44, wherein the one or more polycationic molecules comprise protamine.

46. The kit according to claim 36, wherein at least one of said at least five different immunostimulatory compositions comprises at least one adjuvant.

47. The kit according to claim 36, wherein at least one of said at least five different immunostimulatory compositions comprises a pharmaceutically acceptable carrier.

48. The kit of claim 36, wherein at least one of said at least five different immunostimulatory compositions comprises RNA that comprises a globin 3' UTR.

49. A method of treating lung cancer in a subject comprising administering an effective amount of said at least five different immunostimulatory compositions of a kit according to claim 36 to the subject.

50. A method of treating lung cancer in a subject comprising administering an effective amount of said at least five different immunostimulatory compositions of a kit according to claim 37 to the subject.

51. The method according to claim 49, wherein the lung cancer is non-small-cell lung cancer (NSCLC).

52. A kit comprising at least five different immunostimulatory compositions, wherein the at least five different immunostimulatory compositions are:
  (a) an immunostimulatory composition comprising an isolated NY-ESO-1 antigen coding RNA comprising a 5' untranslated region (5'UTR) and/or a 3' untranslated region (3'UTR) that is modified compared to a wild-type RNA encoding the antigen;
  (b) an immunostimulatory composition comprising an isolated MAGE-C1 antigen coding RNA comprising a 5'UTR and/or a 3'UTR that is modified compared to a wild-type RNA encoding the antigen;
  (c) an immunostimulatory composition comprising an isolated MAGE-C2 antigen coding RNA comprising a 5'UTR and/or a 3'UTR that is modified compared to a wild-type RNA encoding the antigen;
  (d) an immunostimulatory composition comprising an isolated 5T4 antigen coding RNA comprising a 5'UTR and/or a 3'UTR that is modified compared to a wild-type RNA encoding the antigen; and
  (e) an immunostimulatory composition comprising an isolated Survivin antigen coding RNA comprising a 5'UTR and/or a 3'UTR that is modified compared to a wild-type RNA encoding the antigen.

53. The kit according to claim 52, further comprising an immunostimulatory composition comprising an isolated MUC-1 antigen coding RNA comprising a 5'UTR and/or a 3'UTR that is modified compared to a wild-type RNA encoding the antigen.

54. The kit according to claim 52, wherein at least one of said at least five different immunostimulatory compositions comprises RNA that is mRNA.

55. The kit according to claim 52, wherein at least one of said at least five different immunostimulatory compositions comprises RNA that is monocistronic RNA.

56. The kit according to claim 52, wherein the antigen coding RNA of said at least five different immunostimulatory compositions is monocistronic RNA.

57. The kit according to claim 54, wherein the mRNA comprises a G/C content of the antigen coding region that is increased compared to the G/C content of a wild-type RNA encoding the antigen.

58. The kit according to claim 54, wherein the mRNA comprises a A/U content in the environment of the ribosome binding site that is increased compared with the A/U content of a wild-type RNA encoding the antigen.

59. The kit according to claim 54, wherein the mRNA comprises a 5' cap structure; a poly(A) tail; a poly(C) tail; and/or a globin 3'UTR.

60. The kit according to claim 52, wherein at least one of said at least five different immunostimulatory compositions comprises RNA that is complexed with one or more polycationic molecules.

61. The kit of claim 60, wherein the one or more polycationic molecules comprise protamine.

62. The kit according to claim 52, wherein at least one of said at least five different immunostimulatory compositions comprises at least one adjuvant.

63. The kit according to claim 52, wherein at least one of said at least five different immunostimulatory compositions comprises a pharmaceutically acceptable carrier.

64. The kit of claim 52, wherein at least one of said at least five different immunostimulatory compositions comprises RNA that comprises a globin 3' UTR.

65. A method of treating lung cancer in a subject comprising administering an effective amount of said at least five different immunostimulatory compositions of a kit according to claim 52 to the subject.

66. A method of treating lung cancer in a subject comprising administering an effective amount of said at least five different immunostimulatory compositions of a kit according to claim 53 to the subject.

67. The method according to claim 65, wherein the lung cancer is non-small-cell lung cancer (NSCLC).

* * * * *